United States Patent
Sakaguchi

(10) Patent No.: US 7,919,674 B2
(45) Date of Patent: Apr. 5, 2011

(54) TRANSGENIC MAMMAL CARRYING GANP GENE TRANSFERRED THEREINTO AND UTILIZATION THEREOF

(75) Inventor: Nobuo Sakaguchi, Kumamoto (JP)

(73) Assignee: Immunokick Incorporation, Kumamoto-shi (JP)

( * ) Notice: Subject to any disclaimer, the term of this patent is extended or adjusted under 35 U.S.C. 154(b) by 35 days.

(21) Appl. No.: 10/534,043

(22) PCT Filed: Nov. 7, 2003

(86) PCT No.: PCT/JP03/14221
§ 371 (c)(1), (2), (4) Date: Mar. 30, 2006

(87) PCT Pub. No.: WO2004/040971
PCT Pub. Date: May 21, 2004

(65) Prior Publication Data
US 2006/0236417 A1    Oct. 19, 2006

(30) Foreign Application Priority Data
Nov. 7, 2002    (JP) ............................ PCT/JP02/11598

(51) Int. Cl.
C12P 21/00 (2006.01)
A01K 67/00 (2006.01)
A01K 67/033 (2006.01)
A01K 67/027 (2006.01)
C12N 5/00 (2006.01)
C12N 5/02 (2006.01)
C12N 5/07 (2006.01)
C12N 5/10 (2006.01)

(52) U.S. Cl. ......... 800/18; 800/4; 800/5; 800/6; 800/13; 800/14; 435/325; 435/326; 435/352; 435/354

(58) Field of Classification Search .................. None
See application file for complete search history.

(56) References Cited

U.S. PATENT DOCUMENTS
2002/0086014 A1    7/2002  Korman et al.
2002/0176855 A1    11/2002 Co et al.

FOREIGN PATENT DOCUMENTS

| EP | 0 974 67 A1 | 1/2000 |
| JP | 2001-78779 A | 3/2001 |
| WO | WO-00/50611 A | 8/2000 |
| WO | WO-00/56771 A1 | 9/2000 |
| WO | WO-01/81587 A1 | 11/2001 |

OTHER PUBLICATIONS

Kuwahara et al., 2001, PNAS, USA, 98: 10279-10283.*
Lao-Sirieix and Bell, 2004, J. Mol. Biol., 344: 1251-1263.*
Franz et al., 1997, J. Mol. Med., 75: 115-129.*
Racay, 2002, Bratisl Lek Listy, 103: 121-126.*
Jakel et al., 2004, Nature Reviews: Genetics, 5: 136-144.*
Li et al., 2004, Genes and Development, 18: 1-11.*
Murray, et al., 1999, Transgenic Animals in Agriculture, CAB International: Oxon, pp. 58-61.*
Kage et al., 2002, Int. J. Cancer, 97, 626-630.*
Kuwahara et al., 2000, Blood, 95: 2321-2328.*
Jaenisch, 1988, Science, 240: 1468-1474.*
Maas et al., 1999, The Journal of Immunology, 162: 6526-6533.*
Henderson et al., 1998, Annu. Rev. Immunol. 16: 163-200.*
Weill et al., 1996, Review: Immunology Today, 17: 92-97.*
Kuwahara K. et al., Proc. Natl. Acad. USA., 2001, vol. 98, No. 18., pp. 10279-10283.
Sakaguchi N, et al., Dev. Immunol., Sep. 2002, vol. 9, No. 3, pp. 169-172.
Kiyoshi Habu et al., "Experimental Medicine separate volume Shin Idenshi Kogaku Handbook", 1996, pp. 269-276.
Kuwahara K. et al., Tanpakushitsu Kakusan Koso., Dec. 2002, vol. 47 (16 Suppl), pp. 2300-2305.

* cited by examiner

*Primary Examiner* — Joanne Hama
(74) *Attorney, Agent, or Firm* — Birch, Stewart, Kolasch & Birch, LLP

(57) ABSTRACT

It is an object of the present invention to provide a high affinity antibody effective as a diagnostic or therapeutic for various diseases; a transgenic mammal for producing the high affinity antibody; and a medicine comprising the high affinity antibody or a cell producing the high affinity antibody. According to the present invention, a transgenic mammal carrying a GANP gene transferred thereinto, its progeny, or a part thereof, and a method of producing a high affinity antibody using the same are provided.

12 Claims, 69 Drawing Sheets
(23 of 69 Drawing Sheet(s) Filed in Color)

Fig. 10

| Pos | 1 | 2 | 3 | 4 | 5 | 6 | 7 | 8 | 9 | 10 | 11 | 12 | 13 | 14 | 15 | 16 | 17 | 18 | 19 | 20 | 21 | 22 | 23 | 24 | 25 | 26 | 27 | 28 | 29 | 30 |
|---|---|---|---|---|---|---|---|---|---|---|---|---|---|---|---|---|---|---|---|---|---|---|---|---|---|---|---|---|---|---|
| WT aa | Q | V | Q | L | Q | Q | P | G | A | E | L | V | K | P | G | A | S | V | K | L | S | C | K | A | S | G | Y | T | F | T |
| WT codon | CAG | GTC | CAA | CTG | CAG | CAG | CCT | GGG | GCT | GAG | CTT | GTG | AAG | CCT | GGG | GCT | TCA | GTG | AAG | CTG | TCC | TGC | AAG | GCT | TCT | GGC | TAC | ACC | TTC | ACC |
| WT-4 | --- | --- | --- | --- | --- | --- | --- | --- | --- | --- | --- | --- | --- | --- | --- | --- | --- | --- | --- | --- | --- | --- | --- | --- | --- | --- | --- | --- | --- | --- |
| WT-5 | --- | --- | --- | --- | --- | --- | --- | --- | --- | --- | --- | --- | --- | --- | --- | --- | --- | --- | --- | --- | --- | --- | --- | --- | --- | --- | --- | --- | --- | --- |
| WT-6 | --- | --- | --- | --- | --- | --- | --- | --- | --- | --- | --- | --- | --- | --- | --- | --- | --- | --- | --- | --- | --- | --- | --- | T | --- | --- | --- | S | --- | --- |
| WT-9 | --- | --- | --- | --- | --- | --- | --- | --- | --- | --- | --- | --- | --- | --- | --- | --- | --- | --- | --- | --- | --- | --- | --- | A- | --- | --- | --- | T- | --- | --- |
| WT-10 | --- | --- | --- | --- | --- | --- | --- | --- | --- | --- | --- | --- | --- | --- | --- | --- | --- | --- | --- | --- | --- | --- | --- | --- | --- | --- | --- | --- | --- | --- |
| WT-11 | --- | --- | --- | --- | --- | --- | --- | --- | --- | --- | --- | --- | --- | --- | --- | --- | --- | --- | --- | --- | --- | --- | --- | --- | --- | --- | --- | --- | --- | --- |
| WT-14 | --- | --- | --- | --- | --- | --- | --- | --- | --- | --- | --- | --- | --- | --- | --- | --- | --- | --- | --- | --- | --- | --- | --- | --- | --- | --- | --- | --- | --- | --- |
| WT-16 | --- | --- | --- | --- | --- | --- | --- | --- | --- | --- | --- | --- | --- | --- | --- | --- | --- | --- | --- | --- | --- | --- | --- | --- | --- | --- | --- | --- | --- | --- |
| WT-17 | --- | --- | --- | --- | --- | --- | --- | --- | --- | --- | --- | --- | --- | --- | --- | --- | --- | --- | --- | --- | --- | --- | --- | --- | --- | --- | --- | --- | --- | --- |
| WT-18 | --- | --- | --- | --- | --- | --- | --- | --- | --- | --- | --- | --- | --- | --- | --- | --- | --- | --- | --- | --- | --- | --- | --- | --- | --- | --- | --- | --- | --- | --- |
| WT-19 | --- | --- | --- | --- | --- | --- | --- | --- | --- | --- | --- | --- | --- | --- | --- | --- | --- | --- | --- | --- | --- | --- | --- | --- | --- | --- | --- | --- | --- | --- |
| WT-20 | --- | --- | --- | --- | --- | --- | --- | --- | --- | --- | --- | --- | --- | --- | --- | --- | --- | --- | --- | --- | --- | --- | --- | --- | --- | --- | --- | --- | --- | --- |
| WT-21 | --- | --- | --- | --- | --- | --- | --- | --- | --- | --- | --- | --- | --- | --- | --- | --- | --- | --- | --- | --- | --- | --- | --- | --- | --- | --- | --- | --- | --- | --- |
| WT-22 | --- | --- | --- | --- | --- | --- | --- | --- | --- | --- | --- | --- | --- | --- | --- | --- | --- | --- | --- | --- | --- | --- | --- | --- | --- | --- | --- | --- | --- | --- |

| | 1 Q CAG | 2 V GTC | 3 Q CAA | 4 L CTG | 5 Q CAG | 6 Q CAG | 7 P CCT | 8 G GGG | 9 A GCT | 10 E GAG | 11 L CTT | 12 V GTG | 13 K AAG | 14 P CCT | 15 G GGG | 16 A GCT | 17 S TCA | 18 V GTG | 19 K AAG | 20 L CTG | 21 S TCC | 22 C TGC | 23 K AAG | 24 A GCT | 25 S TCT | 26 G GGC | 27 Y TAC | 28 T ACC | 29 F TTC | 30 T ACC |
|---|---|---|---|---|---|---|---|---|---|---|---|---|---|---|---|---|---|---|---|---|---|---|---|---|---|---|---|---|---|---|
| Tg-3 | --- | --- | --- | --- | --- | --- | --- | --- | --- | --- | --- | --- | --- | --- | --- | --- | --- | --- | --- | --- | --- | --- | --- | --- | --- | --- | --- | --- | --- | --- |
| Tg-4 | --- | --- | --- | --- | --- | --- | --- | --- | --- | -A- | --- | --- | --- | --- | --- | --- | --- | --- | --- | --- | --- | --- | --- | --- | --- | --- | --- | --- | --- | --- |
| Tg-5 | --- | --- | --- | --- | --- | --- | --- | --- | --- | --- | --- | --- | --- | --- | --- | --- | --- | --- | --- | --- | --- | --- | --- | --- | --- | --- | --- | --- | --- | --- |
| Tg-7 | --- | --- | --- | --- | --- | --- | --- | --- | --- | --- | --- | --- | --- | --- | --- | --- | --- | --- | --- | --- | --- | --- | --- | --- | --- | --- | --- | --- | --- | --- |
| Tg-8 | --- | --- | --- | --- | --- | --- | --- | --- | --- | --- | --- | --- | --- | --- | --- | S T- | --- | --- | --- | --- | --- | --- | --- | --- | --- | --- | --- | --- | --- | --- |
| Tg-9 | --- | --- | --- | --- | --- | --- | --- | --- | --- | --- | --- | --- | --- | --- | --- | --- | --- | --- | --- | --- | --- | --- | --- | --- | --- | --- | --- | --- | --- | --- |
| Tg-10 | --- | --- | --- | --- | --- | --- | --- | --- | --- | --- | --- | --- | --- | --- | --- | S T- | --- | --- | --- | --- | --- | --- | --- | P C- | --- | --- | --- | --- | --- | --- |
| Tg-11 | --- | --- | --- | --- | --- | --- | --- | --- | --- | --- | --- | --- | --- | --- | --- | --- | --- | --- | --- | --- | --- | --- | --- | --- | --- | --- | --- | --- | --- | --- |
| Tg-12 | --- | --- | --- | --- | --- | --- | --- | --- | --- | --- | --- | --- | --- | --- | --- | --- | --- | --- | --- | --- | --- | --- | --- | --- | --- | --- | --- | --- | --- | N -A |
| Tg-13 | --- | --- | --- | --- | --- | --- | --- | --- | --- | --- | --- | --- | --- | S T- | --- | --- | --- | --- | --- | --- | --- | --- | --- | --- | --- | --- | --- | --- | --- | --- |
| Tg-14 | --- | --- | R -G- | --- | --- | --- | --- | --- | --- | --- | --- | --- | --- | --- | --- | --- | --- | --- | --- | --- | --- | --- | -A- | --- | --- | --- | --- | --- | --- | --- |
| Tg-15 | --- | --- | --- | --- | --- | --- | --- | --- | --- | --- | --- | --- | --- | --- | --- | --- | --- | --- | --- | --- | --- | --- | --- | --- | --- | --- | --- | --- | --- | --- |
| Tg-16 | --- | --- | --- | --- | --- | --- | --- | --- | --- | --- | --- | --- | --- | --- | --- | --- | --- | --- | --- | --- | --- | --- | --- | --- | --- | --- | --- | --- | --- | --- |
| Tg-17 | --- | --- | --- | --- | --- | --- | --- | --- | --- | --- | --- | --- | --- | --- | --- | --- | --- | --- | --- | --- | --- | --- | --- | --- | --- | --- | --- | --- | --- | N -AT |
| Tg-18 | --- | --- | --- | --- | --- | --- | --- | --- | --- | --- | --- | --- | --- | --- | --- | --- | --- | --- | --- | --- | --- | --- | --- | --- | --- | --- | --- | I -TT | --- | --- |
| Tg-20 | --- | --- | --- | --- | --- | --- | --- | --- | --- | --- | --- | --- | --- | --- | --- | --- | --- | --- | --- | --- | --- | --- | --- | --- | --- | --- | --- | --- | --- | --- |
| Tg-21 | --- | --- | --- | --- | --- | --- | --- | --- | --- | --- | --- | --- | --- | --- | --- | --- | --- | --- | --- | --- | --- | --- | --- | --- | --- | --- | --- | --- | --- | --- |
| Tg-23 | --- | --- | --- | --- | --- | --- | --- | --- | --- | --- | --- | --- | --- | --- | --- | --- | --- | --- | --- | --- | --- | --- | --- | --- | --- | --- | --- | --- | --- | --- |

Cre-flox/+

|   | 1 | 2 | 3 | 4 | 5 | 6 | 7 | 8 | 9 | 10 | 11 | 12 | 13 | 14 | 15 | 16 | 17 |
|---|---|---|---|---|---|---|---|---|---|----|----|----|----|----|----|----|----|
|   | Q | V | Q | L | Q | Q | P | G | A | E  | L  | V  | K  | P  | G  | A  | S  |
|   | CAG | GTC | CAA | CTG | CAG | CAG | CCT | GGG | GCT | GAG | CTT | GTG | AAG | CCT | GGG | GCT | TCA |
| 1-5 | --- | --- | --- | --- | --- | --- | --- | --- | --- | --- | --- | --- | --- | --- | --- | --- | --- |
| 1-6 | --- | --- | --- | --- | --- | --- | --- | --- | --- | -A- | --- | --- | --- | --- | --- | --- | --- |
| 3-1 | --- | --- | --- | --- | --- | --- | --- | --- | --- | --- | --- | --- | --- | --- | --- | --- | --- |
| 3-2 | --- | --- | --- | --- | --- | --- | --- | --- | --- | --- | --- | --- | R/-G- | --- | --- | --- | --- |
| 3-3 | --- | --- | --- | --- | --- | --- | --- | --- | --- | --- | --- | --- | --- | --- | --- | --- | --- |
| 4-2 | --- | --- | --- | --- | --- | --- | --- | --- | --- | --- | --- | --- | --- | --- | --- | G/-G- | --- |
| 4-4 | --- | --- | --- | --- | --- | --- | --- | --- | --- | --- | --- | --- | --- | --- | --- | G/-G- | --- |
| 4-6 | --- | --- | --- | --- | --- | --- | --- | --- | --- | --- | --- | --- | --- | --- | --- | --- | --- |
| 1-8 | --- | --- | --- | --- | --- | --- | --- | --- | --- | --- | --- | --- | --- | --- | --- | --- | --- |
| 1-10 | --- | --- | --- | --- | --- | --- | --- | --- | --- | --- | --- | --- | --- | --- | --- | --- | --- |
| 4-7 | --- | --- | --- | --- | --- | --- | --- | --- | --- | --- | --- | --- | --- | --- | --- | G/-G- | --- |
| 6-1 | --- | --- | --- | --- | --- | --- | --- | --- | T/A-- | --- | --- | --- | --- | --- | --- | --- | --- |
| 6-2 | --- | --- | --- | --- | --- | --- | --- | --- | --- | --- | -A- | -G- | --- | --- | --- | --- | --- |
| 7-1 | --- | --- | --- | --- | --- | --- | --- | --- | --- | --- | --- | --- | --- | --- | --- | --- | --- |

Cre-flox/+

Fig. 20C

Cre-flox/+

| | 36 | 37 | 38 | 39 | 40 | 41 | 42 | 43 | 44 | 45 | 46 | 47 | 48 | 49 |
|---|---|---|---|---|---|---|---|---|---|---|---|---|---|---|
| | W | V | K | Q | R | P | G | R | G | L | E | W | I | G |
| | TGG | GTG | AAG | CAG | AGG | CCT | GGA | CGA | GGC | CTT | GAG | TGG | ATT | GGA |
| | --- | --- | --- | --- | --- | --- | --- | --- | --- | --- | --- | --- | --- | --- |
| | --- | --- | --- | --- | --- | --- | --- | --- | --- | --- | --- | --- | --- | --- |
| | --- | --- | --- | --- | --- | --- | --- | --- | --- | --- | --- | --- | --- | --- |
| | --- | --- | --- | --- | --- | --- | --- | --- | --- | --- | --- | --- | --- | --- |
| | --- | --- | --- | --- | --- | --- | --- | --- | --- | --- | --- | --- | --- | --- |
| | --- | --- | --- | --- | --- | --- | --- | --- | --- | --- | --- | --- | --- | --- |
| | --- | --- | --- | --- | --- | --- | --- | --- | --- | --- | --- | --- | --- | --- |
| | --- | --- | --- | --- | --- | --- | --- | --- | --- | --- | --- | --- | --- | --- |
| | --- | --- | --- | --- | --- | --- | --- | --- | --- | --- | --- | --- | --- | --- |
| | --- | --- | --- | --- | --- | --- | --- | --- | --- | --- | --- | --- | --- | --- |
| | --- | --- | --A | --- | --- | --- | --- | --- | --- | --- | --- | --- | --- | --- |
| | --- | --- | --- | --- | --- | --- | --- | --- | --- | --- | --- | --- | --- | --- |
| | --- | --- | --- | --- | --- | --- | --- | --- | --- | --- | --- | --- | --- | --- |

Fig. 20D

Cre-flox/+

| | 50<br>R<br>AGG | 51<br>I<br>ATT | 52<br>D<br>GAT | 53<br>P<br>CCT | 54<br>N<br>AAT | 55<br>S<br>AGT | 56<br>G<br>GGT | 57<br>G<br>GGT | 58<br>T<br>ACT | 59<br>K<br>AAG | 60<br>Y<br>TAC | 61<br>N<br>AAT | 62<br>E<br>GAG | 63<br>K<br>AAG | 64<br>F<br>TTC | 65<br>K<br>AAG | 66<br>S<br>AGC | 67<br>K<br>AAG |
|---|---|---|---|---|---|---|---|---|---|---|---|---|---|---|---|---|---|---|
| 1-5 | --- | --- | --- | --- | --- | --- | --- | --- | --- | --- | --- | --- | --- | --- | --- | --- | --- | --- |
| 1-6 | --- | --- | --- | --- | --- | --- | --- | --- | --- | --- | --- | --- | --- | --- | --- | --- | --- | --- |
| 3-1 | --- | --- | --- | --- | --- | --- | --- | D<br>-A- | —A— | --- | --- | --- | --- | --- | --- | --- | --- | --- |
| 3-2 | --- | --- | --- | --- | M<br>-TG | --- | --- | —C | S<br>-G- | R<br>-G- | --- | --- | --- | Y<br>T-C | --- | --- | --- | --- |
| 3-3 | --- | --- | --- | --- | --- | --- | --- | --- | --- | --- | --- | --- | --- | --- | --- | --- | --- | --- |
| 4-2 | --- | --- | --- | --- | --- | --- | --- | --- | --- | --- | --- | --- | --- | --- | --- | --- | --- | --- |
| 4-4 | --- | --- | --- | --- | --- | --- | --- | --- | --- | --- | --- | --- | --- | --- | --- | --- | --- | --- |
| 4-6 | --- | --- | --- | --- | --- | --- | --- | --- | --- | --- | --- | --- | --- | --- | --- | --- | --- | --- |
| 1-8 | --- | --- | --- | --- | K<br>-A- | --- | --- | --- | --- | --- | --- | --- | S<br>-G- | --- | --- | --- | --- | --- |
| 1-10 | --- | V<br>G-- | --- | --- | --- | T<br>-C- | --- | --- | --- | --- | --- | --- | --- | --- | --- | --- | --- | --- |
| 4-7 | --- | --- | --- | --- | --- | --- | --- | D<br>-A- | --- | --- | --- | --- | --- | --- | --- | --- | --- | --- |
| 6-1 | --- | --- | --- | --- | --- | --- | --- | --- | --- | --- | --- | --- | --- | T<br>-C- | --- | --- | N<br>-A- | --- |
| 6-2 | --- | --- | --- | --- | --- | --- | --- | S<br>A-- | --- | --- | --- | --- | --- | --- | --- | --- | T<br>-C- | --- |
| 7-1 | --- | --- | --- | --- | --- | --- | --- | --- | --- | --- | --- | --- | --- | T<br>-C- | --- | --- | N<br>-A- | --- |

Fig. 20E

Cre-flox/+

| 68 | 69 | 70 | 71 | 72 | 73 | 74 | 75 | 76 | 77 | 78 | 79 | 80 | 81 | 82 | 83 | 84 |
|----|----|----|----|----|----|----|----|----|----|----|----|----|----|----|----|----|
| A | T | L | T | V | D | K | P | S | S | T | A | Y | M | Q | L | S |
| GCC | ACA | CTG | ACT | GTA | GAC | AAA | CCC | TCC | AGC | ACA | GCC | TAC | ATG | CAG | CTC | AGC |

| | | | | | | | | | | | | | | | | |
|---|---|---|---|---|---|---|---|---|---|---|---|---|---|---|---|---|
| — | — | — | — | — | — | — | — | — | — | — | — | — | — | — | — | — |
| — | — | — | — | — | — | — | — | — | — | — | — | — | — | — | — | — |
| — | — | — | — | — | — | — | — | — | — | — | — | — | — | — | — | — |
| — | — | — | — | — | — | — | — | — | — | — | — | — | — | — | — | — |
| — | — | T— | — | — | — | — | — | — | — | — | — | — | — | — | — | — |
| — | — | — | — | I A— | — | — | — | — | — | — | — | — | — | — | — | — |
| — | — | — | — | I A— | — | — | — | — | — | — | — | — | — | — | — | — |
| — | — | — | — | I A— | — | — | — | — | — | — | — | — | — | — | — | — |
| — | — | — | — | — | — | Q C— | — | — | — | — | — | — | — | — | F T— | — |
| — | — | — | — | — | — | — | — | — | — | — | — | — | — | — | — | — |
| — | — | — | — | — | — | — | — | — | — | — | — | — | — | — | — | N -A- |
| — | — | — | — | — | — | — | — | — | — | — | — | — | — | — | — | — |
| — | — | — | — | — | — | — | — | — | — | —T | — | — | — | — | — | — |
| — | — | — | — | — | — | — | — | — | — | — | — | — | — | — | — | — |

Fig. 20F

Cre-flox/+

| | 85 | 86 | 87 | 88 | 89 | 90 | 91 | 92 | 93 | 94 | 95 | 96 | 97 | 98 |
|---|---|---|---|---|---|---|---|---|---|---|---|---|---|---|
| | S | L | T | S | E | D | S | A | V | Y | Y | C | A | R |
| | AGC | CTG | ACA | TCT | GAG | GAC | TCT | GCG | GTC | TAT | TAT | TGT | GCA | AGA |
| | --- | --- | --- | --- | --- | --- | --- | --- | --- | --- | --- | --- | --- | --- |
| | --- | --- | --- | --- | --- | --- | --- | --- | --- | --- | --- | --- | --- | --- |
| | --- | --- | --- | --- | --- | --- | --- | --- | --- | --- | --- | --- | --- | --- |
| | --- | --- | --- | --- | --- | --- | T<br>A--- | --- | D<br>G--- | --- | --- | --- | --- | --- |
| | --- | --- | --- | --- | --- | --- | --- | --- | --- | --- | --- | --- | --- | --- |
| | --- | --- | --- | --- | --- | --- | --- | --- | --- | --- | --- | --- | --- | --G |
| | --- | --- | --- | --- | --- | --- | --- | --- | --- | --- | --- | --- | --- | --G |
| | --- | --- | --- | --- | --- | --- | --- | --- | --- | --- | --- | --- | --- | --G |
| | --- | --- | --- | --- | --- | --- | --- | --- | --- | --- | --- | --- | --- | --- |
| | --- | --- | --- | --- | --- | --- | --- | --- | --- | --- | --- | --- | --- | --- |
| | --- | --- | --- | --- | --- | --- | --- | --- | --- | --- | --- | --- | --- | --- |
| | --- | --- | --- | --- | --- | --- | --- | --- | --- | --- | --- | --- | --- | --- |
| | --- | --- | --- | --- | --- | --- | --- | --- | --- | --- | --- | --- | --- | --- |

Fig. 20G

B-Ganp⁻/⁻

|     | 1<br>Q<br>CAG | 2<br>V<br>GTC | 3<br>Q<br>CAA | 4<br>L<br>CTG | 5<br>Q<br>CAG | 6<br>Q<br>CAG | 7<br>P<br>CCT | 8<br>G<br>GGG | 9<br>A<br>GCT | 10<br>E<br>GAG | 11<br>L<br>CTT | 12<br>V<br>GTG | 13<br>K<br>AAG | 14<br>P<br>CCT | 15<br>G<br>GGG | 16<br>A<br>GCT | 17<br>S<br>TCA |
|-----|---|---|---|---|---|---|---|---|---|---|---|---|---|---|---|---|---|
| 1-1 | --- | --- | --- | --- | --- | --- | --- | --- | --- | --- | --- | --- | --- | --- | --- | --- | --- |
| 1-5 | --- | --- | --- | --- | --- | --- | --- | --- | --- | --- | --- | --- | --- | --- | --- | --- | --- |
| 1-6 | --- | --- | --- | --- | --- | --- | --- | --- | --- | --- | --- | --- | --- | --- | --- | --- | --- |
| 2-2 | --- | --- | --- | --- | --- | --- | --- | --- | --- | --- | --- | --- | --- | --- | --- | --- | --- |
| 2-3 | --- | --- | --- | --- | --- | --- | --- | --- | --- | --- | --- | --- | --- | --- | --- | --- | --- |
| 4-3 | --- | --- | --- | --- | --- | --- | --- | --- | A-T- | --A | --G | --- | --- | --- | --- | --- | --- |
| 4-4 | --- | --- | --- | --- | --- | --- | --- | --- | --- | --- | --- | --- | --- | --- | --- | --- | --- |
| 6-1 | --- | --- | --- | --- | --- | --- | --- | --- | --- | --- | --- | --- | --- | --- | --- | --- | --- |
| 6-2 | --- | --- | --- | --- | --- | --- | --- | --- | --- | --- | --- | --- | --- | --- | --- | --- | --- |
| 7-1 | --- | --- | --- | --- | --- | --- | --- | --- | --- | --- | --- | --- | --- | --- | --- | --- | --- |
| 8-1 | --- | --- | --- | --- | --- | --- | --- | --- | --- | --- | --- | --- | --- | --- | --- | --- | --- |
| 8-2 | --- | --- | --- | --- | --- | --- | --- | --- | --- | --- | --- | --- | --- | --- | --- | --- | --- |
| 9-1 | --- | --- | --- | --- | --- | --- | --- | --- | --- | --- | --- | --- | --- | --- | --- | --- | --- |
| 9-3 | --- | --- | --- | --- | --- | --- | --- | --- | --- | --- | --- | --- | --- | --- | --- | --- | --- |
| 9-4 | --- | --- | --- | --- | --- | --- | --- | --- | --- | --- | --- | --- | --- | --- | --- | --- | --- |

Fig. 20H

B-Ganp⁻/⁻

| 18 | 19 | 20 | 21 | 22 | 23 | 24 | 25 | 26 | 27 | 28 | 29 | 30 | 31 | 32 | 33 | 34 | 35 |
|----|----|----|----|----|----|----|----|----|----|----|----|----|----|----|----|----|----|
| V | K | L | S | C | K | A | S | G | Y | T | F | T | S | Y | W | M | H |
| GTG | AAG | CTG | TCC | TGC | AAG | GCT | TCT | GGC | TAC | ACC | TTC | ACC | AGC | TAC | TGG | ATG | CAC |

| | | | | | | | | | | | | | | | | | |
|---|---|---|---|---|---|---|---|---|---|---|---|---|---|---|---|---|---|
| --- | --- | --- | --- | --- | --- | --- | --- | --- | --- | --- | --- | --- | --- | --- | --- | --- | --- |
| --- | I -TT | --- | --- | --- | --- | --- | --- | A -C- | --- | --- | --- | --- | --- | -T | --- | --- | --- |
| --- | --- | --- | --- | --- | --- | --- | --- | --- | --- | --- | --- | --- | --- | --- | --- | --- | --- |
| --- | --- | --- | --- | --- | --- | -G | --- | --- | --- | --- | --- | --- | N -A- | -T | --- | --- | --- |
| --- | --- | --- | --- | --- | --- | --- | --- | --- | --- | --- | --- | --- | N -A- | --- | --- | --- | --- |
| --- | --- | --- | --- | --- | --- | --- | --- | --- | --- | --- | --- | --- | --- | --- | L -T- | --- | --- |
| --- | --- | --- | --- | --- | --- | --- | --- | --- | --- | --- | --- | --- | N -A- | --- | --- | --- | --- |
| --- | --- | --- | --- | --- | --- | --- | --- | --- | --- | --- | -T | F -A | --- | --- | --- | --- | --- |
| --- | --- | --- | --- | --- | --- | --- | --- | --- | --- | --- | -T | F -A | --- | --- | --- | --- | --- |
| --- | --- | --- | --- | --- | --- | --- | --- | --- | --- | --- | --- | --- | --- | C -G- | --- | --- | --- |
| --- | --- | --- | --- | --- | --- | --- | --- | --- | --- | --- | --- | --- | N -A- | --- | L -T- | --- | --- |
| --- | --- | --- | --- | --- | --- | --- | --- | --- | --- | --- | --- | --- | --- | --- | --- | --- | --- |
| --- | --- | --- | --- | --- | --- | --- | --- | --- | --- | --- | --- | --- | N -A- | --- | --- | --- | --- |
| --- | --- | --- | --- | T A-- | --- | --- | --- | --- | --- | --- | --- | --- | T -C- | --- | --- | L C-- | --- |
| --- | --- | --- | --- | --- | --- | --- | --- | --- | --- | --- | --- | --- | --- | -T | --- | --- | --- |

Fig. 20 I

B-Ganp⁻/⁻

| 36 | 37 | 38 | 39 | 40 | 41 | 42 | 43 | 44 | 45 | 46 | 47 | 48 | 49 |
|----|----|----|----|----|----|----|----|----|----|----|----|----|----|
| W  | V  | K  | Q  | R  | P  | G  | R  | G  | L  | E  | W  | I  | G  |
| TGG | GTG | AAG | CAG | AGG | CCT | GGA | CGA | GGC | CTT | GAG | TGG | ATT | GGA |
| --- | --- | --- | --- | --- | --- | --- | --- | --- | --- | --- | --- | --- | --- |
| --- | --- | --- | --- | --- | --- | --- | --- | --- | --- | --- | --- | --- | --- |
| --- | --- | --- | --- | --- | --- | --- | --- | --- | --- | --- | --- | --- | --- |
| --- | --- | --- | --- | --- | --- | --- | --- | --- | --- | --- | --- | --- | --- |
| --- | --- | --- | --- | --- | --- | --- | --- | --- | --- | --- | --- | --- | --- |
| --- | --- | --- | --- | --- | --- | --- | --- | --- | --- | --- | --- | --- | --- |
| --- | --- | --- | --- | --- | --- | --- | --- | --- | --- | --- | --- | --- | --- |
| --- | --- | --- | --- | --- | --- | --- | --- | --- | --- | --- | --- | --- | --- |
| --- | --- | --- | --- | --- | --- | --- | --- | --- | --- | --- | --- | --- | --- |
| --- | --- | --- | --- | --- | --- | --- | --- | --- | --- | --- | --- | --- | --- |
| --- | --- | --- | --- | --- | --- | --- | --- | --- | --- | --- | --- | --- | --- |
| --- | --- | --- | --- | --- | --- | --- | --- | --- | --- | --- | --- | --- | --- |
| --- | --- | --- | --- | --- | --- | --- | --- | --- | --- | --- | --- | --- | --G |
| --- | --- | --- | --- | --- | --- | --- | --- | --- | --- | --- | --- | --- | --- |

Fig. 20J

B-Ganp⁻/⁻

| | 50 R AGG | 51 I ATT | 52 D GAT | 53 P CCT | 54 N AAT | 55 S AGT | 56 G GGT | 57 G GGT | 58 T ACT | 59 K AAG | 60 Y TAC | 61 N AAT | 62 E GAG | 63 K AAG | 64 F TTC | 65 K AAG |
|---|---|---|---|---|---|---|---|---|---|---|---|---|---|---|---|---|
| 1-1 | --- | --- | --- | --- | K -A- | --- | --- | --- | --- | --- | --- | --- | --- | --- | --- | --- |
| 1-5 | --- | --- | --- | --- | --- | --- | --- | --- | --- | --- | --- | --- | --- | --- | --- | --- |
| 1-6 | --- | --- | --- | --- | --- | --- | --- | --- | --- | --- | --- | --- | --- | --- | --- | --- |
| 2-2 | --- | --- | --- | --- | --- | --- | --- | --- | S T-- | --- | --- | --- | --- | --- | --- | --- |
| 2-3 | --T | --- | --- | --- | --- | --- | --- | --- | --- | --- | --- | --- | --- | --- | --- | --- |
| 4-3 | N -AT | --- | N A-- | --- | --- | --- | --- | --- | --- | --- | --- | N -C | --- | --- | --- | --- |
| 4-4 | --- | --- | --- | --- | --- | G G-- | --- | --- | --- | --- | --- | --- | --- | --- | --- | --- |
| 6-1 | --- | --- | --- | --- | --- | --- | --- | --- | --- | --- | --T | --- | --- | E G-- | --- | --- |
| 6-2 | --- | --- | --- | --- | --- | --- | --- | --- | --- | --- | --T | --- | --- | --- | --- | --- |
| 7-1 | --- | --- | --- | --- | --- | G G-- | --- | --- | --- | --- | F -T- | D G-- | --- | --- | --- | --- |
| 8-1 | --- | --- | --- | --- | --- | --- | --- | --- | --- | --- | --- | --- | --- | --- | --- | --- |
| 8-2 | --- | --- | --- | --- | --- | G G-- | --- | --- | --- | --A | --- | --- | --- | E -G- | --- | --- |
| 9-1 | --- | --- | --- | --- | --- | --- | --- | --- | A G-C | --- | --- | --- | --- | --- | --- | --- |
| 9-3 | --- | --- | --- | --- | --- | -C | --- | --- | --- | --- | --- | --- | --- | --- | --- | --- |
| 9-4 | --- | --- | --- | --- | --- | --- | --- | --- | --- | --- | --- | --- | --- | --- | --- | --- |

Fig. 20K

B-Ganp$^{-/-}$

| 66 | 67 | 68 | 69 | 70 | 71 | 72 | 73 | 74 | 75 | 76 | 77 | 78 | 79 | 80 | 81 | 82 |
|---|---|---|---|---|---|---|---|---|---|---|---|---|---|---|---|---|
| S | K | A | T | L | T | V | D | K | P | S | S | T | A | Y | M | Q |
| AGC | AAG | GCC | ACA | CTG | ACT | GTA | GAC | AAA | CCC | TCC | AGC | ACA | GCC | TAC | ATG | CAG |
| --T | --- | --- | --- | --- | --- | --- | --- | --- | --- | --- | --- | --- | --- | --- | --- | --- |
| --- | --- | --- | --- | --- | --- | --- | --- | --- | --- | --- | --- | --- | --- | --- | --- | --- |
| --- | --- | --- | --- | --- | --- | --- | --- | --- | --- | --- | --- | --- | --- | --- | --- | --A |
| | | | | | | A | | | | | | | | | | |
| --- | --- | --- | --- | --- | --- | -C- | --- | --- | --- | --- | --- | --- | --- | --- | --- | --- |
| N | | | | | | | | | | | | | | | | |
| -A- | --- | --- | --- | --A | --- | --G | --- | --- | --- | --- | --- | --- | --- | --- | --- | --- |
| | | | | | | | | | S | | | | | | | |
| --- | --- | --- | --- | --- | --- | --- | --- | --- | T-- | --- | --- | --- | --- | --- | --- | --- |
| T | | | | | | | | | | | | | | | | |
| -C- | --- | --- | --- | --- | --- | --- | --- | --- | --- | --- | --- | --- | --- | --- | --- | --- |
| --- | --- | --- | --- | --- | --- | --- | --- | --- | --- | --- | --- | --- | --- | --- | --- | --- |
| --- | --- | --- | --- | --- | --- | --- | --- | --- | --- | --- | --- | --- | --- | --- | --- | --- |
| --- | --- | --- | --- | --- | --- | --- | --- | --- | --- | --- | --- | --- | --- | --T | --- | --A |
| --- | --- | --- | --- | --- | --- | --- | --- | --- | --- | --- | --- | --- | --- | --- | --- | --- |
| --- | --- | --- | --- | --- | --- | --- | --- | --- | --T | --- | --- | --- | --- | --- | --- | --- |
| --- | --- | --- | --- | --- | --- | --- | --- | --- | --- | --- | --- | --- | --- | --- | --- | --- |
| | | | | | | | | | S | | | | | | | |
| --- | --- | --- | --- | --- | --- | --- | --- | --- | T-- | --- | --- | --- | --- | --- | --- | --- |

Fig. 20L

B-Ganp⁻/⁻

| 83 | 84 | 85 | 86 | 87 | 88 | 89 | 90 | 91 | 92 | 93 | 94 | 95 | 96 | 97 | 98 |
|----|----|----|----|----|----|----|----|----|----|----|----|----|----|----|----|
| L  | S  | S  | L  | T  | S  | E  | D  | S  | A  | V  | Y  | Y  | C  | A  | R  |
| CTC | AGC | AGC | CTG | ACA | TCT | GAG | GAC | TCT | GCG | GTC | TAT | TAT | TGT | GCA | AGA |

| --- | --- | --- | --- | --- | --- | --- | --- | --- | --- | --- | --- | --- | --- | --- | --- |
| --- | --- | --- | --- | --- | --- | --- | --- | --- | --- | --- | --- | --- | --- | C-- | --- |
| --- | --- | --- | --- | --- | --- | --- | --- | --- | --- | --- | --- | --- | --- | --- | --- |
| --- | --- | --- | --- | --- | --- | --- | --- | --- | --- | --- | --- | --- | --- | --- | --- |
| --- | --- | --- | --- | --- | --- | --- | --- | --- | --- | --- | --C | --- | --- | --- | --- |
| --- | --- | --- | --- | --- | --- | --- | --- | --- | --- | --- | --- | --- | --- | --- | --- |
| --- | --- | --- | --- | --- | --- | --- | --- | --- | --- | --- | --C | --- | --- | --- | --- |
| --- | --- | --- | --- | --- | --- | --- | --- | --- | --- | --- | --- | --- | --- | --- | --- |
| --- | --- | --- | --- | --- | --- | --- | --- | --- | --- | --C | --- | --- | --- | --- | --- |
| --- | --- | --- | --- | --- | --- | --- | --- | --- | --- | --C | --- | --- | --- | --- | --- |
| --- | --- | --- | --- | --- | --- | --- | --- | --- | --- | --- | --- | --- | --- | --- | --- |
| --- | --- | --- | --- | --- | --- | --- | --- | --- | --- | --- | --- | --- | --- | --- | --- |
| F   |     |     |     |     |     |     |     |     |     |     |     |     |     |     |     |
| T-- | --- | --- | --- | --- | --- | --- | --- | --- | --- | --- | --- | --- | --- | --- | --- |
| --- | --- | --- | --- | --- | --- | --- | --- | --- | --- | --- | --- | --- | --- | --- | --- |
| --- | --- | --- | --- | --- | --- | --- | --- | --- | --- | --- | --- | --- | --- | --- | --- |

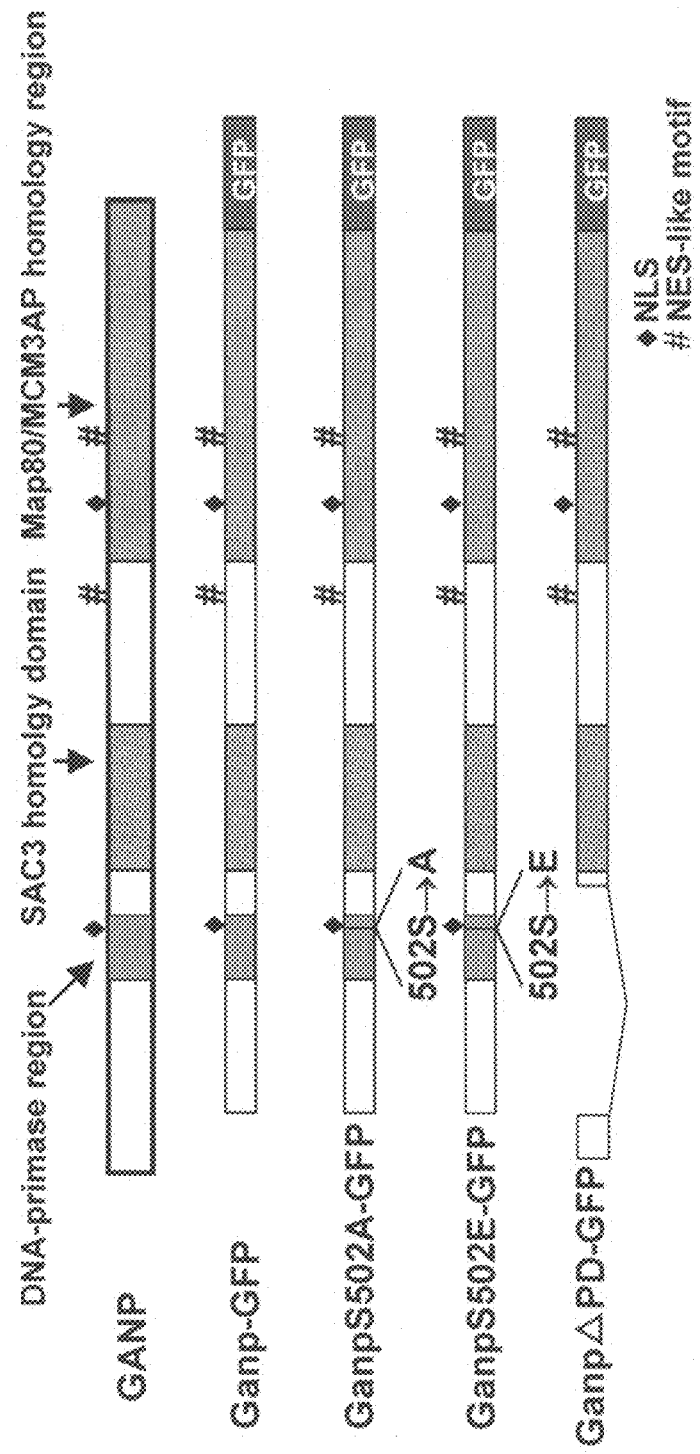

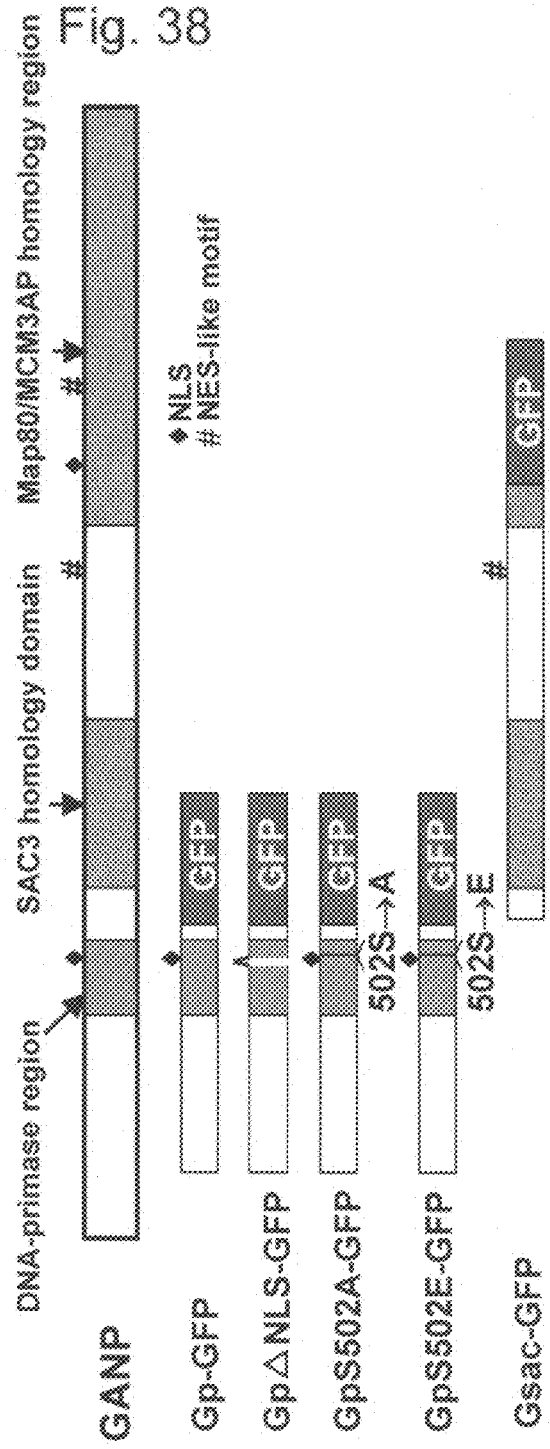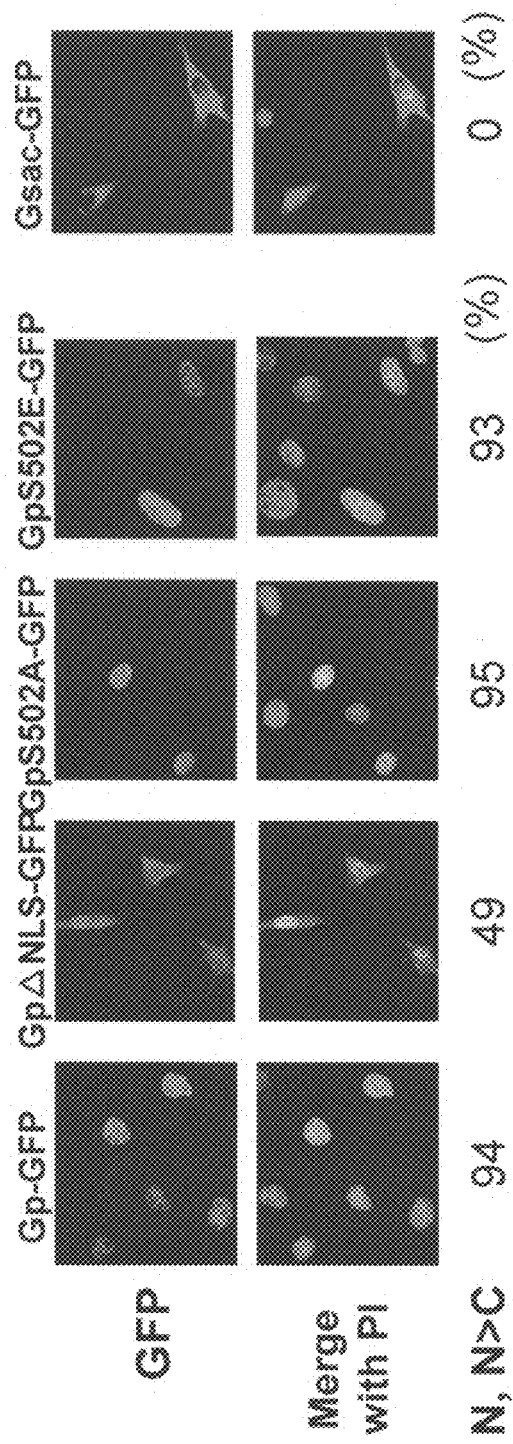
Fig. 38

Fig. 43
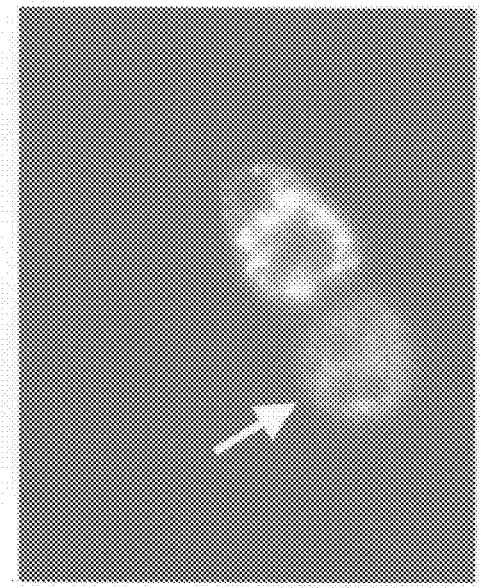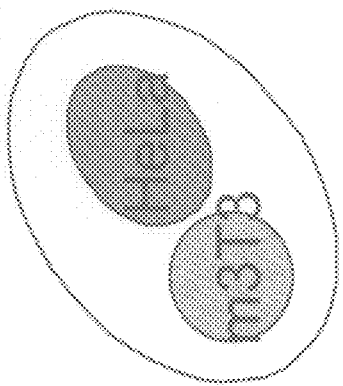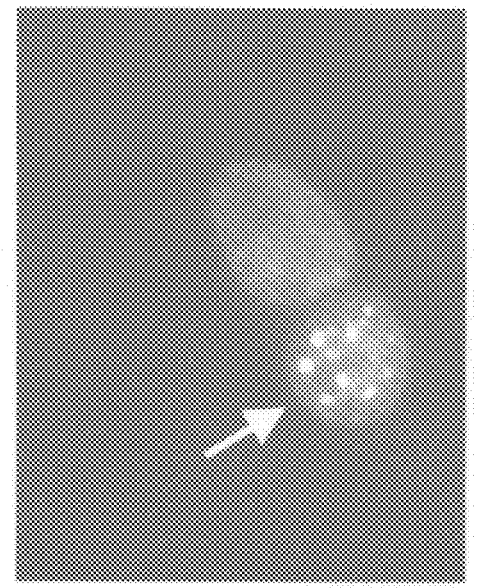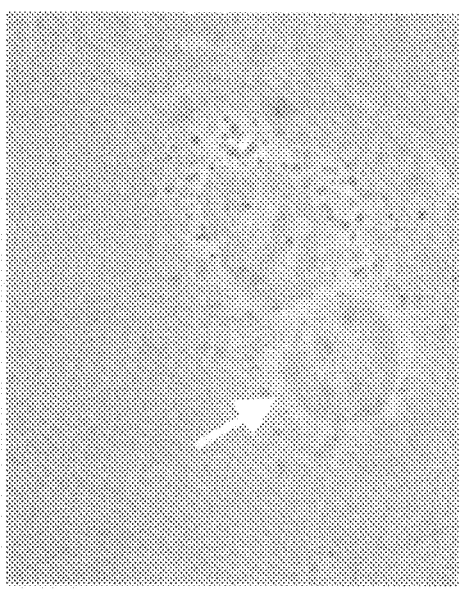

TRANSGENIC MAMMAL CARRYING GANP GENE TRANSFERRED THERETO AND UTILIZATION THEREOF

TECHNICAL FIELD

The present invention relates to a transgenic mammal carrying a GANP gene transferred thereinto and utilization thereof. More specifically, the present invention relates to a transgenic mammal that expresses a high level of GANP and is capable of producing high affinity antibodies; a method of producing a high affinity antibody using the transgenic mammal; and utilization of the resultant high affinity antibody.

BACKGROUND ART

The functions of the immune system are classified into the function based on cellular immune responses caused mainly by the effect of T cells and the function based on humoral immunity caused mainly by the effect of antibodies. Actually, these two functions co-operate with each other to perform immune responses. Antibodies are present as cell surface receptors on the surfaces of B cells produced in the bone marrow. It is said that the number of diverse antigens recognized by the first antibody produced in the living body reaches the order of $10^9$ to $10^{11}$. Such antibodies (antigen receptors) recognize all antigenic determinants that may exist in environments. However, these diverse antigen receptors are generally low in their ability to bind to antigens, and in many occasions, low affinity antibodies are produced. Such antibodies can not cause sufficient immune responses.

Lymphocytes, especially B cells/immunoglobulins (antibodies) are used in various applications based on their immune responses, e.g. they are used in kits for detecting the antigens of pathogens, or as diagnostics or therapeutics. If an antibody that has high reactivity with antigen is used in such antigen-detecting drugs or various therapeutics, sensitivity to antigen will be excellent and efficacy as a therapeutic at a same dose will be great. However, no means to enhance the affinity of antibodies have been known.

When pathogens or foreign substances have entered the living body, the body recognizes them as antigens and induces highly frequent somatic mutations in the genes of the V regions of antibodies which bind directly to those antigens. Such changes require stimulation from T cells, and it is considered that stimulation is provided from activated T cells in the germinal center region. Recently, the present inventors have found a molecule designated GANP whose expression increases selectively in activated B cells of this region (WO 00/50611). This molecule directly binds to a molecule called MCM (minichromosome maintenance) having DNA helicase activity, and has RNA primase activity. Therefore, it is suggested that this molecule GANP is involved in DNA replication. However, functions of GANP in the immune system have not yet been elucidated.

DISCLOSURE OF THE INVENTION

It is an object of the present invention to provide a high affinity antibody effective as a diagnostic or therapeutic for various diseases; a transgenic mammal for producing the high affinity antibody; and a medicine comprising the high affinity antibody or a cell producing the high affinity antibody.

As a result of extensive and intensive researches toward the solution of the above-described problems, the present inventor has found that a GANP gene-transferred transgenic animal is capable of producing a high affinity antibody when immunized with an antigen. Thus, the present invention has been achieved.

The present invention relates to the following.

(1) A transgenic mammal carrying a GANP gene transferred thereinto or its progeny.

The transferred GANP gene is capable of being expressed in B cells. The transgenic mammal of the invention or its progeny may be generated from GANP gene-infected ES cells. As the mammal, mouse may be given, for example.

(2) A part of the above-described transgenic mammal or its progeny.

(3) A method of producing a high affinity antibody, comprising administering an antigen to the above-described transgenic mammal or its progeny and recovering the antibody from the resultant mammal or progeny.

(4) A high affinity antibody obtainable by the method of (3) above, or a fragment thereof.

The antibody of the present invention is $1 \times 10^{-7}$ M or less as expressed as a dissociation constant. The antibody of the present invention may be either a polyclonal antibody or a monoclonal antibody.

(5) A humanized antibody or human antibody, or a fragment thereof, comprising the V region of the above-described antibody or a fragment thereof.

(6) A pharmaceutical composition comprising at least one selected from the group consisting of the above-described antibody or a fragment thereof, and the above-described humanized antibody or human antibody, or a fragment thereof.

(7) A high affinity antibody-producing cell which is taken from the transgenic mammal according to any one of claims 1 to 4 or its progeny, wherein the transgenic mammal or its progeny has been administered an antigen.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 10 (SEQ ID NOS: 37-72) shows the results of analyses of somatic mutations in transgenic (Tg) mice overexpressing GANP and wild-type mice.

FIG. 20A-F shows the results of sequence analyses of VH186.2 in Cre-flox/+ mice after PCR amplification (sequences (SEQ ID NOS: 73-88) continue from A to F in this order).

FIG. 20G-L shows the results of sequence analyses of VH186.2 in Cre-flox/+ mice after PCR amplification (sequences (SEQ ID NOS: 89-105) continue from G to L in this order).

FIG. 36A-B shows the binding of individual GANP constructs to MCM by immunoprecipitation.

FIG. 38 shows intracellular distributions of GANP constructs.

FIG. 43 shows the nucleus-cytoplasm shuttling of MCM3 detected by a heterokaryon assay.

BEST MODE FOR CARRYING OUT THE INVENTION

Figure 1:
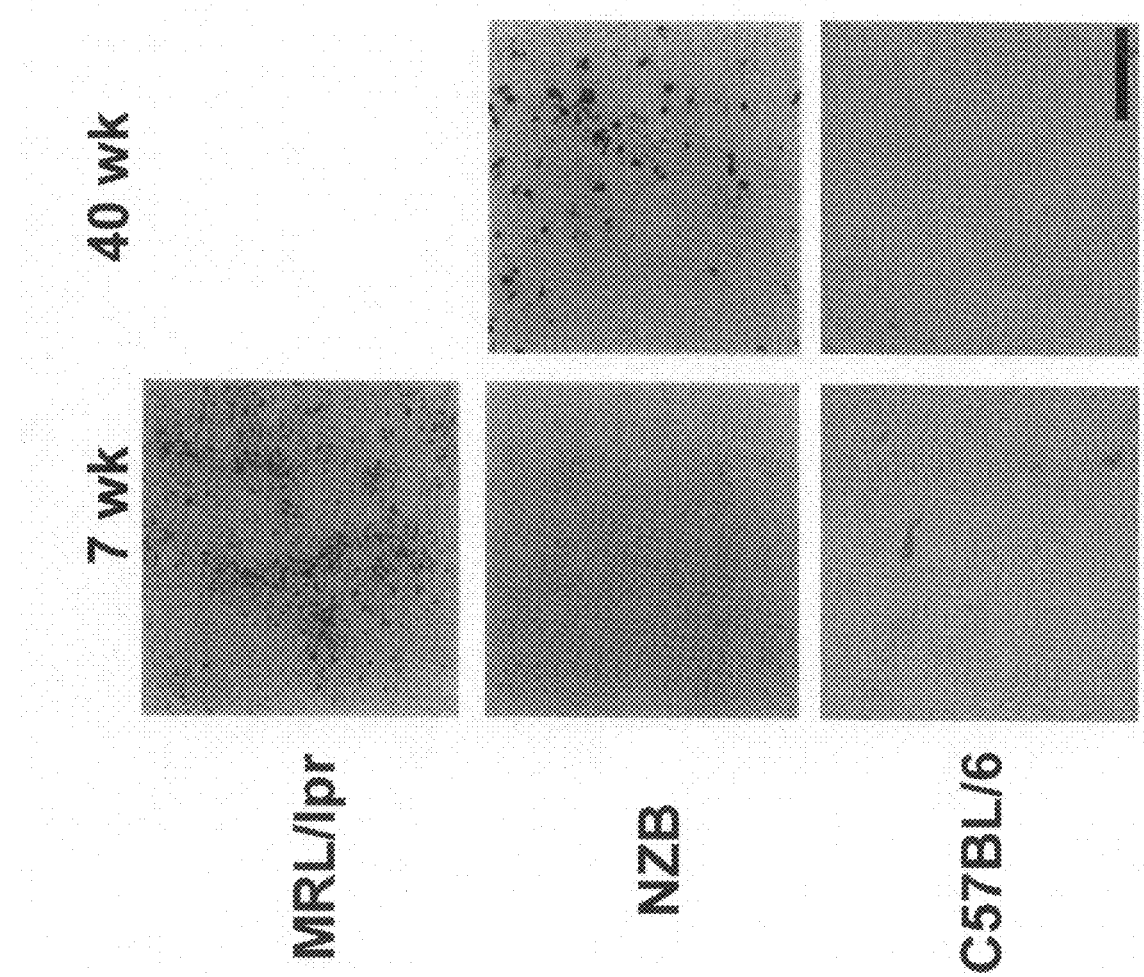
FIG. 1 shows the results of immunohistochemical analyses using anti-GANP monoclonal antibody and ALP-conjugated anti-rat Ig antibody. Scale bar is 100 μm.

Hereinbelow, the present invention will be described in detail.

The present invention has been achieved based on a finding that it is possible to obtain a high affinity antibody by preparing a transgenic animal by transferring a GANP gene into a non-human mammal and immunizing the resultant transgenic animal with an antigen.

1. GANP

GANP which is called "germinal center-associated nuclear protein" is a 210 kDa nuclear protein having homology to yeast Sac3 protein (WO 00/50611). SAC3 is characterized as an inhibitory substance against actin formation. It is known that GANP is selectively up-regulated in germinal center (GC) B cells surrounded by follicular dendritic cells: FDC), has phosphorylation-dependent RNA primase activity, and is involved in the regulation of the cell cycle of B cells (Kuwahara, K. et al., (2000) *Blood* 95: 2321-2328).

In the present invention, the amino acid sequence for mouse GANP protein is shown in SEQ ID NO:2 and the amino acid sequence for human GANP protein is shown in SEQ ID NO: 4. With respect to the gene encoding the GANP protein (hereinafter, referred to as "GANP gene"), the nucleotide sequence for mouse GANP gene is shown in SEQ ID NO: 1 and the nucleotide sequence for human GANP gene is shown in SEQ ID NO: 3. The above-mentioned amino acid sequences and nucleotide sequences are also described in WO 00/50611.

GANP proteins may be mutant proteins; they may be those proteins which consist of the amino acid sequence as shown in SEQ ID NO: 2 or 4 wherein one or a plurality of amino acids have been deleted, substituted or added and have RNA primase activity. For example, a GANP mutant protein may also be used which consists of the amino acid sequence as shown in SEQ ID NO: 2 or 4 wherein one or a plurality of amino acids (preferably, one or several (e.g. one to ten, more preferably one to five) amino acids) have been deleted, one or a plurality of amino acids (preferably, one or several (e.g. one to ten, more preferably one to five) amino acids) have been substituted with other amino acids, and/or one or a plurality of other amino acids (preferably, one or several (e.g. one to ten, more preferably one to five) amino acids) have been added thereto, and yet has the same RNA primase activity as that of the above-described GANP protein.

"RNA primase activity" means the enzyme activity synthesizing a short primer RNA which will be a starting point for strand elongation when a strand extending opposite to the 5'→3' direction (lagging strand) is synthesized. Usually, a molecule called α primase which binds to DNA polymerase α is used. In germinal center B cells, GANP primase which is the second primase is also induced.

GANP protein includes a protein having the amino acid sequence as shown in SEQ ID NO: 2 or 4, or a mutant amino acid sequence thereof, and a protein having a part of the N-terminal sequence of those sequences (e.g. positions 1-600, preferably 139-566 of the amino acid sequence as shown in SEQ ID NO: 2) or a mutant amino acid sequence thereof.

In the present invention, a GANP gene to be transferred into an animal may be a gene encoding the above-described GANP protein, a part of the N-terminal sequence of the GANP protein, or a mutant GANP protein. Specific examples of such a gene include a gene having the nucleotide sequence as shown in SEQ ID NO: 1 or 3. A gene having only the coding region of the nucleotide sequence as shown in SEQ ID NO: 1 or 3 may also be used. Alternatively, it is also possible to use a gene that has a sequence hybridizable to a complementary sequence to the nucleotide sequence as shown in SEQ ID NO: 1 or 3 under stringent conditions, and encodes a protein having RNA primase activity.

"Stringent conditions" refers to washing conditions after hybridization; specifically, the salt (sodium) concentration is 150-900 mM and the temperature is 55-75° C., preferably salt (sodium) concentration is 250-450 mM and the temperature is 68° C.

Introduction of mutations into a gene may be performed according to known techniques such as the Kunkel method or the gapped duplex method, using mutation introducing kits utilizing site-directed mutagenesis, such as GeneTailor™ Site-Directed Mutagenesis System (Invitrogen) or TaKaRa Site-Directed Mutagenesis System (Mutan-K, Mutan-Super Express Km, etc.; Takara Bio).

Details of mutant genes and methods for obtaining the same are also described in WO 00/50611.

In vitro stimulation of B cells with anti-μ antibody and anti-CD40 monoclonal antibody induces not only the up-regulation of GANP expression but also the phosphorylation of a specific serine residue in the amino acid sequence of GANP protein (e.g. serine at position 502: S502). This reaction is a key reaction for the RNA primase activity of GANP (Kuwahara, K. et al. (2001) *Proc. Natl. Acad. Sci. USA*, 98, 10279-10283). The N-terminal primase domain of GANP protein contains a serine residue whose phosphorylation is catalyzed by Cdk2 in vitro. GANP binds to MCM3 replication licensing factor due to its C-terminal domain (Kuwahara, K. et al., (2000) *Blood* 95: 2321-2328; Abe, E. et al., (2000) *Gene* 255: 219-227).

2. Transgenic Mammal Carrying GANP Gene Transferred Thereinto

The present invention relates to a transgenic mammal carrying a GANP gene transferred thereinto. Preferably, the transgenic mammal is capable of expressing the transferred GANP gene in its B cells.

(1) GANP Gene and its Related Molecules

Complexes formed by GANP gene and its related molecules are needed directly or indirectly in the process of induction of mutations in genes. When repairing genetic mutations, GANP protein has the ability to promote induction of mutations in the V region so that high affinity antibodies are obtained. Therefore, the transgenic mammal of the invention carrying the GANP gene or a mutant thereof transferred thereinto is capable of promoting the production of high affinity antibodies of acquired immunity. Further, a transgenic non-human mammal overexpressing this GANP gene is capable of promptly producing an antibody with high binding strength to an antigen. Therefore, by immunizing the above-described transgenic non-human mammal with a specific antigen, it is possible to obtain easily an antibody with a high affinity that has been unachievable by conventional methods. As a result, it becomes possible to obtain polyclonal or monoclonal antibodies capable of eliminating obstinate pathogenic microorganisms or foreign substances. Further, by preparing humanized antibodies using the transgenic mammal of the invention, or by preparing single chain antibodies comprising the V region of the antibody produced by the transgenic mammal of the invention, it becomes possible to sharply increase the effect of antibody therapy.

Because of the GANP gene or its mutant transferred thereinto, the transgenic mammal of the invention is capable of promoting the production of high affinity antibodies in B cells, and the high affinity antibody-producing cells have resistance to apoptosis induction signals.

In order to confirm that GANP is a molecule functioning in the antibody production in acquired immune responses, the present inventors have created a GANP gene deficient mouse so that GANP is deficient B cell selectively. The results revealed that the deficiency of GANP gene did not influence the development, differentiation and proliferation of cells in the immune system and that no big change is observed in the total yield of antibodies.

It should be noted here that only when B cells have reacted with limited types of antigens, they proliferate and differentiate into antibody-producing cells without T cells. For producing antibodies to ordinary antigens, co-existence of T cells is necessary. Antigens to which antibodies are produced even in the absence of T cells are called T cell-independent antigens. On the other hand, general antigens other than T cell-independent antigens are called T cell-dependent antigens. When B cells have reacted with T cell-dependent antigens, the differentiation of B cells into antibody-producing cells is assisted by helper T cells.

Many of the antigenic determinants (also called antigenic epitopes) of pathogenic viruses are weak in immunogenicity by themselves and activated by the peptide antigens of carrier proteins recognized by T cells.

In the present invention, in order to examine that GANP gene-transferred animals are capable of producing high affinity antibodies highly frequently in those antibody-producing responses to soluble antigens where ordinary animals cannot produce strong antibodies, an antigen designated NP-CG was prepared by coupling a nitrophenyl group (NP group) (which has been extensively analyzed as a hapten) to chicken gamma globulin, followed by examination of responses to T cell-dependent antigen.

It is known that C57BL/6 mice's generate high affinity antibody to NP only when utilized a single V region. This response is dominated by only the V region of IgG heavy chain (called $V_H186.2$) and lambda 1 light chain of an antibody. With this system, it is possible for antibodies of $IgG_1$ isotype to examine genetic mutations in high affinity antibodies by analyzing the amino acid sequence of $V_H186.2$. Furthermore, it is reported that the highest affinity is induced when the amino acid residue tryptophan (W) at position 33 of the amino acid sequence of the heavy chain V region ($V_H186.2$) has been mutated into leucine (L) ($W^{33}$ to L mutation).

Then, the present inventor examined whether high affinity antibodies could be induced in GANP gene deficient mice and its defect might be associated with W33 to L mutation event or not. As a result, high affinity antibody production was hardly observed in GANP gene deficient mice, compared to the control Cre-flox/+ mice. Therefore, it has been demonstrated that GANP gene has a key function in the production of high affinity antibodies. To investigate this function further, the inventor has created GANP gene-overexpressing mice. Overexpression of GANP gene was achieved by linking a mouse immunoglobulin promoter moiety and a human immunoglobulin gene intron enhancer moiety upstream (5') of GANP gene so that the gene is expressed selectively in B cells.

The GANP-overexpressing mice were born normally, and no particular change was observed in the development, differentiation and proliferation of their lymph tissues. However, a remarkable increase was observed in the high affinity type V region gene ($W^{33}$ to L) in responses to NP-CG. Although the functional role of RNA primase activity here has not yet been established, it is believed that the RNA primase activity of GANP gene or the phosphorylation of the 502 serine residue involved in the primase activity is related to the production of high affinity antibodies in view of the following: (i) the phosphorylation of serine residue at position 502 (which is an indicator for the primase activity of GANP molecule) is high in cells present at the region of the germinal center where high affinity B cells are produced (centrocytes), and (ii) the frequency of the mutation at the V region induced by experiments to transfer a ganp gene into Daudi cells is high. These results show that high expression of GANP molecule and activation of RNA primase activity are necessary for high affinity antibody production by immune response.

(2) Mammals for Use in GANP Gene Transfer

The term "mammal" used in the present invention means any of non-human mammals such as bovine, horse, pig, goat, rabbit, dog, cat, mouse, rat, hamster and guinea pig. Preferably, mouse, rabbit, rat or hamster is used. Most preferably, mouse is used.

The transgenic mammal of the invention may be prepared by introducing a GANP gene into fertilized eggs, unfertilized eggs, embryonic cells comprising spermatozoa and protocells thereof, preferably into cells of embryogenesis stage (more preferably, the single cell or fertilized egg cell stage and yet generally before eight-cell stage) in the development of non-human mammals, by a method such as the calcium phosphate method, electric pulsing, lipofection, aggregation, microinjection, the particle gun method, or the DEAE-dextran method. Further, it is also possible to transfer a GANP gene of interest into somatic cells, organs of the living body, tissue cells, etc. by the above-mentioned gene transfer methods to use the resultant cells, etc. for cell culture or tissue culture. Further, it is possible to create transgenic mammals by fusing these cells with the above-described embryonic cells according to known cell fusion methods.

When a GANP gene is transferred into an animal of interest, it is preferred that the gene be transferred in the form of a gene construct in which the gene is ligated downstream of a promoter capable of directing expression of this gene in cells of the animal of interest. Specifically, a vector in which a GANP gene is ligated downstream of various promoters capable of directing expression of the GANP gene derived from various mammals may be microinjected into fertilized eggs of the mammal of interest (e.g. mouse fertilized eggs) to thereby create a transgenic mammal capable of high expression of the GANP gene of interest.

(3) Expression Vector

Examples of expression vectors for GANP gene include plasmids derived from *Escherichia coli*; plasmids derived from *Bacillus subtilis*; plasmids derived from yeast; bacteriophages such as λ-phage; retroviruses such as Moloney leukemia virus; and animal or insect viruses such as vaccinia virus or baculovirus.

As promoters for regulating gene expression, promoters of viruses-derived genes; promoters of various mammals (such as human, rabbit, dog, cat, guinea pig, hamster, rat and mouse)-derived genes; and promoters of birds (such as chicken)-derived genes may be used.

Examples of promoters of viruses-derived genes include promoters of cytomegalovirus-, Moloney leukemia virus-, JC virus- or breast cancer virus-derived genes.

Examples of promoters of various mammals- and birds-derived genes include promoters of such as albumin, insulin II, erythropoietin, endothelin, osteocalcin, muscle creatine kinase, platelet-derived growth factor β, keratin K1, K10 and K14, collagen type I and type II, atrial natriuretic factor, dopamine β-hydroxylase, endothelial receptor tyrosine kinase, sodium/potassium-dependent adenosinetriphosphatase, neurofilament light chain, metallothionein I and IIA, metalloproteinase I tissue inhibitor, MHC Class I antigen, smooth muscle α-actin, polypeptide chain elongation factor 1α (EF-1α), β-actin, α- and β-myosin heavy chains, myosin light chains 1 and 2, myelin basic polypeptide, serum amyloid P component, myoglobin and renin genes.

The above-described vector may have a terminator which terminates the transcription of a messenger RNA of interest in a transgenic mammal. For the purpose of achieving still higher expression of GANP gene, the splicing signal of each gene, enhancer region, or a part of an intron of an eukaryotic gene may be ligated upstream (5') of the promoter region, between the promoter region and the translation region, or downstream (3') of the translation region, if desired.

In a preferred embodiment of the invention, it is possible to allow selective expression of the transferred GANP gene in B cells by ligating the GANP gene downstream of an immunoglobulin promoter or by ligating a human immunoglobulin gene intron enhancer moiety upstream (5') of the GANP gene.

(4) Transfer of GANP Gene

The transfer of GANP gene at the fertilized egg cell stage is preferably carried out in such a manner that excessive presence of GANP gene is secured in all the embryonic cells and somatic cells of the mammal of interest. Excessive presence of GANP gene in the embryo cells of the created animal after gene transfer means that all the progeny of that animal has excessive GANP gene in all the embryonic cells and somatic cells. The progeny of this kind of animal which inherited the GANP gene has excessive GANP protein in all the embryonic cells and somatic cells.

In the present invention, first, heterozygotes which have the transferred GANP gene in one of the homologous chromosomes are prepared; then, homozygotes which have the transferred GANP gene in both of the homologous chromosomes are obtained by mating the heterozygotes with each other. Subsequently, by mating female homozygotes with male homozygotes, all the resultant progeny retains the transferred GANP gene stably. After confirmation of the excessive presence of GANP gene, the progeny may be sub-bred in usual breeding environments.

Fertilized eggs of a non-human mammal of interest (preferably, mouse) or its ancestor (back-crossing) to be used for transferring a foreign GANP gene different from the endogenous gene of the mammal of interest are obtained by mating allogenic male and female mammals.

Although fertilized eggs may be obtained by natural mating, it is preferred that female mammals after artificial adjustment of their sexual cycle be mated with male mammals. As a method for artificially adjusting the sexual cycle of female mammals, such a method may be used preferably in which follicle-stimulating hormone (pregnant mare serum gonadotropin (PMSG)) and then luteinizing hormone (human chorionic gonadotropin (hCG)) are administered by, e.g., intraperitoneal injection.

After the transfer of a foreign GANP gene into the resultant fertilized eggs by the methods described above, the eggs are artificially transferred/implanted in female mammals. As a result, non-human mammals having a foreign gene-integrated DNA are obtained. In a preferable method, fertilized eggs are transferred/implanted artificially in pseudo-pregnant female mammals in which fertility has been induced by mating with male mammals after administration of luteinizing hormone-releasing hormone (LHRH). As totipotent cells into which a GANP gene is to be transferred, fertilized eggs or early embryos may be used if the mammal of interest is mouse. As a method of gene transfer into cultured cells, DNA microinjection is preferable in view of the production efficiency of transgenic mammal individuals and the transmittance efficiency of the transgene to the subsequent generation.

Subsequently, the gene-injected fertilized eggs are transplanted into the oviduct of a recipient female mammal. Those animals which have developed from the eggs up to individuals and have been successively born are bred under foster parents. Then, DNA is extracted from a part of their bodies (e.g. the tail end in the case of mouse) and subjected to Southern analysis, PCR, etc. Thus, it is possible to confirm the presence of the transgene. Those animals in which the presence of the transgene has been confirmed are designated founder animals. The transgene is transmitted to 50% of their offspring (F1). Further, by mating F1 individuals with wild-type animals or other F1 individuals, F2 individuals which have the transgene in one (heterozygote) or both (homozygote) of the diploid chromosomes can be produced.

Alternatively, transgenic mammals expressing high levels of GANP protein may also be created by introducing the above-described GANP gene into ES (embryonic stem) cells. For example, the GANP gene is introduced into HPRT negative (i.e. lacking hypoxanthine-guanine phosphoribosyltransferase gene) ES cells derived from normal mouse blastocysts. Then, those ES cells in which the GANP gene has been integrated through homologous recombination induced in a mouse endogenous gene are selected by HAT selection. The thus selected ES cells are microinjected into fertilized eggs (blastocysts) obtained from other normal mouse. The resultant blastocysts are transferred into the uterus of other normal mouse as a recipient. Subsequently, chimeric transgenic mice are born from the recipient mouse. By mating these chimeric transgenic mice with normal mice, heterotransgenic mice can be obtained. Further, by mating the heterotransgenic mice with each other, homotransgenic mice can be obtained.

The present invention encompasses not only the above-described transgenic mammal but also its progeny and a part of the transgenic mammal or its progeny in the scope of the invention. As a part of the transgenic mammal, a tissue, organ, cell or the like of the transgenic mammal or its progeny may be enumerated. Specific examples of organs or tissues include the spleen, thymus, lymph nodes, bone marrow or tonsil; and specific examples of cells include B cells.

The transgenic mammal of the invention may be mated with a mammal that further activates B cells. As a result of such mating, antibodies of still higher affinity can be produced.

Recently, it has been reported that when B cells are activated in peripheral lymph nodes in MRL/lpr mouse, induction of mutations in the V region is further increased in the T cell region after B cells passed through the germinal center. The inventors have also found that non-immunized MRL/lpr mouse shows high expression of GANP equivalent to the GANP expression observed in ganp transgenic mouse which was created by ligating a GANP gene downstream of Ig promoter and enhancer. This suggests a possibility that, while high affinity antibodies are not produced against autoantigens normally, high affinity antibodies to autoantigens may be produced in this autoimmune disease mouse because of the abnormal activation of GANP molecule.

Still higher induction of mutations can be expected if such mouse as MRL/lpr, NZB or (NZB×NZW)F1 (all of them are considered as autoimmune disease mice) is used as the above-mentioned animal that still activates B cells.

By creating a GANP transgenic mouse from MRL/lpr mouse utilizing what has been described above, it may be possible to create a super high affinity antibody-producing mouse. In other words, by mating the GANP gene overexpressing transgenic mammal of the invention with various autoimmune disease model animals, it is possible to create mammals capable of producing high affinity antibodies.

3. Preparation of High Affinity Antibodies

The term "antibody" used in the invention means a protein having activity to specifically bind to an antigen, preferably a protein produced by B cells. In the present invention, an antibody having high reactivity with an antigen is called high affinity antibody. The term "high affinity" used herein means that the ability of an antibody to bind to an antigen is high. In the present invention, a high affinity antibody refers to an antibody which has higher ability to bind to an antigen than those antibodies prepared using conventional animals such as mouse, and which is slow in dissociating from that antigen. This means that such an antibody is high and specific in the ability to bind to an antigenic determinant (epitope) sterically and closely. Besides, the binding of such an antibody to the antigenic determinant induces changes not only in the determinant but also the structure of the antigen itself, to thereby show strong activities eventually (e.g. biological activities such as neutralization of toxicity, prevention of viral infection, deactivation of pathogens, promotion of elimination of pathogens from the body, or induction of denaturation in antigen molecules).

The binding ability of an antibody (i.e. affinity) may be measured as a dissociation constant (KD), dissociation rate constant (Kdiss) or association rate constant (Kass) by Scatchard analysis or with a surface plasmon resonance sensor called Biacore. Biacore systems in which three technologies of sensor chip, microflow system and SPR detection system are integrated are to measure the strength, rate and selectivity of molecular binding. This apparatus enables real time detection of biological molecules and monitoring of interactions among a plurality of molecules without using labels. Specific examples of useful Biacore systems include Biacore 3000, Biacore 2000, Biacore X, Biacore J and Biacore Q (all of them are manufactured by Biacore).

With the above-described Biacore system, parameters showing the affinity of antibodies, i.e. dissociation constant (KD), dissociation rate constant (Kdiss) (1/Sec) and association rate constant (Kass) (1/M.Sec) are measured.

Antibodies with smaller dissociation constant (KD) values are preferable because the smaller the dissociation constant value, the higher the affinity. The binding ability of an antibody (affinity) is determined by the two parameters of Kdiss and Kass, and is represented by the following formula:

$$KD\ (M) = Kdiss/Kass$$

Although the affinity of the resultant antibody varies depending on a plurality of factor such as the type of the antigen, generally, its KD value is preferably $1 \times 10^{-7}$ (M) or less. For example, preferable KD values are $1 \times 10^{-8}$ (M) or less, $1 \times 10^{-10}$ (M) or less, or $1 \times 10^{-11}$ (M) or less.

In the present invention, when the resultant antibody reveals any of the above-described effects or natures, the antibody is judged as a "high affinity" antibody.

Enhancement in the affinity of antibody molecules is produced by inducing somatic hypermutations (SHM) in genes of the variable regions (V region) of antibodies. Although specificities of antibodies to antigens are recognized from the beginning of immunization of the living body with antigens, most of early antibodies are IgM class antibodies; their binding affinity to antigens is not high and their ability to remove or deactivate pathogens or foreign substances is low. However, if an antigen is administered to the living body to give several boosters, the binding affinity of antibody to the antigen is enhanced. At this time, B cells need stimulation from T cells, and this activation is considered to take place in the germinal center region in peripheral lymph tissues. Recently, the RNA editing molecule AID expressed in the germinal center has been reported as a molecule necessary to induce mutations in V region genes. Further, it is reported that uracil DNA glycosidase and, as DNA polymerases necessary for DNA replication, DNA polymerases zeta ($\zeta$) and iota ($\iota$) which easily produce errors are also involved in the above activation. However, the molecule(s) which control(s) these functions has/have not been elucidated. The function of GANP molecule as a novel SHM-inducing molecule has been elucidated. Increase in the expression of this molecule plays a key role in SHM induction. Among all, it has been demonstrated that GANP molecule is important in producing high affinity antibodies.

Antibodies induced by immunizing C57BL/6 mice with nitrophenyl-chicken γ globulin as a hapten carrier antigen have $V_H186.2$ locus as the H chain and $\lambda 1$ as the L chain. In this system, it is known that antibodies obtained after boosters were given are $IgG_1$ antibodies, and that the mutation induced in the V region sequence of those antibodies with particularly high binding affinity among them is mutation from tryptophan to leucine at position 33. In the Examples of the present specification, this high affinity-type V region mutation is induced highly. This can be said definite evidence at the molecule level showing that high affinity antibodies have been induced.

Therefore, it is possible to obtain high affinity antibodies by administering an antigen to the above-described transgenic mammal or its progeny and letting the resultant mammal or progeny produce antibodies. Briefly, an antigen of interest is administered by conventional methods to an animal that is engineered to express high levels of GANP protein. Then, high affinity antibodies may be prepared form lymphocytes of a tissue such as blood or spleen (not limited to these tissues) of the immunized animal. These high affinity antibodies may be either polyclonal or monoclonal antibodies.

As a method for producing polyclonal antibodies, for example, polyclonal antibodies may be obtained by administering an antigen to the transgenic mammal of the invention, taking blood from the immunized mammal, and then separating and purifying antibodies from the resultant blood.

Methods of immunization are known to those skilled in the art. For example, immunization may be performed by administering an antigen once or more.

The types of the antigen are not particularly limited. All substances which may have a steric structure as an antigenic determinant fall under antigen. In addition to all biological components such as proteins, enzymes, peptides, sugars, lipids, DNAs, RNAs and prions, any substance such as cancer antigens, virus antigens, organic or inorganic synthetic antigens may be used.

The antigen may be administered, for example, two or three times at intervals of 7 to 30 days. The dose may be, for example, about 0.05 to 2 mg of the antigen per administration. The route of administration is not particularly limited. For example, subcutaneous administration, dermal administration, intraperitoneal administration, intravenous administration or intramuscular administration may be selected appropriately. Preferably, the antigen is administered by intravenous, intraperitoneal or subcutaneous injection. The antigen may be used in solution in an appropriate buffer, e.g. a buffer containing conventional adjuvants such as complete Freund's adjuvant or aluminium hydroxide, but the antigen may be used without adjuvant depending on the administration route or other conditions.

After immunized mammals have been bred for a specific period of time, serum samples are obtained from them and antibody titers thereof are measured. When the antibody titer begins to rise, boosters may be given using, for example, 100 µg to 1000 µg of the antigen. One to two months after the final administration, blood is taken from the immunized mammals and subjected to various conventional methods used for protein isolation, e.g. centrifugation, precipitation using ammonium sulfate or polyethylene glycol, and chromatography such as gel filtration chromatography, ion exchange chromatography or affinity chromatography. Thus, polyclonal antibodies may be obtained as polyclonal anti-sera.

As a method for producing monoclonal antibodies, the hybridoma method may be used. First, a peptide constituting an antigen of interest is suspended in an adjuvant. The resultant suspension is administered subcutaneously or intradermally into animals to be immunized (i.e. the transgenic mammal of the invention). The types of the antigen used here are the same as described above. Examples of the adjuvant used here include complete Freund's adjuvant, BCG, trehalose dimycolate (TDM), lipopolysaccharide (LPS), alum adjuvant and silica adjuvant. Preferably, a combination of complete Freund's adjuvant (CFA) and incomplete Freund's adjuvant (IFA) is used in view of the ability to induce antibodies.

In the production of monoclonal antibodies, preferably, animals which have undergone the first immunization with an antigen are boosted several times; after passage of appropriate number of days, blood samples are taken and antibody titers thereof are measured. Since antibodies produced by the method of the invention are high affinity antibodies, the first immunization may be sufficient without booster. Antibody titers may be measured by known methods such as enzyme-linked immunosorbent assay (hereinafter, referred to as ELISA).

Subsequently, the spleens are removed from the immunization-completed animals to obtain B cells. Obtaining B cells capable of binding to antigens is preferable because it could reduce subsequent screening. The B cells obtained at this point are high affinity antibody-producing cells, which may be used as an immunopotentiator without any processing. It is also possible to obtain V region genes directly from these B cells and to measure somatic hypermutations in the V region.

Subsequently, the resultant B cells are fused with myeloma cells by conventional methods to thereby prepare an antibody-producing hybridoma. For example, if the animal is mouse, the spleen is removed and placed in a solution such as Hanks' balanced salt solution (HBSS). Cells are pushed out with tweezers to obtain spleen lymphocytes (B cells). The resultant spleen lymphocytes are stained with trypanblue or the like to count the number of viable cells, and then fused with myeloma cells to prepare a hybridoma.

The myeloma cell used for the cell fusion is not particularly limited. Known myeloma cells such as P3-X63.Ag8 (X63), P3-X63.Ag8.U1 (P3U1), P3/NS I/1-Ag4-1(NSI) or Sp2/0-Ag14(Sp2/0) may be used. In the selection of the myeloma cell, compatibility with antibody-producing cells should be considered appropriately.

Cell fusion is carried out as described below. Briefly, $1\times10^6$-$1\times10^7$ cells/ml of antibody-producing cells are mixed with $2\times10^5$-$2\times10^6$ cells/ml of myeloma cells (preferable cell ratio of antibody-producing cells to myeloma cells is 5:1) in an animal cell culture medium such as serum-free DMEM or RPMI-1640 and fused in the presence of a cell fusion promoter.

As the method of cell fusion, any of the methods known in the art (the Sendai virus method, the polyethylene glycol method, or the protoplast method) may be selected. Preferably, the polyethylene glycol method is used in view of relatively low cytotoxicity and simple fusion operations. Polyethylene glycol with a mean molecular weight of 1000-6000 daltons may be used as a cell fusion promoter. When production of a large quantity of antibodies is desired, a hybridoma prepared by fusing antibody-producing cells stimulated with a vinyl pyridine derivative with myeloma cells is used preferably.

The resultant hybridoma is cultured in HAT medium (containing hypoxanthine, aminopterin and thymidine) for an appropriate period of time according to conventional methods, followed by selection of hybridoma clones. Subsequently, those hybridoma clones producing an antibody of interest are screened, followed by cloning of the hybridoma clones.

As the screening method, known methods for antibody detection, such as ELISA, radio immunoassay (hereinafter, referred to as RIA), the plaque method, or the aggregation reaction method, may be used. As the cloning method, known methods in the art such as the limiting dilution-culture method, the soft agar method or FACS, may be used. The resultant hybridoma is cultured in an appropriate culture broth, or administered into the abdominal cavity of an animal (e.g. mouse) compatible with the hybridoma. From the thus obtained culture broth or abdominal dropsy, the monoclonal antibody of interest may be isolated and purified by methods such as salting out, ion exchange chromatography, gel filtration or affinity chromatography.

It should be noted that fragments and single chain antibodies of the V region of the above-described antibody are also within the scope of the present invention. A fragment of the antibody means a portion of the above-described polyclonal or monoclonal antibody. Specific examples of such a fragment include $F(ab')_2$, Fab', Fab, Fv (variable fragment of antibody), sFv, dsFv (disulphide stabilized Fv) or dAb (single domain antibody). $F(ab')_2$ and Fab' mean those antibody fragments which are prepared by treating an immunoglobulin (monoclonal antibody) with proteolytic enzymes pepsin and papain, respectively, and are generated through digestion around the disulfide bond present between the two H chains in the hinge region. For example, when IgG is treated with papain, this molecule is cut upstream of the disulfide bond present between the two H chains in the hinge region to yield two homologous antibody fragments in which an L chain consisting of $V_L$ (L chain variable region) and $C_L$ (L chain constant region) and an H chain fragment consisting of $V_H$ (H chain variable region) and $C_H\gamma1$ ($\gamma1$ region in H chain constant region) are coupled by a disulfide bond in the C-terminal region. Each of these two homologous antibody fragments is called Fab'. When IgG is treated with pepsin, this molecule is cut downstream of the disulfide bond present between the two H chains in the hinge region to yield an antibody fragment which is slightly larger than the above-described two Fab' fragments ligated at the hinge region. This antibody fragment is called $F(ab')_2$. A single chain antibody has a structure in which VL and $V_H$ are linked by a linker.

The high affinity antibody of the invention may be a humanized antibody or human antibody. These human antibodies may be prepared by using mammals whose immune system has been replaced with the human immune system. After immunizing such mammals, human antibodies may be prepared directly in the same manner as used in the preparation of conventional monoclonal antibodies.

For the preparation of humanized antibodies, reconstructed variable regions consisting of human-derived framework regions and mouse-derived CDRs (complementarity determining regions) is prepared by transferring the CDRs of the variable regions in a mouse antibody into the human variable regions.

Subsequently, these humanized, reconstructed human variable regions are ligated to human constant regions. Portions derived from non-human amino acid sequences in the finally reconstructed humanized antibody are only CDRs and extremely small parts of FRs. CDRs are composed of hypervariable amino acid sequences. Since these sequences do not show species specific sequences, it is possible to use humanized antibodies having mouse CDRs. Methods for preparing humanized antibodies are well-known in the art.

Human antibodies may be produced using any animal (e.g. mouse, rat, etc.) in terms of structure, though generally the antigen binding site in the variable region (i.e. hyper variable region) may raise some problem with respect to specificity and binding affinity. On the other hand, it is desirable that the structures of the remaining portion of the variable region and the constant region should be the same as the structures in human antibodies. With respect to genetic sequences common in human, genetic engineering techniques to prepare them have been established.

The isotype of the antibody of the invention is not particularly limited. The antibody of the invention may have any isotype, e.g. IgG ($IgG_1$, $IgG_2$, $IgG_3$, $IgG_4$), IgM, IgA ($IgA_1$, $IgA_2$), IgD or IgE.

4. Use of High Affinity Antibodies

The high affinity antibody of the invention is useful as a drug for diagnosing, treating or preventing diseases.

(1) Diagnosis of Diseases

Diagnosis of various diseases using the antibody of the invention is carried out as described below. Briefly, samples (e.g. sera) taken from subjects suspected of having various diseases are bound to the antibody of the invention by antigen-antibody reaction. Then, the amount of an antigen of interest in the sample is detected from the amount of bound antibody. The detection of the amount of bound antibody may be performed by conventional immunological measuring methods. For example, immunoprecipitation, immunoaggregation, labeled immunoassay, immunonephelometry, immunoturbidimetry, or the like may be used. Labeled immunoassay is especially preferable from the viewpoint of simplicity and high sensitivity. In labeled immunoassay, antibody titers in samples may be expressed directly as the amounts of label detected using a labeled antibody. Alternatively, antibody titers may be expressed relatively using as a standard solution an antibody of known concentration or known titer. Briefly, the standard solution and a sample may be measured simultaneously in the same measuring system, followed by expression of the antibody titer in the sample relatively based on the value of the standard solution.

In labeled immunoassay, any of known measurement methods, such as ELISA, RIA, fluoroimmunoassay, or chemiluminescence immunoassay, may be used. The labeling substance may be appropriately selected depending on the above-mentioned assay method; for example, an enzyme, radioisotope, fluorescent compound, or chemiluminescent compound may be selected. Specific examples of the enzyme useful in the invention include peroxidase, alkaline phosphatase, acid phosphatase and glucose oxidase. Detection sensitivity of the above-mentioned labeling substances may be increased by using avidin-biotin complex. As a specific example of the radioisotope useful in the invention, $^{125}I$ may be given at first. Specific examples of the fluorescent compound useful in the invention include fluoresceine isothiocyanate (FITC) and tetramethylrhodamine isothiocyanate (TRITC). Specific examples of the chemiluminescent compound useful in the invention include lophine, luminol and lucigenin. The labeling of antibodies with the above-mentioned substances may be performed according to conventional methods. Hereinbelow, labeled immunoassay using labeled antibodies will be described.

As a method of detection of various diseases according to labeled immunoassay, a method using a known non-competitive reaction system or competitive reaction system may be possible. Non-competitive reaction systems require solid phase (solid phase method). Competitive reaction systems do not necessarily require solid phase (liquid phase method), but use of solid phase is preferable since that will make measuring operations simple. Specific examples of materials for the solid phase include polystyrene, nylon, glass, silicon rubber and cellulose. As the shape of the solid phase, spheres, wells, tubes, sheets, or the like may be enumerated. However, the material and the shape useful in the invention are not limited to those enumerated above. Known materials and shapes used in labeled immunoassay may be used at discretion.

In non-competitive reaction systems, measurement operations are carried out as follows. Briefly, a sample or the antibody of the invention is immobilized on a solid support and then reacted with the antibody of the invention or a sample. Subsequently, a pre-labeled anti-immunoglobulin antibody (secondary antibody) is added to react with the above antibody reacting with the immobilized sample. With the labeling substance of this secondary antibody, it is possible to detect the amount of the antibody bound to the sample. Since the amount of the labeled secondary antibody detected is directly correlated with the amount of the antigen of interest in the sample, the amount of this antigen can be obtained from the amount of the labeled secondary antibody.

In competitive reaction systems, a sample and a specific amount of an antigen of interest are reacted with a specific amount of an antibody. For example, after immobilization of a sample on a solid support, the sample is reacted with the antibody of the invention which has been pre-reacted with an antigen of interest. Subsequently, the antibody which has reacted with the immobilized sample is reacted with a pre-labeled anti-immunoglobulin antibody (secondary antibody), followed by detection of the amount of the antibody by the labeling substance. The amount of the labeling substance is inversely correlated with the amount of the antigen of interest added. Other types of competitive reaction systems may also be used where the antibody of the invention is immobilized, reacted with a sample, and then reacted with a pre-labeled antigen of interest. The amount of the labeling substance detected is inversely correlated with the amount of GANP protein in the sample bound to the antibody.

As the method of immobilization of an antigen or antibody on a solid support, known methods such as physical adsorption, covalent binding, ionic bonding or crosslinking may be used. Physical adsorption is especially preferable because of its simplicity. As examples of the anti-immunoglobulin antibody (secondary antibody) useful in the invention, anti-IgG antibody or anti-IgM antibody may be given. These antibodies may be used as an entire molecule. Alternatively, antibody fragments Fab, Fab' and F(ab')$_2$ comprising the antigen binding site obtained by treating antibodies with enzymes may be used. Further, instead of the labeled anti-immunoglobulin antibody, a substance having specific affinity for antibody molecules (e.g. protein A which has specific affinity for IgG) may be labeled and used.

As a preferable example of the above-described labeled immunoassay, ELISA may be given which is an immunoassay using an enzyme as a label. Briefly, a sample or a dilution thereof is placed in 96-well plates or the like and incubated at 4° C. to room temperature overnight or at 37° C. for about 1-3 hrs so that GANP protein to be detected is adsorbed and immobilized on the plates. Then, the antibody of the invention is reacted. Subsequently, an enzyme-preconjugated anti-immunoglobulin antibody (secondary antibody) is reacted. Finally, an appropriate color-developing substrate reactive with the enzyme (e.g. if the enzyme is phosphatase, p-nitrophenylphosphate or the like) is added to thereby detect the antibody with its color development.

By using the high affinity antibody of the invention, it is possible to evaluate the efficacies of therapeutics for various diseases. The evaluation method using the high affinity antibody of the invention is performed as follows. Briefly, a drug is administered to various disease patients or disease model animals. Then, using the antibody of the invention, the amounts of the antigen (such as virus) in these living bodies are detected. By comparing the amounts, the efficacy of the drug as a therapeutic for various diseases can be evaluated based on the amounts of the antigen in living bodies.

The high affinity antibody of the invention may be provided in the form of a diagnosis kit for various diseases. This kit may be used in the diagnosis method of the invention or the efficacy evaluation method of the invention. The kit of the invention comprises as least one selected from the following (a) and (b).

(a) the antibody of the invention or that antibody labeled (b) immobilized reagent in which the antibody or labeled antibody of (a) above is immobilized on a solid support The "labeled antibody" means an antibody labeled with an enzyme, radioisotope, fluorescent compound or chemiluminescent compound. As the material of a solid support on which the antibody or labeled antibody is immobilized in the kit of the invention, polystyrene, nylon, glass, silicon rubber, cellulose or the like may be used. As the shape of such a solid support, spheres, wells, tubes or sheets may be enumerated. However, the material and the shape useful in the invention are not limited to these ones. Instead of the immobilized reagent, a solid phase and an immobilizing agent may be attached to the kit. As the immobilizing agent, if immobilization by physical adsorption is intended, a coating liquid such as 50 mM carbonate buffer (pH 9.6), 10 mM Tris-HCl buffer (pH 8.5, containing 100 mM sodium chloride) or PBS and, if necessary, a blocking liquid (which is a coating liquid containing 0.5% gelatin) may be enumerated, for example.

The antibody contained in the kit of the invention may be in a state of solution in PBS or the like, or in a state where the antibody is linked to a gel (hereinafter, abbreviated to "absorption gel"). This absorption gel may be pre-packed in 0.5-2 ml microcentrifuge-precipitation tubes for absorption by the batch method. Alternatively, the absorption gel may be pre-packed in 0.1-5 ml mini-columns for absorption by the column method.

In addition to the above-described components, the kit of the invention may contain other reagents for carrying out the detection of the invention, e.g. the substrate of an enzyme (color developing substrate, etc.), the substrate in solution, enzymatic reaction-terminating liquid or the like when the labeling substance is an enzyme, and diluents for samples. Specific examples of diluents for samples include 20 mM Tris-HCl buffer (pH 7.4) containing PBS (phosphate-buffered physiological saline, pH 7.4), 137 mM sodium chloride and 3 mM potassium chloride (hereinafter abbreviated to "TBS"); and PBS or TBS containing 0.05% Tween 20 and 0.1-1% BSA. These diluents for samples may be used for diluting other substances such as antibodies.

(2) Pharmaceutical Compositions for Treating or Preventing Diseases

When the high affinity antibody of the invention has an effect of neutralizing the activity of an antigen which will become the pathogen of a disease, the antibody of the invention is useful in a pharmaceutical composition for treating or preventing the disease. The pharmaceutical composition of the invention comprises the high affinity antibody of the invention or a fragment thereof as an active ingredient and, is provided, preferably, in the form of a pharmaceutical composition comprising a pharmacologically acceptable carrier.

The "pharmacologically acceptable carrier" used herein includes excipients, diluents, fillers, disintegrants, stabilizers, antiseptics, buffers, emulsifiers, aromatics, coloring agents, sweetening agents, thickening agents, flavoring agents, dissolution aids and other additives. By using one or more of these carriers, various forms of pharmaceutical compositions may be prepared, e.g. tablets, pills, powders, granules, injections, solutions, capsules, troches, elixirs, suspensions, emulsions and syrups. These pharmaceutical compositions may be administered orally or parenterally. Other forms for parenteral administration include solutions for external use which comprise one or more active substances and are prescribed by conventional methods, suppositories for enteric administration, and pessaries.

The dose of the pharmaceutical composition of the invention varies depending on the age, sex, body weight and conditions of the patient, treatment effect, the method of administration, time period for treatment, or the type of the high affinity antibody (the active ingredient) contained in the composition. Usually, the pharmaceutical composition of the invention may be administered to adult patients in the range from 10 µg to 1000 mg per administration, preferably in the range from 10 µg to 100 mg per administration. However, the dose is not limited to this range.

For example, in the case of injections, the pharmaceutical composition of the invention may be dissolved or suspended in a pharmacologically acceptable carrier (such as physiological saline or commercial distilled water for injection) so that the concentration of the antibody in the carrier is from 0.1 µg /mil to 10 mg/ml. The thus prepared injection may be administered to human patients in need of treatment at a rate of 1 µg –100 mg/kg body weight, preferably at a rate of 50 µg –50 mg/kg body weight, per administration once to several times per day. The route of administration may be intravenous injection, subcutaneous injection, intradermal injection, intramuscular injection or intraperitoneal injection, for example. Among all, intravenous injection is preferable. Optionally, injections may be prepared in the form of a non-aqueous diluent (e.g. propylene glycol, polyethylene glycol, vegetable oil such as olive oil, alcohol such as ethanol), suspension or emulsion. Sterilization of such injections may be performed by filter-sterilization through a bacteria removal filter, addition of antiseptics, or irradiation. Injections may take a form that is prepared into an injection at the time of use. Briefly, a solid composition is prepared by lyophilization or the like, and this solid composition may be dissolved in aseptic distilled water for injection or other solvent at the time of use.

5. Application of the Present Invention

The present inventors have induced overexpression of GANP in B cell tumor strains and analyzed them. As a result, the B cell tumor strains showed that GANP gene transfer has a remarkable effect in inducing somatic hypermutations in V region genes. Since this effect is not observed when a mutant gene in which phosphorylation of serine at position 502 (required for the primase activity of GANP) does not occur is used, it is suggested that RNA primase activity is necessary for the remarkable induction of somatic hypermutations in V region genes. These results demonstrate that GANP has an effect of enhancing the production of specific antibodies as a clinical, supplemental immunopotentiator.

It is also effective for clinical, supplemental immunopotentiation to use a retrovirus vector as a vector and a combination of GANP and a stimulation mediated by TNF family molecules such as DC40 or BAFF. Further, by transferring a GANP gene at the bone marrow cell level, induction of high affinity binding in T cells is also expected. It is expected that this gene transfer will manifest an excellent effect in such diseases as AIDS, hepatitis C, adult T cell leukemia or Bovine Spongeform Encepharopathy where high affinity antibodies are not obtained or, even if obtained, the production of high affinity antibodies cannot be maintained because mutations promptly occur in antigens.

The GANP gene overexpressing mammal of the invention is useful in developing monoclonal antibodies useful in the preparation of biological research reagents and clinical test reagents. For example, the preparation of a monoclonal antibody to a specific signal transduction molecule in a functional domain- or functional motif-specific manner and as a high affinity antibody with high binding ability easily is very widely applicable. Since many antibodies are not screened many times, sometimes it is impossible to use them in Western analysis and immunoprecipitation. When the transgenic mammal of the invention is used for antibody production, high affinity antibody-producing cells may be selected from a relatively small number of clones. Thus, the effect of the present invention in the reduction of cost, time and labor is great. In particular, the preparation of phosphorylated antibodies and specific antibodies to mutated sites of genes is applicable to diagnostics, or the selective injection method for medicines using antibodies. The production of high affinity antibodies which selectively bind to a specific gene sequence or nucleotide portion will also become possible.

A part of the steric structure of any substance (such as inorganic substance, carbohydrate, or chemically synthesized substance) is recognized as an antigen motif. Although no high affinity antibodies have been obtained to date, mice created by mating with autoimmune mice are effective for obtaining high affinity antibodies to all antigens. There is a possibility that high affinity antibodies whose binding ability is on the order of $10^{-11}$ M might be obtained by this method. By introducing the developed technology of ELISA, it is possible to develop a technology to detect trace substances easily.

According to the present invention, it is also possible to provide a gene therapeutic for allergic diseases or autoimmune diseases, comprising an RNA primase inactivated-type GANP gene. The "RNA primase inactivated-type GANP gene" means a GANP gene in which the RNA primase domain is deficient or mutated. Due to mutations of the serine residue at position 502 and neighboring residues in the gene, the structure and function of GANP molecule encoded by this gene has been altered.

The gene therapeutic of the invention may be prepared by combining a recombinant vector comprising an RNA primase inactivated-type GANP gene with a base to be used in the gene therapeutic. As a vector for use in the construction of the recombinant vector, a viral vector such as retrovirus vector, adenovirus vector, adeno-associated vector, vaculovirus vector or vaccinia virus vector may be enumerated. Alternatively, an animal expression plasmid may be used. Preferably, the vector is a viral vector. When an RNA primase inactivated-type GANP gene has been integrated into a viral vector, viral particles containing the recombinant protein may be produced and combined with a base for the gene therapeutic to thereby prepare the gene therapeutic.

Specific examples of the base to be used in the gene therapeutic include those bases conventionally used in injections, e.g. distilled water; solution of sodium chloride or solution of a mixture of sodium chloride and inorganic salt; solution of mannitol, lactose, dextran or glucose; solution of amino acid such as glycine or arginine; mixed solution consisting of organic acid solution or salt solution and glucose solution. Alternatively, injections may be prepared as solutions, suspensions or dispersions by combining those bases with auxiliary agents such as osmoregulator, pH regulator, vegetable oil, surfactant, etc. according to conventional methods well known to those skilled in the art. It is also possible to powder or lyophilize these injections and dissolve them at the time of use.

The gene therapeutic of the invention may be administered systemically by conventional intravenous or intra-arterial administration, or administered locally by local injection or oral administration. The dose of the gene therapeutic of the invention varies depending on the age, sex, conditions of the patient, the route of administration, the number of times of administration, and the dosage form. Generally, the gene therapeutic of the invention may be administered to adult patients in the range from 1 µg/kg to 1000 mg/kg per day, preferably in the range from 10 µg/kg to 100 mg/kg per day, in the amount of the recombinant gene. The number of times of administration per day is not particularly limited.

EXAMPLES

Hereinbelow, the present invention will be described more specifically with reference to the following Examples which should not be construed as limiting the present invention.

Example 1

Expression and Function of GANP in Autoimmune Disease Model Animals (Materials and Methods)
1. Animals
NZB, NZW, B/WF1, MRL/lpr and BXSB mice were purchased from Japan SLC Co.
C57BL/6 and BALB/c mice were purchased from Charles River Japan. NOD mice were kindly supplied from Dr. Miyazaki, the graduate school of Osaka University.

2. Antibodies and Reagents
Rat monoclonal antibodies to mouse B220 (RA3-6B2), mouse IgM (AM/3) and mouse IgD (CS/15) were purified from hybridoma culture supernatant and labeled with D-biotin-N-hydroxysuccinimide ester (Roche diagnostics, Branchburg, N.J.). Biotin-labeled rat anti-mouse Syndecan-1 and anti-mouse CD5 monoclonal antibodies were purchased (BD PharMingen, San Diego, Calif.). Biotin-labeled peanut agglutinin (PNA) was purchased from Vector Laboratories (Burlingame, Calif.).

3. Immunization
Trinitrophenyl keyhole limpet hemocyanin (TNP-KLH) and TNP-Ficoll were purchased from Biosearch Technologies (Novato, Calif.). Briefly, 100 µg of TNP-KLH emulsified in complete Freund's adjuvant or 25 µg of TNP-Ficoll was injected into the abdominal cavity of the mouse. Fourteen days thereafter, lymph organs were removed and frozen with OCT compound to be used in immunohistological analysis.

4. Immunohistological Analysis
Six-micrometer cryosections of organs were fixed in acetone for 5 min, blocked with 3% BSA in PBS for 15 min, and incubated for 1 hr with rat anti-mouse GANP monoclonal antibody (42-23) [Kuwahara, K. et al., 2000, Blood 95: 2321-2328] or rat anti-pSer$^{502}$ GANP monoclonal antibody (PG/103) [Kuwahara, K. et al., 2001, Proc. Natl. Acad. Sci. USA 98: 10279-10283]. Sections were mounted on slide glasses, which were washed with PBS several times and then incubated with alkali phosphatase (ALP)-conjugated goat anti-rat IgG antibody (ICN Pharmaceuticals, Costa Mesa, Calif.). Color development was carried out with Vector Blue kit (Vector). Double staining was carried out using biotin-labeled antibodies in combination with horse radish peroxidase (HRP)-conjugated streptavidin (Kirkegaard & Perry Laboratories, Gaithersburg, Md.). After color development with 3,3'-diaminobenzidine tetrahydrochloride (DAB; Dojin Kagaku), sections were fixed in 1% glutaraldehyde in PBS for 1 min. For mounting, Aquatex (Merck, Darmstadt, Germany) was used. In order to detect cells with proliferation activity in vivo, bromodeoxyuridine (BrdU) (Sigma Chemicals Co., St. Louis, Mo.; 1 mg/mouse) was injected intravenously 2 hrs before slaughter. Cells which synthesize DNA were stained with a combination of anti-BrdU monoclonal antibody (BD PharMingen) and ALP-conjugated goat anti-mouse Ig antibody (sigma), followed by color development with Vector Red (Vector) for detection. PAS staining was carried out as described previously [Jiang, Y. et al., 1997, J. Immunol. 158: 992-997].

5. Results
(1) Appearance of GANP$^{hi}$ Cells in MRL/lpr Mouse Lymph Nodes
GANP is expressed highly in autoimmune-prone, highly active B cells. High level GANP-expressing lymphocytes (GANP$^{hi}$ cells) appear spontaneously in peripheral lymph nodes of MRL/lpr mice in a non-immunized state.

Immunohistochemical analysis was performed on popliteal lymph nodes from autoimmune disease model (MRL/lpr and NZB) female mice and normal C57BL/6 female mice using anti-GANP monoclonal antibody and ALP-conjugated anti-rat Ig antibody.

The results are shown in FIG. 1. While GANP$^{hi}$ cells stained with Vector Blue (ALP substrate) were observed in lymph nodes of MRL/lpr mice at week 7, such cells were not observed in NZB mice of the same age and appeared at week 40 (FIG. 1). In normal C57BL/6 mice, an extremely small number of GANP$^{hi}$ cells were observed throughout the period of experiment.

Compared to C57BL/6 mice, autoimmune disease model mice revealed a remarkable increase in lymphocytes but showed no GANP$^{hi}$ cells under non-immunized conditions (FIG. 1). The appearance of such GANP$^{hi}$ cells was examined in lymph nodes of NZB mice which develop autoimmune conditions little by little as they get older. While young NZB mice (7 week old) did not have GANP$^{hi}$ cells in their popliteal lymph nodes, aged NZB mice (40 week old) had a great number of GANP$^{hi}$ cells.

It is considered that GANP RNA primase activity may play an important role in the activation and differentiation of B cells. Then, inventor compared the states of phosphorylation of Ser$^{502}$ (which is a key phosphorylation site for RNA primase activity) in NZB mice using anti-pSer$^{502}$ monoclonal antibody.

The expressions of GANP and pSer$^{502}$ GANP were compared in lymph nodes of NZB mice. Briefly, pSer$^{502}$ GANP was detected with anti-pSer$^{502}$ GANP (PG/103) monoclonal antibody (blue) and all sections were stained with biotin-labeled anti-B220 monoclonal antibody, followed by detection with a combination of HRP-conjugated streptavidin and DAB (brown). Representative data obtained from two independent experiments are shown in FIG. 2.

Figure 2:
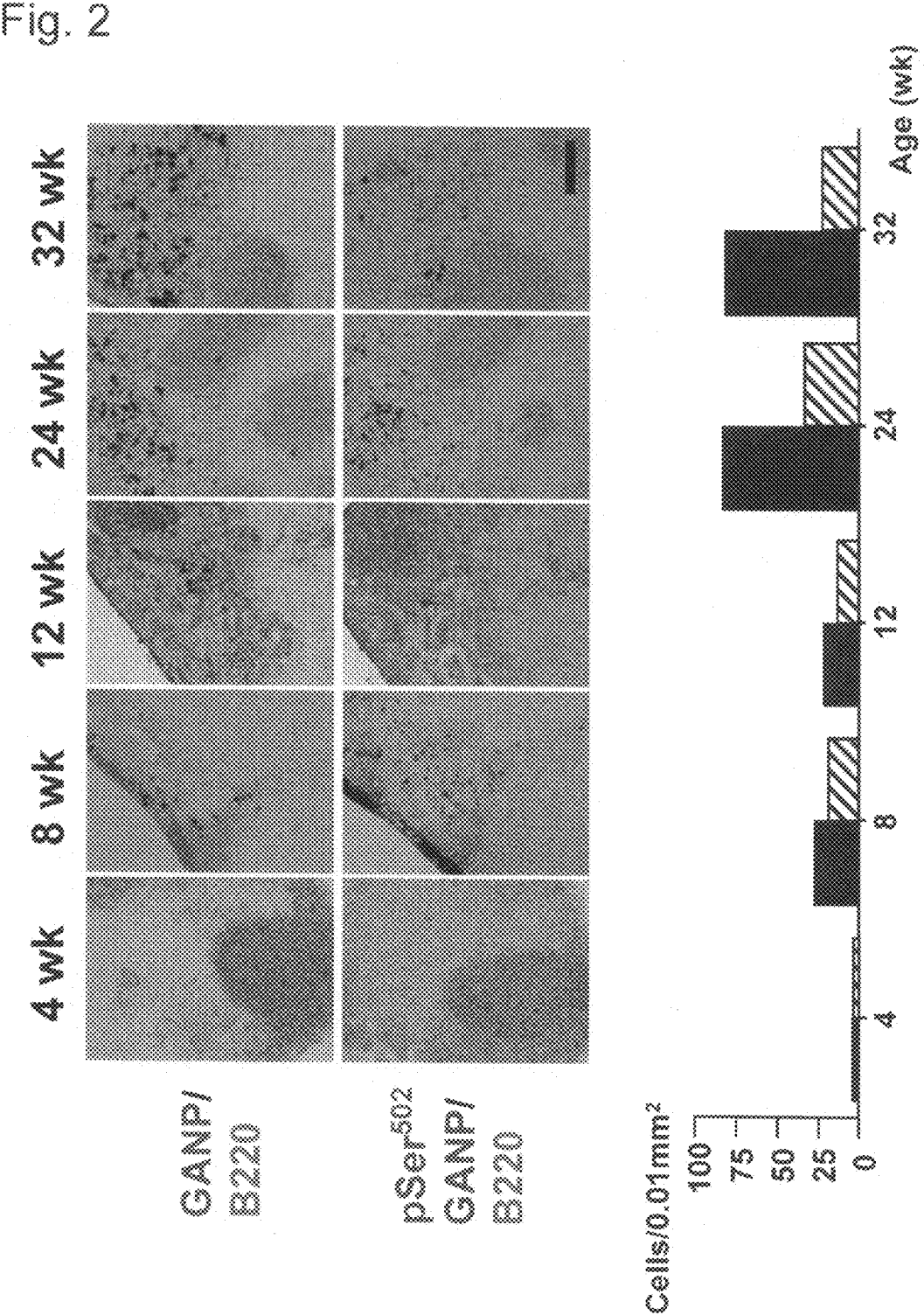
FIG. 2 shows the rates of appearance of $GANP^{hi}$ cells in popliteal lymph nodes of female NZB mice. Scale bar is 100 μm.

In FIG. 2, the bottom panel (graph) shows the time course of the numbers of GANP$^{hi}$ cells (black column) and pSer$^{502}$ GANP$^{hi}$ cells (column with slant lines) in extrafollicular regions.

GANP expression is remarkable at week 8; GANP$^{hi}$ cells were detected throughout the experiment period up to week 32 (FIG. 2, upper panel). In contrast, pSer$^{502}$ positive cells reached the peak at week 8 and then sharply decreased (FIG. 2, middle panel). The numbers of reactive cells based on peak age obtained by microscopic observation are shown (FIG. 2, bottom panel). From these results, it is understood that GANP expression is accompanied by RNA primase activity at the beginning but this activity is not regulated for a long period of time.

(2) Spontaneous Appearance of GANP$^{hi}$ Cells in the Red Pulp of the Spleen in Autoimmune-Prone Mice Whether or not the GANP$^{hi}$ cells detected in popliteal lymph nodes of autoimmune-prone NZB mice appear in the spleen under non-immunized conditions was examined.

Figure 3:
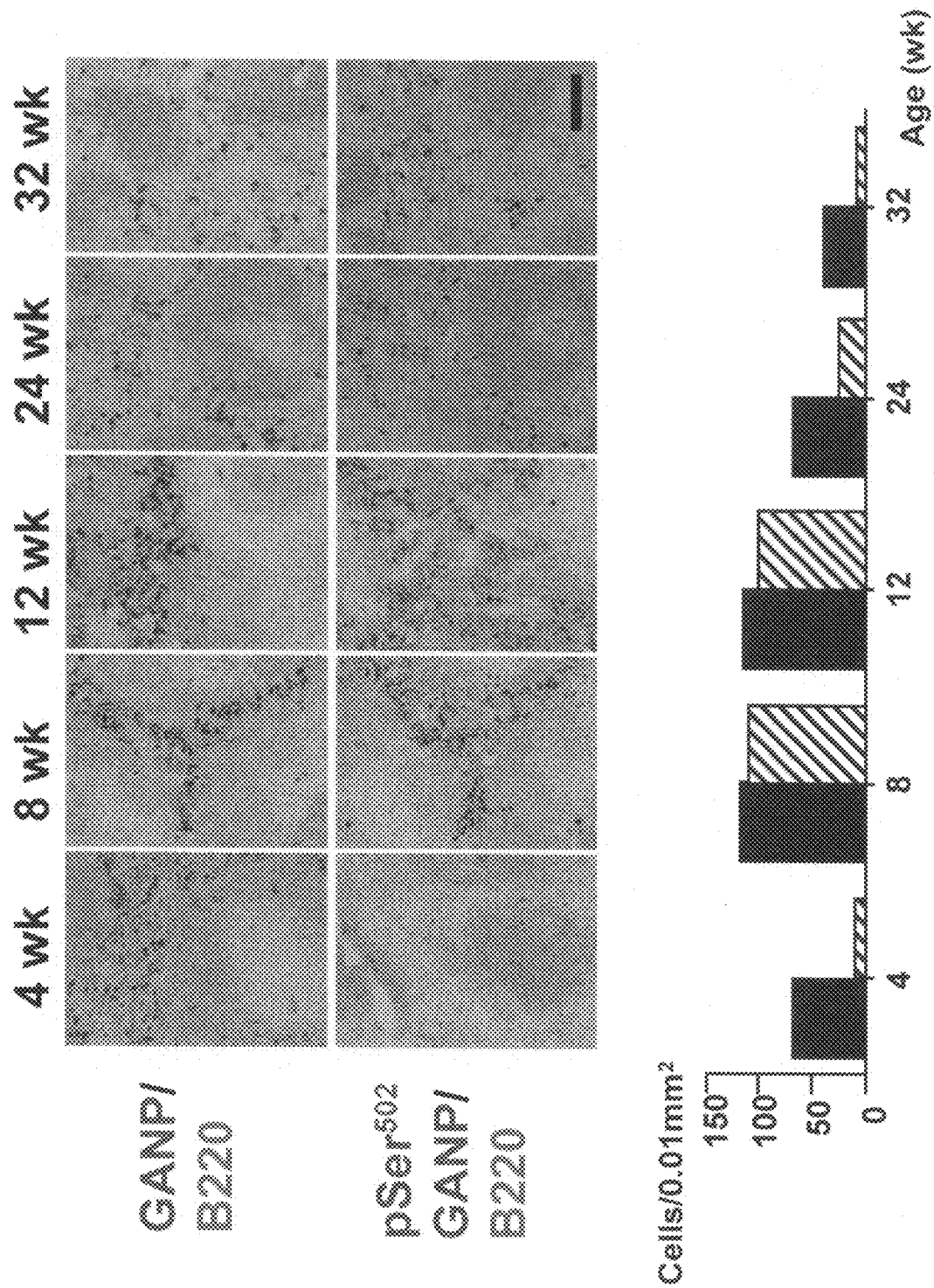
FIG. 3 shows the rates of appearance of $GANP^{hi}$ cells in the spleens of female NZB mice. Scale bar is 100 μm.

Immuno-staining was carried out in the same manner as described in (1) above (FIG. 2). Representative data from three independent experiments are shown in FIG. 3.

GANP$^{hi}$ cells appeared in the spleen at week 4. The cell count reached its maximum at week 12 but GANP$^{hi}$ cells disappeared at week 24 (FIG. 3, upper panel). The expression of pSer$^{502}$ GANP was also detected at weeks 8 and 12 (FIG. 3, middle panel). From the results of comparison with relative cell counts in the red pulp, it is understood that the GANP$^{hi}$ cells which had appeared in the spleen moved to peripheral lymph nodes 12 weeks thereafter. The increase of GANP$^{hi}$ cells is proportional to the yield of autoantibody prior to the occurrence of autoimmune disease (FIGS. 2 and 3; Theofilopoulos, A. N. et al., 1985, *Adv. Immunol.* 37: 269-390).

The appearance of GANP$^{hi}$ cells may be associated with abnormalities in B cells in autoimmune-prone mice. Therefore, the appearance of GANP$^{hi}$ cells was examined in various autoimmune-prone mice (8 week old) under non-immunized conditions.

Figure 4:
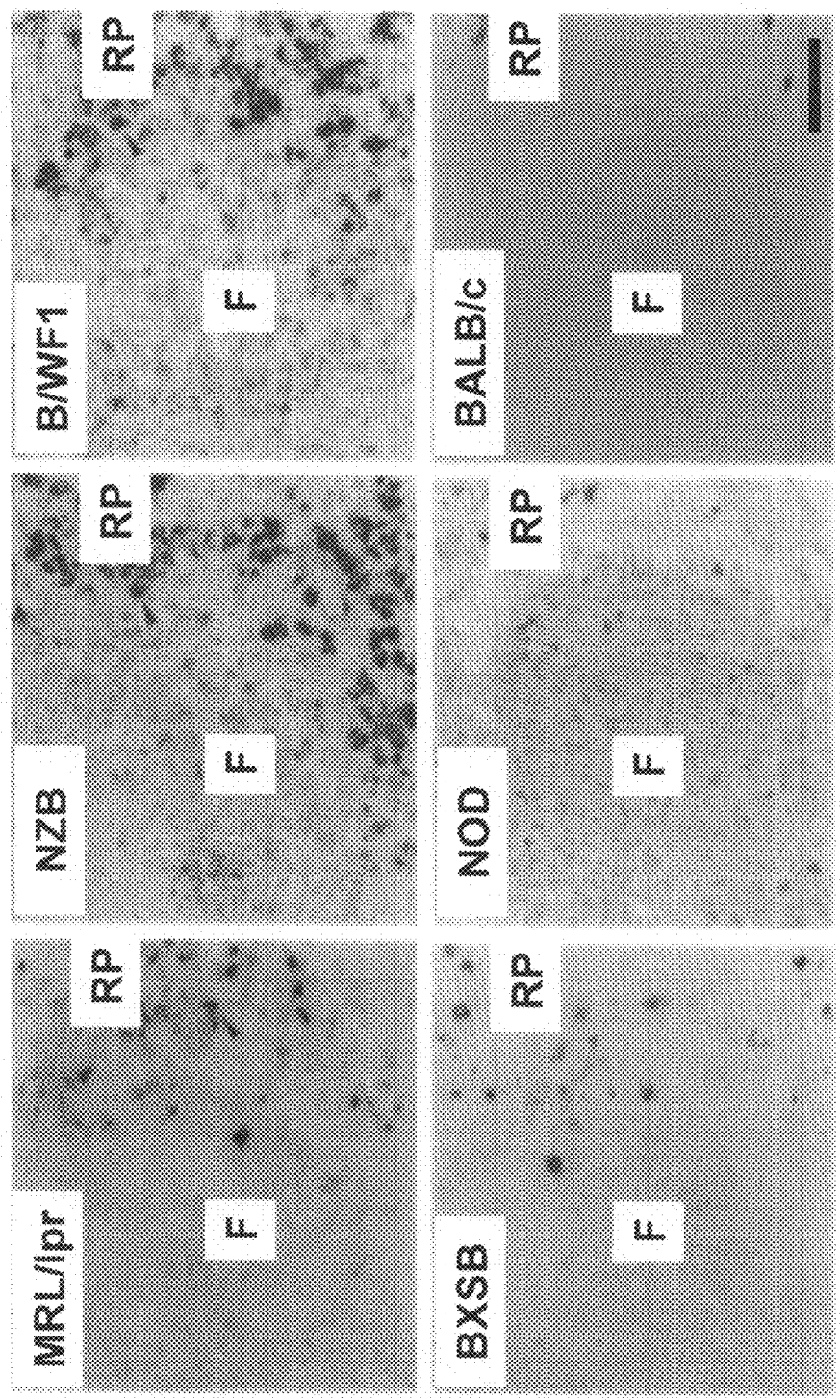
FIG. 4 shows the results of the staining of plural lineage mice-derived spleen sections with anti-GANP monoclonal antibody. RP: red pulp; F: follicles. Scale bar is 100 μm.

The results are shown in FIG. 4. GANP$^{hi}$ cells appeared remarkably in the red pulps of MRL/lpr, NZB and B/WF1 mice.

Although the number of GANP$^{hi}$ cells did not show a remarkable increase in the spleens of BXSB and NOD mice (both are SLE model mice), the number showed an increase when compared to the control mice, i.e. BALB/c mouse (FIG. 4) and C57BL/6 mouse (FIG. 1). Spleen sections showed, as a GC-like structure, or immature association of PNA$^+$ B cells. GANP expression in the GC-like region was not high compared to GANP expression in the GC which was created by immunizing normal C57BL/6 mouse and BALB/c mouse with T cell-dependent antigens (TD-Ags). However, GANP$^{hi}$ cells appeared remarkably in the red pulp region in autoimmune-prone mice (FIG. 4).

Further, GANP$^{hi}$ cell population was analyzed with markers of lymphoid cells.

Spleen sections from NZB mice were double-stained with biotin-labeled B220 monoclonal antibody, biotin-labeled Syndecan-1 monoclonal antibody, biotin-labeled IgM monoclonal antibody and anti-IgG antibody to thereby identify GANP$^{hi}$ cells.

Figure 5:
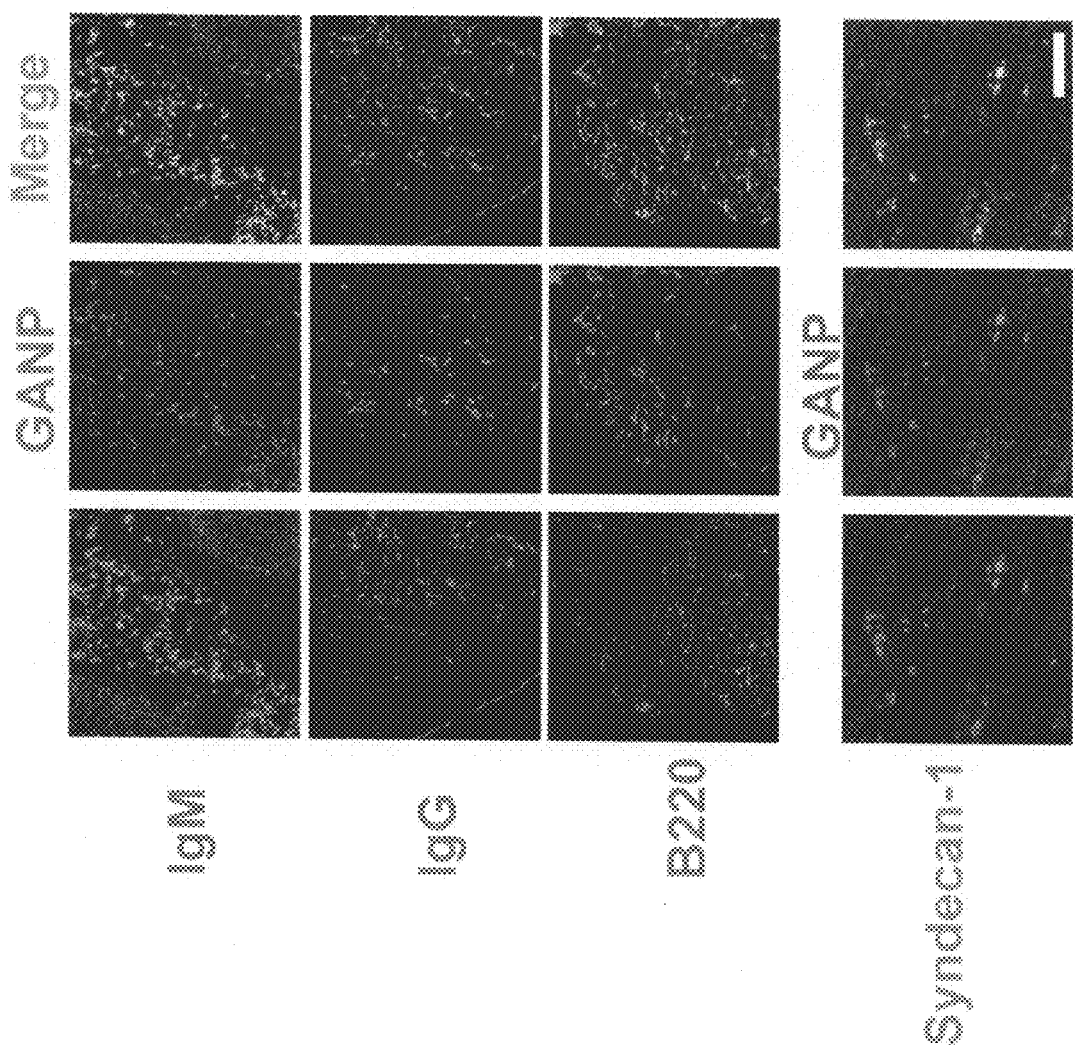
FIG. 5 shows the identification of $GANP^{hi}$ cells in the spleen red pulp.

The results are shown in FIG. 5. The photographs in the left side panel of FIG. 5 show sections when biotin-labeled IgM monoclonal antibody, anti-IgG antibody, biotin-labeled B220 monoclonal antibody and biotin-labeled Syndecan-1 monoclonal antibody were used, respectively. The photographs in the central panel show GANP expression in the same sections as described above. The right side panel is a superposition of the left side panel and the central panel. Those cells which are double-stained in the right side panel indicate that GANP$^{hi}$ cells are B220$^-$ Syndecan1$^+$ IgM$^+$. GANP expression is shown in red when IgM, IgG and B220 antibodies were used, and shown in green when Syndecan-1 antibody was used. Markers are indicated in green when IgM, IgG and B220 antibodies were used, and indicated in red when Syndecan-1 antibody was used.

GANP$^{hi}$ cells show the phenotype of B220$^-$ Syndecan-1$^+$ and express a large quantity of IgM within cells (FIG. 5). GANP$^{hi}$ cells are negative with respect to CR1, Thy-1, GL-7, CD23 and PNA. From these results, it is shown that GANP$^{hi}$ cells are B-lineage cells of late maturing stage, perhaps plasma cells. In order to examine whether or not these GANP$^{hi}$ cells are proliferative plasmablast cells, BrdU (1 mg/mouse) was intravenously injected into NZB mice, which were then incubated for 2 hrs so that BrdU was taken in vivo. Subsequently, spleen sections were prepared from the resultant mice.

Sections were double-stained with anti-GANP monoclonal antibody (blue) and anti-BrdU monoclonal antibody (red). PAS staining was carried out according to conventional methods.

Figure 6:
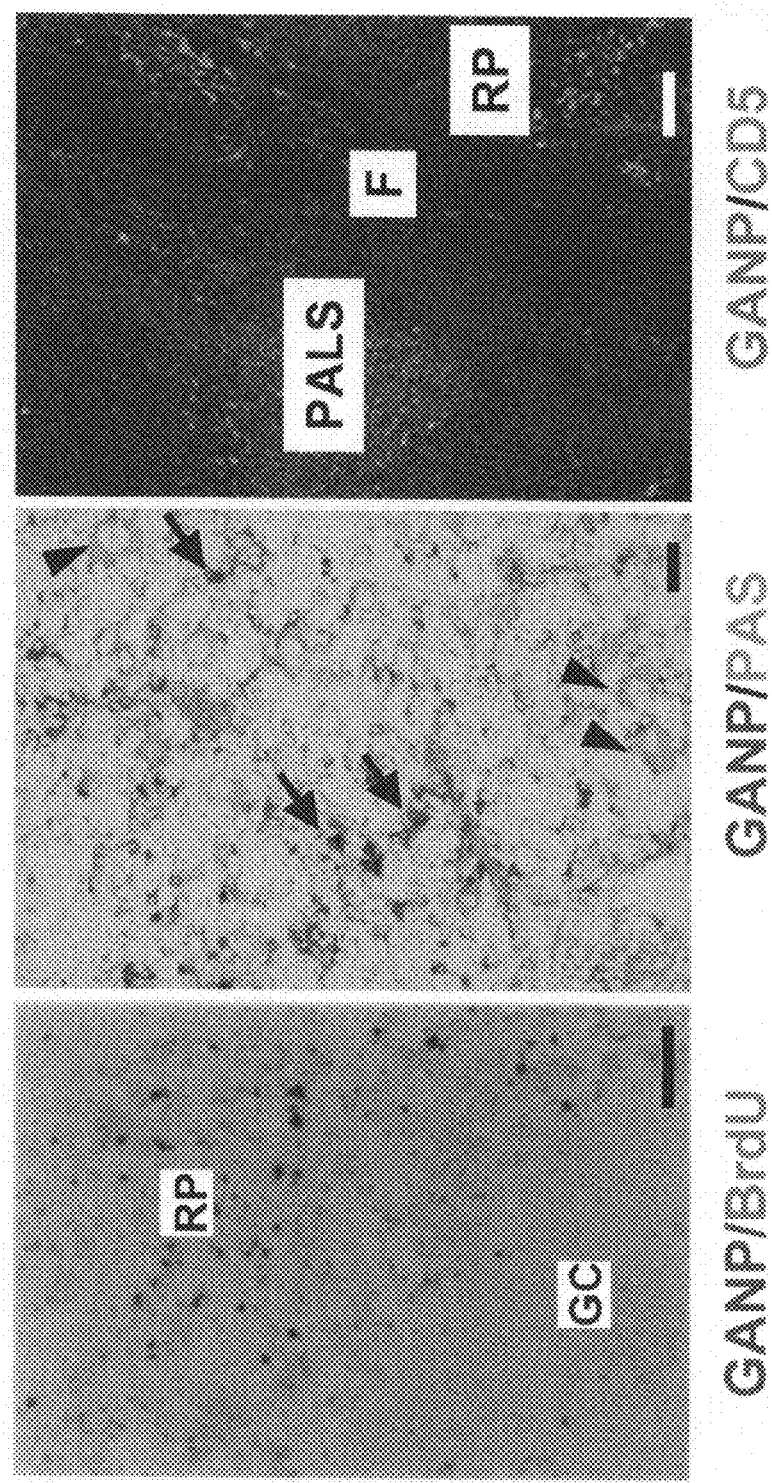
FIG. 6 shows the identification of plasma cell markers in $GANP^{hi}$ cells. Scale bar is 100 μm.

The results are shown in FIG. 6. GC represents germinal center (left panel). GANP singly positive cells are shown with arrows; and PAS singly positive cells are shown with arrow heads (central panel).

Also, sections were stained with biotin-labeled anti-CD-5 monoclonal antibody. The PALS region represents the periarterial sheath in lymph nodes (right panel). FIG. 6 shows representative data obtained from three independent experiments.

Since GANP$^{hi}$ cells are not positive with respect to BrdU intake (FIG. 6), it is suggested that these cells are not proliferative and are more mature than plasmablast stage.

As abnormal differentiation of B-1 cells, Mott cell formation is observed in autoimmune-prone mice. Mott cell is an abnormal morphology of plasma cell; a large number of IgM molecules are accumulated in rough-surfaced endoplasmic reticulum-associated follicles which are detected as intracytoplasmic Russell bodies by PAS staining [Jiang, Y. et al., 1997, *J. Immunol.* 158: 992-997]. GANP$^{hi}$ cells are not stained by PAS staining (FIG. 6), and thus can be distinguished from Mott cells which are B-1 cell-derived plasma cells. Since the GANP$^{hi}$ polulation in the spleen was negative in CD5 expression (FIG. 6) and peritoneal cells obtained from NZB mice (12 week) were negative with respect to GANP$^{hi}$ cells, it is suggested that B-1 cells are not expressing a large quantity of GANP. From these results, GANP$^{hi}$ cells are classified into highly active B cells of autoimmune sate, and it is suggested that this population is of a lineage whose origin is different from the origin of B-1 cells.

(3) Induction of GANP$^{hi}$ Cells in Normal Mice by Immunization with TD-Ag

Whether or not the appearance of GANP$^{hi}$ plasma cells in secondary lymph organs is limited to autoimmune-prone mice was examined.

Figure 7:
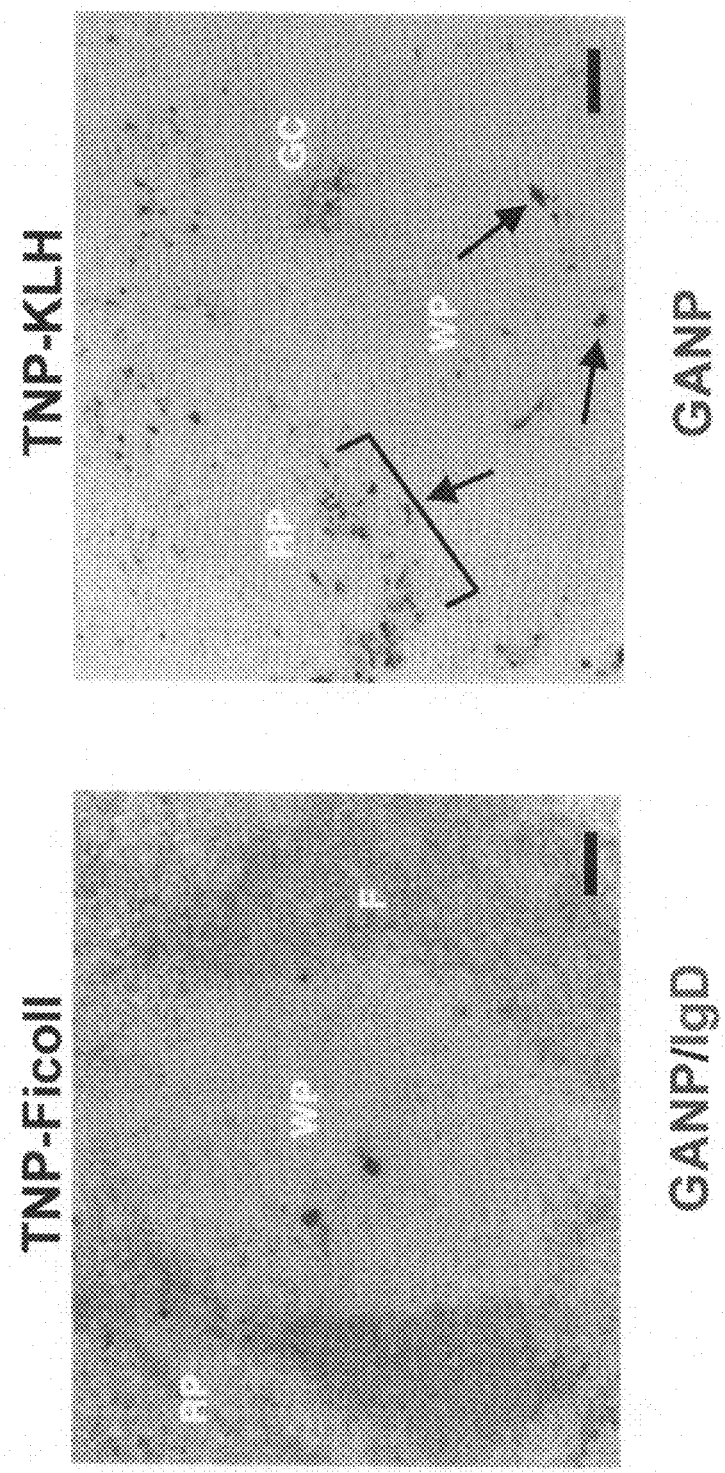
FIG. 7 shows the appearance of $GANP^{hi}$ cells in the red pulp region of the spleens of C57BL/6 mice as a result of immunization with TD-Ag. Scale bar is 100 μm.

Female C57BL/6 mice (7 week old) were immunized intraperitoneally with TNP-Ficoll (TI-2-Ag) or TNP-KLH (TD-Ag). Their spleens were removed on day 14. Those mice immunized with TNP-Ficoll did not show GANP$^{hi}$ cells in the red pulp region when counter-stained with biotin-labeled anti-IgD monoclonal antibody (FIG. 7, left panel). Those mice immunized with TNP-KLH showed the induction of GANP$^{hi}$ cells in the red pulp region (FIG. 7, right panel). In FIG. 7, GANP$^{hi}$ cells are marked with arrows. WP represents the white pulp region.

GANP$^{hi}$ plasma cell population is also induced in the spleens of normal C57BL/6 and BALB/c mice by immunization with TD-Ag, though the number of cells is very small (FIG. 7). Immunization with T cell-independent Ag (TI-Ag) has only a small effect in inducing such cells. The GANP$^{hi}$ cell population showed a phenotype similar to B220$^{lo}$IgM$^{hi}$IgD$^{lo}$GL-7$^{lo}$PNA$^{lo}$CD5$^{lo}$CD40$^{lo}$, but was Syndecan-1$^{+}$.

These results indicate that the generation of GANP$^{hi}$ plasma cells in autoimmune-prone mice is induced by stimulation similar to the stimulation supplied for immune responses to TD-Ag. Ag-driven B cells which have undergone proliferation and differentiation in the GC may be localized in the red pulp region as the plasma cell stage for a longer period, while expressing GANP.

Example 2

Excessive Expression of GANP (Methods)
1. Stable Transfection into Daudi Cells

Ten micrograms of linearized pCXN-2 mouse GANP or GANPS/A502 cDNA was electroporated into Daudi cells with Gene Pulser II (Bio-Rad). After 48 hrs, selection started with G418 (Promega; 1 mg/ml) to thereby obtain Daudi cells which express mouse GANP stably.

2. Analysis of the IgV$_H$ Transcript of Daudi Transfectants

Total RNA was extracted from total cells with Trizol (Invitrogen). cDNA was obtained as described previously (Kuwahara, K. et al., Blood 95, 2321-2328 (2000)). LV$_H$3-C$_H$1Cμ transcript was amplified using the following primers and the reaction solution. For amplification, Pfu Turbo (Stratagene) was used.

```
5'-LV_H3 primer:
                                         (SEQ ID NO: 5)
5'-CTATAACCATGGACCATGGACATACTTTGTTCC-3'

3'-XbaI-C_H1-Cμ primer:
                                         (SEQ ID NO: 6)
5'-TGCATGCATTCTAGAGTTGCCGTTGGGGTGCTGGAC-3'
```

Composition of the Reaction Solution:

| | |
|---|---|
| cDNA | 0.5 μl |
| 10x buffer | 2.5 μl |
| 10 mM dNTP mix | 0.5 μl |
| 5'-LVH3 primer (10 μM) | 1 μl |
| 3'-Xba I-CH1-Cμ primer (10 μM) | 1 μl |
| Pfu Turbo | 0.5 μl |
| dH$_2$O | 19.5 μl |

Reaction Conditions:
94° C. for 1 min
[94° C. for 1 min; 62° C. for 1 min; 72° C. for 1 min]×35 cycles
72° C. for 10 min
4° C.

The resultant PCR product was digested with NcoI and XbaI, purified in a gel, and ligated to a plasmid digested with NcoI-XbaI. After transformation into competent bacterial cells, a small quantity of plasmid DNA was prepared with QIAprep kit (Qiagen). The nucleotide sequence of this plasmid DNA was determined with an automated sequencer (Applied Biosystems).

3. Preparation of GANP-Transgenic (Tg) Mouse

A transgene was prepared by inserting a 5.6 kb mouse GANP gene into the XhoI site of pLG vector. This vector having a human immunoglobulin intron enhancer domain (2 kb EcoRI fragment) is a specific vector that directs strong expression in B cells. This gene was linearized and transferred into mice. Briefly, a linearized pLG vector (Koike, M. et al., Int. Immunol. 7, 21-30 (1995)) comprising the full-length mouse GANP cDNA was micro-injected into fertilized eggs of C57BL/6 mice. The presence of the transferred gene was screened using genomic DNA obtained from mouse tail vein, the following primers and the reaction solution.

```
                                         (SEQ ID NO: 7)
1-5' primer: 5'-TCCCGCCTTCCAGCT GTGAC-3'

(SEQ ID NO: 8)
1-3' primer: 5'-GTGCTGCTGTGTTATGTCCT-3'
```

Composition of the Reaction Solution:

| | |
|---|---|
| DNA (50 ng/μl) | 1 μl |
| 10x buffer | 2.0 μl |
| 2.5 mM dNTP mix | 2.0 μl |
| 1-5' primer (10 μM) | 0.8 μl |
| 1-3' primer (10 μM) | 0.8 μl |
| Z-Taq DNA polymerase | 0.1 μl |
| dH$_2$O | 13.3 μl |

Reaction Conditions:
[98° C. for 5 sec; 59° C. for 5 sec; 72° C. for 10 sec]×35 cycles
4° C.

4. RT-PCR

Total RNA was extracted from the spleen or spleen B cells using Trizol (Invitrogen). RT-PCR was performed with two primers (1-5' primer and 1-3' primer) to synthesize cDNA (Kuwahara, K. et al., Blood 95, 2321-2328 (2000)). GANP transcript was detected by agarose gel electrophoresis. β-actin transcript was used as a control.

5. Results (1) Somatic Hypermutations (SHMs) in V Region Genes of Daudi Transfectants Expressing GANP Stably A GANP gene was transferred into various human B lymphocytes used in SHM analysis in vitro (Rogozin, I. B., et al., *Nat. Immunol.* 2: 530-536 (2001); Kuwahara, K. et al. *Blood* 95: 2321-2328 (2000); and Denepoux, S. et al., *Immunity* 6: 35-46 (1997)). Although a great number of B cell strains were incapable of transfection, it was possible to transfer a GANP gene into Daudi B cells which express AID that usually does not generate SHMs while maintained.

The resultant clones showed highly frequent SHMs ($5 \times 10^{-4}$/bp) in the V regions, compared to wild-type cells and pseudo-transfectants.

$V_H3$-$C_H1C\mu$ fragment was amplified by PCR and subcloned into a plasmid, followed by sequencing.

Figure 8A:
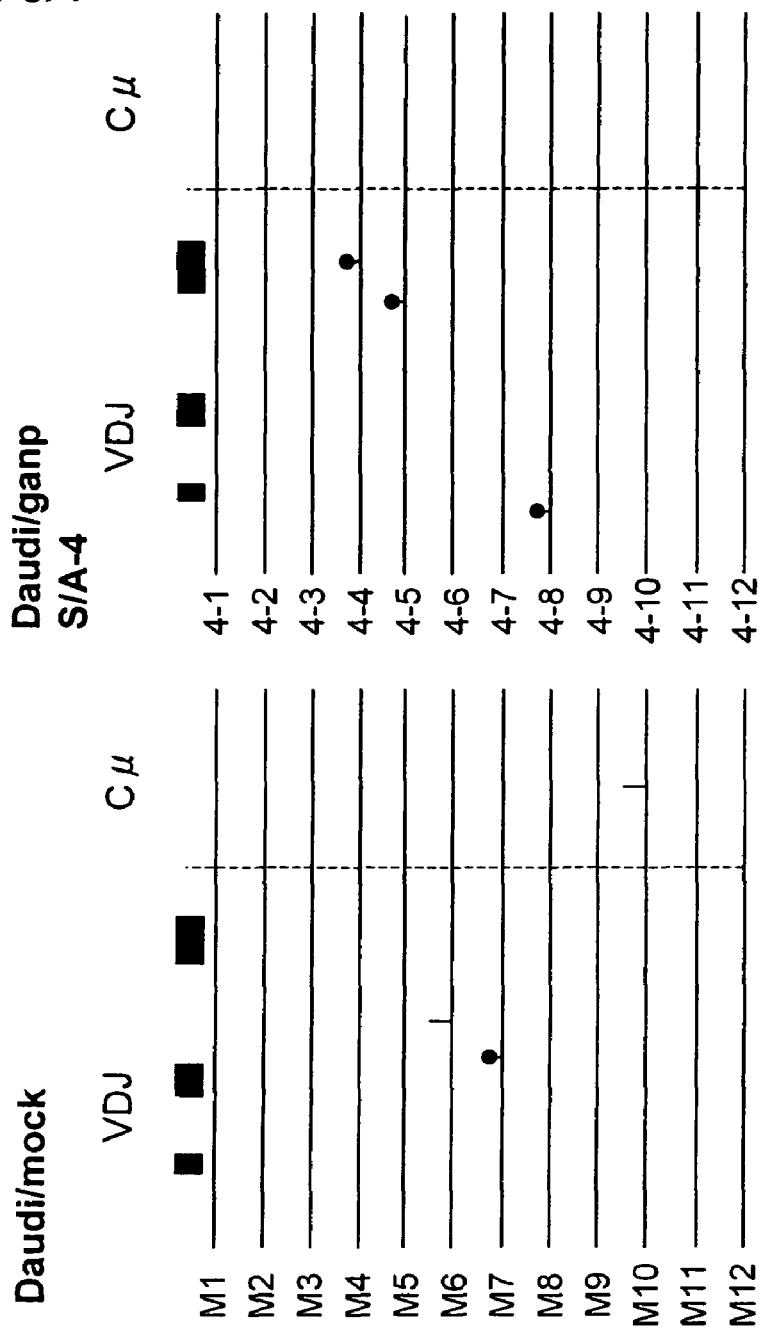
FIG. 8A-C shows somatic mutations in Daudi cell transfectants which are engineered to express mouse GANP stably.
Figure 8B:
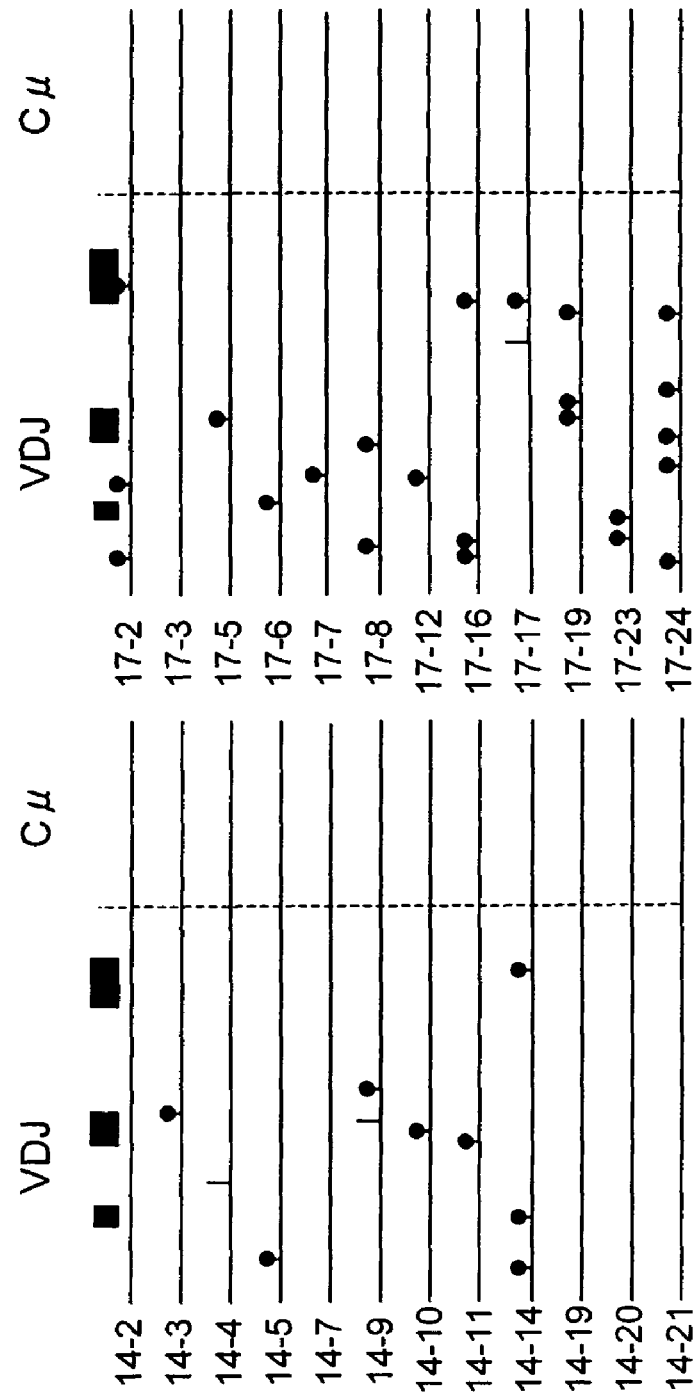
Figure 8C:
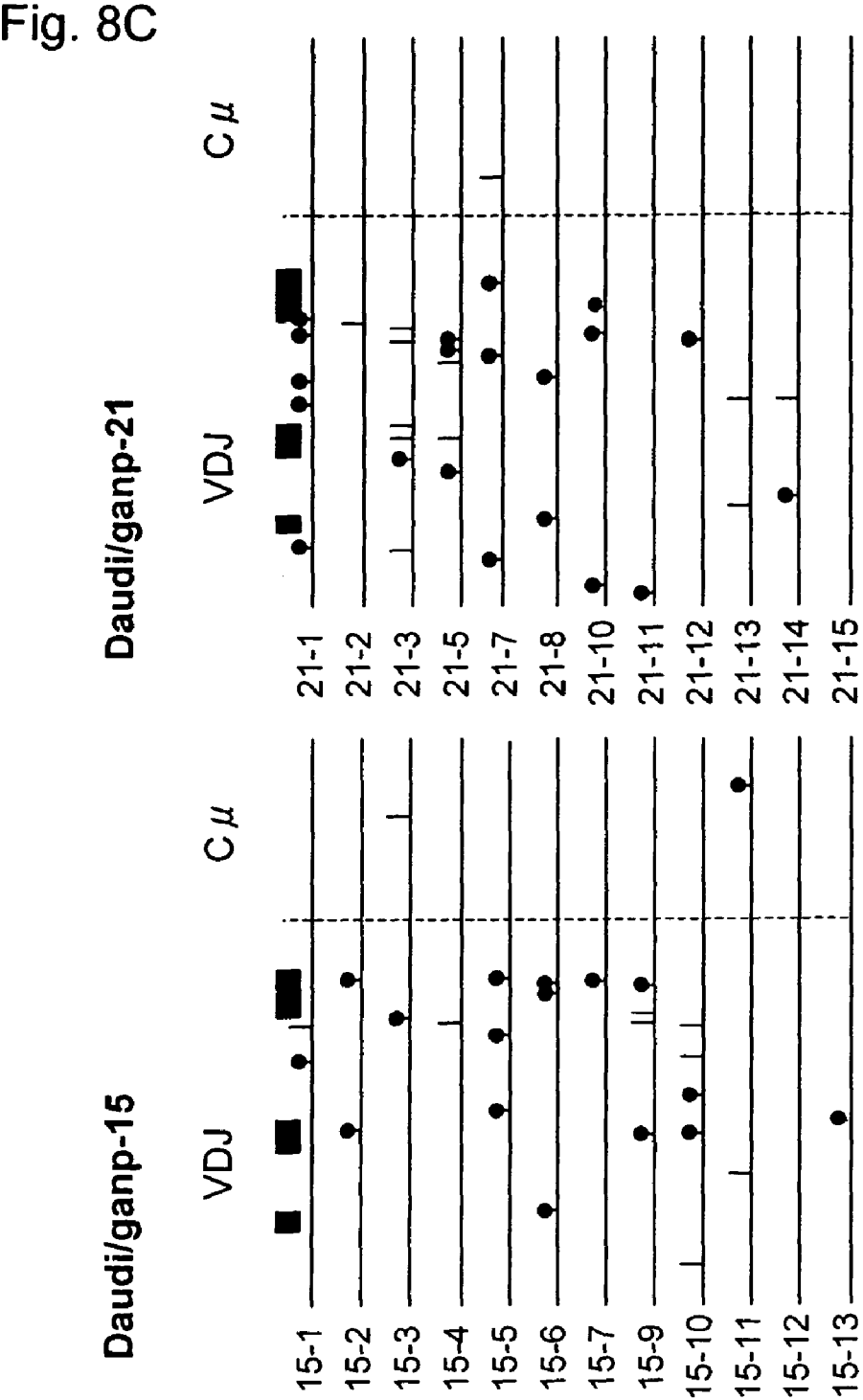

Schematic diagrams of somatic hypermutations are shown in FIG. 8: A-C. Vertical line "|" represents a silent mutation (where the amino acid is not changed), and the other mark (short vertical line with black circle) represents a mutation where the amino acid is replaced. While Daudi/mock shows few mutations, four clones of Daudi/DANP-14, -15, -17 and -21 more of less show a great number of mutations. The efficiency of inducing mutations is decreased in the transfectant into which a mutant (GANP S/A) has been introduced; in this mutant, $Ser^{502}$ involved in the control of DNA primase activity is replaced with alanine.

SHMs were not induced in constant region genes (FIG. 8: A-C). The RNA primase activity of GANP is regulated by the phosphorylation of S502, and this phosphorylation can be detected with a specific monoclonal antibody (Kuwahara, K. et al., *Proc. Natl. Acad Sci. USA* 98: 10279-10283 (2001)). Since both in vivo and in vitro stimulation of B cells induce the phosphorylation of $Ser^{502}$ (Kuwahara, K. et al., *Proc. Natl. Acad. Sci. USA* 98: 10279-10283 (2001)), whether or not this phosphorylation is involved in the generation of SHMs in Daudi B cells was examined.

When a non-phosphorylated GANP mutant (GANP-S502A) was introduced, SHMs were not induced (FIG. 8A). Therefore, it is suggested that the phosphorylation of S502 is important for the generation of SHMs in GC-B cells.

(2) Transgenic Mouse Overexpressing GANP in B Cells

Figure 9A:
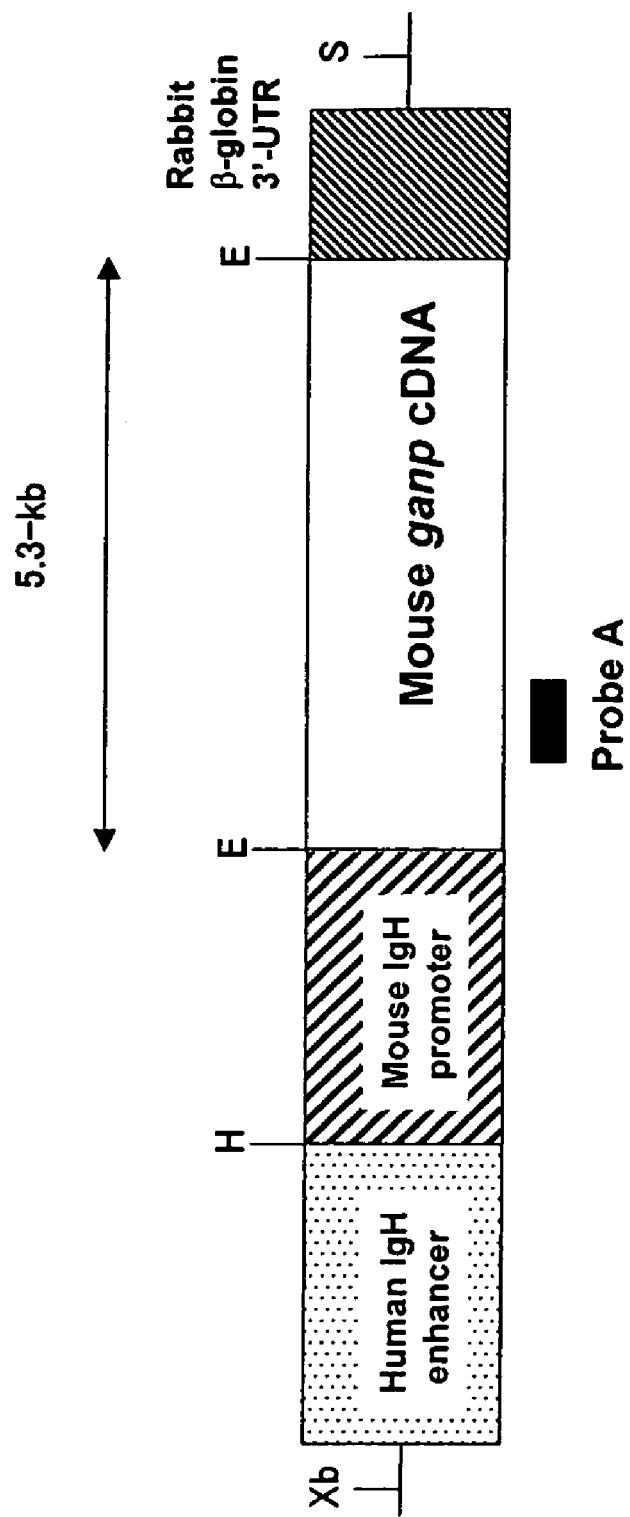
FIG. 9A-C shows an outline of the preparation of a transgenic mouse which is engineered to overexpress GANP in its B cells.
Figure 9B:
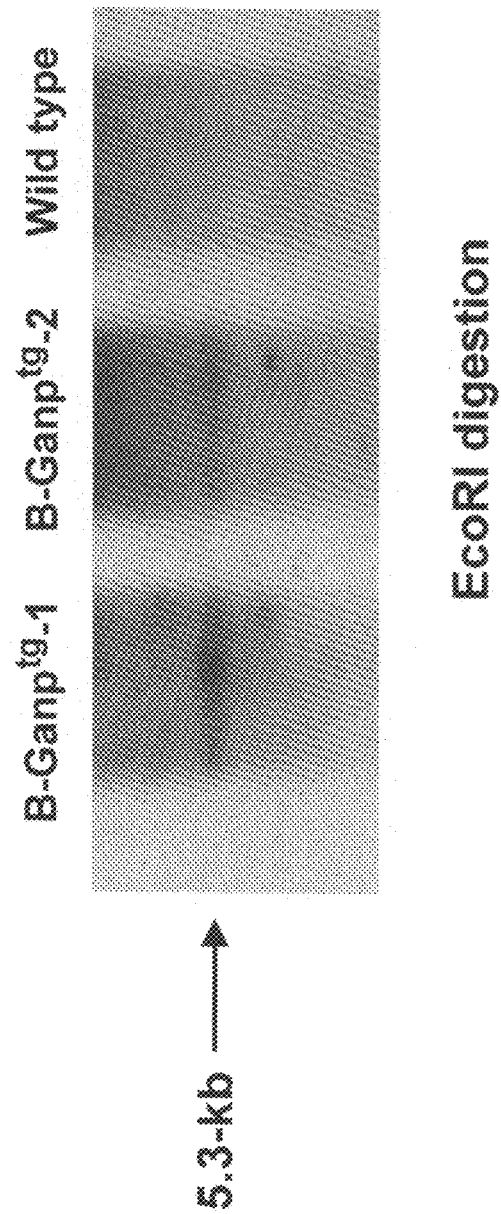
Figure 9C:
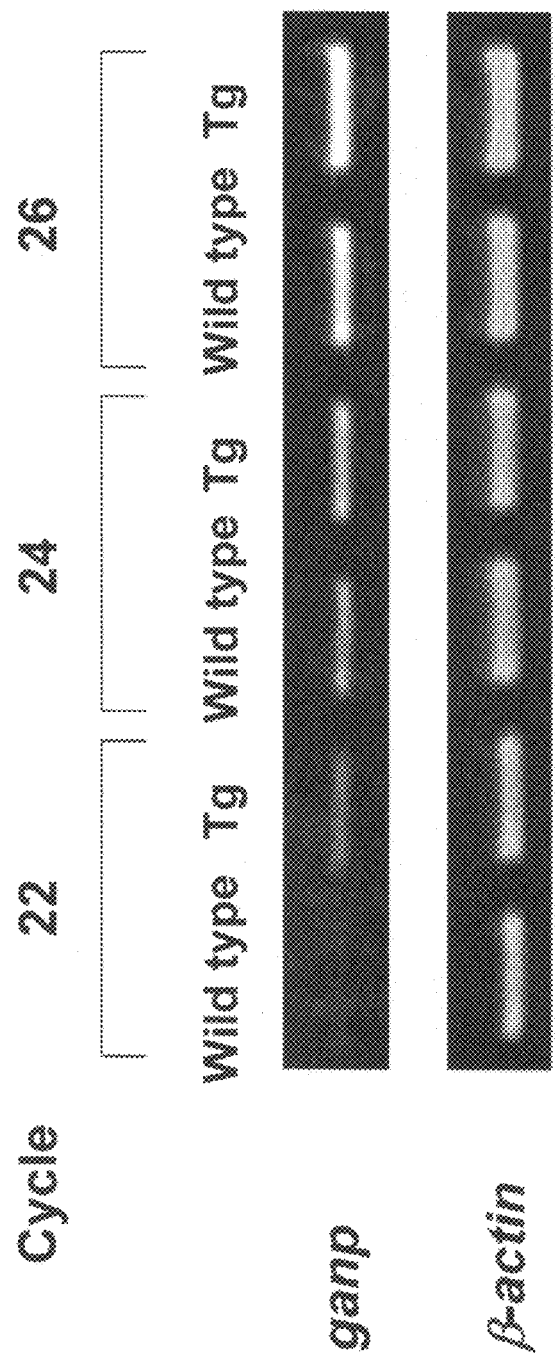
Figure 11A:
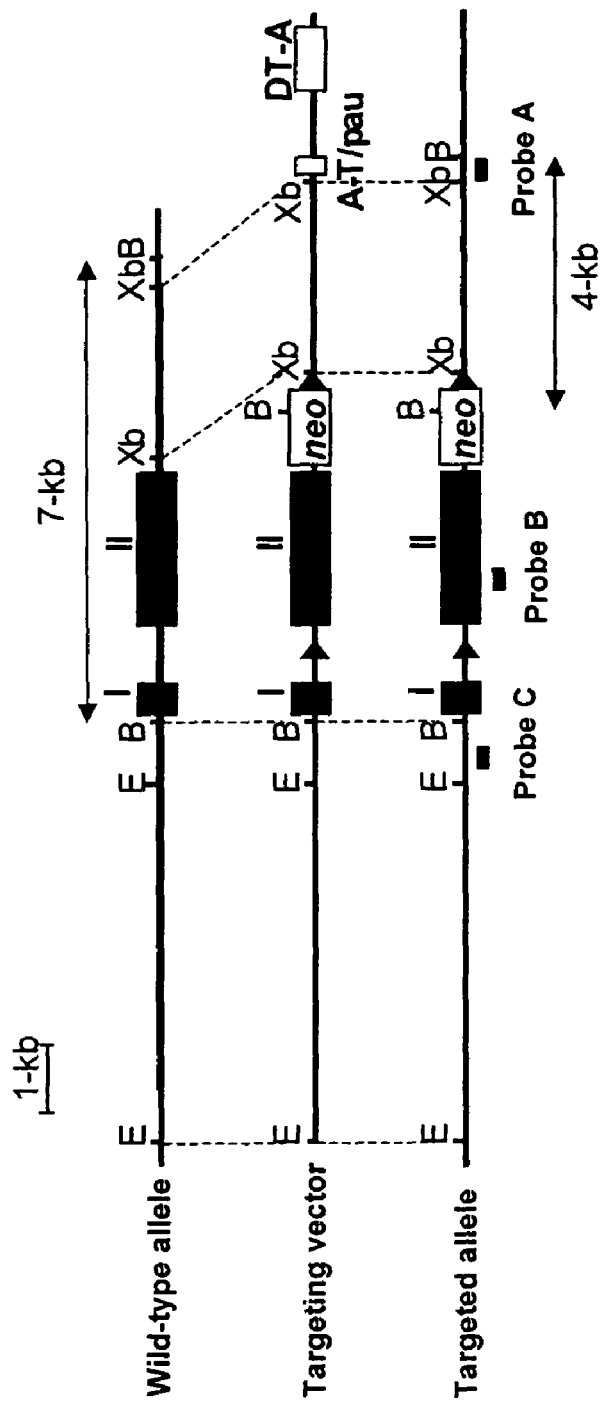
FIG. 11A-E shows an outline of the preparation of a B cell-specific GANP deficient mouse (B-GANP$^{-/-}$).
Figure 11B:
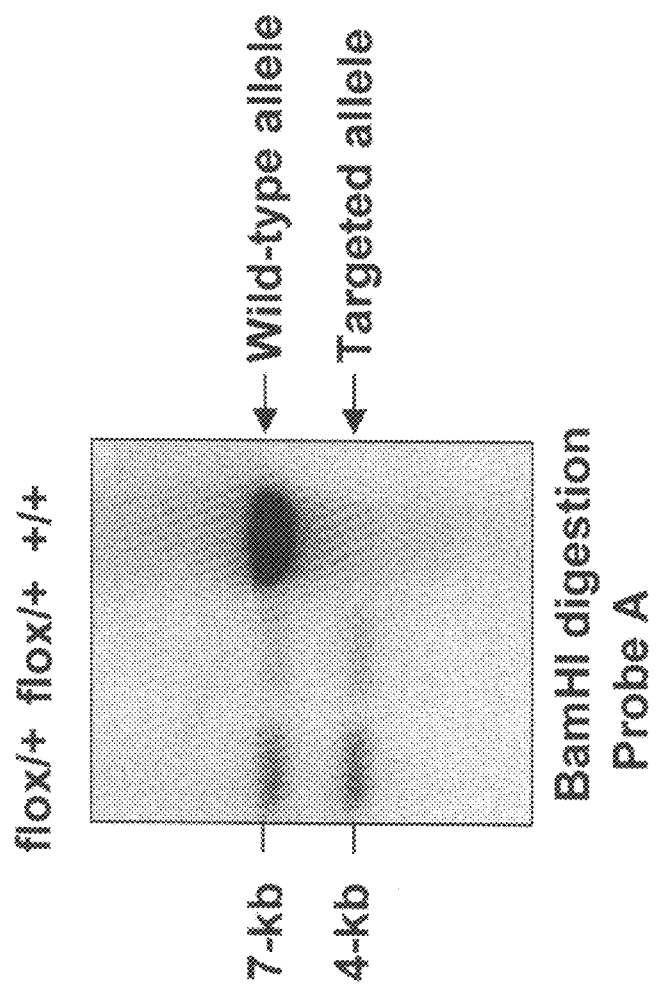
Figure 11C:
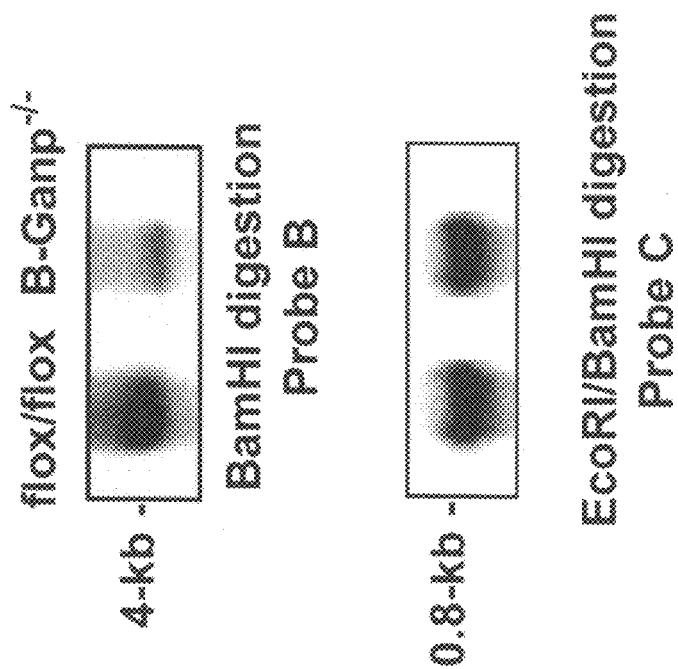
Figure 11D:
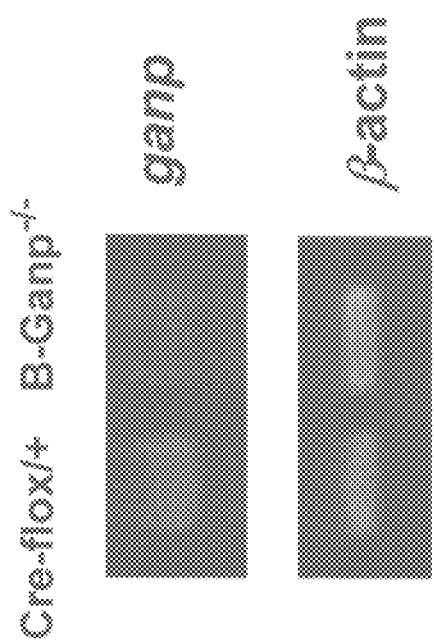
Figure 11E:
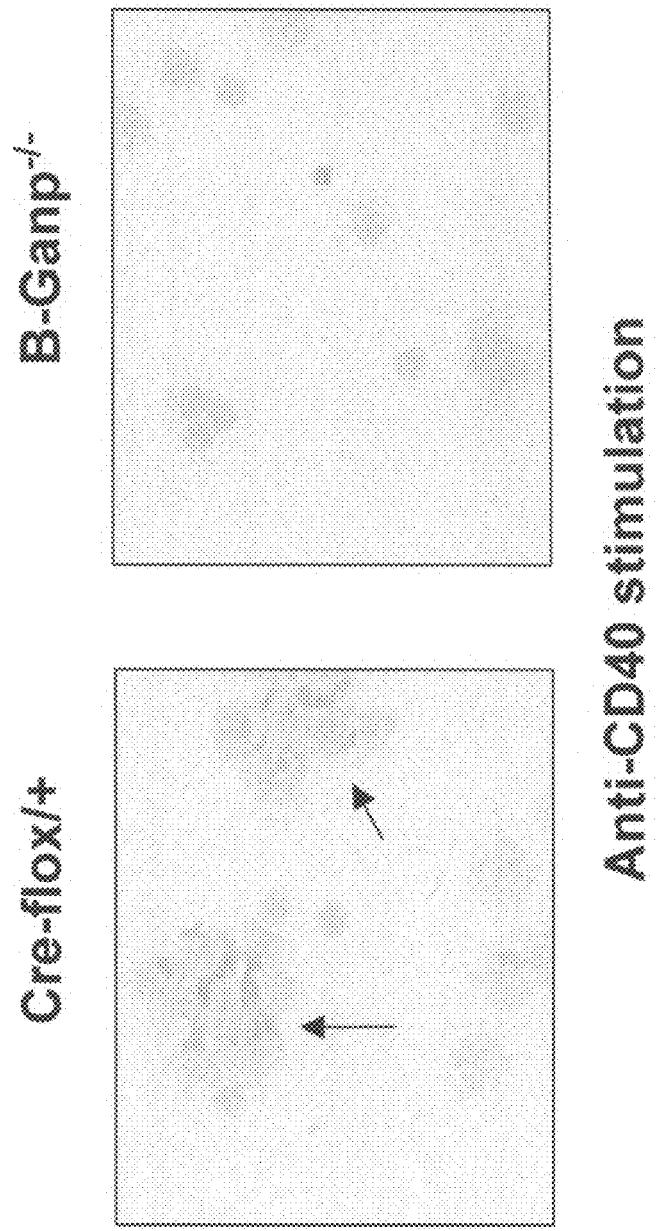

In order to examine the involvement of GANP in immune responses, GANP-transgenic (Tg) mouse which overexpresses GANP under the control of human Ig enhancer and promoter was created (FIG. 9: A-B). Enhancement in GANP mRNA expression was confirmed by RT-PCT.

This mouse showed an increase in GANP expression in B cells (FIG. 9C), and showed normal differentiation of B lineage cells in surface marker analysis of bone marrow, spleen and lymph node cells.

In order to investigate into the in vivo role of GANP in SHMs, the $V_H186.2$ region was examined after immunization with NP-CG (which is TD-Ag). Briefly, 50 µg of NP-CG was administered to GANP-overexpressing transgenic (Tg) mice three times at intervals of two weeks. Then, the $V_H186.2$ region was amplified by PCR, followed by analysis of somatic hypermutations.

Figure 10:
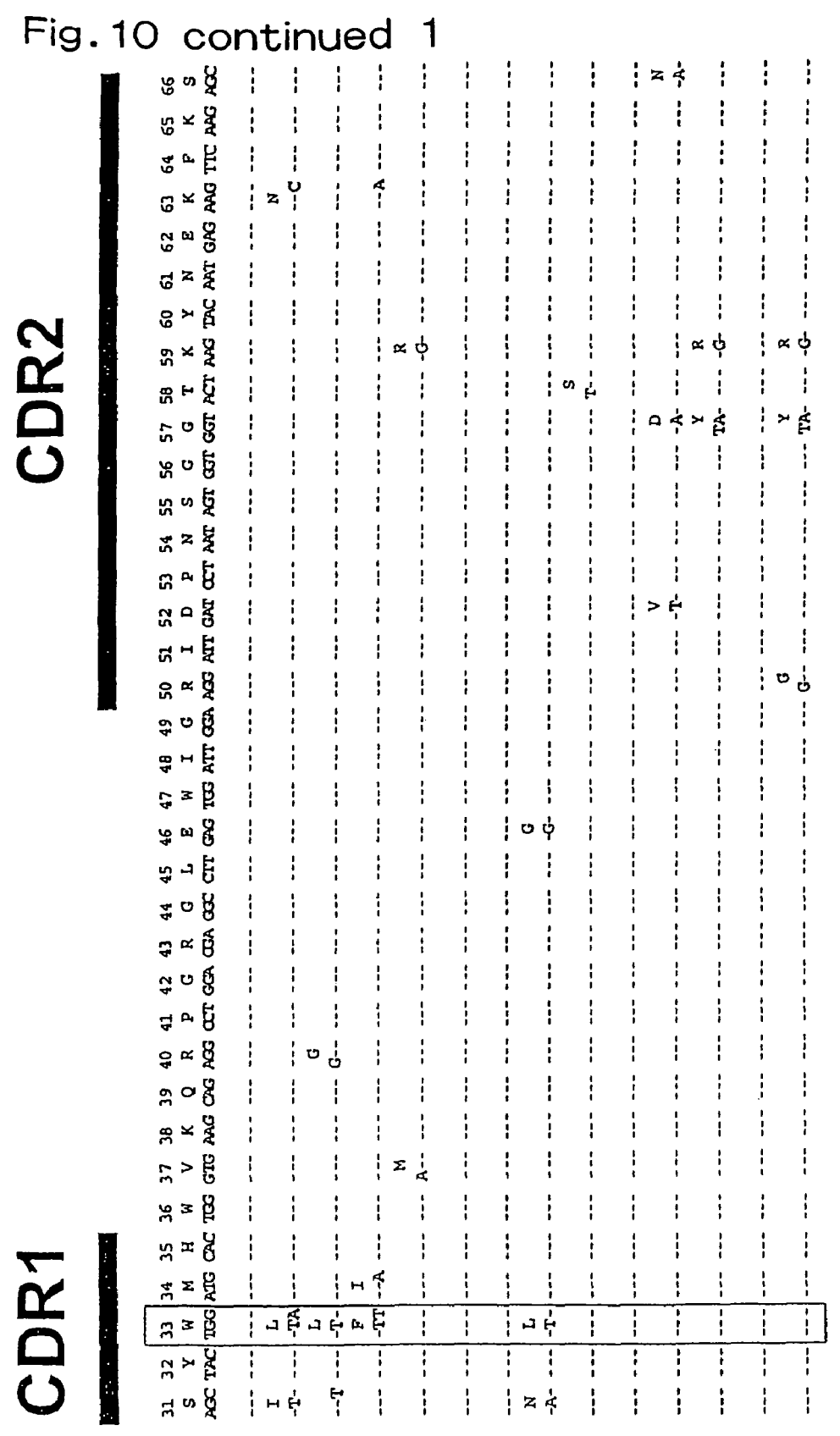
Figure 10:
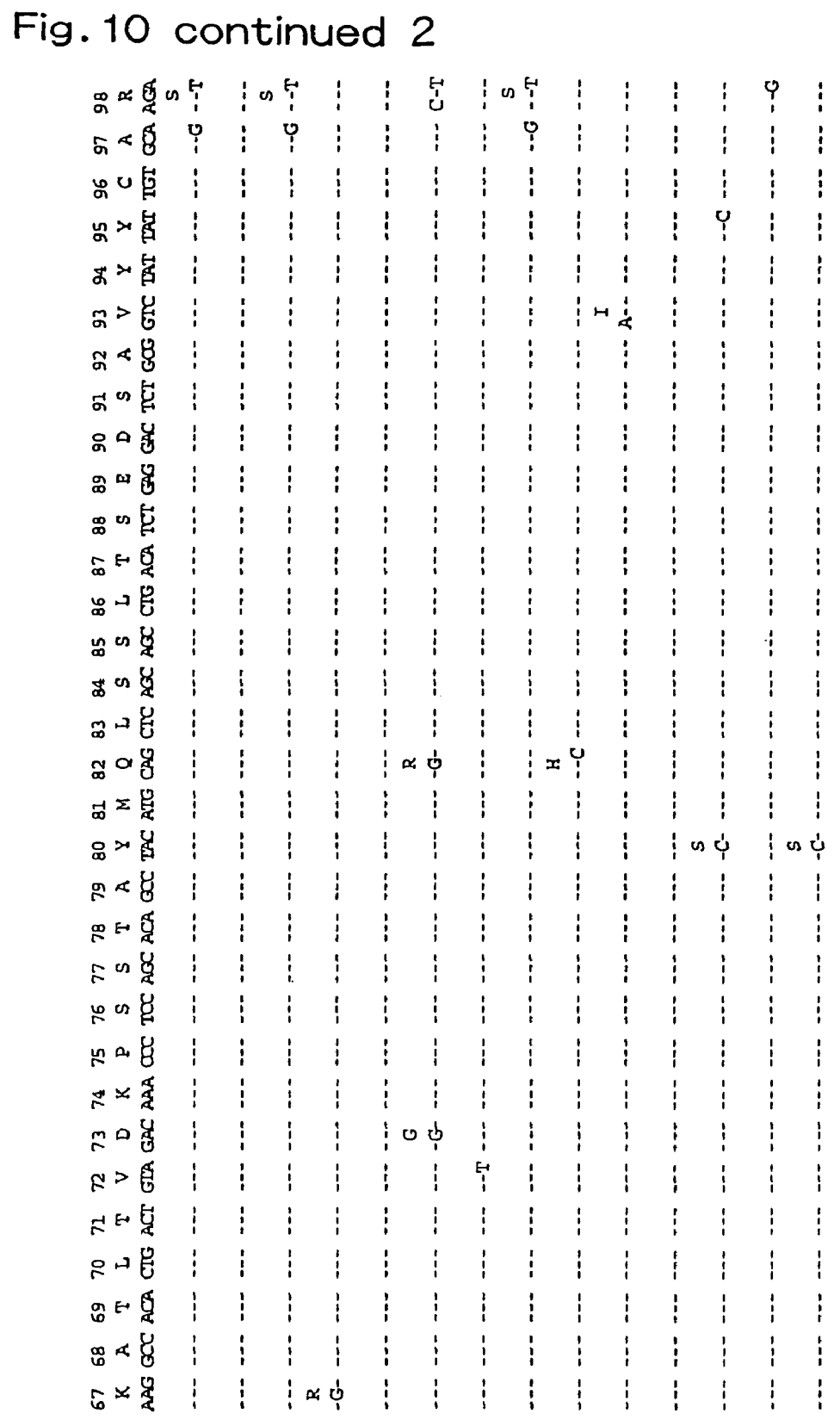
Figure 10:
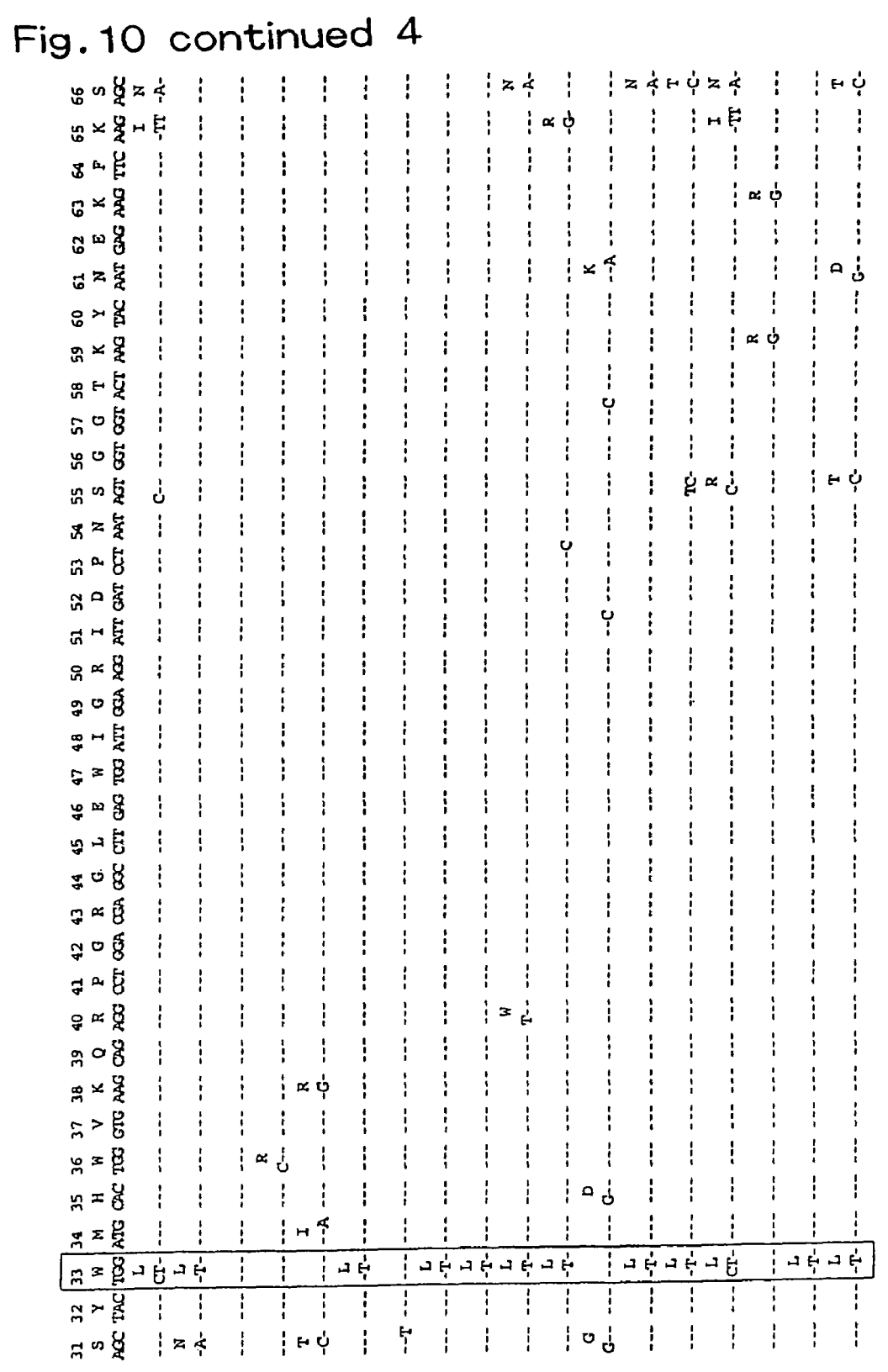
Figure 10:
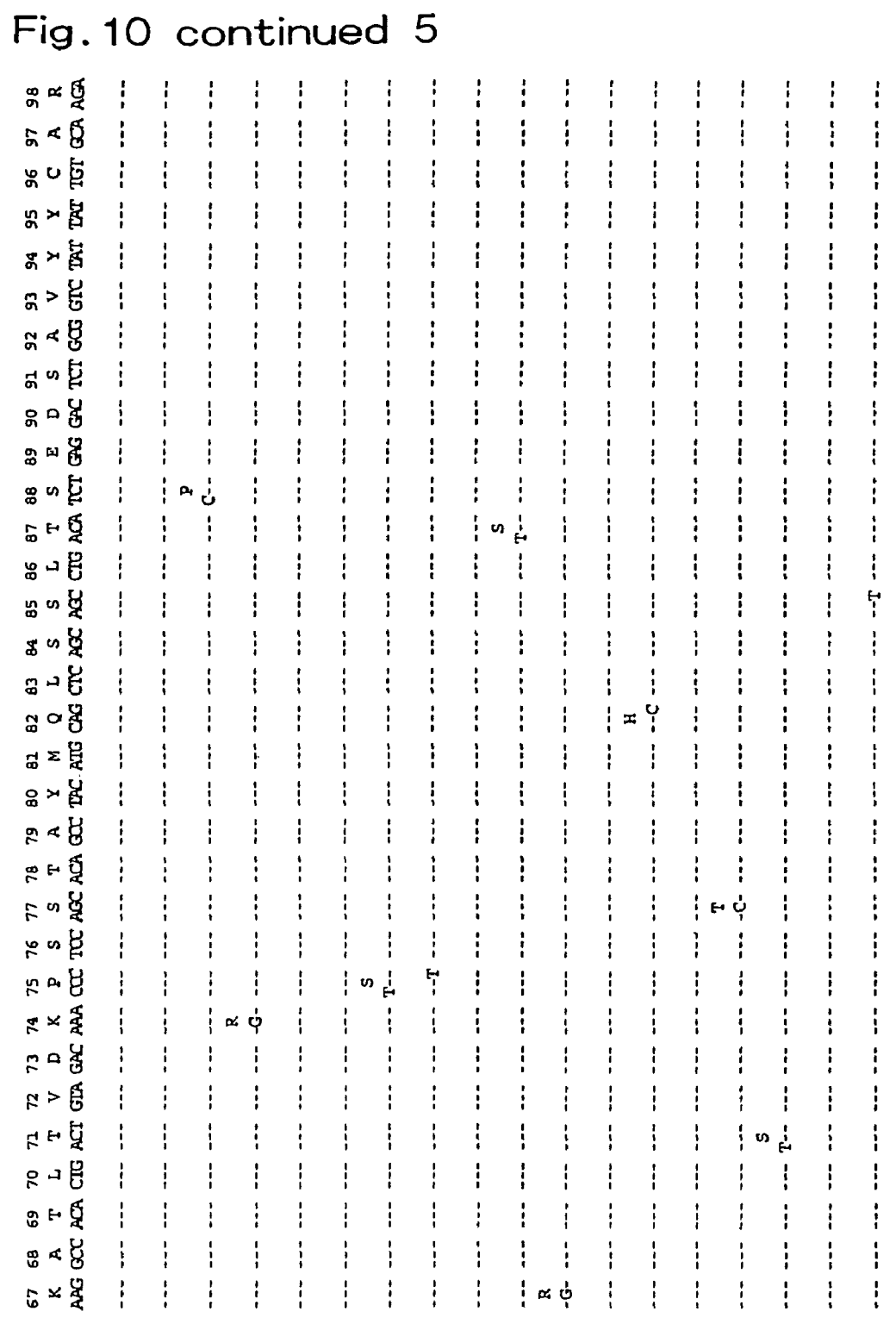

The results are shown in FIG. 10. The number of mutations was slightly increased in Tg mice. However, the somatic hypermutation of $W^{33}$ to L which indicates high affinity was increased almost 3-fold in Tg mice. "CDR" represents complementarity determining region.

The $V_H186.2$ locus shows SHMs of a peculiar pattern for high affinity IgG($\gamma 1\lambda 1$)NP response. The sequence analysis on the total spleen B cells after immunization with NP-CG revealed that SHM frequency is slightly increased in GANP-Tg mice compared to wild-type mice (FIG. 10).

It has been shown previously that these somatic hypermutations are important for affinity maturation of hapten specific B cells (Allen, D. et al., *EMBO J.* 1995-2001 (1988)).

Example 3

Preparation of B Cell Specific GANP-Deficient Mice
(B-GANP$^{-/-}$ Mice)

(Methods)
1. Establishment of CD19-Cre/+GANP Flox Mice

Using genomic DNA encoding GANP, neomycin resistance gene (neo) was inserted downstream of exon II to thereby construct a targeting vector. LoxP sites were introduced into the 3' flanking region to neo and the intron between exons I and II, respectively.

Briefly, flox mice in which GANP exon II is sandwiched by two loxP sequences were prepared. These mice were crossed with CD19-Cre mice to thereby establish B cell specific GANP-deficient mice (FIG. 11: A and B).

The targeting vector was linearized and electroporated into TT2 ES cells (Yagi, T. et al., *Anal. Biochem.* 214: 70-76 (1993)) for transfection. After selection with G418, ES colonies were picked up and incubated with proteinase K. Homologous recombinants were screened for with the following neo2 primer and CGK3'-2 primer.

(SEQ ID NO: 9)
neo2 primer: 5'-GCCTGCTTGCCGAATATCATGGTGGAAAAT-3'

(SEQ ID NO: 10)
CGK3'-2 primer: 5'-GGCACCAAGCATGCACGGAGTACACAGA-3'

Homologous recombination was confirmed by analyzing the BamHI-digested DNAs of ES clones by Southern blotting using probe A. Using three positive clones showing a 4 kb band, microinjection into ICR blastocysts was carried out to prepare chimeric first generation mice. The absence of GANP expression in B cells was confirmed by Southern blotting, RT-PCR and cell staining (FIG. 11: C, D and E).

GANP flox/+ mice were backcrossed with C57BL/6 mice at least 10 times. In order to delete GANP gene in B cells, GANP-floxed mice were crossed with CD19-Cre knock-in mice (Rickert, R. C., et al., *Nucleic Acids Res.* 25, 1317-1318 (1997)).

2. FACS Analysis

Lymph organ-derived single cell suspensions were stained with each biotin-labeled monoclonal antibody for 1 hr on ice. After washing with staining buffer, cells were incubated with FITC-conjugated streptavidin (Amersham Bioscience) and PE-conjugated monoclonal antibody for 1 hr. Lymphocytes were analyzed with FACScan (Becton Dickinson) using Cell Quest software.

3. Purification of B Cells

Spleen cells were isolated from Cre-flox/+ mice and B-GANP$^{-/-}$ mice (7 to 8 week old) and treated with 0.15 M ammonium chloride buffer to remove erythrocytes. After incubation at 37° C. for 30 min on plastic dishes, unadhered cells were recovered as lymphocytes. Then, T cells were removed therefrom using Dynabeads-anti-mouse Thy1.2 monoclonal antibody (Dynal) according to the protocol attached thereto. The purity of B cells (90% or more) was confirmed by cell surface staining with FITC-conjugated B220 monoclonal antibody (BD Pharmingen).

4. In vitro Proliferation Assay

Purified B cells were incubated in RPMI-1640 medium (with or without cell division promoter) containing 10% thermo-inactivated FCS (JRH Biosciences), 2 mM L-glutamine and $5 \times 10^{-5}$ M 2-mercaptoethanol in 96-well microplates at $2 \times 10^5$ cells/well for 48 hrs. Cells were recovered after pulsing with [$^3$H]-thymidine at 0.2 µCi/well for 16 hrs. Then, the radioactivity taken up was measured with a scintillation counter.

As the cell division promoter, affinity-purified goat anti-mouse µ-chain-specific antibody (10 µg/ml) [F(ab')$_2$] (ICN), rat anti-mouse CD40 monoclonal antibody (LB429; 10 µg/ml) and LPS (Sigma; 10 µg/ml) were used.

5. Antigens and Immunization

TNP-KLH, TNP-Ficoll and nitrophenyl-chicken γ globulin (NP-CG) (23:1) were purchased from Biosearch Technologies. Fifty micrograms of TNP-KLH and NP-CG (precipitated with aluminium) or 25 µg of TNP-Ficoll (dissolved in PBS) was injected into the abdominal cavities of Cre-flox/+ mice and B-GANP$^{-/-}$ mice.

6. Measurement of Antigen Specific Antibody Production

At day 10 or 14 after the immunization, sera were recovered from immunized mice. ELISA plates were coated with 5 µg/well of TNP-BSA (Biosearch Technology). Each well was blocked with 3% BSA in PBS, and incubated with serially diluted serum. After washing with PBS-0.1% Tween 20, each well was incubated with biotin-conjugated isotype-specific monoclonal antibody and alkaline phosphatase (ALP)-conjugated streptavidin (Southern Biotechnology). Color development was performed in the presence of substrates.

In order to determine the affinity of NP-binding antibodies in the sera, the ratio of NP2-binding antibody to NP25-binding antibody was calculated by differential ELISA using NP2-BSA (two NPs are bound to BSA per molecule) and NP25-BSA (25 NPs are bound to BSA per molecule) (Biosearch Technology) as coated antigens.

7. Immunohistochemistry

Spleen sections (8 µm) from immunized mice were fixed lightly in acetone. These samples were blocked with 3% BSA in PBS-Tween 20 and incubated with anti-IgD monoclonal antibody and ALP-conjugated anti-rat IgG (ICN) antibody. The first color development was performed with Vector Blue kit (Vector). The second color development was performed by incubating the sample with biotin-conjugated peanut agglutinin (PNA) (Vector) and horseradish peroxidase-conjugated streptavidin (Kirkegaard & Perry) and then incubating with 3,3'-diaminobenzidine tetrahydrochloride (Dojindo). Samples were fixed with 1% glutaraldehyde in PBS and then mounted with Aquatex (Merck).

8. Sequence Analysis of $V_H186.2$ Gene

NP-binding IgG1$^{dull}$CD38$^{low}$ B cells from NP-CG-immunized Cre-flox/+ and B-GANP$^{-/-}$ mice were fractioned with FACS Vantage (Becton Dickinson Biosciences) using (4-hydroxy-5-iode-3-nitrophenyl)acetyl (NIP) and incubated with proteinase K at 37° C. overnight. Using the resultant lysate, PCR was performed two times as described previously (Takahashi, Y. et al., *Immunity* 14: 181-192 (2001)). The genetic DNA of $V_H186.2$ was ligated to pBluescript, followed by determination of the sequence with an automated sequencer.

9. Detection of Apoptotic Cells

B cells purified from Cre-flox/+ and B-GANP$^{-/-}$ mice were stimulated with various reagents for 40 hrs (Watanabe, N. et al., (1998) *Scand. J. Immunol.* 47: 541-547). For detection of AICD, anti-µ antibody (50 µg/ml) was immobilized on 24-well plates. For detection of other types of apoptosis, purified B cells was stimulated with various stimulants and the incubated with anti-Fas monoclonal antibody (Jo2; BD Pharmingen) for 4 hrs (Wang, J. et al., (1996) *J. Exp. Med.* 184, 831-838). Cells were incubated in propidium iodide (PI) solution (50 µg/ml PI, 0.1% Triton X-100, 0.1% sodium citrate) at room temperature for 1 hr, and apoptotic cells were calculated (percent) as sub-$G_1$ area by FACScan. Further, apoptotic cells were also confirmed microscopically after trypan blue staining.

10. TUNEL Assay

Cre-flox/+ and B-GANP$^{-/-}$ mice were immunized with SRBC (sheep red blood cells). Spleen cryosections were prepared therefrom and fixed in 4% paraformaldehyde in PBS. Section samples were treated with MEBSTAIN Apoptosis Kit II (MBL) and counter-stained with PI. For use in an experiment conducted together with TdT-mediated dUTP-biotin nick-end labeling (TUNEL) assay, section samples were also stained with ant-IgG$_1$ monoclonal antibody (BD Pharmingen) and Alexa 546-conjugated goat anti-rat IgG antibody (Molecular Probes). Positive signals were detected and the results were confirmed with a fluorescence microscope (BX51; Olympus).

11. Results (1) The Role of RNA Primase GANP

Figure 12:
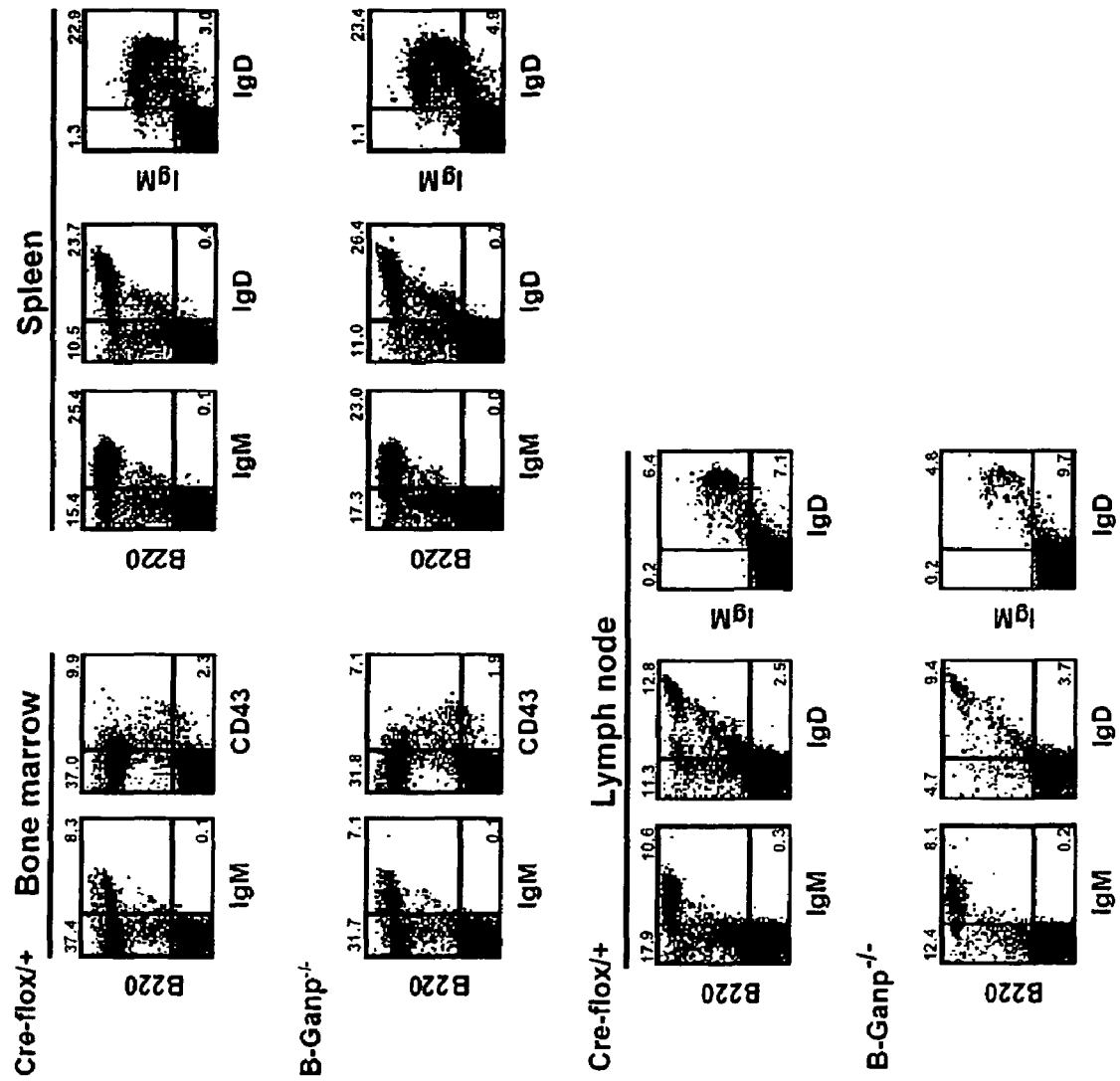
FIG. 12 shows the results of analyses (flowcytometry) of cell surface staining using the B cell-specific GANP deficient mouse (B-GANP$^{-/-}$).

In order to investigate into the role of RNA primase GANP, B-GANP$^{-/-}$ mice which are deficient in GANP gene in their CD19$^+$ B cells were prepared using Cre-loxP system (FIG. 11: A and B). The GANP gene of the B-GANP$^{-/-}$ mice lacked most of exon II (FIG. 11C). B-GANP$^{-/-}$ cells did not express GANP mRNA (FIG. 11D) and, according to immunostaining, expressed little GANP protein (FIG. 11E). B-GANP$^{-/-}$ mice grew normally, showing normal numbers of lymphocytes in the bone marrow, spleen, thymus and lymph nodes. According to flow cytometry, B-GANP$^{-/-}$ mice showed surface marker profiles on cells of the bone marrow, spleen and lymph nodes similar to those observed in the control Cre-flox/+ mice (FIG. 12); there was no difference between B-GANP$^{-/-}$ mice and Cre-flox/+ mice.

Figure 13:
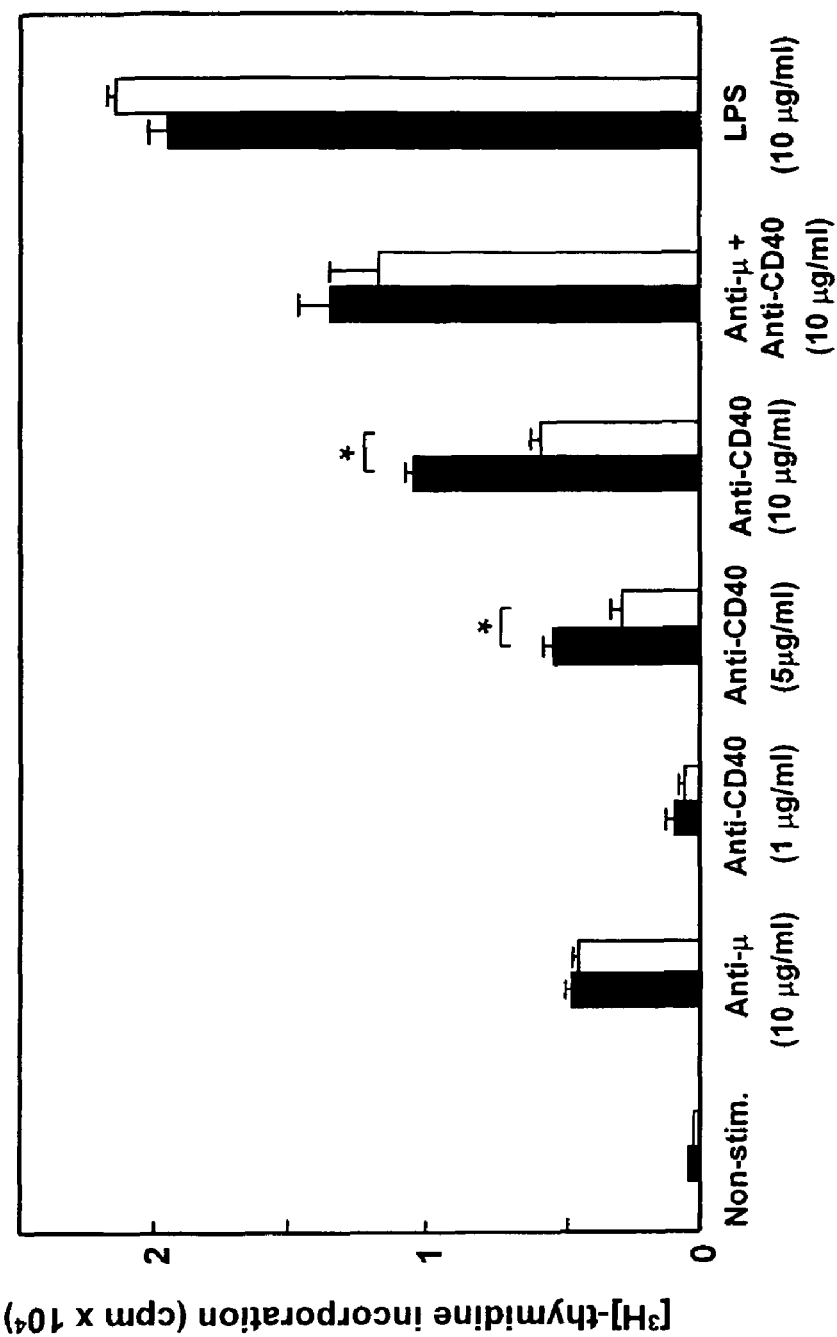
FIG. 13 shows the results of B cell proliferation assays. Almost no difference was observed, but only the proliferation caused by anti-CD40 antibody stimulation was decreased to about ½.
Figure 14:
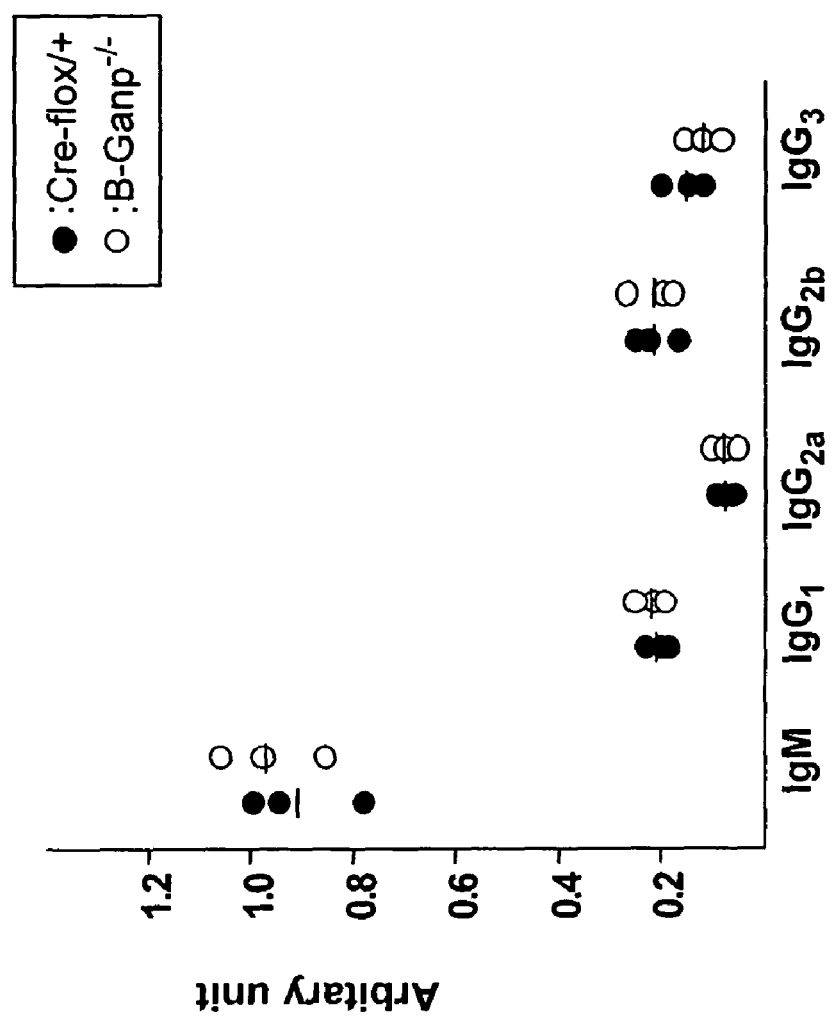
FIG. 14 shows antibody titers in the sera from non-immunized Cre-flox/+ mice and B-GANP$^{-/-}$ mice. No difference was observed among the antibody titers of individual isotypes.

The number of mature B cells expressing sIgM$^{low}$sIgD$^{high}$ (IgM$^+$IgD$^+$) was decreased in the lymph nodes of B-GANP$^{-/-}$ mice. B cells from B-GANP$^{-/-}$ mice showed normal proliferation responses after in vitro stimulation with anti-µ antibody, anti-µ antibody+anti-CD40 monoclonal antibody, or lipopolysaccharide (FIG. 13: white column represents B-GANP$^{-/-}$ and black column represents Cre-flox/+). On the other hand, B cells from B-GANP$^{-/-}$ mice showed a decrease in proliferation activity after stimulation with anti-CD40 monoclonal antibody (5 and 10 µg/ml) (FIG. 13). This indicates that responses to CD40/CD145 interaction are slightly impaired in B cell proliferation in B-GANP$^{-/-}$ mice. The amounts of serum Ig in B-GANP$^{-/-}$ mice were similar to those in Cre-flox/+ mice (FIG. 14).

(2) Antigen Specific Antibody Production in B-GANP$^{-/-}$ Mice

Figure 15:
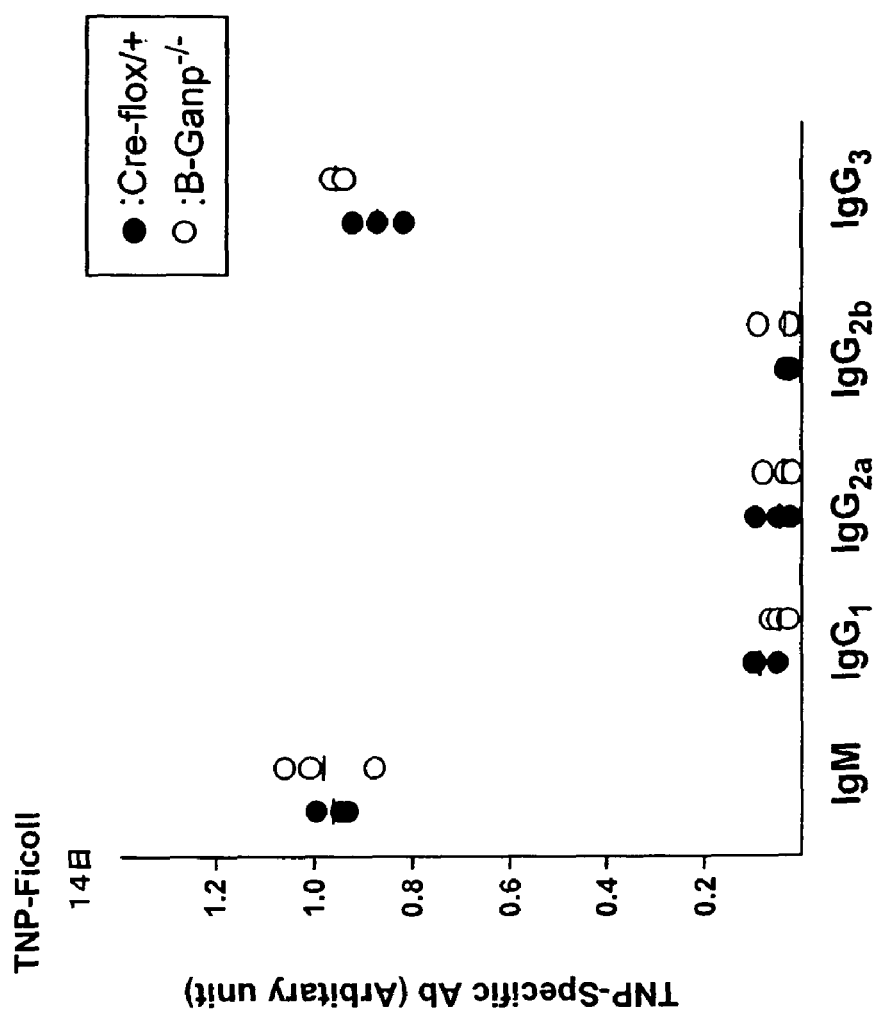
FIG. 15 shows the results of measurement of antibody production in B-GANP$^{-/-}$ mice.

Immunoresponses of B-GANP$^{-/-}$ mice after immunization of TI-Ag or TD-Ag were examined. At day 14 after immunization with a TI antigen trinitrophenyl (TNP)-Ficoll, anti-TNP antibody titers were measured by ELISA. As a result, TNP-Ficoll induced similar responses in B-GANP$^{-/-}$ mice and Cre-flox/+ mice; no particular difference was observed (FIG. 15).

When germinal center (GC) formation was examined, mutant mice showed delayed GC formation in response to TD-Ags such as TNP-keyhole limpet hemocyanin (KLH) or NP-CG, compared to Cre-flox/+ mice.

Figure 16:
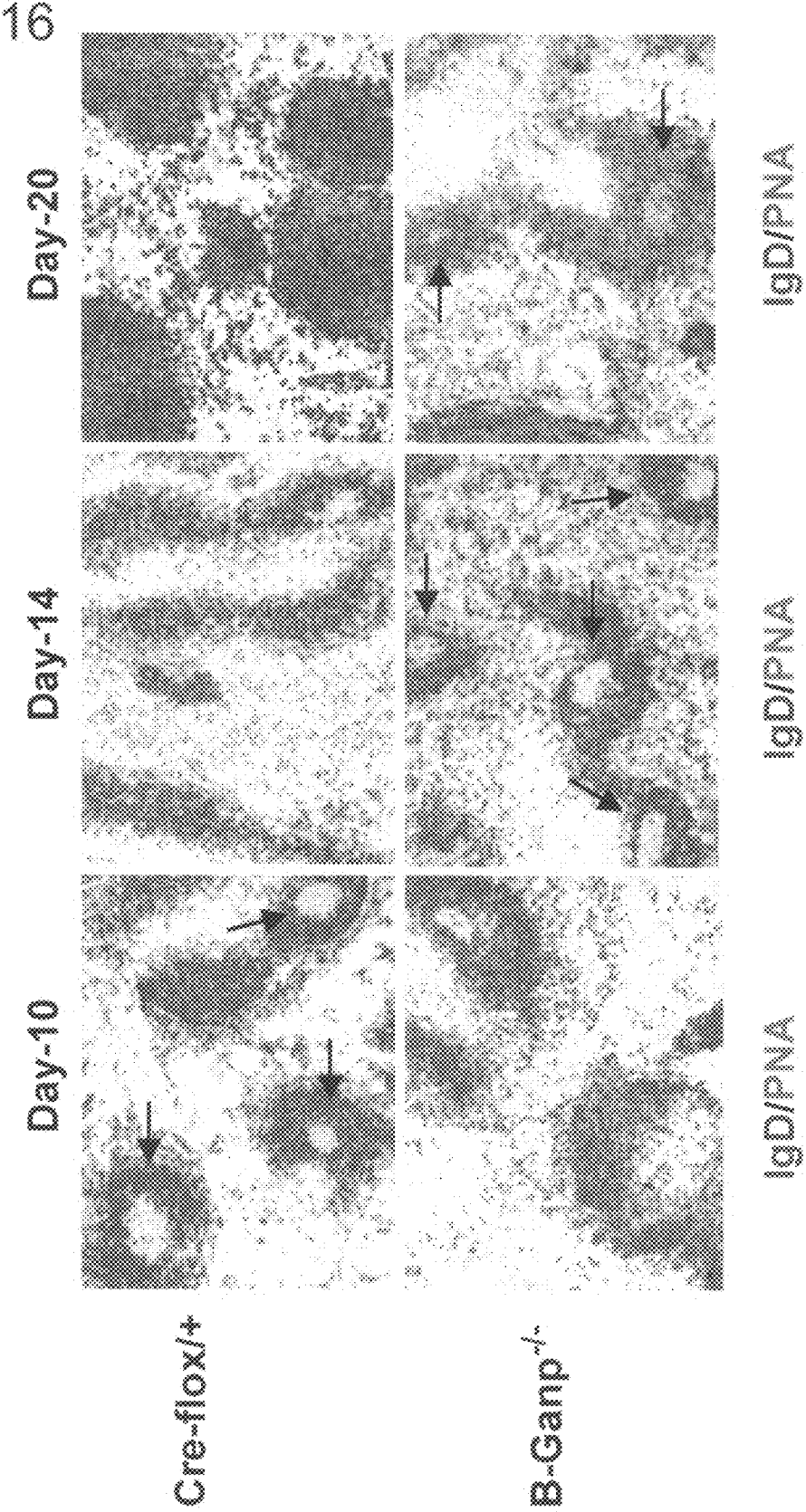
FIG. 16 shows the results of the staining of GC with peanut agglutinin.

With respect to the peak response on GC formation, Cre-flox/+ mice showed large matured GCs stained with peanut agglutinin (a marker for GC-B cells) at day 10 (arrow marks in FIG. 16). At day 10 after immunization, GC formation in B-GANP$^{-/-}$ mice was slightly less. However, B-GANP$^{-/-}$ mice showed more GC formation than Cre-flox/+ mice at day 14, and they still showed vigorous GC formation even at day 20 (arrow marks in FIG. 16).

Figure 17:
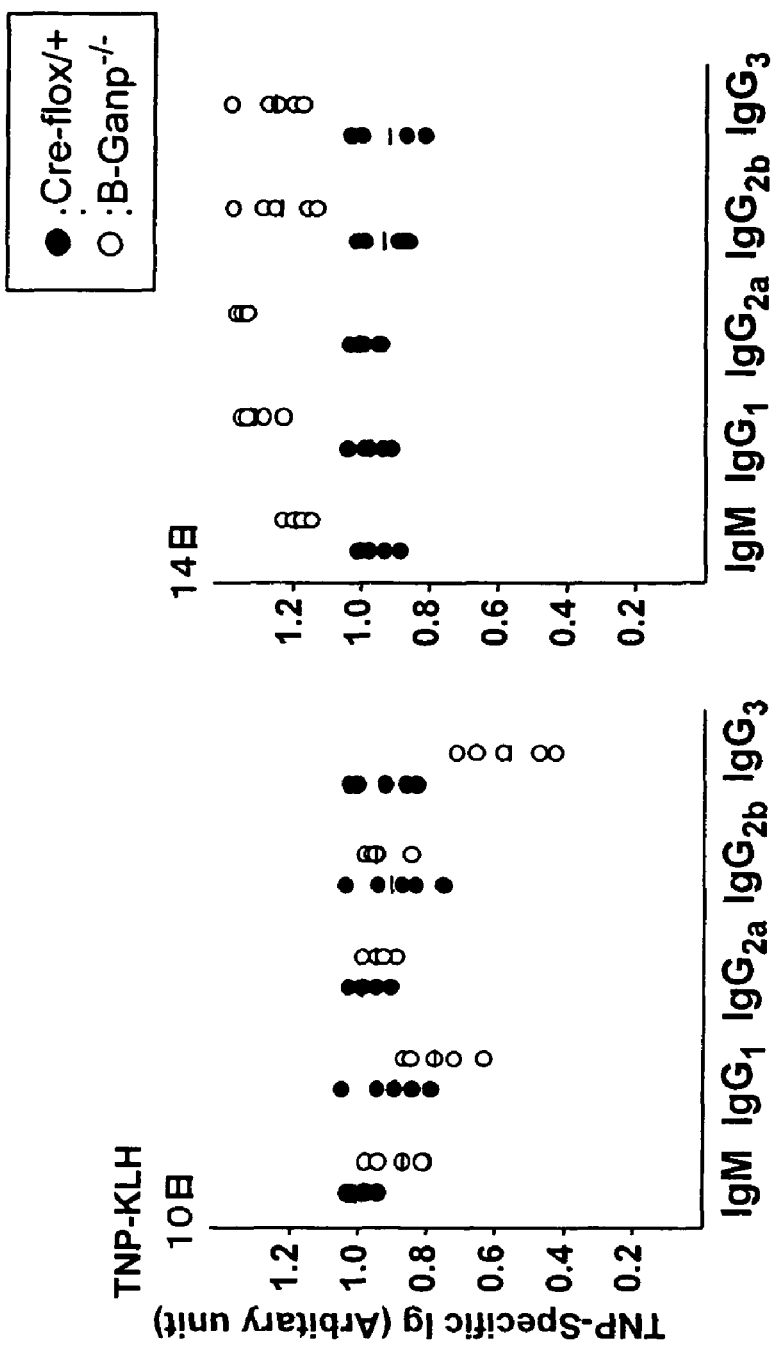
FIG. 17 shows the results of measurement of antigen-specific antibody production in B-GANP$^{-/-}$ mice.

Since B-GANP$^{-/-}$ mice showed definite GC formation at day 14, their antigen specific antibody responses were measured (FIG. 17). When immunized with TNP-KLH (a TD antigen), B-GANP$^{-/-}$ mice did not show definite GCs until day 10 after the immunization; no difference was observed in antibody titers between B-GANP$^{-/-}$ mice and Cre-flox/+ mice. At day 14, however, B-GANP$^{-/-}$ mice showed gradual increase and expansion of GCs (FIG. 17). Mutant mice showed antibody responses to TNP-KLH similar to those shown by Cre-flox/+ mice.

(3) Obstacles to Affinity Maturation in B-GANP$^{-/-}$ Mice

In order to further investigate into the characteristic of the GC in B-GANP$^{-/-}$ mice (i.e. antibody response is of low affinity), antigen specific IgG1$^+$ GC-B cells were examined after immunization with NP-CG By differential ELISA using conjugates of NP hapten with different molecular weights and a protein, responses to NP2-BSA conjugate were compared to responses to multi-hapten NP25-BSA conjugate.

Figure 18:
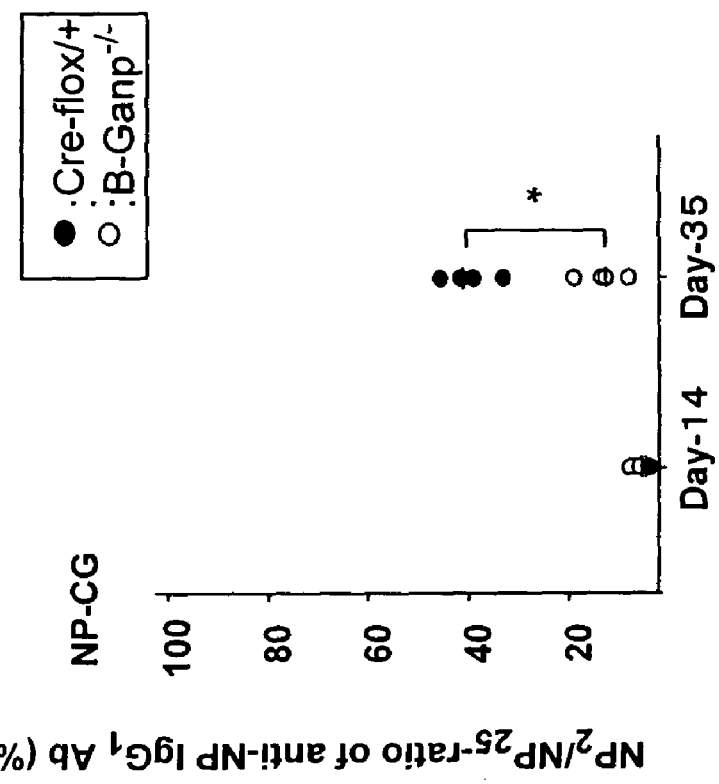
FIG. 18 shows the results of measurement by differential ELISA of the degrees of maturation of affinity in mice 14 and 35 days after immunization with 100 μg of NP-GC.

In B-GANP$^{-/-}$ mice, antibody responses to NP2-BSA conjugate were of low affinity (13%) at day 35 after immunization with NP-CG. This value was remarkably lower than the value of Cre-flox/+ mice (42%) (FIG. 18).

Figure 19:
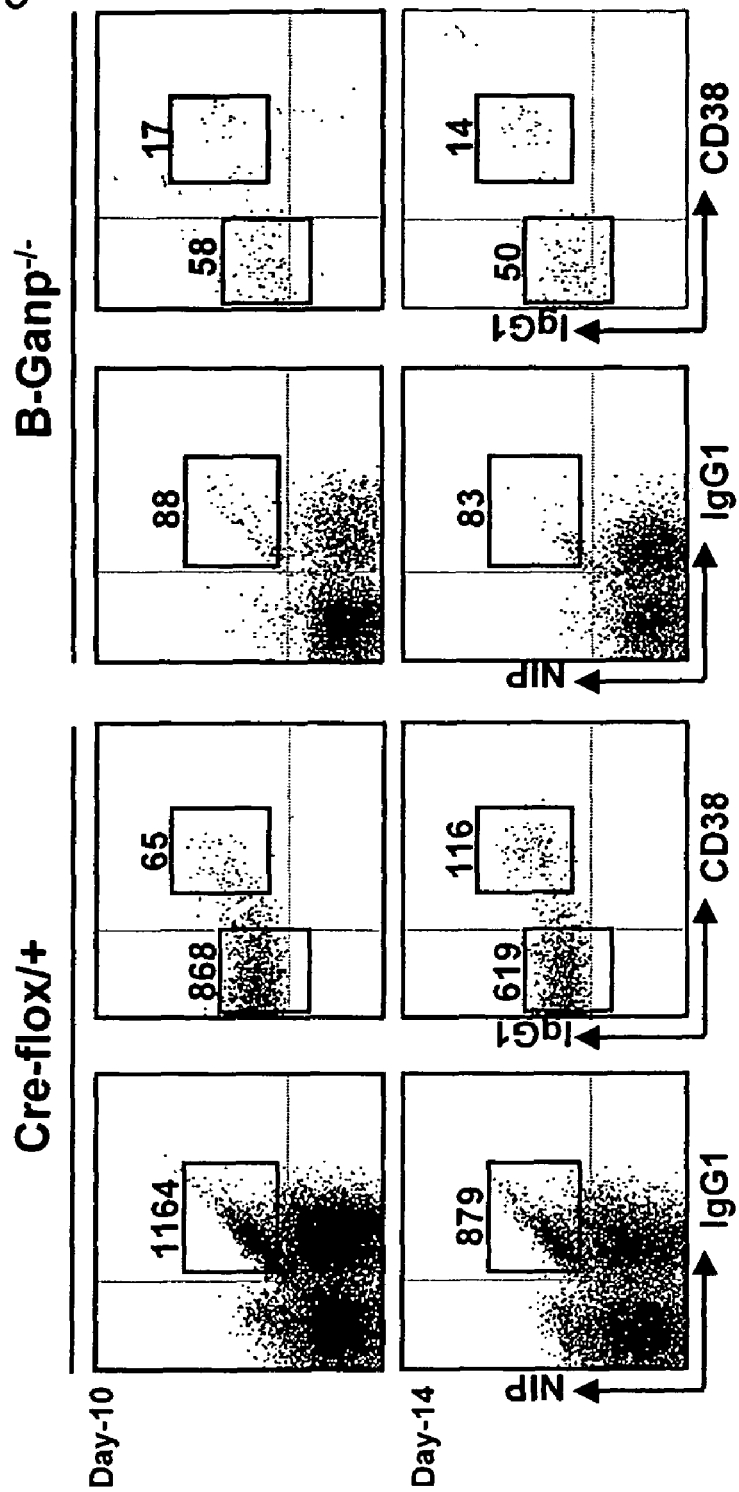
FIG. 19 shows the results of flowcytometry on GC-B cells.

Further, as shown in FIG. 19, NP-specific IgG1$^{dull}$CD38$^{low}$ B cells were remarkably decreased in B-GANP$^{-/-}$ mice. Specifically, while the ratio of these B cells was 1,164 cells/10$^6$ cells in Cre-flox/+ mice at day 10 after immunization, it was 88 cells/10$^6$ cells in B-GANP$^{-/-}$ mice. At day 14, while Cre-flox/+ mice had 879 cells/10$^6$ cells, B-GANP$^{-/-}$ mice had 83 cells/10$^6$ cells. This tendency was unchanged at day 20.

In contrast, IgG1$^{high}$CD38$^{high}$ memory B cells were not decreased. These results indicate that the mutation of no GANP expression caused defect in B cell differentiation at the stage of IgG1$^{high}$CD38$^{low}$ GC-B cells.

In order to confirm the reduced affinity maturation in antibodies of B-GANP$^{-/-}$ mice, the sequence of the V$_H$186.2 region in spleen B cells was examined after immunization with NP-CG.

Since somatic hypermutations occur at this stage of B cell differentiation, a variety of purified B cells were examined on SHMs in V$_H$186.2 locus. It should be noted that V$_H$186.2 locus is used for high affinity IgG ($\gamma 1\lambda 1$) NP-responses (Cumano, A. & Rajewsky, K. (1985) *Eur. J. Immunol.* 15, 512-520). With respect to IgM locus, no difference was observed between B-GANP$^{-/-}$ mice and Cre-flox/+ mice.

Figure 20B:
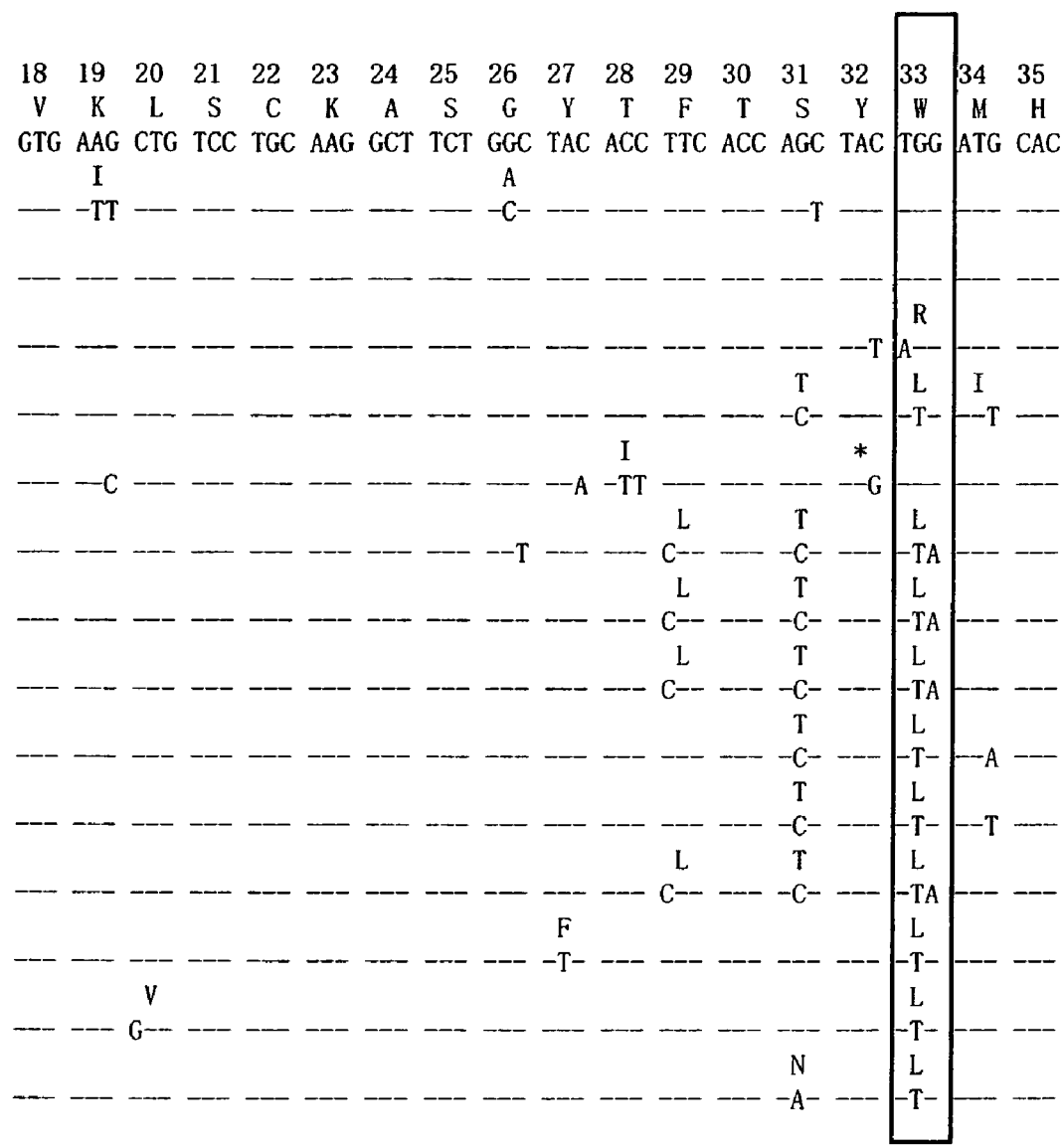

Subsequently, B-GANP$^{-/-}$ mice or Cre-flox/+ mice were immunized with NP-CG, followed by sorting for NP-binding IgG$_1$ weakly positive CD38 weakly positive GC-B cells (i.e. Ag-binding IgG$_1$ B cells) (FIG. 19). After the sorting, genomic DNA was extracted from the resultant cells. V$_H$186.2 was amplified by PCR and subjected to sequence analysis. Then, V$_H$186.2 sequences were compared (FIG. 20: A-L). Panels A-F in FIG. 20 show comparison of V$_H$186.2 sequences of Cre-flox/+ mice. Panels G-L in FIG. 20 show comparison of V$_H$186.2 sequences of B-GANP$^{-/-}$ mice.

Figure 21:
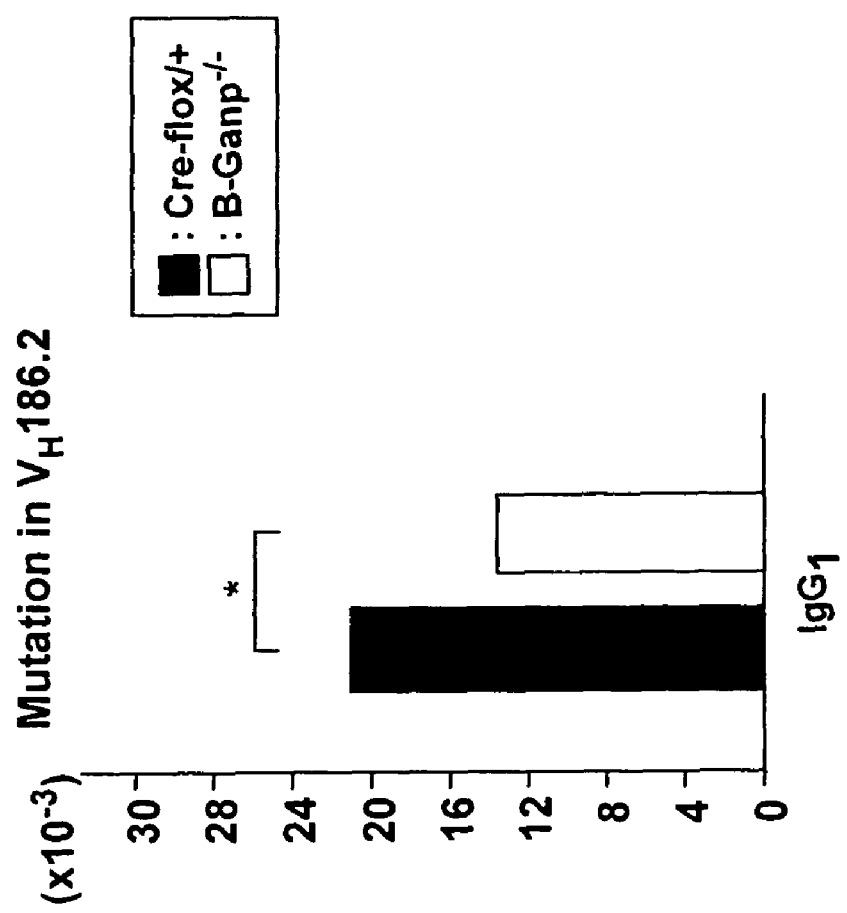
FIG. 21 shows the frequencies of IgG1 mutation in Cre-flox/+ mice and B-GANP$^{-/-}$ mice.
Figure 22:
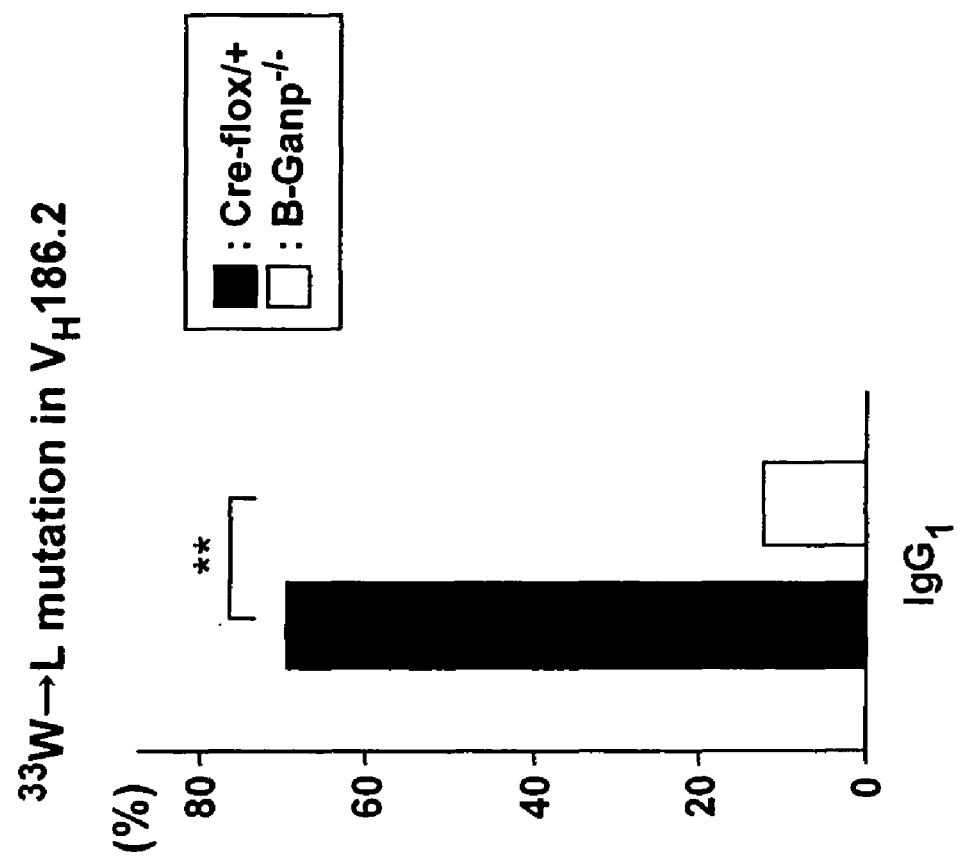
FIG. 22 shows the frequencies of $^{33}$W to L mutation in $V_H$186.2 in Cre-flox/+ mice and B-GANP$^{-/-}$ mice.

In B-GANP$^{-/-}$ mice, the frequency of mutations in the entire IgV region sequence was 14×10$^{-3}$, showing a decrease compared to Cre-flox/+ mice (21×10$^{-3}$) (FIG. 21). Further, the high affinity type mutation of W$^{33}$ to L (i.e. mutation of the 33rd amino acid residue tryptophan to lysine, which is observed remarkably in C57BL/6 mice) was 13% (2/15 V regions), showing a remarkable decrease compared to Ce-flox/+ mice (71%, 10/14 V regions) and the lowering of affinity to ⅓ (FIG. 22).

From these results, it was demonstrated that GANP is essential for the affinity maturation of antibodies.

(4) Protective Function from Apoptosis in B-GANP$^{-/-}$ Mouse B Cells

It is considered that the decrease in high affinity antibody production in B-GANP$^{-/-}$ mice is caused because B cells after antigen stimulation are unstable. Then, in order to examine the suceptibility of B cells, the apoptosis of B cells in vitro was studied.

Figure 23:
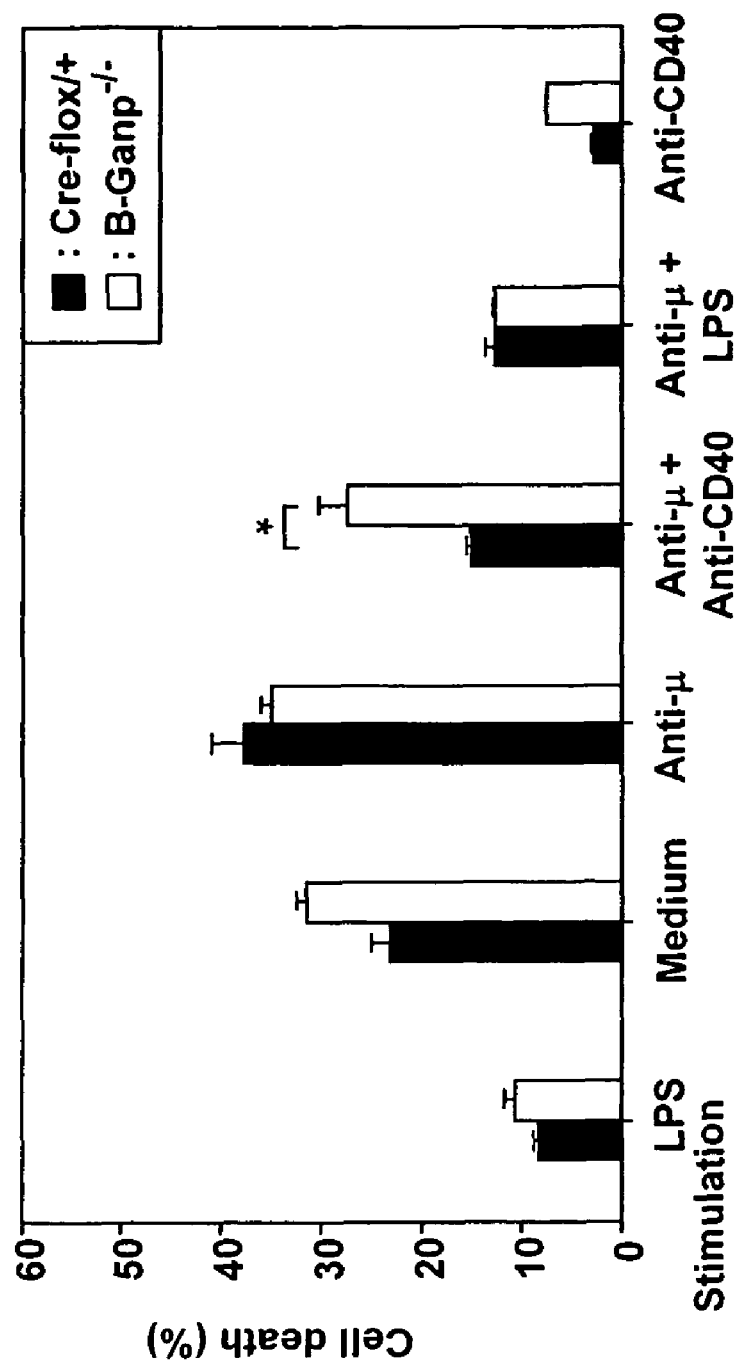
FIG. 23 shows the results of measurement of activation-induced cell death (AICD) and the results of apoptosis inhibition.

In normal B cells, activation-induced cell death (AICD) was induced by strongly cross-linked B cell antigen receptor, and this AICD was prevented by stimulation by CD40. In B-GANP$^{-/-}$ B cells, though the susceptibility to AICD stimulation was equivalent to that of normal B cells (control), inhibition of anti-CD40-mediated apoptosis was inferior to Cre-flox/+ control B cells (FIG. 23). This means that B-GANP$^{-/-}$ mice lack the protective function for antigen-reactive B cells during GC formation.

In GCs, B cells stimulated with Ag and CD40/CD 154 interaction induce the surface expression of Fas/CD95 and become susceptible to Fas-induced apoptosis. Then, the inventor measured the susceptibility of B-GANP$^{-/-}$ B cells to anti-CD95 stimulation.

First, spleen B cells were stimulated with anti-CD40 monoclonal antibody (LB429), anti-μ antibody+anti-CD40 monoclonal antibody, IL-4+anti-CD40 monoclonal antibody, and anti-μ antibody+IL4+anti-CD40 monoclonal antibody for 48 hrs, and then anti-CD95 monoclonal antibody was added to the culture medium.

Figure 24:
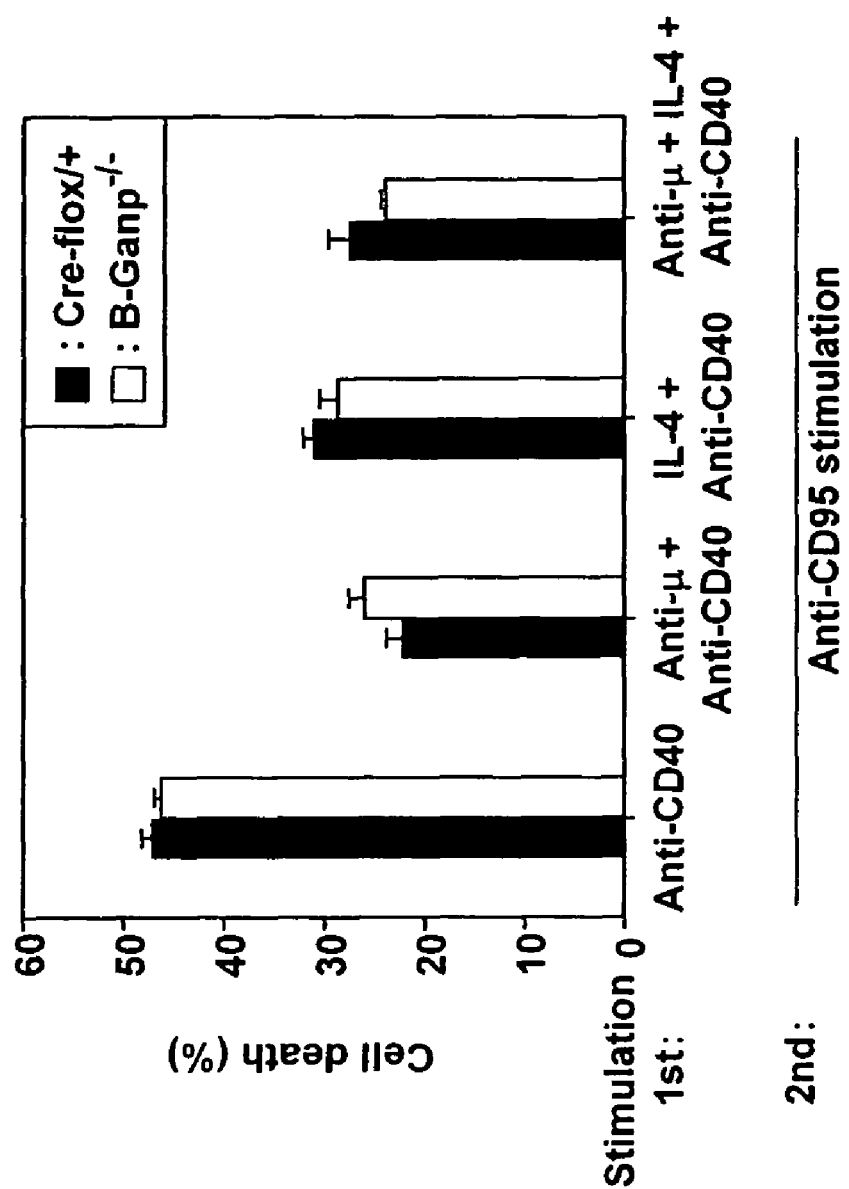
FIG. 24 shows the results of measurement of the apoptosis sensitivities of cells to anti-CD40 and anti-CD95 stimulations.

As a result, apoptotic responses of B-GANP$^{-/-}$ mouse B cells were similar to the responses of Cre-flox/+ mouse B cells; no difference was observed between B-GANP$^{-/-}$ mice and Cre-flox/+ mice (FIG. 24).

As described above, the stimulation with anti-CD95 after anti-CD40 (LB429) treatment did not show any difference between B-GANP$^{-/-}$ mice and Cre-flox/+ mice in the induction of expression. This suggests that B-GANP$^{-/-}$ B cells may be susceptible to the apoptotic stimulation normally received by GC-B cells in vivo. Therefore, TUNEL assay was carried out using tissue sections from mice immunized with SRBC as TD-Ag.

Figure 25:
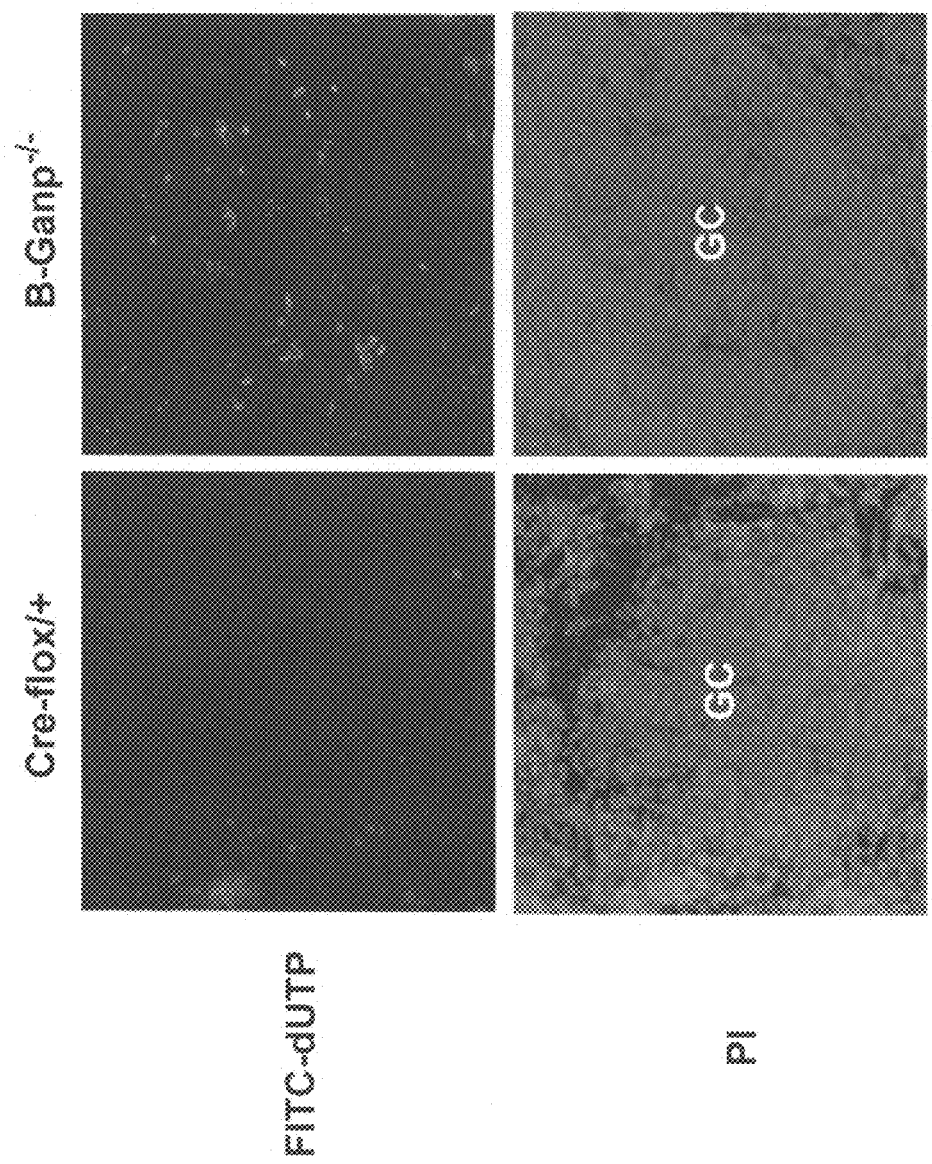
FIG. 25 shows the results of detection of apoptosis cells by TUNEL assay.
Figure 26:
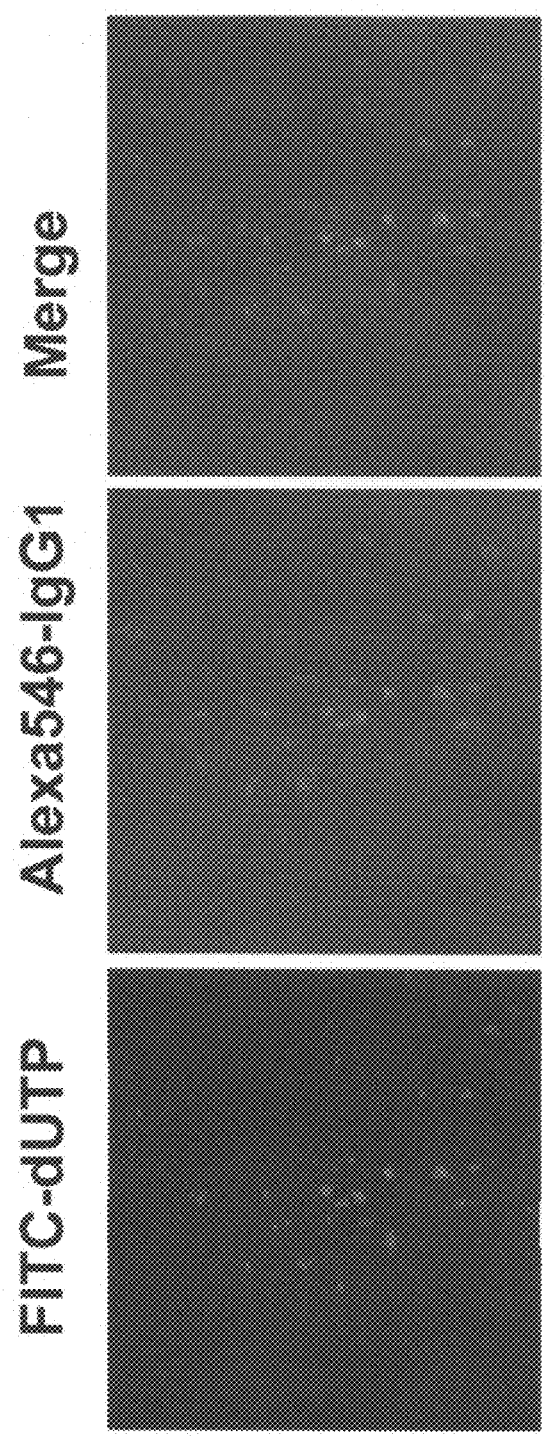
FIG. 26 shows the results of detection of apoptosis cells by TUNEL assay.

As a result, TUNEL-positive cells increased in the GC region of B-GANP$^{-/-}$ mice, and most of them also showed IgG$_1$ expression (FIGS. 25 and 26). These results revealed that most of the apoptotic cells of B-GANP$^{-/-}$ mice are GC-B cells (FIGS. 25 and 26).

Subsequently, the inventor examined the RNA expression of Bcl-2 family members which are recognized to be the molecules necessary for CD40-mediated inhibition of apoptosis of various malignant lymphoma cells and normal B cells.

Figure 27:
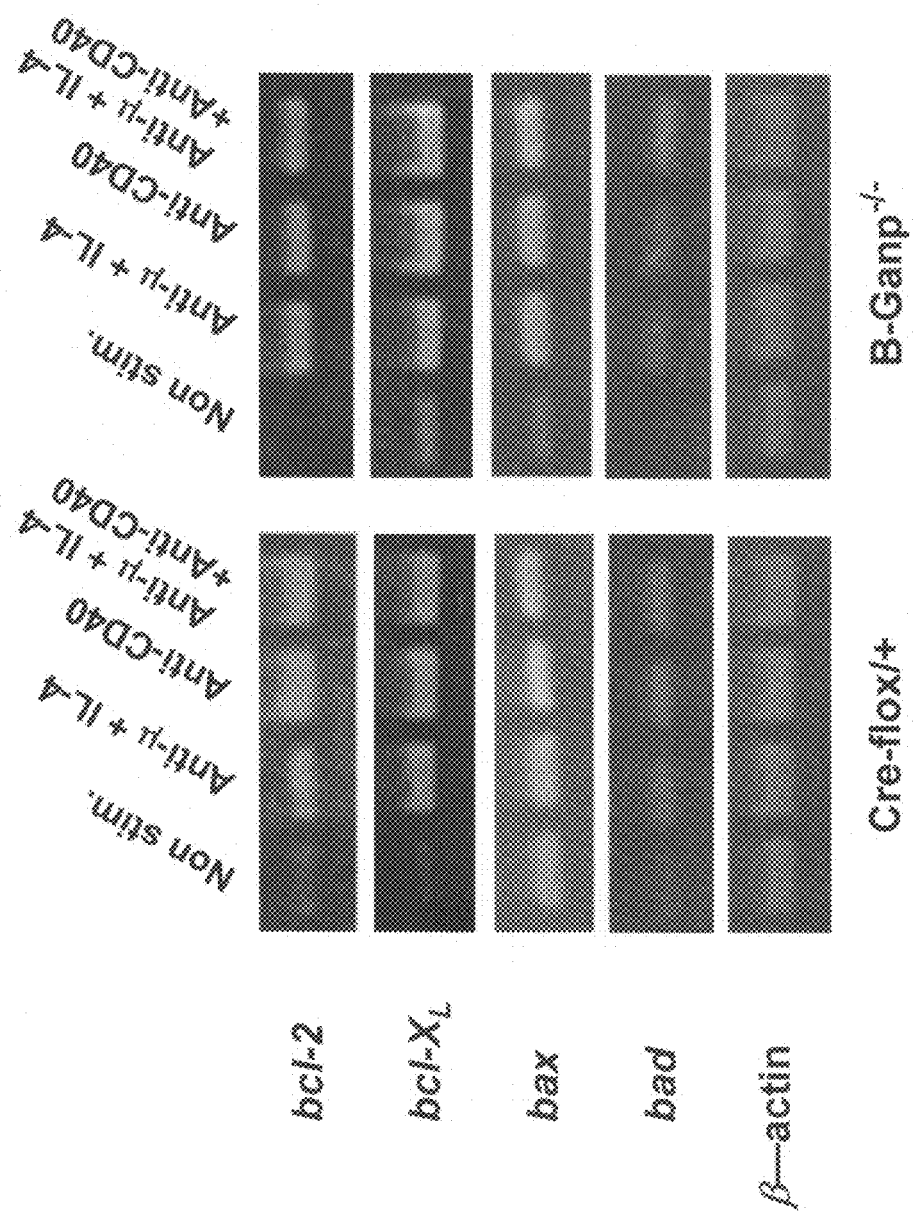
FIG. 27 shows the RNA expression levels of Bcl-2 family involved in apoptosis inhibition.

Stimulation with anti-μ antibody+IL-4 induced an apparent increase in bcl-2 transcription in Cre-flox/+ B cells, and anti-CD40 mAb further up-regulated this expression (FIG. 27). The B-GANP$^{-/-}$ B cells showed similar up-regulation of bcl-2 transcripts by stimulation with anti-μ antibody, but the response to anti-CD40 mAb (anti-CD40 mAb alone or anti-μ Ab+IL-4+anti-CD40 mAb) was not as high as the response in Cre-flox/+ B cells (FIG. 27). In other words, the RNA expression levels of Bcl-2 family involved in apoptosis inhibition were decreased in B-GANP$^{-/-}$ B cells compared to the control (FIG. 27).

With respect to bcl-$X_L$, bax and bad in mutant B cells, the expression levels were equivalent to those in Cre-flox/+ B cells.

These results suggest that GANP regulates the signal transduction of CD40-mediated induction of Bcl-2 expression in GC-B cells, which greatly contributes to the survival of high-affinity BCR+ B cells in vivo.

(5) Conclusion

The results obtained from B-GANP$^{-/-}$ mice and GANP-Tg mice demonstrate that GANP is involved in the generation of high affinity B cells after immunization with TD-Ag. As a role of GANP, GANP may mediate efficient recruit and regulation of DNA polymerase in GC-B cells. Once GC-B cells with V-region SHMs have acquired high-affinity BCRs, they should be positively selected and further SHMs in the V regions might be suppressed to thereby guarantee the production of high affinity antibodies in vivo. Since AID expression in GC-B cells may generate DNA mutations continuously, regulation of AID activity might be necessary for maintaining high affinity BCRs in B cells. The results obtained from B-GANP$^{-/-}$ mice suggest that GANP is necessary for SHM process.

Example 4

Production of High Affinity Antibodies Using GANP Transgenic Mice

1. Comparison of Antibody Titers by Differential ELISA

Each two wild-type (WT) mice and GANP transgenic (Tg) mice were immunized with 100 μg of NP-CG. At day 28 after the immunization, serum samples were taken from them and subjected to ELISA. Briefly, ELISA plates were coated with 20 μg/ml of NP2-BSA or NP17-BSA overnight at 4° C. Then, the plates were blocked with 3% BSA/PBS-0.1% Tween 20 for 1 hr, followed by reaction with the serum for 1 hr. After washing with PBS-0.1% Tween 20 three times, biotin-labeled anti-mouse IgG$_1$ antibody (Southern Biotechnology) was reacted for 1 hr. Then, after washing with PBS-0.1% Tween 20 three times, alkaline phosphatase-labeled streptavidin (Southern Biotechnology) was reacted for 30 min. After washing with PBS-0.1% Tween 20 three times and with TBS once, color was developed using p-nitrophenyl phosphate as a substrate. Absorbance was measured at 405 nm.

Figure 28:
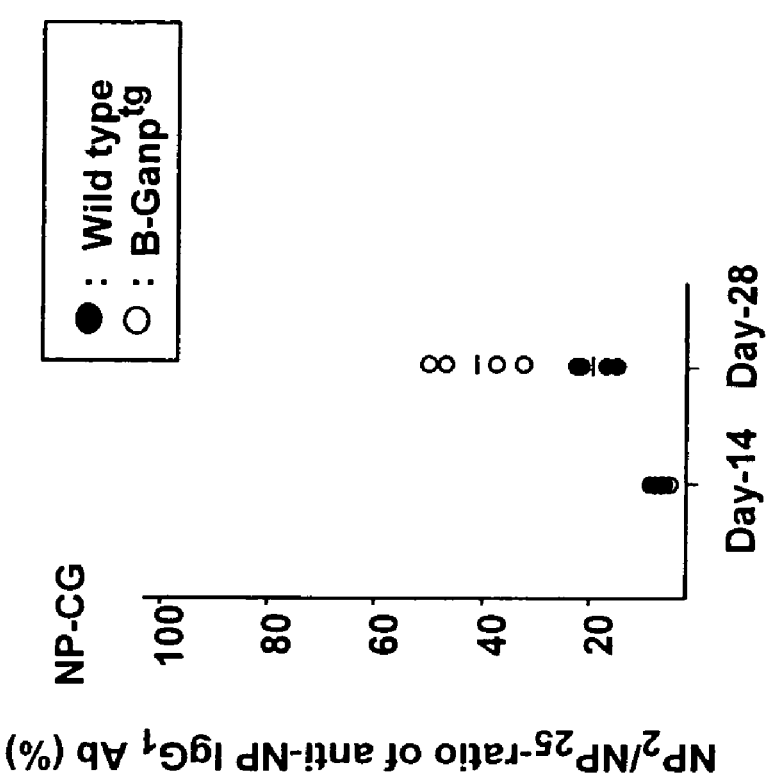
FIG. 28 shows the results of production of a high affinity antibody using a GANP transgenic mouse.

The results are shown in FIG. 28. From these results, it is understood that a high affinity antibody is produced by using GANP transgenic mice.

2. Analysis of Antigen-Antibody Binding Affinity Using ELISA and Biacore

Wild-type (WT) mice and GANP transgenic (Tg) mice were immunized with NP-CG. Cells from them were subjected to cell fusion to obtain hybridomas. Using the culture supernatants of positive hybridoma clones, binding curves of antibodies responding to the antigen were obtained by ELISA and with Biacore. The utility of Tg mice was shown from the resultant binding curves.

(1) Materials
(a) Animals
Wild-type (WT) mice and GANP transgenic (Tg) mice.
(b) Antibodies and Reagents
NP16-CG (16 NPs are coupled to CG (chicken immunoglobulin) per molecule), NP2-BSA (2 NPs are coupled to BSA (bovine serum albumin) per molecule), NP17-BSA (17 NPs are coupled to BSA per molecule), HRP-labeled anti-mouse IgG, IgA and IgM were used.

(2) Methods and Results

Each five wild-type (WT) mice and GANP transgenic (Tg) mice were immunized with NP16-CG three times at intervals of two weeks. After the 3rd immunization, the mice were exsanguinated, and antibody titers were compared using antisera. The results also confirmed the utility of GANP-Tg mice as the results described in (1) above.

Spleen cells from those mice which showed a high valence among them were fused with P3U1 myeloma cells, and plated at a density of $1 \times 10^5$ cells/well based on the numbers of spleen cells from GANP-Tg mice ($6.0 \times 10^7$) and from WT mice ($4.8 \times 10^7$). GANP-Tg mice-derived 600 hybridoma clones and WT mice-derived 480 hybridoma clones were cultured in HAT medium.

At day 9 of HAT culture, the culture supernatant was recovered and subjected to ELISA using NP2-BSA (1 μg/ml) as an immobilized antigen. Upper 2.5% clones showing production of high affinity antibodies as determined by measurement of absorbance in ELISA were selected from both culture supernatants derived from GANP-Tg mice and WT mice. Then, cloning was carried out using HT medium.

At day 9 of HT culture, culture supernatants were recovered and subjected to ELISA using NP2-BSA (1 μg/ml) as an immobilized antigen. As a result, 6 hybridoma clones (G2-6, G2-9, G2-12, G2-14, G2-15 and G2-16) were established from GANP-Tg mice and one hybridoma clone (W2-7) from WT mice.

Individual clones from GANP-Tg mice and WT mice were cultured in RPMI medium, and 1 ml each of culture supernatant appropriate for use in the following experiment was secured. Using this culture supernatant, the following evaluation and examination were carried out.

(a) ELISA

For the evaluation of antibody titers, antigens different in nature (i.e. substances different in NP content per CG molecule) were used, and antibody titers were evaluated based on the ratios of ELISA reactivities.

This method is useful for measuring the affinity of NP. It is simple and capable of testing a large number of samples. Therefore, this method is appropriate and reliable as primary screening.

First, NP2-BSA (1 μg/ml) and NP17-BSA (1 μg/ml) were separately immobilized as antigens at 4° C. overnight. The antigen-immobilized plates were washed with PBS-Tween 20 and blocked with skim milk-PBS-Tween 20. After washing further with PBS-Tween 20, RPMI culture supernatants from GANP-Tg mice-derived 6 clones (G2-6, G2-9, G2-12, G2-14, G2-15 and G2-16) and WT mice-derived 1 clone (W2-7) (stock solution to 256-fold dilution) were reacted with the immobilized antigen at room temperature for 1 hr. Subsequently, the plates were washed with PBS-Tween 20. Then, HRP-conjugated anti-mouse IgG, IgA and IgM were reacted at room temperature for 1 hr. After washing with PBS-Tween 20, color was developed with ortho-phenylene diamine (OPD) for 5 min, followed by termination of the reaction with 2N sulfuric acid.

Absorbance was meatured with an ELISA reader at 490 mm.

Figure 29:
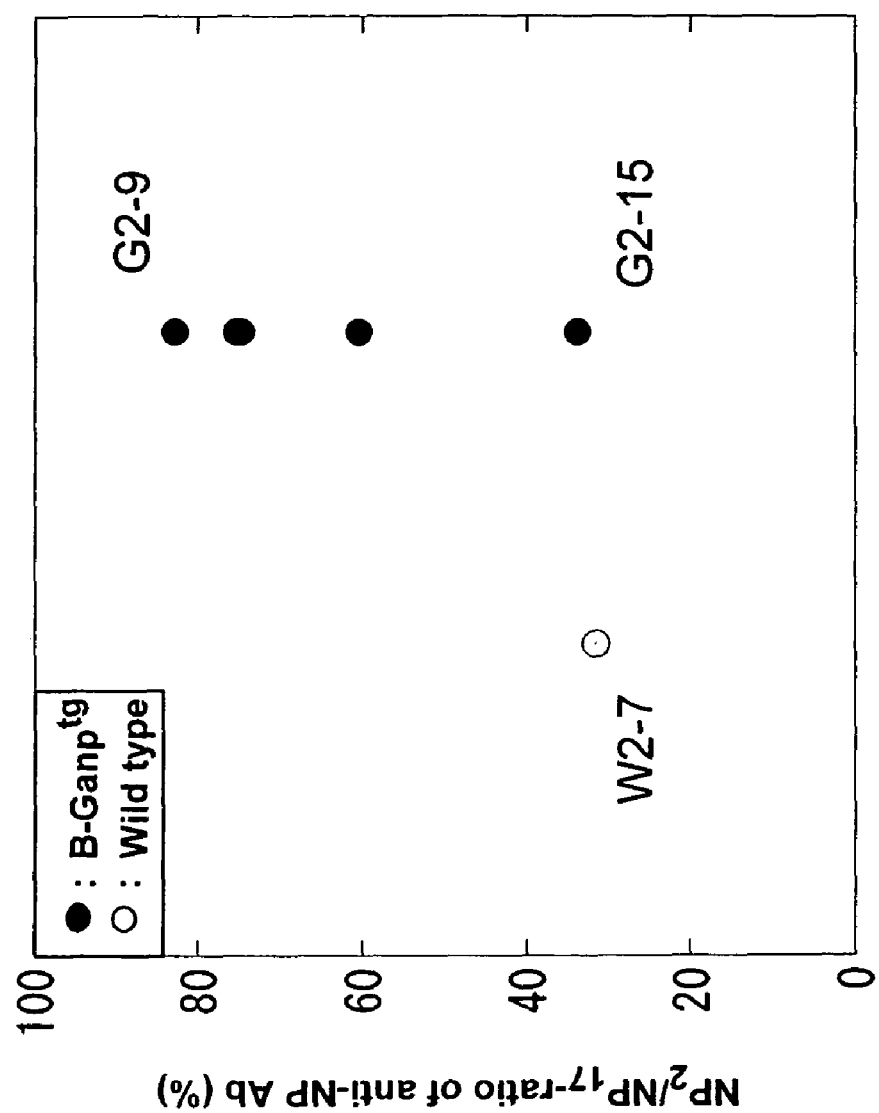
FIG. 29 shows the results of production of a high affinity antibody using the GANP transgenic mouse-derived hybridoma clones.

The results of ELISA are shown in FIG. 29. From these results, it is understood that high affinity antibodies are produced by using GANP-Tg mice.

(b) High Affinity Analysis Using Biacore

Using the clone which is predicted to be most high in affinity from the results of ELISA described above, physicochemical binding ability was examined with Biacore.

Analysis with Biacore was performed as described below. Briefly, NP2-BSA (1 μg/ml) was bound to Biacore chip as a ligand. As analyte solutions, RPMI culture supernatants from clone Tg (G2-9) which was predicted to be highest in affinity, clone Tg (G2-15) which was predicted to be lowest in affinity, and clone WT (W2-7) were used. Association rate constant (k ass), dissociation rate constant (k diss) and dissociation constant KD (KD=k diss/k ass) that is an indicator of affinity were calculated for each of the above culture supernatants. The smaller the KD value is, the higher the affinity is evaluated.

Figure 30:
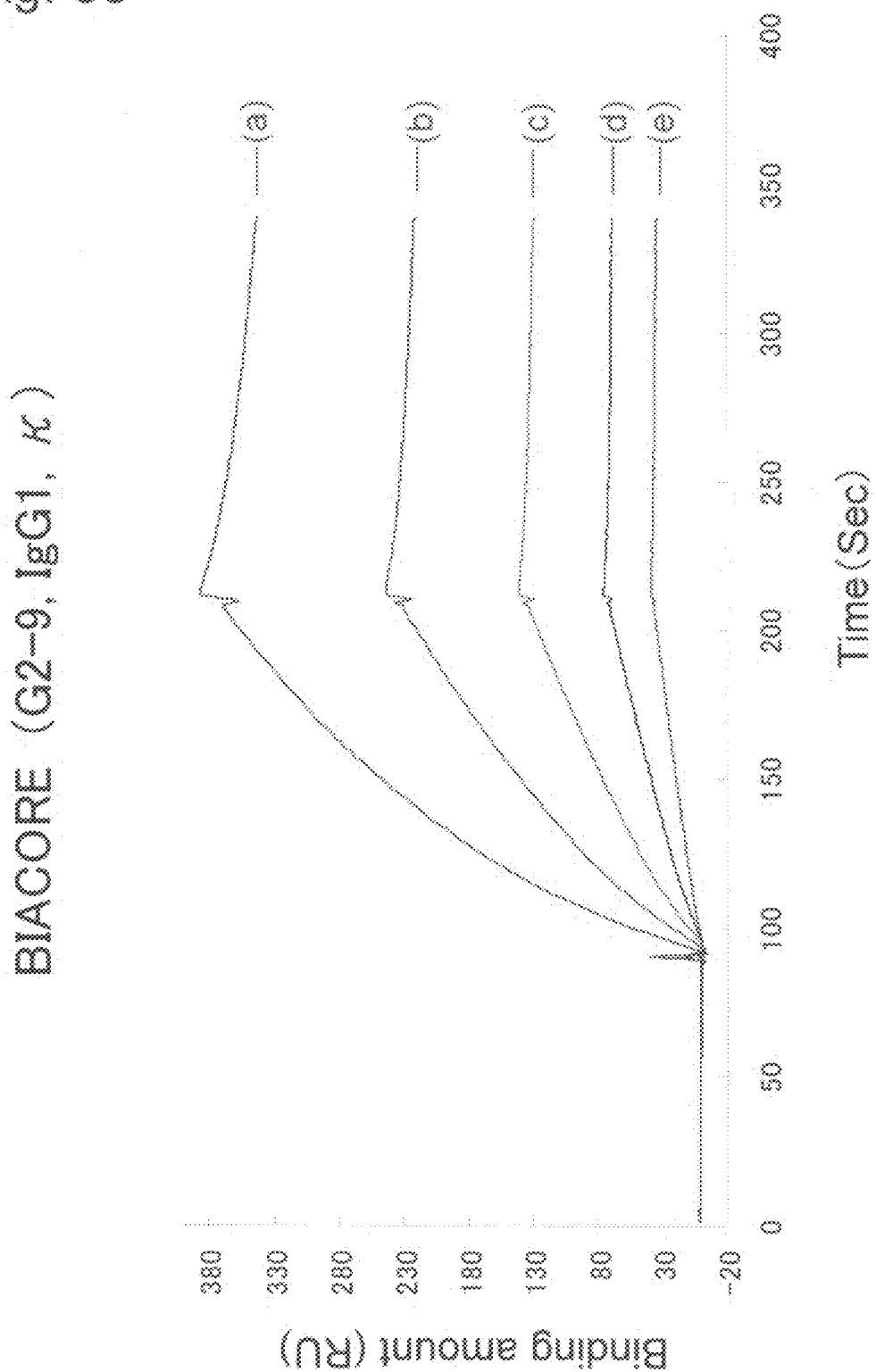
FIG. 30 shows association-dissociation curves obtained with Biacore on culture supernatants of the GANP transgenic mouse-derived hybridoma clones.

As a result, the Biacore pattern of G2-9 (ELISA: 82.9% NP2/NP17 ratio) is shown in FIG. 30. Curves (a) to (e) appearing in FIG. 30 correspond to antibody concentrations of 26.6, 13.3, 6.65, 3.33 and 1.66 nM, respectively. From the above results, the following values were obtained: association rate constant (k ass)=$1.48 \times 10^5$, dissociation rate constant (k diss)=$9.63 \times 10^{-4}$, and dissociation constant (indicator of affinity) KD (KD=k diss/k ass)=$6.50 \times 10^{-9}$.

Figure 31:
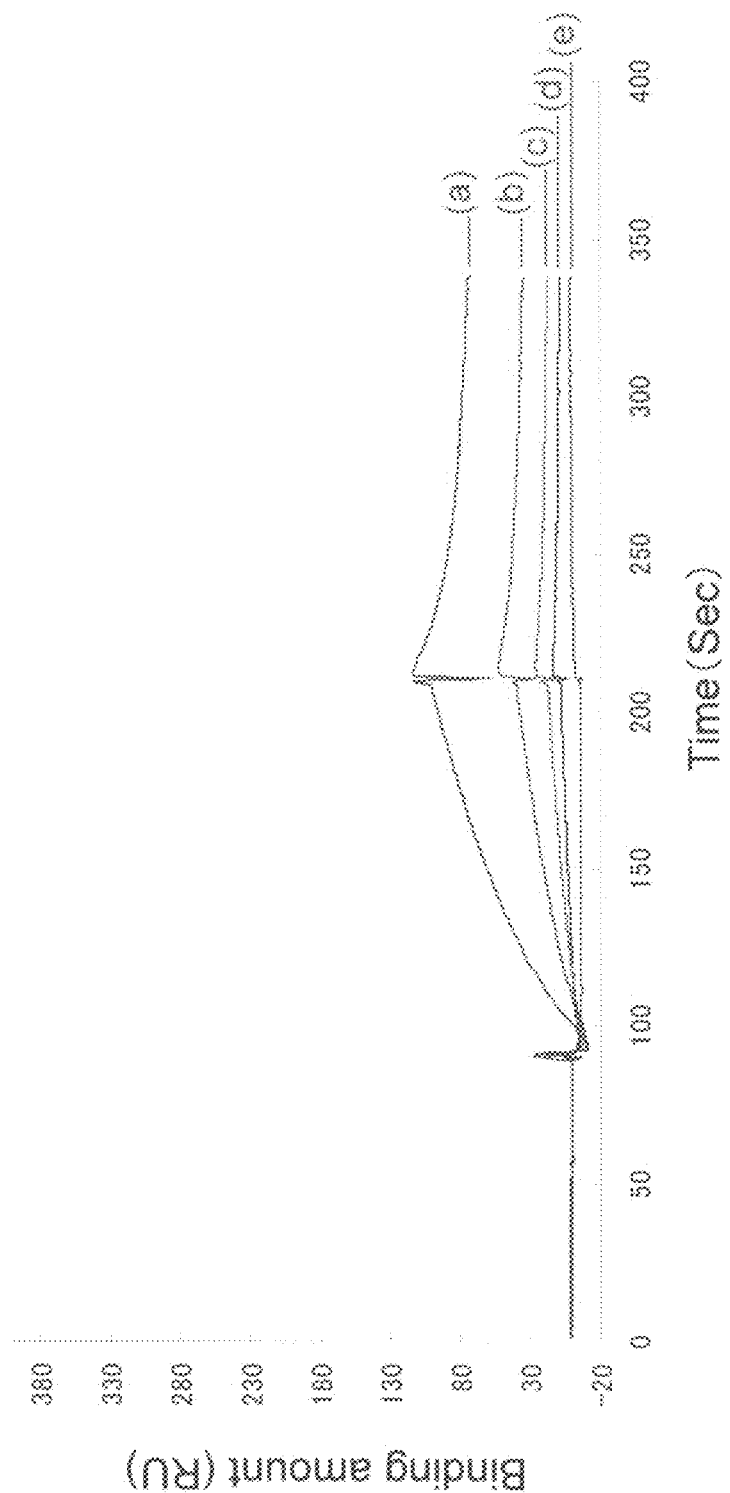
FIG. 31 shows association-dissociation curves obtained with Biacore on culture supernatants of the GANP transgenic mouse-derived hybridoma clones.

On the other hand, the Biacore pattern of G2-15 (ELISA: 33.9% NP2/NP17 ratio) which is predicted to be relatively low in affinity from the results of ELISA is shown in FIG. 31. Curves (a) to (e) appearing in FIG. 31 correspond to antibody concentrations of 23.0, 11.5, 5.75, 2.88 and 1.44 nM, respectively.

The following values were obtained: association rate constant (k ass)=$5.33 \times 10^4$, dissociation rate constant (k diss)=$1.56 \times 10^{-2}$, and dissociation constant (indicator of affinity) KD (KD=k diss/k ass)=$2.92 \times 10^{-7}$. This KD value was close to the KD value of $1.67 \times 10^{-7}$ shown by W2-7 which also showed an equivalent affinity in ELISA (ELISA: 31.6% NP2/NP 17 ratio).

From what have been described above, it is clear that high affinity antibodies are produced by using GANP transgenic (Tg) mice.

Example 5

Association of GANP with MCM3, and Shuttling Between Nucleus and Cytoplasm During Cell Cycle 1. Outline In this Example, the present inventor determined the MCM3 binding domain of GANP by using truncated-type mutant GANPs, and characterized the localization of GANP in NIH-3T3 cells using a monoclonal antibody specific to the phosphorylation of serine at position 502 (pSer$^{502}$) in the GANP specific domain.

The binding of a primase to MCM is a linked function, and the molecular complex resulting from their binding has an action of unwinding the DNA double strand. Therefore, it is believed that if a GANP partial fragment has bound to MCM, that GAMP fragment also reveals primase activity and has an action of producing high affinity antibodies.

Then, the localization of GANP and partial fragments thereof, Map80 and MCM3 in the nucleus/cytoplasm compartment was analyzed by cDNA transfection and cell fusion experiment.

The resultant data show that GANP binds to MCM3 and that the localization of GANP is influenced by MCM3 expression. GANP associates with MCM3 by a binding mode different from that by which Map80 associates with MCM3. These results suggest that GANP bound to MCM3 mediates a unique function different from the function of Map80/MCM3AP.

2. Materials and Methods 2.1. Cells and Cell Cultures

NIH-3T3, COS7, HeLa and Swiss-3T3 cells were maintained in D-MEM medium (Invitrogen) supplemented with 10% thermo-inactivated FCS (Dainippon Pharmaceutical), 2 mM L-glutamine (Biowhittaker), 100 µg/ml streptomycin, 100 U/ml penicillin and 50 µM 2-mercaptoethanol at 37° C. under 5% $CO_2$ (Takei, Y. et al., (1998) *J. Biol. Chem.* 273, 22177-22180; Sakaguchi, N. et al., (1988) *EMBO J.* 7, 3457-3464, Kimura, H. et al., (1995) *Nucl. Acids Res.* 23, 2097-2104). BAL17 cells were cultured in RPMI-1640 medium (Invitrogen).

2.2. Intracellular Localization of Phosphorylated GANP and MCM3

NIH-3T3 cells were fixed in 3.7% paraformaldehyde in PBS (pH 7.4) for 5 min and made transparent using 0.2% Triton X-100 (Kimura, H. et al., (1994) *EMBO J.* 13, 4311-4320). As primary antibodies, rat anti-pSer$^{502}$ GANP monoclonal antibody (Kuwahara, K. et al., (2001) *Proc. Natl. Acad. Sci. USA* 98, 10279-10283) and rabbit anti-MCM3 antibody (Kimura, H. et al., (1994) EMBO J. 13, 4311-4320) were used. As secondary antibodies, Alexa 488-conjugated goat anti-rat IgG antibody (Molecular Probes) was used against GANP and Alexa 546-conjugated goat anti-rabbit IgG antibody (Molecular Probes) was used against MCM3. Counterstaining was carried out using TOTO-3 iodide (Molecular Probes), followed by observation with a confocal laser scanning microscope (FV500; Olympus).

2.3. cDNA Constructs for Expression pSRα-MCM3-HA is described in the literature (Kimura, H. et al., (1995) *Nucl. Acids Res.* 23, 2097-2104). A vector pECFP-Nuc carrying the three nuclear localization signals (NLSs) of SV40 T-Ag was purchased from Clontech. PCR fragments obtained by using the following combinations of 3' and 5' primers were introduced into pGEX-4T-1 (Amersham). Using the resultant plasmids, different forms of mouse ganp cDNAs were expressed as fusion proteins with glutathione-S-transferase (GST).

```
GANP1-5': 5'-GGGGATCCATACCCGG TGAACCCCTT-3'      (SEQ ID NO: 11)

GANP1-3': 5'-GGGTCGACGCGCACAGACTTTCCCCTGA-3'      (SEQ ID NO: 12)

GANP2-5': 5'-GGGAATTCTCCCGCCTTCCAGCTGTGAC-3'      (SEQ ID NO: 13)

GANP2-3': 5'-GGGTCGACGTGCTGCTGTGTTATGTCCT-3'      (SEQ ID NO: 14)

GANP3-5': 5'-GGGAATTCCATGAGCT GAGACCCTCAGC-3'     (SEQ ID NO: 15)

GANP3-3': 5'-GGGTCGACTGAGGATGCAGGAGGCGGCT-3'      (SEQ ID NO: 16)

GANP4-5': 5'-GGGAATTCTACGTTGGAGAGAGCCTGGC-3'      (SEQ ID NO: 17)

GANP4-3': 5'-GGGTCGACCATGCTGTCATCTCCTGTGA-3'      (SEQ ID NO: 18)
```

-continued

```
GANP5-5': 5'-GGGAATTCGAGAA CCTGGCCAAGGGTCT-3'      (SEQ ID NO: 19)

GANP5-3': 5'-GGGTCGACGAAAAACCGACGGCTGA ACT-3'      (SEQ ID NO: 20)

GANP6-5': 5'-GGGAATTCAAGCCCTTCCAGCCTGCCCT-3'      (SEQ ID NO: 21)

GANP6-3': 5'-GGGTCGACCGAGGGAACGTGGTATTTTC-3'      (SEQ ID NO: 22)

GANP7-5': 5'-GGCCCGGGCC CGTGGGATGACATCATCA-3'     (SEQ ID NO: 23)

GANP7-3': 5'-GGCTCGAGCATGTCCACCATCTC CAGCA-3'     (SEQ ID NO: 24)
``` cDNA constructs were prepared by introducing PCR fragments into pSVEGFP pA to thereby obtain green fluorescence protein (GFP)-tagged Ganp mutants (Kuwata, N. et al., (1999) *J. Immunol.* 163, 6355-6359). Subsequently, these constructs were introduced into a mammalian expression vector pCXN2 (Niwa, H. et al., (1991) *Gene* 108, 193-200). Primer sequences were designed as described below so that they encode Ganp.

```
Gp-gfp-5':
5'-GGGGATCCGAATTCCACCATGGCAGTCTTCA  (SEQ ID NO: 25)
AACCGATA CC-3'

Gp-gfp-3':
5'-GCAGGGGCTCCTCCTGATCT-3'          (SEQ ID NO: 26)

Gsac-gfp-5':
5'-GGGGATC CGAATTCCACCATGTCCGAGGGC  (SEQ ID NO: 27)
CTTGGTTCTTG-3'

Gsac-gfp-3':
5'-CTGTCTT GTTTCTAAGCCGC-3'         (SEQ ID NO: 28)

Gmap80-gfp-5':
5'-GGGGATCCGAATTCCACCATGGAGA ACCTG  (SEQ ID NO: 29)
GCCAAGGGTCT-3'

Gmap80-gfp-3':
5'-GAGGACTTGTAGATGTTTTCAC CATGG-3'  (SEQ ID NO: 30)
```

FLAG-tagged Ganp mutants were prepared by introducing into pCXN2 the cDNA fragments obtained by PCR using the following primers.

```
FLAG-Gp-5':
5'-GGGAATTCCACCATGGATTACAAGGATGACG  (SEQ ID NO: 31)
ACGATAAGGCAGTCTTCAA CCGATACC-3'

FLAG-Gp-3':
5'-GGGAATTCCTCCGGGTCTCCCTCAAGTA-3'  (SEQ ID NO: 32)

FLAG-Gsac-5':
5'-GGGAATTCCACCATGGATTACAAGGATGACG  (SEQ ID NO: 33)
ACGATAAGTCCGAGGGCCTTGGTTCTTG-3'

FLAGGsac-3':
5'-GGGAATTCGCTGTCTTGTTTCTAAGCCG-3'  (SEQ ID NO: 34)

FLAG-Gmap-5':
5'-GGGAATTCCACCATGGATTACAAGGATGACG  (SEQ ID NO: 35)
ACGATAAGGAGAACCTGGCCAAGGGTCT-3'

FLAG-Gmap-3':
5'-GGGAATTCTGAGGACTTGTAGATGTTTT-3'  (SEQ ID NO: 36)
```

Internal deletion mutant GpΔNLS-GFP and I3 mutant (MCMΔNLS-HA) were prepared as described in the literature (Imai, Y. et al., (1991) *Nucl. Acids Res.* 19, 2785-2785). All of the constructs were sequenced to confirm that they have the proper orientation and that the reading frame of codons will be correct when they are expressed as tagged fusion proteins. Thus, their quality was controlled. Expression vectors comprising a mutant RNA/DNA primase domain (PD) are described in the literature (Gp mutant from $Ser^{502}$ to Ala [GpS502A] or Glu [GpS502E]) (Kuwahara, K. et al., (2001). *Proc. Natl. Acad. Sci. USA* 98, 10279-10283).

2.4. Detection of Transgene Product with Confocal Microscope

NIH-3T3 cells were transfected with pCXN2-ganp-gfp and/or pSRα-MCM3-HA using FuGENE 6 (Roche Diagnostics). Sixteen hours before fixation, leptomycin B (LMB) (Kudo, N. et al., (1999) *Proc. Natl. Acad. Sci. USA* 96, 9112-9117) was added to the medium. In the co-transfection experiment, rabbit anti-HA antibody (Santa Cruz) and Alexa 546-conjugated goat anti-rabbit IgG antibody were used. In the single transfection experiment, Alexa 488-conjugated goat anti-rabbit IgG antibody (Molecular Probes) was used. Thus, exogenous MCM3 protein was stained. Nuclear acid was counter-stained with TOTO-3 iodide in the co-transfection experiment and with propidium iodide (PI; Sigma) in the single transfection experiment.

2.5. GST Pull Down Assay

GST fusion proteins were purified as described in the literature (Kuwahara, K. et al., (2000) *Blood* 95, 2321-2328). Various GST fusion proteins (5 μg each) immobilized on glutathione-Sepharose beads (Amersham) were incubated with BAL17 lysate prepared with TNE buffer (10 mM Tris-HCl [pH 7.8], 150 mM NaCl, 1 mM EDTA, 1% Nonidet P-40, 10 μg of aprotinin, 1 mM phenylmethyl-sulfonylfluoride [PMSF]). Bound proteins were separated by 8% SDS-PAGE, transferred onto a nitrocellulose filter and blocked. Subsequently, the filter was incubated with rabbit anti-mouse MCM3 antibody (Kimura, H. et al., (1994) *EMBO J.* 13, 4311-4320) and then with peroxidase-labeled protein A (Amersham) serially. Finally, signals were visualized with ECL detection kit (Amersham). For direct binding assay, radiolabeled MCM3 was prepared with $^{35}S$-methionin (Amersham) using In vitro Transcription and Translation Binding System (Novagen) according to the manufacturer's instructions. Thus, [$^{35}S$]-labeled MCM3 was detected by autoradiography.

2.6. Immunoprecipitation and Western Blotting of Transgene Product

COS7 cells were transfected with pCXN2-FLAG-ganp and/or pSRα-MCM3-HA using FuGENE 6. After 26 hrs, cells were lysed in TNE buffer. The resultant lysate was incubated with a combination of protein A-Sepharose (Amersham) and anti-HA antibody. The resultant immunoprecipitates were separated by 8% SDS-PAGE, transferred on a nitrocellulose filter, and blocked. Subsequently, the filter was incubated with anti-mouse FLAG M2 antibody (Stratagene) and then with peroxidase-labeled goat anti-mouse IgG (H+L) antibody (Zymed). For the detection of Gp-GFP and mutants thereof, the blotted filter was probed with rabbit anti-GFP antibody (Santa Cruz) and peroxidase-conjugated protein A (Zymed).

2.7. Heterokaryon Assay

HeLa cells were transfected with pSRα-MCM3-HA using FuGENE 6. After 20 hrs, transfected HeLa cells and untransfected mouse Swiss-3T3 cells were treated with trypsin and seeded in culture dishes at a ratio of 1:1. After 24 hrs, cells were fused using polyethylene glycol 1500 (Roche Diagnostics) at room temperature for 2 min (Schmidt-Zachmann, M. S. et al., (1993) *Cell* 74, 493-504). The culture dishes were washed with the medium 4 times. Then, cycloheximide-containing medium was added thereto (at a final concentration of 20 μg/ml), and the cells were incubated in $CO_2$ incubator at 37° C. for 5 hrs. Subsequently, the cells were fixed with 4% paraformaldehyde in 250 mM HEPES-NaOH (pH 7.4) for 20 min, made transparent using 0.5% Triton X-100 in PBS for 30 min, and washed with PBS. The cells were stained using anti-HA antibody (12CA5; Covence Research Products) and Cy3-conjugated donkey anti-mouse Ig antibody (Jackson). Also, DNA was counter-stained with 100 ng/ml of Hoechst 33342 (Sigma) in PBS for 20 min. Images were collected using Zeiss Axioplan equipped with 100× PlanNeofluar phase-contrast objective lens (NA 1.3) and SpotII CCD.

3. Results and Observations

3.1. Association of GANP with MCM3

Figure 32:
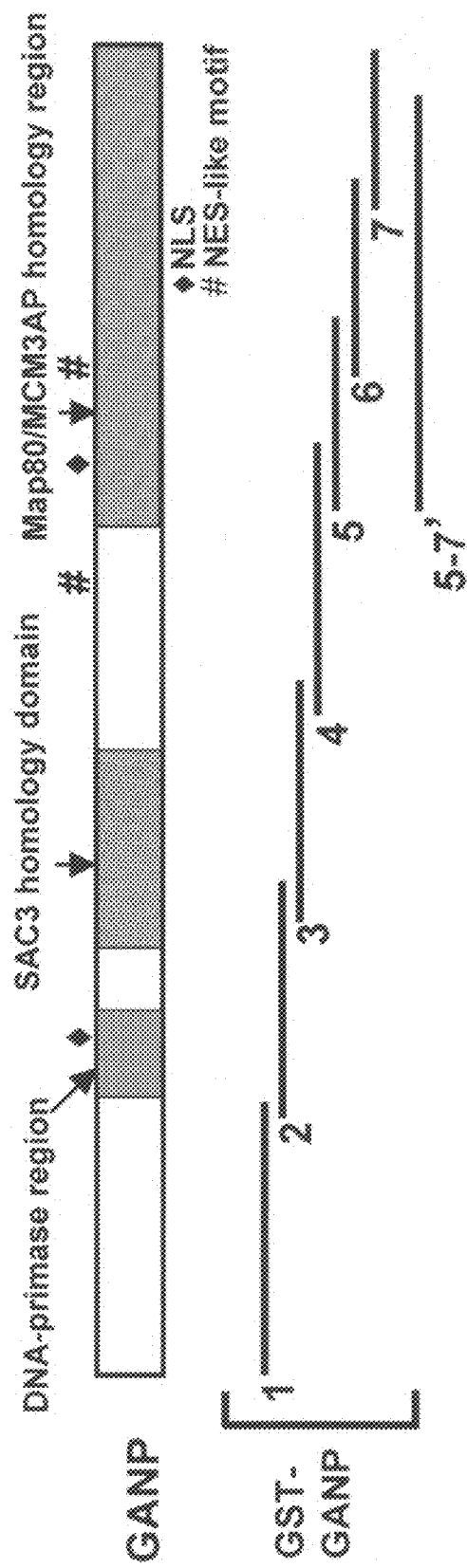
FIG. 32 shows an outline of the structure of GANP-GST fusion protein.

The interaction between GANP and MCM3 in B cell lineage has been already demonstrated by immunoprecipitation (Kuwahara, K. et al., (2000) *Blood* 95, 2321-2328). Since a C-terminal domain of GANP is identical with total Map80 protein, it is predicted that GANP associates with MCM3 at this domain. In order to determine which domain of GANP associates with MCM3, the present inventor performed a pull down assay using GST fusion proteins containing the various truncated GANP proteins as shown in FIG. 32. Briefly, GST was fused to the N-terminus of each of the truncated GANP proteins designated 1 to 7 and 5-7' in FIG. 32. In the lower panel of FIG. 33, Map80 domain (designated GANP5-7') pulled down MCM3 from cell extract as described previously (Kimura, H. et al., (1994) *EMBO J.* 13, 4311-4320).

Figure 33:
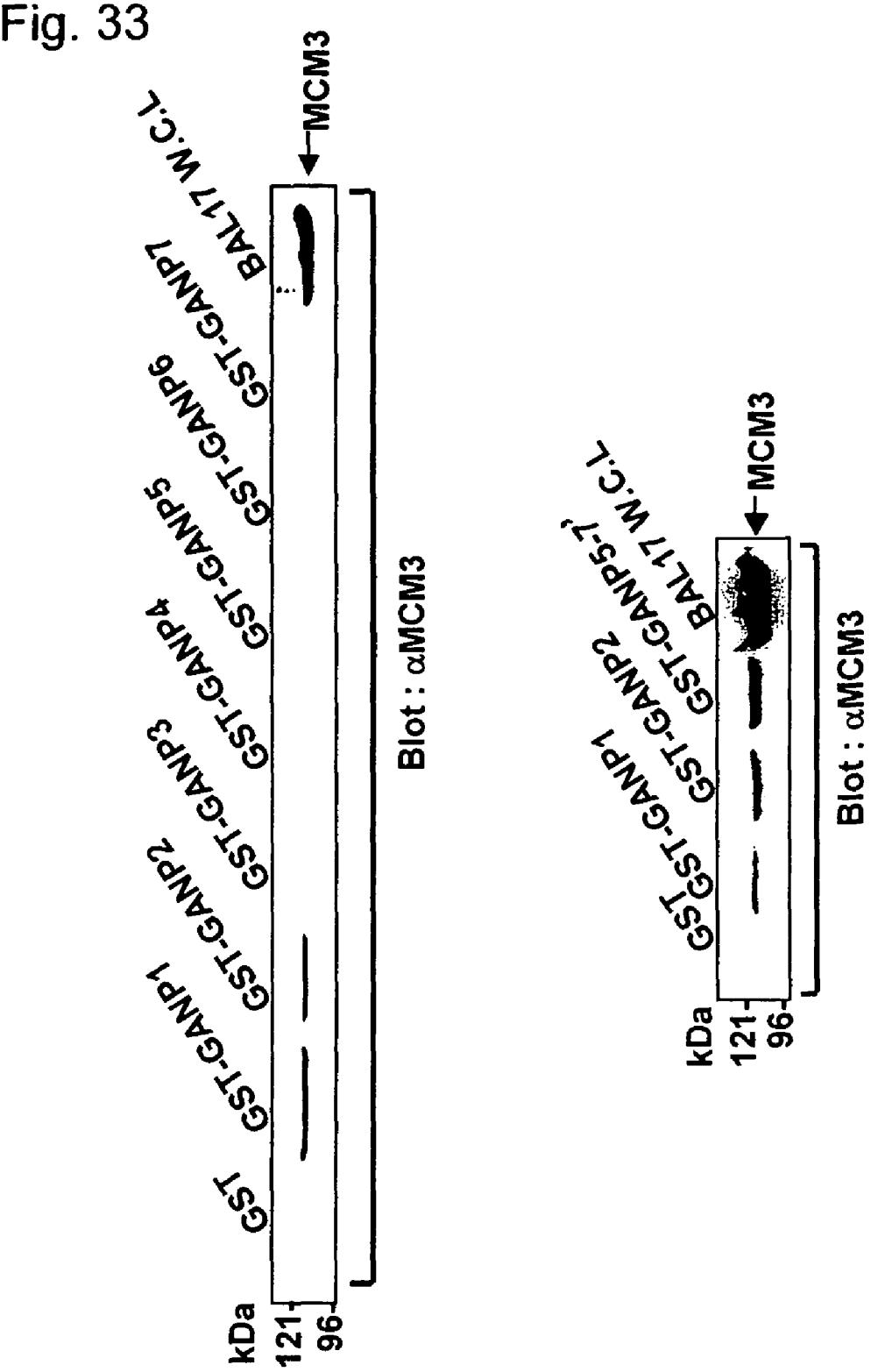
FIG. 33 shows the results of a pull-down assay for determining the region of GANP which directly binds to MCM. Shown on the left side of each panel are the positions of size standards.

Surprisingly, GANP1 and GANP2 (which are partial fragments of GANP) also pulled down MCM3 (FIG. 33: upper and lower panels).

Figure 34:
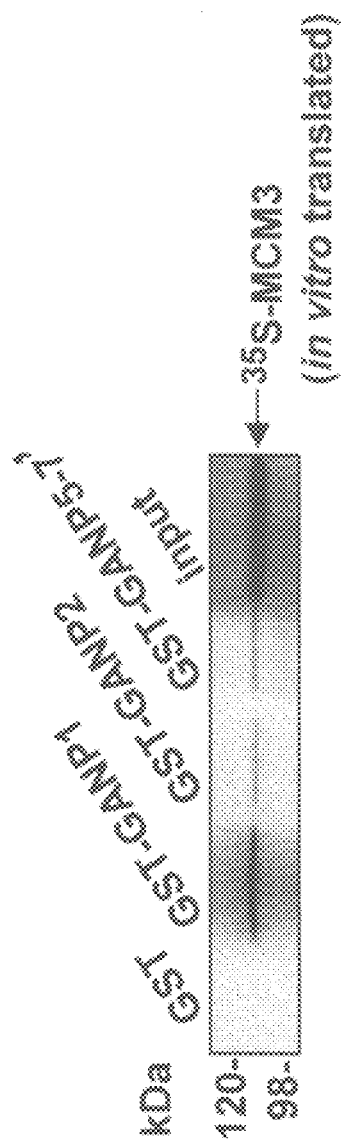
FIG. 34 shows the results of a pull-down assay using in vitro translated MCM.

Subsequently, this binding was examined using MCM3 synthesized in vitro in a reticulocyte lysate system (FIG. 34). GST-GANP1 and GST-GANP2 also pulled down [$^{35}$S]-MCM3 from the in vitro translation cocktail.

GST alone (negative control: first lane) or GST fused with an irrelevant protein did not show any signal. Further, the binding to GST-GANP1 was stronger than the binding to Map80 domain (GST-GANP5-7'). This binding was also confirmed in cells by a DNA transfection experiment using FLAG-tagged constructs (FIG. 35).

Briefly, COS7 cells were co-transfected with pCXN2-FLAG-Ganp, pCXN2-FLAG-Gp and pCXN2-FLAG-Gmap80 in combination with pSRα-MCM3-HA or pSRa-I3-HA. After immunoprecipitation with anti-HA antibody, Western blotting was performed using anti-FLAG monoclonal antibody. The predicted sizes of FLAG-labeled proteins are shown in individual lanes with triangle marks. In the left and right panels, the migration of bands is similar, but the light exposure for ECL detection was 1 min for the left panel and 3 min for the right panel (FIG. 35).

Figure 35:
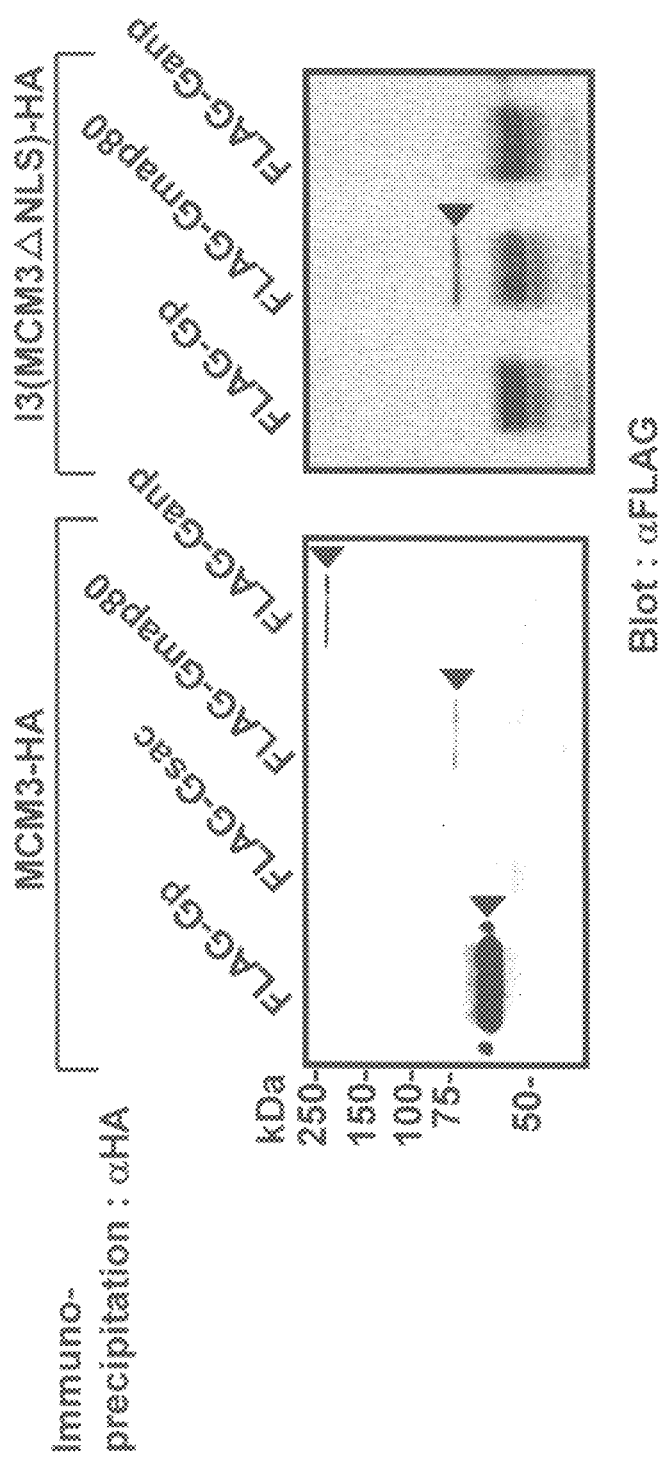
FIG. 35 shows the binding of individual GANP constructs to MCM by immunoprecipitation.

FLAG-Ganp, FLAG-Gp and FLAG-Gmap80 bound to wild-type MCM3-HA (HA epitope-tagged MCM3) (FIG. 35: left panel). Only FLAG-Gsac did not bind thereto. With respect to the binding with I3 mutant MCM3 (MCM3ΔNLS), only FLAG-Gmap80 showed a positive result (FIG. 35: right panel). Gp domain carrying the N-terminal NLS associates with MCM3 consistently in cells containing a large quantity of MCM3 (FIG. 35: left panel). These results suggest that GANP associates with the NLS domain of MCM3 through Gp domain.

The present inventor further examined whether the state of phosphorylation of Ser$^{502}$ in Gp domain influences the binding GANP to MCM3 or not. A GANP mutant lacking primase site (GanpΔPD-GFP) and other GANP mutants prepared as GanpS502A and GanpS502E having a mutation at Ser$^{502}$ were fused with GFP (FIG. 36A). Cells were co-transfected with pCXN2-Ganp-gfp and pSRα-MCM3-HA, and cell lysate was used in immunoprecipitation with anti-HA antibody.

Figure 36B:
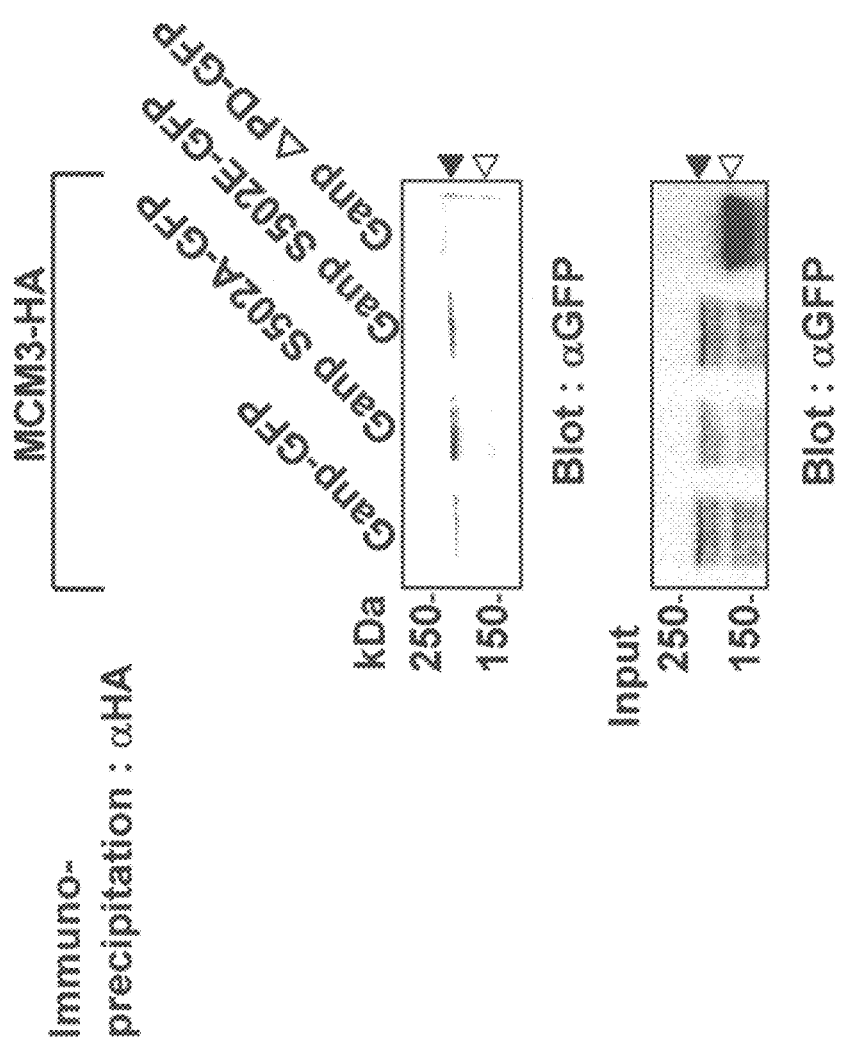

GFP signals were detected with anti-GFP antibody (FIG. 36B: upper panel). This means that GANP has bound to MCM.

Co-transfection using Ganp-GFP mutants was also performed in the same manner. In order to determine the predicted position of each protein, lysates were separated by SDS-PAGE and blotted with anti-GFP antibody in the same manner (FIG. 36B: lower panel).

The non-phosphorylated mutant (GanpS502A-GFP) bound to MCM3 as wild-type Ganp-GFP and GanpS502E-GFP (a mutant much resembling phosphoserine) did (FIG. 36B: upper panel). Interestingly, GanpΔPD-GFP does not co-precipitate with MCM3-HA (FIG. 36B: upper panel).

Regardless of the latent binding activity of Map80 domain, GANP molecule as a whole needs RNA primase domain (PD) for its binding to MCM3. Open triangle in FIG. 36B indicates the position of GanpΔPD-GFP. The size of Ganp-GFP, which is equal to the sizes of Ganp S502A-GFP and Ganp S502E-GFP, is indicated with filled triangle (FIG. 36B: lower panel). These results suggest that the binding of GANP to MCM3 is mediated by its PD domain, but phosphorylation at Ser$^{502}$ does not influence this binding.

The experiment using truncated constructs revealed the association of GANP with MCM3 in a wide region. However, the association of the entire GANP (involving its N-terminal 600 amino acid region) with MCM3 requires the NLS of MCM3. NLS-deficient MCM3 mutant was unable to effectively associate with entire GANP molecule in cells. Map80 domain bound to NLS-negative MCM3, suggesting that GANP mainly binds to a domain of MCM3 other than the domain required for the interaction with Map80. Although Map80 is considered to be an MCM3 import factor, GANP may play a different role in cooperation with MCM3. It seems that GANP has many potential phosphorylation sites and has many association components in cells (Kuwahara, K. et al., (2000) *Blood* 95, 2321-2328). Therefore, it will be necessary to specify a domain whose state of phosphorylation influences the GANP/MCM3 association and transport between the cytoplasm and the nuclear compartment.

3.2. Intracellular Localization of Map80 and Ganp Mutants Shown by Transfection GANP has two potential NLSs. One is located in the N-terminal primase domain and the other in the C-terminal Map80 domain. GANP also has two nuclear export signal (NES)-like motifs. On is located between SAC3 homologous domain and Map80 domain and the other within Map80 domain.

Figure 37:
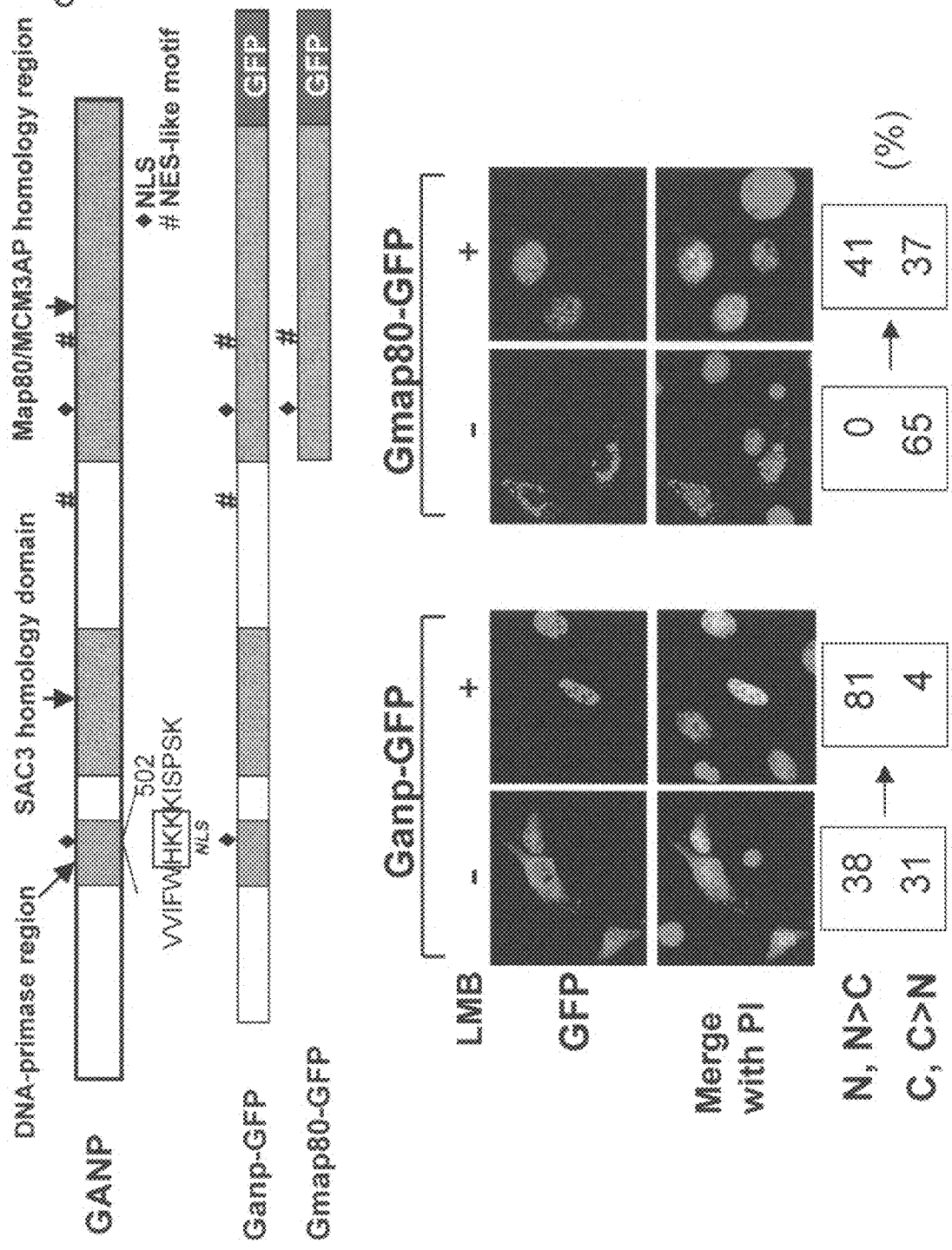
FIG. 37 shows an outline of the structures of GANP constructs and their intracellular distributions.

NIH-3T3 cells were transfected with pCXN2-Ganp-gfp or pCXN2-Gmap80-gfp, followed by fixation 48 hrs later. LMB was added 16 hrs before the fixation. Nuclei were pre-stained with PI, and images were collected with a confocal microscope. Representative expression properties are shown in FIG. 37. The numbers of cells were counted by property and expressed in % (FIG. 37).

It was found that Ganp-GFP (almost full-length GANP tagged with GFP) is present in both the cytoplasm and the nuclear compartment, though the ratio of cells showing nuclear dominant expression (N and N>C: 38%) or cells showing cytoplasm dominant expression (C and C>N: 31%) was varied (% from total 500 cells) (FIG. 37: Ganp-GFP, LMB-). In contrast, Gmap80-GFP was found in the cytoplasm for the most part, showing no nuclear dominant expression according to the inventor's classification (N>C, 0%; N=C, 35%; C and C>N, 65%) (FIG. 37: Gmap80-GFP, LMB-). The localization of Ganp-GFP is different from the localization of Gmap80-GFP.

In order to examine whether the N-terminal NLS motif is functional or not, 5' 1-kb DNA fragment comprising RNA/DNA primase domain and the N-terminal NLS (but not NES-like motif) was fused with GFP (FIG. 38: Gp-GFP). Although this Gp-GFP product was present in the nucleus alone (N and N>C: 94%) (FIG. 38), NLS-deficient mutant GpGFP (Gp-ΔNLS-GFP; as shown in FIG. 38, amino acids from position 497 to 500 are deleted) was found to be cytoplasmic. Thus, it was confirmed that the N-terminal NLS is involved in the nuclear localization.

The present inventor examined whether or not the mutation of the adjacent $Ser^{502}$ to alanine (GpS502A-GFP; non-phosphorylated type) or to glutamic acid (GpS502E-GFP; phosphoserine-mimic type) influences this localization (FIG. 38). Then, the present inventor observed that these mutations do not alter the localization of Gp. This suggests that the N-terminal NLS is functional regardless of the state of phosphorylation of $Ser^{502}$ (FIG. 38). In contrast, it seems that Gac-GFP having neither N-terminal NLS nor C-terminal NLS is present in the cytoplasm for the most part (N and N>C: 0%; N=C: 3%; C and C>N: 97%) (FIG. 38).

These results suggest that the N-terminal NLS plays a functional role for Ganp to enter into the nucleus. However, the NLS may not be so strong to maintain GANP expression within the nucleus, because Ganp-GFP is also present in the cytoplasm (FIG. 37). In order to examine this issue further, cells were treated with leptomycin B (LMB) after cDNA transfection in order to inhibit the Crm1-mediated export to the nucleus (Kudo, N. et al., (1999) Proc. Natl. Acad. Sci. USA 96, 9112-9117).

In LMB-treated cells, Ganp-GFP localized in the nucleus for most of the transfectants (FIG. 37). The cell fraction showing cytoplasm dominant expression decreased from 31% to 4%, while the cell fraction showing nuclear dominant expression increased from 38% to 81%. Therefore, it appears that the movement of Ganp to the cytoplasm is inhibited by LMB.

The localization of Gmap80-GFP has also changed dramatically after LMB treatment (FIG. 37). The cell fraction showing cytoplasm dominant expression decreased from 65% to 37%, and the cell fraction showing nuclear dominant expression increased from 0% to 41%. These findings were reproduced in other cell systems including COS7 and Ltk⁻ cells, suggesting that the export of GANP from the nucleus to the cytoplasm is regulated by Crm1-dependent passway. Therefore, GANP and Map80 seem to shuttle between the nucleus and the cytoplasm, and their localization seem to depend on the balance between nuclear import and export mechanisms maintained in cooperation with other molecules.

3.3. Localization of MCM3 and GANP in Cotransfected Cells

Subsequently, the present inventor examined whether or not the movement of GANP is related to MCM3 expression. Mammal MCM3 alters the state of binding with chromatin during cell cycle, but it is present only in the nucleus throughout the interphase (Kimura, H. et al., (1994) EMBO J. 13, 4311-4320). NIH-3T3 cells were transfected with pSRα-MCM3-HA or pSRα-I3-HA, fixed, immunolabeled with anti-HA antibody (Alexa 488) and stained with PI.

Figure 39:
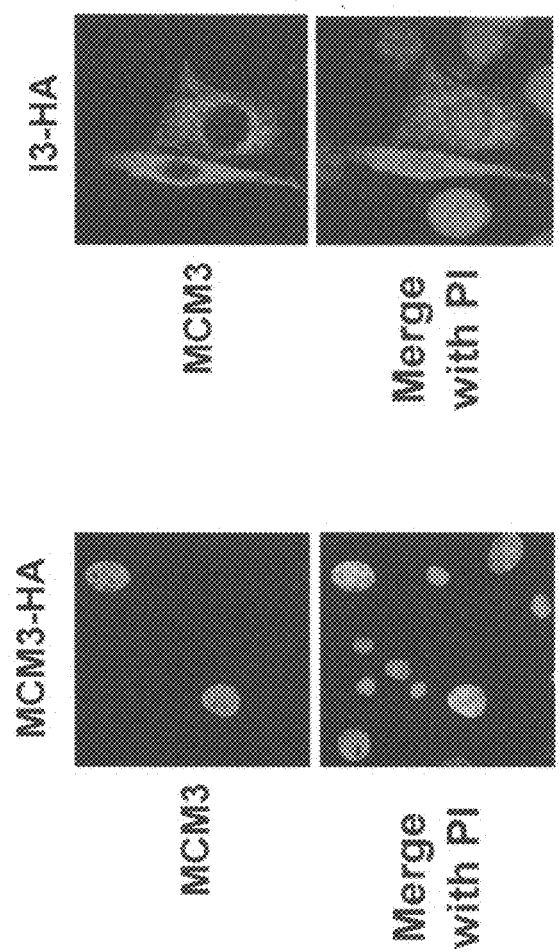
FIG. 39 shows the nuclear localization of MCM3.

MCM3-HA in transfected cells agreed with the representative presence of NLS (Kimura, H. et al., (1994) EMBO J. 13, 4311-4320, Takei, Y. et al., (1998) J. Biol. Chem. 273, 22177-22180) and localized in the nucleus (FIG. 39). This nuclear localization was dependent on the NLS of MCM3, because an MCM3 mutant lacking this NLS (I3; MCM3ΔNLS-HA) was expressed only in the cytoplasm (FIG. 39: right panel).

Figure 40:
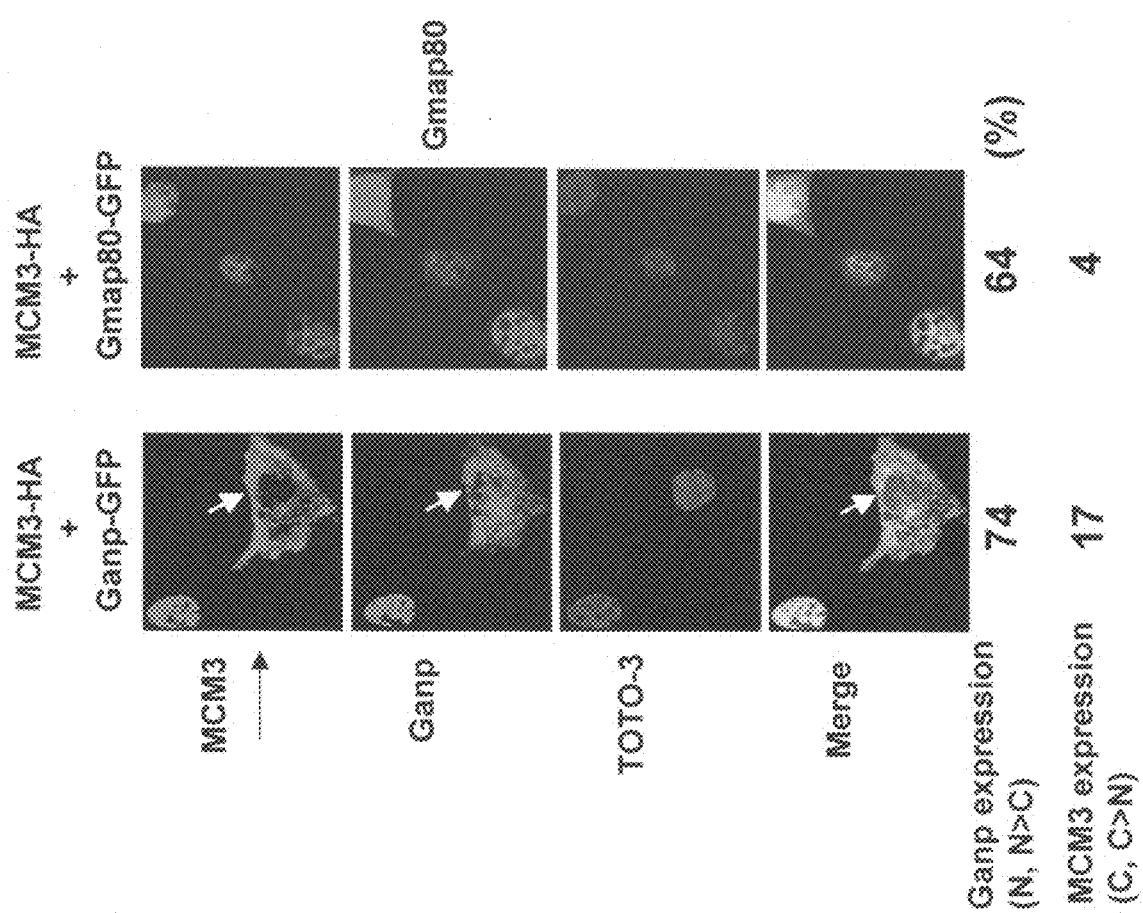
FIG. 40 shows the cytoplasmic localization of MCM3 induced by GANP expression.

Cells were cotransfected with pCXN2-Ganp-gfp or pCXN2-Gmap80-gfp and pSRα-MCM3-HA, fixed and immunolabeled with anti-HA antibody (Alexa 546), and nuclei were pre-stained with TOTO-3 (FIG. 40). Cell counts are shown below the panel (FIG. 40).

Interestingly, when cells were cotransfected with Ganp-GFP, cytoplasmic localization of MCM3 was induced in 17% of the cells (FIG. 40: marked with white arrows). When cells were cotransfected with Gmap80-GFP or Gp-GFP, such a result was not observed.

Figure 41:
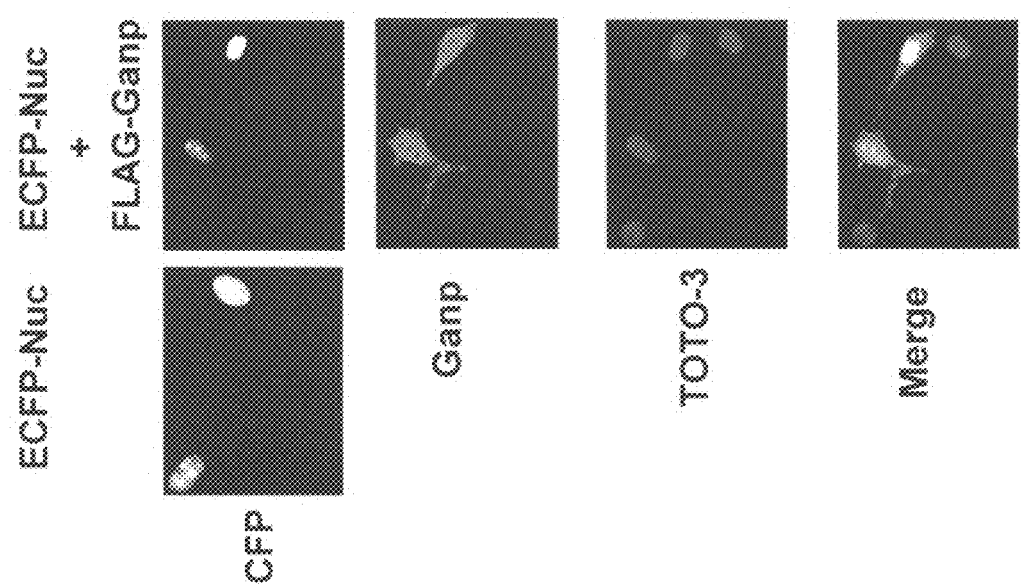
FIG. 41 shows a control protein localized in the nucleus.

In order to prove that the effect of Ganp on MCM3 is specific, expression of ECFP-Nuc which appears in the nucleus was examined before and after transfection using different ganp-gfp constructs. Representative images obtained from transfection with Ganp-GFP are shown in FIG. 41. The localization of ECFP-Nuc in the nucleus was not influenced by any cotransfection using Ganp-GFP (FIG. 41) or Gmap80-GFP or Gp-GFP.

Figure 42:
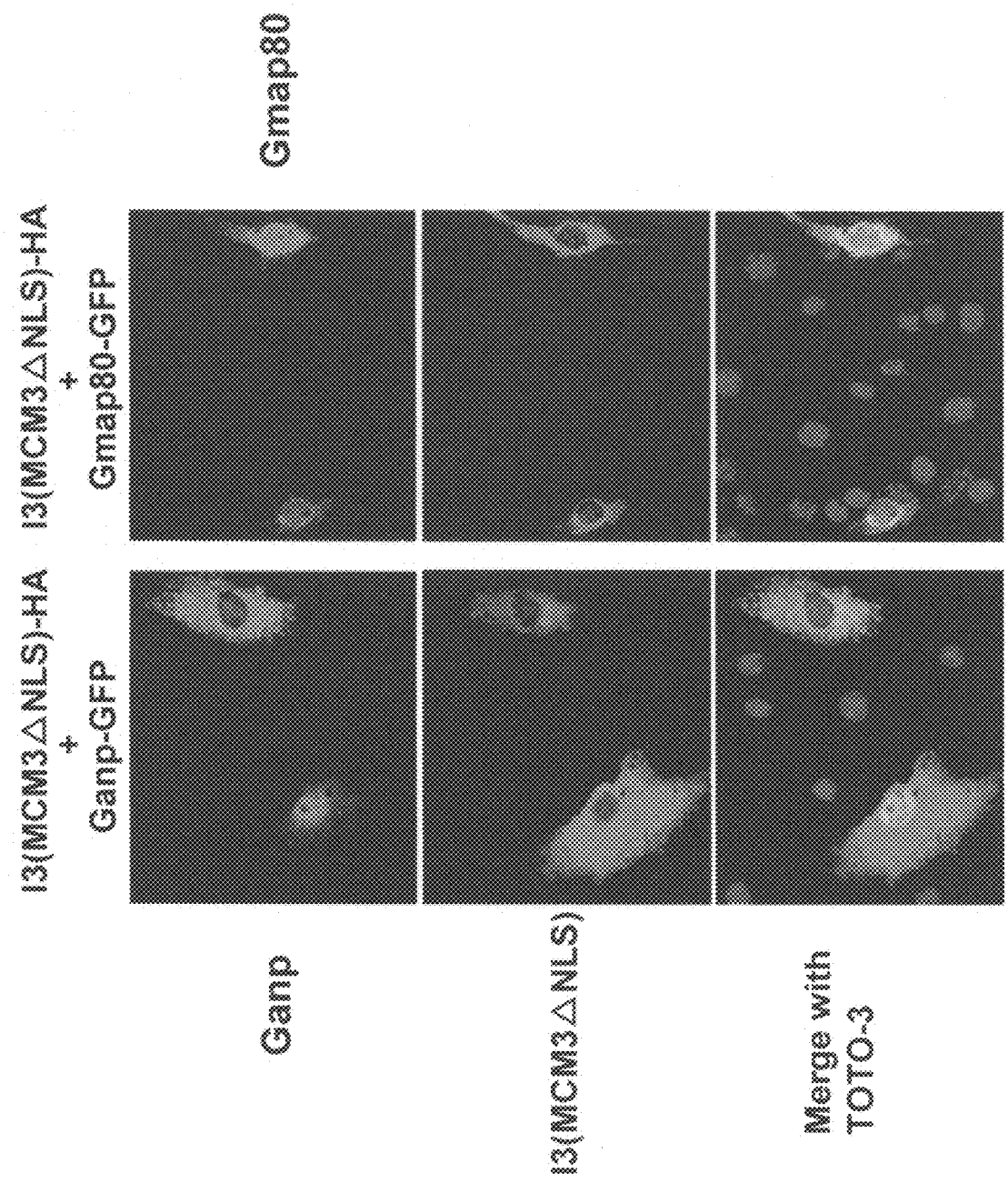
FIG. 42 shows the effect of GANP construct in the localization of MCM3 mutants.

Coexpression of Ganp and MCM3 has also altered the localization of GANP. Compared to the transfection with Ganp-GFP alone (38%) or with Gmap80-GFP alone (0%) (FIG. 37), cotransfection using MCM3 raised the nuclear expression levels of Ganp-GFP (74%) and Gmap80-GFP (64%) (FIG. 40). MCM3 retained GANP and Map80 within the nucleus, but overexpression of Ganp alone enhanced the expression of MCM3 in the cytoplasm (FIG. 40: 17% by Ganp-GFP expression). On the other hand, Gmap80 did not enhance the expression of MCM3 in the cytoplasm (4% by Gmap80-GFP expression). The mutation of MDM3 at its NLS (I3; MCM3ΔNLS-HA) (as a result, MCM3 is present in the cytoplasm) did not induce the accumulation of Ganp-GFP or Gmap80-GFP in the nucleus (FIG. 42).

Unlike wild-type MCM3, I3 mutant (MCM3ΔNLS-HA) does not associate with Ganp or Ga (FIG. 35). Considering this fact together, it is suggested that the NLS motif of MCM3 is necessary for the functional association with GANP and for the transport of GANP between the nucleus and the cytoplasm.

DNA transfection experiments demonstrated that Ganp-GFP is accumulated in the nuclear compartment when co-introduced with MCM3, suggesting the formation of GANP/MCM3 complex in the nucleus. MCM3 does not contain a definite common NES-like motif recognizable by Crm1. Therefore, the export of MCM3 from the nucleus probably depends on other binding molecules having an NES-like motif or a different export mechanism. The two NES-like motifs on GANP seems to be involved in an LMB sensitive, Crm1 dependent export passway (FIG. 37). The two NES-like motifs carried by GANP (these might be recognized by Crm1) might possibly be involved in the transport of the complex.

Recently, it was shown that yeast SAC3 carrying a GANP homologous domain is involved in the export of a specific protein from the nucleus and associates with a component of nuclear pore complex (Jones, A. L. et al., (2000) Proc. Natl. Acad. Sci. USA 97, 3224-3229). Coexpression with GANP altered the localization of MCM3 in the cytoplasmic compartment.

The nuclear-cytoplasmic shuttling of MCM3 was examined using cell fusion techniques (Schmidt-Zachmann, M. S. et al., (1993) *Cell* 74, 493-504). HeLa cells were transfected with MCM3-HA and then fused with untransfected mouse Swiss-3T3 cells. After a 5-hour incubation in the presence of cycloheximide to inhibit protein synthesis, cells were fixed and immunolabeled with MCM3-HA. Heterokaryons were examined by Hoechst staining. This staining discriminates mouse nuclei (marked with arrows) with "mottled" heterochromatins from human HeLa nuclei.

As representative images are shown in FIG. 43, MCM3-HA was found in both human nuclei and mouse nuclei in heterokaryons. Unfused mouse cells do not exhibit such staining. This suggests that MCM3-HA has been exported from the HeLa nucleus to the cytoplasm, and then imported into the mouse nucleus.

From these results, it is concluded that MCM3-HA is a shuttling protein. It should be noted here that proving the movement of an endogenous protein from the nucleus to the cytoplasm with a sensitivity similar to the sensitivity achieved when transgene products are handled is often difficult (Kimura, H., Ohtomo, T. et al., (1996) *Genes Cells* 1, 977-993; Mizuno, T. et al., (1999) *Mol. Cell. Biol.* 19, 7886-7896). That was the case with the results shown in the present Example. It is also difficult to prove the movement of endogenous MCM protein from the nucleus to the cytoplasm in mammal cells with a sensitivity achieved in more primitive cells such as yeast.

However, the results of the present inventor suggest that the nuclear-cytoplasmic shuttling of MCM protein is probably important in untreated cells (though experiments were performed by DNA transfection). To facilitate definite understanding of the nuclear-cytoplasmic shuttling of the MCM complex during cell cycle, discovery of a further component may be necessary.

3.4. Localization of GANP During Cell Cycle

Figure 44:
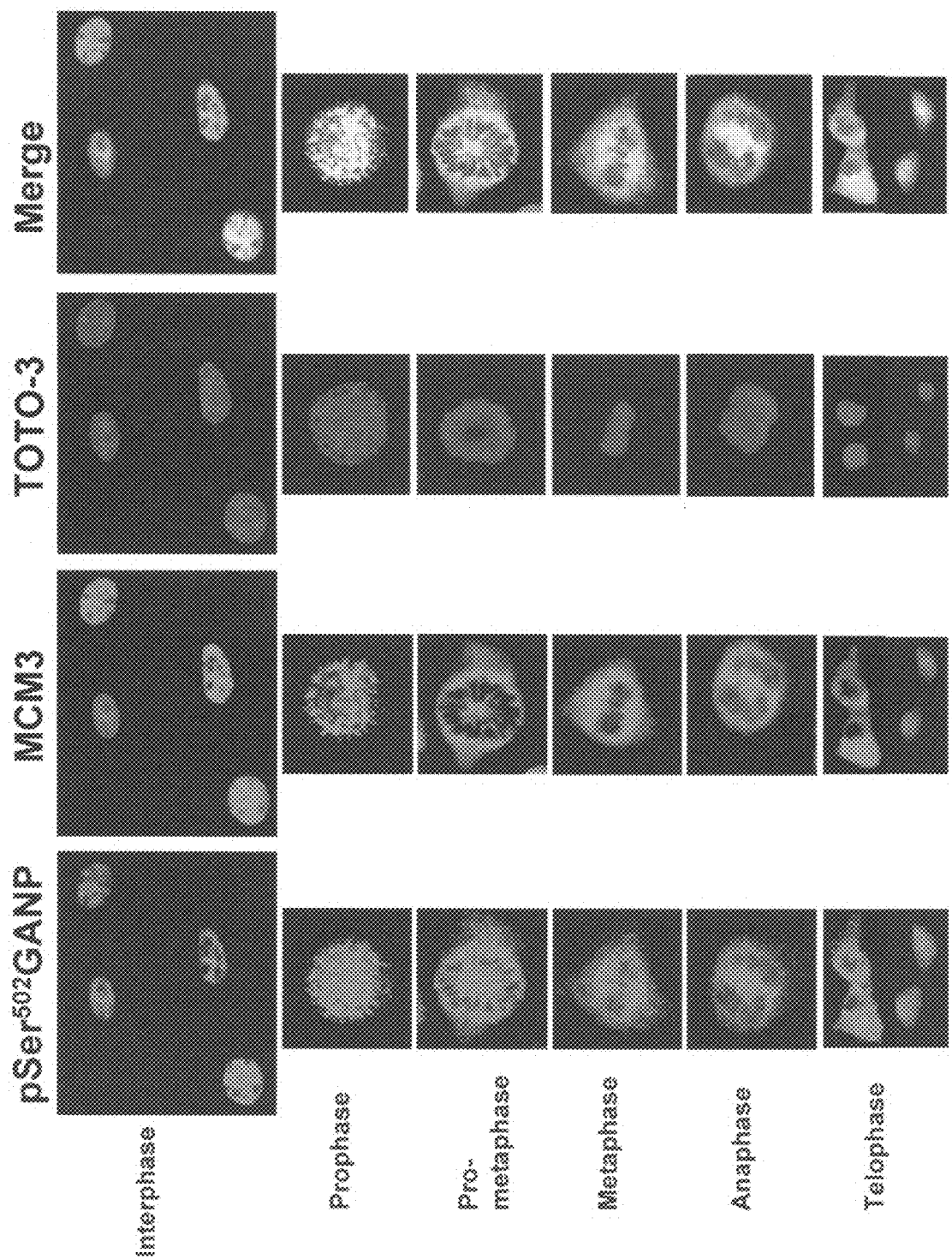
FIG. 44 shows the localization of GANP during the cell cycle.

Using a monoclonal antibody specific to the epitope of RNA/DNA primase domain (pSer$^{502}$ GANP) peculiar to GANP, the localization of GANP in NIH-3T3 cells was examined under a confocal laser scanning microscope (Kuwahara, K. et al., (2001) *Proc. Natl. Acad. Sci. USA* 98, 10279-10283). NIH-3T3 cells at different stages of cell cycle were immunostained with anti-pSer$^{502}$ GANP (Alexa 488; green) and anti-MCM3 (Alexa 546; red) antibodies. Nuclei were pre-stained with TOTO-3 iodide (blue). During the interphase, the above-described monoclonal antibody reacted everything within the nucleus except for the nucleolus (FIG. 44).

By the triple labeling with anti-MCM3 antibody and TOTO-3 for staining nucleic acid, the localization of GANP during mitosis was analyzed in detail. As cells proceed from the prometaphase to the metaphase, GANP seems to be dissociated from concentrated chromatin (FIG. 44). The yellow signal in the superimposed image indicates colocalization of GANP and MCM3, but some blue staining shows that GANP alone is also observed in the central part of the prometaphase image. At this stage, GANP and MCM3 are not superimposed with the concentrated chromosome. In metaphase cells, GANP is detected in the spindle region. This signal decreases when chromosomes are separated into two daughter cells in the anaphase.

In the anaphase of mitosis, most of GANP molecules are found in the cytoplasmic compartment until nuclei are formed (telophase). These results suggest that the behaviors of GANP and MCM3 are similar and that they are almost colocalized in the nucleus throughout the interphase. This is consistent with the interassociation of these two molecules. However, as shown by the confocal microscopic examination during mitosis, GANP and MCM3 may be present separately (FIG. 44).

The biological meaning of the nuclear-cytoplasmic shuttling of GANP with respect to the second type RNA/DNA primase remains to be investigated. The shuttling may be associated with the generation of RNA primer at the final stage of DNA repairing. Although the expression level of GANP is low in normal cells, GANP expression is up-regulated in the germinal center where cells rapidly proliferate (Kuwahara, K. et al., (2000) *Blood* 95, 2321-2328; Kuwahara, K. et al., (2001). *Proc. Natl. Acad. Sci. USA* 98, 10279-10283). Further, GANP is expressed at higher levels in certain types of cells having rapid cell cycle. This suggests the possibility that association into MCM complex may stimulate DNA replication (Kuwahara, K. et al., (2001). *Proc. Natl. Acad. Sci. USA* 98, 10279-10283). The expression of GANP having RNA/DNA primase activity, MCM3 binding ability and an acetyltransferase domain (Takei, Y. et al., (2001) *EMBO Rep.* 2, 119-123) may be involved in the regulation of cell cycle progress.

Sequence Listing Free Text

SEQ ID NO: 5: primer
SEQ ID NO: 6: primer
SEQ ID NO: 7: primer
SEQ ID NO: 8: primer
SEQ ID NO: 9: primer
SEQ ID NO: 10: primer
SEQ ID NO: 11: primer
SEQ ID NO: 12: primer
SEQ ID NO: 13: primer
SEQ ID NO: 14: primer
SEQ ID NO: 15: primer
SEQ ID NO: 16: primer
SEQ ID NO: 17: primer
SEQ ID NO: 18: primer
SEQ ID NO: 19: primer
SEQ ID NO: 20: primer
SEQ ID NO: 21: primer
SEQ ID NO: 22: primer
SEQ ID NO: 23: primer
SEQ ID NO: 24: primer
SEQ ID NO: 25: primer
SEQ ID NO: 26: primer
SEQ ID NO: 27: primer
SEQ ID NO: 28: primer
SEQ ID NO: 29: primer
SEQ ID NO: 30: primer
SEQ ID NO: 31: primer
SEQ ID NO: 32: primer
SEQ ID NO: 33: primer
SEQ ID NO: 34: primer
SEQ ID NO: 35: primer
SEQ ID NO: 36: primer

INDUSTRIAL APPLICABILITY

By using the GANP overexpressing mouse of the invention, it is possible to rapidly prepare antibodies specific to viral antigens and having high affinity therefor, which could not be obtained by conventional methods. Therefore, it is expected that specific and potent antibodies can be obtained rapidly enough to keep up with the mutations of viral antigens in order to prevent the worsening of conditions caused by prolonged infection such as AIDS or hepatitis C. Further, with the transgenic animal of the invention, it is possible to prepare tailored, specific antibodies corresponding to the mutations of viral antigens from infected patients. The period of immunization necessary for antibody preparation is about only 10 days, and the efficiency of producing antibodies with high affinity mutations reaches almost 60%. High affinity antibody production protocol using bed side patients' samples is expected to become a new immunotherapy that will take the place of vaccine therapy.

The invention claimed is:

1. A transgenic mouse, comprising a transferred recombinant mouse GANP gene encoding and expressing a protein of SEQ ID NO: 2 or progeny thereof encoding and expressing said protein, wherein said transgenic mouse produces high affinity antibody-producing B cells.

2. The transgenic mouse according to claim 1, wherein the GANP gene is expressed in B cells of the transgenic mouse, or its progeny.

3. A part of a transgenic mouse, comprising a transferred recombinant mouse GANP gene encoding and expressing a protein of SEQ ID NO: 2, or progeny thereof encoding and expressing said protein, wherein said part of the transgenic mouse produces high affinity antibody-producing B cells.

4. A method of producing a high affinity antibody, comprising:
   administering an antigen to the transgenic mouse according to claim 1 or its progeny; waiting for a time sufficient for said mouse to generate antibodies to said antigen; and recovering the antibody from the resultant mouse or progeny.

5. A high affinity-antibody producing cell which is taken from a transgenic mouse, comprising a transferred recombinant mouse GANP gene encoding and expressing a protein comprising SEQ ID NO: 2, or progeny thereof encoding and expressing said protein, and wherein said transgenic mouse or its progeny has been administered an antigen.

6. The method according to claim 4, comprising:
   obtaining blood from the mouse after administration of the antigen, separating and purifying antibodies from the blood to recover the antibody.

7. The method according to claim 4, wherein the antigen is administered two to three times at intervals of from 7 to 30 days.

8. The method according to claim 4, wherein an administration dose of the antigen is from 0.05 mg to 2 mg.

9. The method according to claim 4, wherein the route of administration is subcutaneous, dermal, intraperitoneal, intravenous or intramuscular.

10. The transgenic mouse according to claim 1, wherein said GANP gene is operably linked to a human IgG enhancer, or its progeny.

11. The method according to claim 4, wherein said GANP gene is operably linked to a human IgG enhancer.

12. The cell according to claim 5, wherein said GANP gene is operably linked to a human IgG enhancer, or its progeny.

* * * * *

SEQUENCE LISTING

```
<160> NUMBER OF SEQ ID NOS: 105

<210> SEQ ID NO 1
<211> LENGTH: 6429
<212> TYPE: DNA
<213> ORGANISM: Mus musculus
<220> FEATURE:
<221> NAME/KEY: CDS
<222> LOCATION: (384)..(6299)

<400> SEQUENCE: 1
gttgcggtgc ggtgggcccg gtagaggctg cacgcagact gtgggcgagc acaagcgctg      60
gcgacagtgg ccgtatctgg cggacttgct cctccctccg cggcctccgc tgtcccttgt     120
gtctttgccg agttgctgaa ggccttcact agtcttcgct cgaaggcgtc tgttaaccta     180
gcggccggct tccggagtgt taagcatcgg ggataaaaag ctattatttc tagaccaggg     240
catcgcaagt tcgagttacc gggagaaaaa tgagatggtc atcctgagga tgaaggagag     300
cttcccctgg caacagataa tttaaagagg agagctactt gtgtatagtc catatttatt     360
gccttcagat aattggcttg aag atg cac ccg gtg aac ccc ttc gga ggc agc     413
                          Met His Pro Val Asn Pro Phe Gly Gly Ser
                           1               5                  10 agc cca agt gct ttt gcg gta tct tcc agc acc acg gga aca tat cag       461
Ser Pro Ser Ala Phe Ala Val Ser Ser Ser Thr Thr Gly Thr Tyr Gln
             15                  20                  25 act aaa tca cca ttt cga ttt ggc cag cct tcc ctt ttt gga cag aac       509
Thr Lys Ser Pro Phe Arg Phe Gly Gln Pro Ser Leu Phe Gly Gln Asn
         30                  35                  40 agc aca ccc agc aag agc ctg gcg ttt tca caa gta cca agc ttt gca       557
Ser Thr Pro Ser Lys Ser Leu Ala Phe Ser Gln Val Pro Ser Phe Ala
     45                  50                  55 aca ccc tct gga gga agc cat tct tcc tcc ttg cca gca ttt gga ctc       605
Thr Pro Ser Gly Gly Ser His Ser Ser Ser Leu Pro Ala Phe Gly Leu
 60                  65                  70 acc caa acc tca agt gtg gga ctc ttc tct agt ctc gaa tcc aca cct       653
Thr Gln Thr Ser Ser Val Gly Leu Phe Ser Ser Leu Glu Ser Thr Pro
75                  80                  85                  90 tct ttc gca gct act tcg agt tcc tct gtg ccc ggc aat acg gca ttc       701
Ser Phe Ala Ala Thr Ser Ser Ser Ser Val Pro Gly Asn Thr Ala Phe
                 95                 100                 105 agc ttt aag tca acc tct agc gtt ggg gtt ttc cca agt ggc gct act       749
Ser Phe Lys Ser Thr Ser Ser Val Gly Val Phe Pro Ser Gly Ala Thr
            110                 115                 120 ttt ggg cca gaa acc gga gaa gta gca ggt tct ggc ttt cgg aag acg       797
Phe Gly Pro Glu Thr Gly Glu Val Ala Gly Ser Gly Phe Arg Lys Thr
        125                 130                 135 gaa ttc aag ttt aaa cct ctg gaa aat gca gtc ttc aaa ccg ata ccg       845
Glu Phe Lys Phe Lys Pro Leu Glu Asn Ala Val Phe Lys Pro Ile Pro
    140                 145                 150 ggg cct gag tca gag cca gaa aaa acc cag agc cag att tct tct gga       893
Gly Pro Glu Ser Glu Pro Glu Lys Thr Gln Ser Gln Ile Ser Ser Gly
155                 160                 165                 170 ttt ttt aca ttt tcc cat ccc gtt ggt agc ggg tct gga ggc ctg acc       941
Phe Phe Thr Phe Ser His Pro Val Gly Ser Gly Ser Gly Gly Leu Thr
```

```
                           175                 180                 185
cct ttt tct ttc cca cag gtg aca aat agt tcg gtg act agc tca agt          989
Pro Phe Ser Phe Pro Gln Val Thr Asn Ser Ser Val Thr Ser Ser Ser
                190                 195                 200 ttt atc ttt tcg aaa cca gtt act agt aat act cct gcc ttt gcc tct         1037
Phe Ile Phe Ser Lys Pro Val Thr Ser Asn Thr Pro Ala Phe Ala Ser
        205                 210                 215 cct ttg tct aac caa aat gta gaa gaa gag aag agg gtt tct acg tca         1085
Pro Leu Ser Asn Gln Asn Val Glu Glu Glu Lys Arg Val Ser Thr Ser
    220                 225                 230 gcg ttt gga agc tca aac agt agc ttc agt act ttc ccc aca gcg tca         1133
Ala Phe Gly Ser Ser Asn Ser Ser Phe Ser Thr Phe Pro Thr Ala Ser
235                 240                 245                 250 cca gga tct ttg ggg gag ccc ttc cca gct aac aaa cca agc ctc cgc         1181
Pro Gly Ser Leu Gly Glu Pro Phe Pro Ala Asn Lys Pro Ser Leu Arg
                255                 260                 265 caa gga tgt gag gaa gcc atc tcc cag gtg gag cca ctt ccc acc ctc         1229
Gln Gly Cys Glu Glu Ala Ile Ser Gln Val Glu Pro Leu Pro Thr Leu
        270                 275                 280 atg aag gga tta aag agg aaa gag gac cag gat cgc tcc ccg agg aga         1277
Met Lys Gly Leu Lys Arg Lys Glu Asp Gln Asp Arg Ser Pro Arg Arg
    285                 290                 295 cat tgc cac gag gca gca gaa gac cct gat ccc ctg tcc agg ggc gac         1325
His Cys His Glu Ala Ala Glu Asp Pro Asp Pro Leu Ser Arg Gly Asp
300                 305                 310 cat ccc cca gat aaa cgg cca gtc cgc ctc aac aga ccc cgg gga ggt         1373
His Pro Pro Asp Lys Arg Pro Val Arg Leu Asn Arg Pro Arg Gly Gly
315                 320                 325                 330 act ttg ttt ggc cgg aca ata cag gag gtc ttc aaa agc aat aaa gag         1421
Thr Leu Phe Gly Arg Thr Ile Gln Glu Val Phe Lys Ser Asn Lys Glu
                335                 340                 345 gca ggc cgc ctg ggc agc aag gaa tcc aag gag agt ggc ttt gcg gaa         1469
Ala Gly Arg Leu Gly Ser Lys Glu Ser Lys Glu Ser Gly Phe Ala Glu
        350                 355                 360 cct ggg gaa agt gac cac gcg gcc gtc cca gga ggg agt cag tcc acc         1517
Pro Gly Glu Ser Asp His Ala Ala Val Pro Gly Gly Ser Gln Ser Thr
    365                 370                 375 atg gta cct tcc cgc ctt cca gct gtg act aaa gag gaa gaa gaa agt         1565
Met Val Pro Ser Arg Leu Pro Ala Val Thr Lys Glu Glu Glu Glu Ser
380                 385                 390 aga gat gag aaa gaa gat tct ctc agg gga aag tct gtg cgc cag agt         1613
Arg Asp Glu Lys Glu Asp Ser Leu Arg Gly Lys Ser Val Arg Gln Ser
395                 400                 405                 410 aag cga agg gaa gag tgg atc tac agc ctc ggg ggc gtg tct tct tta         1661
Lys Arg Arg Glu Glu Trp Ile Tyr Ser Leu Gly Gly Val Ser Ser Leu
                415                 420                 425 gag ctc aca gcc atc cag tgc aag aac atc ccc gac tac ctc aac gac         1709
Glu Leu Thr Ala Ile Gln Cys Lys Asn Ile Pro Asp Tyr Leu Asn Asp
        430                 435                 440 aga gcc atc ctg gag aaa cac ttc agc aaa atc gct aaa gtc cag cgg         1757
Arg Ala Ile Leu Glu Lys His Phe Ser Lys Ile Ala Lys Val Gln Arg
    445                 450                 455 gtc ttc acc aga cgc agc aag aag ctc gcc gtg att cat ttt ttc gac         1805
Val Phe Thr Arg Arg Ser Lys Lys Leu Ala Val Ile His Phe Phe Asp
460                 465                 470 cac gca tcg gca gcc ctg gct agg aag aag ggg aaa ggt ctg cat aag         1853
His Ala Ser Ala Ala Leu Ala Arg Lys Lys Gly Lys Gly Leu His Lys
475                 480                 485                 490 gac gtg gtt atc ttt tgg cac aag aag aaa ata agt ccc agc aag aaa         1901
Asp Val Val Ile Phe Trp His Lys Lys Lys Ile Ser Pro Ser Lys Lys
```

-continued

|  |  |  |
|---|---|---|
| 495 | 500 | 505 |

| | | |
|---|---|---|
| ctc ttt ccc ctg aag gag aag ctt ggt gag agt gaa gcc agc cag ggc<br>Leu Phe Pro Leu Lys Glu Lys Leu Gly Glu Ser Glu Ala Ser Gln Gly<br>510               515               520 | 1949 |
| atc gag gac tcc ccc ttt cag cac tcg cct ctc agc aag ccc atc gtg<br>Ile Glu Asp Ser Pro Phe Gln His Ser Pro Leu Ser Lys Pro Ile Val<br>525               530               535 | 1997 |
| agg cct gca gcc ggc agc ctc ctc agc aaa agc tct cca gtg aag aag<br>Arg Pro Ala Ala Gly Ser Leu Leu Ser Lys Ser Ser Pro Val Lys Lys<br>540               545               550 | 2045 |
| ccg agt ctt ctg aag atg cac cag ttt gag gcg gat cct ttt gac tct<br>Pro Ser Leu Leu Lys Met His Gln Phe Glu Ala Asp Pro Phe Asp Ser<br>555               560               565               570 | 2093 |
| gga tct gag ggc tcc gag ggc ctt ggt tct tgc gtg tca tct ctt agc<br>Gly Ser Glu Gly Ser Glu Gly Leu Gly Ser Cys Val Ser Ser Leu Ser<br>575               580               585 | 2141 |
| acc ctg ata ggg act gtg gca gac aca tct gag gag aag tac cgc ctt<br>Thr Leu Ile Gly Thr Val Ala Asp Thr Ser Glu Glu Lys Tyr Arg Leu<br>590               595               600 | 2189 |
| ctg gac cag aga gac cgc atc atg cgg caa gct cga gtg aag agg acg<br>Leu Asp Gln Arg Asp Arg Ile Met Arg Gln Ala Arg Val Lys Arg Thr<br>605               610               615 | 2237 |
| gac ctg gac aaa gcc agg gca ttt gtt ggg act tgc cct gac atg tgt<br>Asp Leu Asp Lys Ala Arg Ala Phe Val Gly Thr Cys Pro Asp Met Cys<br>620               625               630 | 2285 |
| ccc gag aag gag cgg tac ttg agg gag acc cgg agc cag ctg agc gtg<br>Pro Glu Lys Glu Arg Tyr Leu Arg Glu Thr Arg Ser Gln Leu Ser Val<br>635               640               645               650 | 2333 |
| ttt gaa gtt gtc cca ggg act gac cag gtg gac cat gca gca gcc gtg<br>Phe Glu Val Val Pro Gly Thr Asp Gln Val Asp His Ala Ala Ala Val<br>655               660               665 | 2381 |
| aag gag tac agc cgg tcc tct gca gat cag gag gag ccc ctg cca cat<br>Lys Glu Tyr Ser Arg Ser Ser Ala Asp Gln Glu Glu Pro Leu Pro His<br>670               675               680 | 2429 |
| gag ctg aga ccc tca gca gtt ctc agc agg acc atg gac tac ctg gtg<br>Glu Leu Arg Pro Ser Ala Val Leu Ser Arg Thr Met Asp Tyr Leu Val<br>685               690               695 | 2477 |
| acc cag atc atg gac caa aag gaa ggc agc ctt cgg gat tgg tat gac<br>Thr Gln Ile Met Asp Gln Lys Glu Gly Ser Leu Arg Asp Trp Tyr Asp<br>700               705               710 | 2525 |
| ttc gtg tgg aac cgc acc cgg ggt ata cgg aag gac ata aca cag cag<br>Phe Val Trp Asn Arg Thr Arg Gly Ile Arg Lys Asp Ile Thr Gln Gln<br>715               720               725               730 | 2573 |
| cac ctc tgt gat ccc ctg acg gtg tct ctg atc gag aag tgt acc cga<br>His Leu Cys Asp Pro Leu Thr Val Ser Leu Ile Glu Lys Cys Thr Arg<br>735               740               745 | 2621 |
| ttt cac att cac tgt gcc cac ttt atg tgt gag gag cct atg tct tcc<br>Phe His Ile His Cys Ala His Phe Met Cys Glu Glu Pro Met Ser Ser<br>750               755               760 | 2669 |
| ttt gat gcc aag atc aac aat gag aac atg acc aag tgt cta cag agt<br>Phe Asp Ala Lys Ile Asn Asn Glu Asn Met Thr Lys Cys Leu Gln Ser<br>765             770               775 | 2717 |
| ctg aag gag atg tac cag gac ctg agg aac aag ggt gtt ttt tgt gcc<br>Leu Lys Glu Met Tyr Gln Asp Leu Arg Asn Lys Gly Val Phe Cys Ala<br>780             785               790 | 2765 |
| agt gaa gca gag ttt cag ggc tac aat gtc ctg ctt aat ctc aac aaa<br>Ser Glu Ala Glu Phe Gln Gly Tyr Asn Val Leu Leu Asn Leu Asn Lys<br>795             800             805               810 | 2813 |
| gga gac att ttg aga gaa gtg cag cag ttc cac cct gac gtt agg aac<br>Gly Asp Ile Leu Arg Glu Val Gln Gln Phe His Pro Asp Val Arg Asn | 2861 |

-continued

```
                815                 820                 825
tcc cca gag gtg aac ttc gct gtc cag gct ttt gct gca ttg aac agc    2909
Ser Pro Glu Val Asn Phe Ala Val Gln Ala Phe Ala Ala Leu Asn Ser
            830                 835                 840 aat aat ttt gtg aga ttt ttc aaa ctg gtt cag tca gct tct tac ctg    2957
Asn Asn Phe Val Arg Phe Phe Lys Leu Val Gln Ser Ala Ser Tyr Leu
            845                 850                 855 aat gcg tgc ctg tta cac tgt tac ttt aat cag atc cgc aag gat gcc    3005
Asn Ala Cys Leu Leu His Cys Tyr Phe Asn Gln Ile Arg Lys Asp Ala
            860                 865                 870 ctc cgg gca ctc aat gtt gct tat act gta agc aca cag cgc tct acc    3053
Leu Arg Ala Leu Asn Val Ala Tyr Thr Val Ser Thr Gln Arg Ser Thr
875                 880                 885                 890 gtc ttc ccc ctg gat ggt gtc gtc cgc atg ctg ctg ttc aga gat agt    3101
Val Phe Pro Leu Asp Gly Val Val Arg Met Leu Leu Phe Arg Asp Ser
                895                 900                 905 gaa gag gcg aca aac ttc ctc aat tac cat ggc ctc act gta gct gat    3149
Glu Glu Ala Thr Asn Phe Leu Asn Tyr His Gly Leu Thr Val Ala Asp
            910                 915                 920 ggc tgt gtt gag ctg aat cgg tcg gca ttc ttg gaa ccg gag gga tta    3197
Gly Cys Val Glu Leu Asn Arg Ser Ala Phe Leu Glu Pro Glu Gly Leu
            925                 930                 935 tgc aag gcc agg aag tca gtg ttt att ggc cgg aag ctg acg gtg tca    3245
Cys Lys Ala Arg Lys Ser Val Phe Ile Gly Arg Lys Leu Thr Val Ser
            940                 945                 950 gtt ggg gaa gtt gtg aat gga ggg ccg ttg ccc cct gtt cct cgc cat    3293
Val Gly Glu Val Val Asn Gly Gly Pro Leu Pro Pro Val Pro Arg His
955                 960                 965                 970 aca cct gtg tgc agc ttc aac tcc cag aat aag tac gtt gga gag agc    3341
Thr Pro Val Cys Ser Phe Asn Ser Gln Asn Lys Tyr Val Gly Glu Ser
                975                 980                 985 ctg gct acg gag ctg ccc atc agc act cag aga gct ggt gga gac cca    3389
Leu Ala Thr Glu Leu Pro Ile Ser Thr Gln Arg Ala Gly Gly Asp Pro
            990                 995                 1000 gca ggt ggt ggc aga gga gag gac tgt gag gca gag gtg gac ttg        3434
Ala Gly Gly Gly Arg Gly Glu Asp Cys Glu Ala Glu Val Asp Leu
            1005                1010                1015 cca aca ttg gcg gtc ctc cca cag ccg cct cct gca tcc tca gcc        3479
Pro Thr Leu Ala Val Leu Pro Gln Pro Pro Pro Ala Ser Ser Ala
            1020                1025                1030 acg ccg gcg ctt cat gtc cag cca ctg gcc cca gcc gca gca ccc        3524
Thr Pro Ala Leu His Val Gln Pro Leu Ala Pro Ala Ala Ala Pro
            1035                1040                1045 agc ctt ctc cag gcc tcc acg cag cct gag gtg ctg ctt cca aag        3569
Ser Leu Leu Gln Ala Ser Thr Gln Pro Glu Val Leu Leu Pro Lys
            1050                1055                1060 cct gcg cct gtg tac tct gac tcg gac ctg gta cag gtg gtg gac        3614
Pro Ala Pro Val Tyr Ser Asp Ser Asp Leu Val Gln Val Val Asp
            1065                1070                1075 gag ctc atc cag gag gct ctg caa gtg gac tgt gag gaa gtc agc        3659
Glu Leu Ile Gln Glu Ala Leu Gln Val Asp Cys Glu Glu Val Ser
            1080                1085                1090 tcc gct ggg gca gcc tac gta gcc gca gct ctg ggc gtt tcc aat        3704
Ser Ala Gly Ala Ala Tyr Val Ala Ala Ala Leu Gly Val Ser Asn
            1095                1100                1105 gct gct gtg gag gat ctg att act gct gcg acc acg ggc att ctg        3749
Ala Ala Val Glu Asp Leu Ile Thr Ala Ala Thr Thr Gly Ile Leu
            1110                1115                1120 agg cac gtt gcc gct gag gaa gtt tcc atg gaa agg cag aga cta        3794
Arg His Val Ala Ala Glu Glu Val Ser Met Glu Arg Gln Arg Leu
```

-continued

|  |  |  |  |  |  |  |  |  |  |  |  |  |
|---|---|---|---|---|---|---|---|---|---|---|---|---|
|  |  | 1125 |  |  | 1130 |  |  |  | 1135 |  |  |  |
| gag | gaa | gag | aag | caa | cga | gct | gag | gag | gaa | cgg | ttg | aag | caa | gag | 3839 |
| Glu | Glu | Glu | Lys | Gln | Arg | Ala | Glu | Glu | Glu | Arg | Leu | Lys | Gln | Glu |  |
|  |  | 1140 |  |  | 1145 |  |  |  | 1150 |  |  |  |
| aga | gaa | ctg | atg | tta | act | cag | ctg | agc | gag | ggt | ctg | gcc | gca | gag | 3884 |
| Arg | Glu | Leu | Met | Leu | Thr | Gln | Leu | Ser | Glu | Gly | Leu | Ala | Ala | Glu |  |
|  |  | 1155 |  |  | 1160 |  |  |  | 1165 |  |  |  |
| ctg | aca | gaa | ctc | acg | gtg | aca | gag | tgt | gtg | tgg | gaa | acc | tgc | tct | 3929 |
| Leu | Thr | Glu | Leu | Thr | Val | Thr | Glu | Cys | Val | Trp | Glu | Thr | Cys | Ser |  |
|  |  | 1170 |  |  | 1175 |  |  |  | 1180 |  |  |  |
| cag | gag | cta | cag | agt | gca | gta | aaa | ata | gac | cag | aag | gtc | cgt | gtg | 3974 |
| Gln | Glu | Leu | Gln | Ser | Ala | Val | Lys | Ile | Asp | Gln | Lys | Val | Arg | Val |  |
|  |  | 1185 |  |  | 1190 |  |  |  | 1195 |  |  |  |
| gcc | cgc | tgt | tgt | gaa | gcc | gtc | tgt | gca | cac | ctg | gtg | gat | ttg | ttt | 4019 |
| Ala | Arg | Cys | Cys | Glu | Ala | Val | Cys | Ala | His | Leu | Val | Asp | Leu | Phe |  |
|  |  | 1200 |  |  | 1205 |  |  |  | 1210 |  |  |  |
| ctt | gct | gag | gaa | att | ttc | cag | act | gca | aaa | gag | aca | ctc | cag | gaa | 4064 |
| Leu | Ala | Glu | Glu | Ile | Phe | Gln | Thr | Ala | Lys | Glu | Thr | Leu | Gln | Glu |  |
|  |  | 1215 |  |  | 1220 |  |  |  | 1225 |  |  |  |
| ctc | cag | tgt | ttc | tgc | aag | tat | cta | caa | cgg | tgg | agg | gag | gct | gtt | 4109 |
| Leu | Gln | Cys | Phe | Cys | Lys | Tyr | Leu | Gln | Arg | Trp | Arg | Glu | Ala | Val |  |
|  |  | 1230 |  |  | 1235 |  |  |  | 1240 |  |  |  |
| gca | gct | cgg | aag | aaa | ttc | cgg | cgt | cag | atg | cgg | gcc | ttc | cct | gca | 4154 |
| Ala | Ala | Arg | Lys | Lys | Phe | Arg | Arg | Gln | Met | Arg | Ala | Phe | Pro | Ala |  |
|  |  | 1245 |  |  | 1250 |  |  |  | 1255 |  |  |  |
| gcg | cca | tgc | tgt | gtg | gat | gtg | aat | gac | cgg | ctg | cag | gca | cta | gtg | 4199 |
| Ala | Pro | Cys | Cys | Val | Asp | Val | Asn | Asp | Arg | Leu | Gln | Ala | Leu | Val |  |
|  |  | 1260 |  |  | 1265 |  |  |  | 1270 |  |  |  |
| ccc | agc | gca | gag | tgc | ccc | att | act | gag | gag | aac | ctg | gcc | aag | ggt | 4244 |
| Pro | Ser | Ala | Glu | Cys | Pro | Ile | Thr | Glu | Glu | Asn | Leu | Ala | Lys | Gly |  |
|  |  | 1275 |  |  | 1280 |  |  |  | 1285 |  |  |  |
| ctt | ttg | gac | ctg | ggc | cac | gca | ggc | aaa | gta | ggc | gtc | tcc | tgt | acc | 4289 |
| Leu | Leu | Asp | Leu | Gly | His | Ala | Gly | Lys | Val | Gly | Val | Ser | Cys | Thr |  |
|  |  | 1290 |  |  | 1295 |  |  |  | 1300 |  |  |  |
| agg | ttg | agg | cgg | ctt | aga | aac | aag | aca | gct | cac | cag | ata | aag | gtc | 4334 |
| Arg | Leu | Arg | Arg | Leu | Arg | Asn | Lys | Thr | Ala | His | Gln | Ile | Lys | Val |  |
|  |  | 1305 |  |  | 1310 |  |  |  | 1315 |  |  |  |
| cag | cac | ttc | cac | cag | cag | ctg | ctg | agg | aat | gct | gca | tgg | gca | cct | 4379 |
| Gln | His | Phe | His | Gln | Gln | Leu | Leu | Arg | Asn | Ala | Ala | Trp | Ala | Pro |  |
|  |  | 1320 |  |  | 1325 |  |  |  | 1330 |  |  |  |
| ctg | gac | ctg | cca | tcc | att | gtg | tct | gag | cac | ctc | ccc | atg | aag | cag | 4424 |
| Leu | Asp | Leu | Pro | Ser | Ile | Val | Ser | Glu | His | Leu | Pro | Met | Lys | Gln |  |
|  |  | 1335 |  |  | 1340 |  |  |  | 1345 |  |  |  |
| aag | cga | agg | ttt | tgg | aaa | ctg | gtg | ctg | gtg | ttg | cct | gat | gtg | gaa | 4469 |
| Lys | Arg | Arg | Phe | Trp | Lys | Leu | Val | Leu | Val | Leu | Pro | Asp | Val | Glu |  |
|  |  | 1350 |  |  | 1355 |  |  |  | 1360 |  |  |  |
| gag | cag | act | cca | gag | agt | cct | ggc | aga | ata | cta | gaa | aac | tgg | cta | 4514 |
| Glu | Gln | Thr | Pro | Glu | Ser | Pro | Gly | Arg | Ile | Leu | Glu | Asn | Trp | Leu |  |
|  |  | 1365 |  |  | 1370 |  |  |  | 1375 |  |  |  |
| aag | gtc | aaa | ttc | aca | gga | gat | gac | agc | atg | gtg | ggt | gac | ata | gga | 4559 |
| Lys | Val | Lys | Phe | Thr | Gly | Asp | Asp | Ser | Met | Val | Gly | Asp | Ile | Gly |  |
|  |  | 1380 |  |  | 1385 |  |  |  | 1390 |  |  |  |
| gat | aat | gct | ggt | gat | atc | cag | acc | ctc | tca | gtc | ttt | aat | aca | ctt | 4604 |
| Asp | Asn | Ala | Gly | Asp | Ile | Gln | Thr | Leu | Ser | Val | Phe | Asn | Thr | Leu |  |
|  |  | 1395 |  |  | 1400 |  |  |  | 1405 |  |  |  |
| agt | agt | aaa | ggg | gat | caa | aca | gtt | tct | gtc | aac | gtg | tgt | ata | aag | 4649 |
| Ser | Ser | Lys | Gly | Asp | Gln | Thr | Val | Ser | Val | Asn | Val | Cys | Ile | Lys |  |
|  |  | 1410 |  |  | 1415 |  |  |  | 1420 |  |  |  |
| gtg | gct | cat | ggc | acc | ctt | agt | gac | agt | gcc | ctt | gat | gct | gtg | gag | 4694 |
| Val | Ala | His | Gly | Thr | Leu | Ser | Asp | Ser | Ala | Leu | Asp | Ala | Val | Glu |  |

|  |  |  |  |  |  |  |  |  |  |  |  |  |
|---|---|---|---|---|---|---|---|---|---|---|---|---|
| | | 1425 | | | 1430 | | | | 1435 | | | |
| acc | cag | aag | gac | ctg | ttg | gga | acc | agt | ggg | ctc | atg | ctg | ctg | ctt | 4739 |
| Thr | Gln | Lys | Asp | Leu | Leu | Gly | Thr | Ser | Gly | Leu | Met | Leu | Leu | Leu | |
| | | 1440 | | | | 1445 | | | | | 1450 | | | | |

| ccc | ccg | aaa | gtg | aag | agt | gag | gag | gtg | gca | gag | gag | gaa | ctg | tcc | 4784 |
| Pro | Pro | Lys | Val | Lys | Ser | Glu | Glu | Val | Ala | Glu | Glu | Glu | Leu | Ser |  |
|     |     | 1455 |     |     |     |     | 1460 |     |     |     |     | 1465 |     |     |     |

| tgg | ctg | tcg | gct | tta | ctg | cag | ctc | aag | cag | ctt | ctg | cag | gcc | aag | 4829 |
| Trp | Leu | Ser | Ala | Leu | Leu | Gln | Leu | Lys | Gln | Leu | Leu | Gln | Ala | Lys |  |
|     |     | 1470 |     |     |     |     | 1475 |     |     |     |     | 1480 |     |     |     |

| ccc | ttc | cag | cct | gcc | ctg | ccg | ctg | gtg | gtc | ctc | gtg | ccc | agc | tcc | 4874 |
| Pro | Phe | Gln | Pro | Ala | Leu | Pro | Leu | Val | Val | Leu | Val | Pro | Ser | Ser |  |
|     |     | 1485 |     |     |     |     | 1490 |     |     |     |     | 1495 |     |     |     |

| aga | ggg | gac | tcc | gcg | ggg | agg | gca | gta | gag | gac | ggt | ctg | atg | tta | 4919 |
| Arg | Gly | Asp | Ser | Ala | Gly | Arg | Ala | Val | Glu | Asp | Gly | Leu | Met | Leu |  |
|     |     | 1500 |     |     |     |     | 1505 |     |     |     |     | 1510 |     |     |     |

| cag | gat | ttg | gtt | tca | gcc | aag | ctg | att | tcc | gat | tac | att | gtt | gtt | 4964 |
| Gln | Asp | Leu | Val | Ser | Ala | Lys | Leu | Ile | Ser | Asp | Tyr | Ile | Val | Val |  |
|     |     | 1515 |     |     |     |     | 1520 |     |     |     |     | 1525 |     |     |     |

| gag | att | cct | gac | tct | gtt | aat | gat | tta | caa | ggc | aca | gtg | aag | gtt | 5009 |
| Glu | Ile | Pro | Asp | Ser | Val | Asn | Asp | Leu | Gln | Gly | Thr | Val | Lys | Val |  |
|     |     | 1530 |     |     |     |     | 1535 |     |     |     |     | 1540 |     |     |     |

| tct | gga | gca | gtc | cag | tgg | ctg | atc | tcc | gga | tgt | cct | caa | gcc | cta | 5054 |
| Ser | Gly | Ala | Val | Gln | Trp | Leu | Ile | Ser | Gly | Cys | Pro | Gln | Ala | Leu |  |
|     |     | 1545 |     |     |     |     | 1550 |     |     |     |     | 1555 |     |     |     |

| gac | ctt | tgc | tgc | cag | acc | ctt | gtt | cag | tat | gtt | gag | gat | ggg | atc | 5099 |
| Asp | Leu | Cys | Cys | Gln | Thr | Leu | Val | Gln | Tyr | Val | Glu | Asp | Gly | Ile |  |
|     |     | 1560 |     |     |     |     | 1565 |     |     |     |     | 1570 |     |     |     |

| agc | cgc | gag | ttc | agc | cgt | cgg | ttt | ttc | cac | gac | agg | aga | gag | agg | 5144 |
| Ser | Arg | Glu | Phe | Ser | Arg | Arg | Phe | Phe | His | Asp | Arg | Arg | Glu | Arg |  |
|     |     | 1575 |     |     |     |     | 1580 |     |     |     |     | 1585 |     |     |     |

| cgc | ctg | gct | agc | ctg | ccc | tcc | cag | gag | cct | agc | acc | att | att | gag | 5189 |
| Arg | Leu | Ala | Ser | Leu | Pro | Ser | Gln | Glu | Pro | Ser | Thr | Ile | Ile | Glu |  |
|     |     | 1590 |     |     |     |     | 1595 |     |     |     |     | 1600 |     |     |     |

| ttg | ttc | aac | agt | gtg | ctg | cag | ttc | ctg | gcc | tct | gtg | gta | tcc | tct | 5234 |
| Leu | Phe | Asn | Ser | Val | Leu | Gln | Phe | Leu | Ala | Ser | Val | Val | Ser | Ser |  |
|     |     | 1605 |     |     |     |     | 1610 |     |     |     |     | 1615 |     |     |     |

| gag | cag | ctg | tgt | gac | atc | tcc | tgg | cct | gtc | atg | gaa | ttt | gcc | gaa | 5279 |
| Glu | Gln | Leu | Cys | Asp | Ile | Ser | Trp | Pro | Val | Met | Glu | Phe | Ala | Glu |  |
|     |     | 1620 |     |     |     |     | 1625 |     |     |     |     | 1630 |     |     |     |

| gtg | gga | ggc | agc | cag | ctg | ctt | cct | cac | ctg | cac | tgg | aac | tca | cca | 5324 |
| Val | Gly | Gly | Ser | Gln | Leu | Leu | Pro | His | Leu | His | Trp | Asn | Ser | Pro |  |
|     |     | 1635 |     |     |     |     | 1640 |     |     |     |     | 1645 |     |     |     |

| gag | cat | cta | gcg | tgg | ctg | aaa | caa | gct | gtg | ctt | ggg | ttc | cag | ctt | 5369 |
| Glu | His | Leu | Ala | Trp | Leu | Lys | Gln | Ala | Val | Leu | Gly | Phe | Gln | Leu |  |
|     |     | 1650 |     |     |     |     | 1655 |     |     |     |     | 1660 |     |     |     |

| cca | cag | atg | gac | ctt | cca | ccc | cca | ggg | gcc | ccc | tgg | ctc | cct | gtg | 5414 |
| Pro | Gln | Met | Asp | Leu | Pro | Pro | Pro | Gly | Ala | Pro | Trp | Leu | Pro | Val |  |
|     |     | 1665 |     |     |     |     | 1670 |     |     |     |     | 1675 |     |     |     |

| tgt | tcc | atg | gtc | att | cag | tac | acc | tcc | cag | att | ccc | agc | tca | agc | 5459 |
| Cys | Ser | Met | Val | Ile | Gln | Tyr | Thr | Ser | Gln | Ile | Pro | Ser | Ser | Ser |  |
|     |     | 1680 |     |     |     |     | 1685 |     |     |     |     | 1690 |     |     |     |

| cag | aca | cag | cct | gtc | ctc | cag | tcc | cag | gcg | gag | aac | ctg | ctg | tgc | 5504 |
| Gln | Thr | Gln | Pro | Val | Leu | Gln | Ser | Gln | Ala | Glu | Asn | Leu | Leu | Cys |  |
|     |     | 1695 |     |     |     |     | 1700 |     |     |     |     | 1705 |     |     |     |

| aga | aca | tac | cag | aag | tgg | aag | aac | aag | agc | ctc | tct | cca | ggc | cag | 5549 |
| Arg | Thr | Tyr | Gln | Lys | Trp | Lys | Asn | Lys | Ser | Leu | Ser | Pro | Gly | Gln |  |
|     |     | 1710 |     |     |     |     | 1715 |     |     |     |     | 1720 |     |     |     |

| gag | ttg | ggg | cct | tct | gtt | gcc | gag | atc | ccg | tgg | gat | gac | atc | atc | 5594 |
| Glu | Leu | Gly | Pro | Ser | Val | Ala | Glu | Ile | Pro | Trp | Asp | Asp | Ile | Ile |  |

```
                1725                1730               1735
acc tta tgc atc aat cat aag ctg agg gac tgg aca ccc ccc agg      5639
Thr Leu Cys Ile Asn His Lys Leu Arg Asp Trp Thr Pro Pro Arg
        1740                1745               1750 ctc cct gtc aca tta gag gcg ctg agt gaa gat ggt caa ata tgt      5684
Leu Pro Val Thr Leu Glu Ala Leu Ser Glu Asp Gly Gln Ile Cys
        1755                1760               1765 gtg tat ttt ttc aaa aac ctt tta aga aaa tac cac gtt ccc tcg      5729
Val Tyr Phe Phe Lys Asn Leu Leu Arg Lys Tyr His Val Pro Ser
        1770                1775               1780 tca tgg gaa cag gcc aga atg cag acg cag cgg gaa ctg cag ctg      5774
Ser Trp Glu Gln Ala Arg Met Gln Thr Gln Arg Glu Leu Gln Leu
        1785                1790               1795 agt cat gga cgt tcg ggg atg agg tcc atc cat cct cct aca agc      5819
Ser His Gly Arg Ser Gly Met Arg Ser Ile His Pro Pro Thr Ser
        1800                1805               1810 act ttt cct act cca ttg ctt cat gta cac cag aaa ggg aag aaa      5864
Thr Phe Pro Thr Pro Leu Leu His Val His Gln Lys Gly Lys Lys
        1815                1820               1825 aag gaa gag agt ggc cga gag ggg agc ctc agt aca gag gac ctc      5909
Lys Glu Glu Ser Gly Arg Glu Gly Ser Leu Ser Thr Glu Asp Leu
        1830                1835               1840 ctg cgg ggg gct tct gca gaa gag ctc ctg gca cag agt ctg tcc      5954
Leu Arg Gly Ala Ser Ala Glu Glu Leu Leu Ala Gln Ser Leu Ser
        1845                1850               1855 agc agt ctt ctg gaa gag aag gaa gag aac aag agg ttt gaa gat      5999
Ser Ser Leu Leu Glu Glu Lys Glu Glu Asn Lys Arg Phe Glu Asp
        1860                1865               1870 caa ctt cag cag tgg tta tcg caa gac tca cag gca ttc aca gag      6044
Gln Leu Gln Gln Trp Leu Ser Gln Asp Ser Gln Ala Phe Thr Glu
        1875                1880               1885 tca act cgg ctt cct ctc tac ctc cct cag acg cta gtg tcc ttt      6089
Ser Thr Arg Leu Pro Leu Tyr Leu Pro Gln Thr Leu Val Ser Phe
        1890                1895               1900 cct gat tct atc aaa act cag acc atg gtg aaa aca tct aca agt      6134
Pro Asp Ser Ile Lys Thr Gln Thr Met Val Lys Thr Ser Thr Ser
        1905                1910               1915 cct cag aat tca gga aca gga aag cag ttg agg ttc tca gag gca      6179
Pro Gln Asn Ser Gly Thr Gly Lys Gln Leu Arg Phe Ser Glu Ala
        1920                1925               1930 tcc ggt tca tcc ctg acg gaa aag ctg aag ctc ctg gaa agg ctg      6224
Ser Gly Ser Ser Leu Thr Glu Lys Leu Lys Leu Leu Glu Arg Leu
        1935                1940               1945 atc cag agc tca agg gcg gaa gaa gca gcc tcc gag ctg cac ctc      6269
Ile Gln Ser Ser Arg Ala Glu Glu Ala Ala Ser Glu Leu His Leu
        1950                1955               1960 tct gca ctg ctg gag atg gtg gac atg tag ctgtctgacg ggagacggat   6319
Ser Ala Leu Leu Glu Met Val Asp Met Met
        1965                1970 ctctaattca taatgctttg tctgtattca attgtgttat agatgctgtt ggaaatgtga    6379
ctattaatta tgcaaataaa ctttttgaat cattccaaaa aaaaaaccat              6429

<210> SEQ ID NO 2
<211> LENGTH: 1971
<212> TYPE: PRT
<213> ORGANISM: Mus musclus

<400> SEQUENCE: 2

Met His Pro Val Asn Pro Phe Gly Gly Ser Ser Pro Ser Ala Phe Ala
1               5                   10                  15
```

-continued

Val Ser Ser Thr Thr Gly Thr Tyr Gln Thr Lys Ser Pro Phe Arg
          20                  25                  30

Phe Gly Gln Pro Ser Leu Phe Gly Gln Asn Ser Thr Pro Ser Lys Ser
         35                  40                  45

Leu Ala Phe Ser Gln Val Pro Ser Phe Ala Thr Pro Ser Gly Gly Ser
 50                  55                  60

His Ser Ser Ser Leu Pro Ala Phe Gly Leu Thr Gln Thr Ser Ser Val
 65                  70                  75                  80

Gly Leu Phe Ser Ser Leu Glu Ser Thr Pro Ser Phe Ala Ala Thr Ser
             85                  90                  95

Ser Ser Ser Val Pro Gly Asn Thr Ala Phe Ser Phe Lys Ser Thr Ser
            100                 105                 110

Ser Val Gly Val Phe Pro Ser Gly Ala Thr Phe Gly Pro Glu Thr Gly
            115                 120                 125

Glu Val Ala Gly Ser Gly Phe Arg Lys Thr Glu Phe Lys Phe Lys Pro
130                 135                 140

Leu Glu Asn Ala Val Phe Lys Pro Ile Pro Gly Pro Glu Ser Glu Pro
145                 150                 155                 160

Glu Lys Thr Gln Ser Gln Ile Ser Ser Gly Phe Phe Thr Phe Ser His
                165                 170                 175

Pro Val Gly Ser Gly Ser Gly Gly Leu Thr Pro Phe Ser Phe Pro Gln
            180                 185                 190

Val Thr Asn Ser Ser Val Thr Ser Ser Phe Ile Phe Ser Lys Pro
            195                 200                 205

Val Thr Ser Asn Thr Pro Ala Phe Ala Ser Pro Leu Ser Asn Gln Asn
210                 215                 220

Val Glu Glu Lys Arg Val Ser Thr Ser Ala Phe Gly Ser Ser Asn
225                 230                 235                 240

Ser Ser Phe Ser Thr Phe Pro Thr Ala Ser Pro Gly Ser Leu Gly Glu
            245                 250                 255

Pro Phe Pro Ala Asn Lys Pro Ser Leu Arg Gln Gly Cys Glu Glu Ala
            260                 265                 270

Ile Ser Gln Val Glu Pro Leu Pro Thr Leu Met Lys Gly Leu Lys Arg
            275                 280                 285

Lys Glu Asp Gln Asp Arg Ser Pro Arg Arg His Cys His Glu Ala Ala
290                 295                 300

Glu Asp Pro Asp Pro Leu Ser Arg Gly Asp His Pro Pro Asp Lys Arg
305                 310                 315                 320

Pro Val Arg Leu Asn Arg Pro Arg Gly Gly Thr Leu Phe Gly Arg Thr
                325                 330                 335

Ile Gln Glu Val Phe Lys Ser Asn Lys Glu Ala Gly Arg Leu Gly Ser
            340                 345                 350

Lys Glu Ser Lys Glu Ser Gly Phe Ala Glu Pro Gly Glu Ser Asp His
            355                 360                 365

Ala Ala Val Pro Gly Gly Ser Gln Ser Thr Met Val Pro Ser Arg Leu
        370                 375                 380

Pro Ala Val Thr Lys Glu Glu Glu Glu Ser Arg Asp Glu Lys Glu Asp
385                 390                 395                 400

Ser Leu Arg Gly Lys Ser Val Arg Gln Ser Lys Arg Arg Glu Glu Trp
                405                 410                 415

Ile Tyr Ser Leu Gly Gly Val Ser Ser Leu Glu Leu Thr Ala Ile Gln
            420                 425                 430

Cys Lys Asn Ile Pro Asp Tyr Leu Asn Asp Arg Ala Ile Leu Glu Lys

```
                435                 440                 445
His Phe Ser Lys Ile Ala Lys Val Gln Arg Val Phe Thr Arg Arg Ser
450                 455                 460

Lys Lys Leu Ala Val Ile His Phe Phe Asp His Ala Ser Ala Ala Leu
465                 470                 475                 480

Ala Arg Lys Lys Gly Lys Gly Leu His Lys Asp Val Val Ile Phe Trp
                485                 490                 495

His Lys Lys Ile Ser Pro Ser Lys Leu Phe Pro Leu Lys Glu
            500                 505                 510

Lys Leu Gly Glu Ser Glu Ala Ser Gln Gly Ile Glu Asp Ser Pro Phe
            515                 520                 525

Gln His Ser Pro Leu Ser Lys Pro Ile Val Arg Pro Ala Ala Gly Ser
            530                 535                 540

Leu Leu Ser Lys Ser Ser Pro Val Lys Lys Pro Ser Leu Leu Lys Met
545                 550                 555                 560

His Gln Phe Glu Ala Asp Pro Phe Asp Ser Gly Ser Glu Gly Ser Glu
                565                 570                 575

Gly Leu Gly Ser Cys Val Ser Ser Leu Ser Thr Leu Ile Gly Thr Val
            580                 585                 590

Ala Asp Thr Ser Glu Glu Lys Tyr Arg Leu Leu Asp Gln Arg Asp Arg
            595                 600                 605

Ile Met Arg Gln Ala Arg Val Lys Arg Thr Asp Leu Asp Lys Ala Arg
610                 615                 620

Ala Phe Val Gly Thr Cys Pro Asp Met Cys Pro Glu Lys Glu Arg Tyr
625                 630                 635                 640

Leu Arg Glu Thr Arg Ser Gln Leu Ser Val Phe Glu Val Val Pro Gly
                645                 650                 655

Thr Asp Gln Val Asp His Ala Ala Ala Val Lys Glu Tyr Ser Arg Ser
            660                 665                 670

Ser Ala Asp Gln Glu Pro Leu Pro His Glu Leu Arg Pro Ser Ala
            675                 680                 685

Val Leu Ser Arg Thr Met Asp Tyr Leu Val Thr Gln Ile Met Asp Gln
690                 695                 700

Lys Glu Gly Ser Leu Arg Asp Trp Tyr Asp Phe Val Trp Asn Arg Thr
705                 710                 715                 720

Arg Gly Ile Arg Lys Asp Ile Thr Gln Gln His Leu Cys Asp Pro Leu
                725                 730                 735

Thr Val Ser Leu Ile Glu Lys Cys Thr Arg Phe His Ile His Cys Ala
            740                 745                 750

His Phe Met Cys Glu Glu Pro Met Ser Ser Phe Asp Ala Lys Ile Asn
            755                 760                 765

Asn Glu Asn Met Thr Lys Cys Leu Gln Ser Leu Lys Glu Met Tyr Gln
770                 775                 780

Asp Leu Arg Asn Lys Gly Val Phe Cys Ala Ser Glu Ala Glu Phe Gln
785                 790                 795                 800

Gly Tyr Asn Val Leu Leu Asn Leu Asn Lys Gly Asp Ile Leu Arg Glu
                805                 810                 815

Val Gln Gln Phe His Pro Asp Val Arg Asn Ser Pro Glu Val Asn Phe
            820                 825                 830

Ala Val Gln Ala Phe Ala Ala Leu Asn Ser Asn Asn Phe Val Arg Phe
            835                 840                 845

Phe Lys Leu Val Gln Ser Ala Ser Tyr Leu Asn Ala Cys Leu Leu His
850                 855                 860
```

-continued

Cys Tyr Phe Asn Gln Ile Arg Lys Asp Ala Leu Arg Ala Leu Asn Val
865                 870                 875                 880

Ala Tyr Thr Val Ser Thr Gln Arg Ser Thr Val Phe Pro Leu Asp Gly
            885                 890                 895

Val Val Arg Met Leu Leu Phe Arg Asp Ser Glu Glu Ala Thr Asn Phe
        900                 905                 910

Leu Asn Tyr His Gly Leu Thr Val Ala Asp Gly Cys Val Glu Leu Asn
            915                 920                 925

Arg Ser Ala Phe Leu Glu Pro Glu Gly Leu Cys Lys Ala Arg Lys Ser
        930                 935                 940

Val Phe Ile Gly Arg Lys Leu Thr Val Ser Val Gly Glu Val Val Asn
945                 950                 955                 960

Gly Gly Pro Leu Pro Pro Val Pro Arg His Thr Pro Val Cys Ser Phe
                965                 970                 975

Asn Ser Gln Asn Lys Tyr Val Gly Glu Ser Leu Ala Thr Glu Leu Pro
            980                 985                 990

Ile Ser Thr Gln Arg Ala Gly Gly Asp Pro Ala Gly Gly Arg Gly
                995                 1000                1005

Glu Asp Cys Glu Ala Glu Val Asp Leu Pro Thr Leu Ala Val Leu
    1010                1015                1020

Pro Gln Pro Pro Pro Ala Ser Ser Ala Thr Pro Ala Leu His Val
    1025                1030                1035

Gln Pro Leu Ala Pro Ala Ala Pro Ser Leu Leu Gln Ala Ser
    1040                1045                1050

Thr Gln Pro Glu Val Leu Leu Pro Lys Pro Ala Pro Val Tyr Ser
    1055                1060                1065

Asp Ser Asp Leu Val Gln Val Val Asp Glu Leu Ile Gln Glu Ala
    1070                1075                1080

Leu Gln Val Asp Cys Glu Glu Val Ser Ser Ala Gly Ala Ala Tyr
    1085                1090                1095

Val Ala Ala Ala Leu Gly Val Ser Asn Ala Ala Val Glu Asp Leu
    1100                1105                1110

Ile Thr Ala Ala Thr Thr Gly Ile Leu Arg His Val Ala Ala Glu
    1115                1120                1125

Glu Val Ser Met Glu Arg Gln Arg Leu Glu Glu Lys Gln Arg
    1130                1135                1140

Ala Glu Glu Glu Arg Leu Lys Gln Glu Arg Glu Leu Met Leu Thr
    1145                1150                1155

Gln Leu Ser Glu Gly Leu Ala Ala Glu Leu Thr Glu Leu Thr Val
    1160                1165                1170

Thr Glu Cys Val Trp Glu Thr Cys Ser Gln Glu Leu Gln Ser Ala
    1175                1180                1185

Val Lys Ile Asp Gln Lys Val Arg Val Ala Arg Cys Cys Glu Ala
    1190                1195                1200

Val Cys Ala His Leu Val Asp Leu Phe Leu Ala Glu Glu Ile Phe
    1205                1210                1215

Gln Thr Ala Lys Glu Thr Leu Gln Glu Leu Gln Cys Phe Cys Lys
    1220                1225                1230

Tyr Leu Gln Arg Trp Arg Glu Ala Val Ala Ala Arg Lys Lys Phe
    1235                1240                1245

Arg Arg Gln Met Arg Ala Phe Pro Ala Ala Pro Cys Cys Val Asp
    1250                1255                1260

Val Asn Asp Arg Leu Gln Ala Leu Val Pro Ser Ala Glu Cys Pro
    1265                1270                1275

-continued

```
Ile Thr Glu Glu Asn Leu Ala Lys Gly Leu Leu Asp Leu Gly His
    1280            1285                1290

Ala Gly Lys Val Gly Val Ser Cys Thr Arg Leu Arg Arg Leu Arg
    1295            1300                1305

Asn Lys Thr Ala His Gln Ile Lys Val Gln His Phe His Gln Gln
    1310            1315                1320

Leu Leu Arg Asn Ala Ala Trp Ala Pro Leu Asp Leu Pro Ser Ile
    1325            1330                1335

Val Ser Glu His Leu Pro Met Lys Gln Lys Arg Arg Phe Trp Lys
    1340            1345                1350

Leu Val Leu Val Leu Pro Asp Val Glu Gln Thr Pro Glu Ser
    1355            1360                1365

Pro Gly Arg Ile Leu Glu Asn Trp Leu Lys Val Lys Phe Thr Gly
    1370            1375                1380

Asp Asp Ser Met Val Gly Asp Ile Gly Asp Asn Ala Gly Asp Ile
    1385            1390                1395

Gln Thr Leu Ser Val Phe Asn Thr Leu Ser Ser Lys Gly Asp Gln
    1400            1405                1410

Thr Val Ser Val Asn Val Cys Ile Lys Val Ala His Gly Thr Leu
    1415            1420                1425

Ser Asp Ser Ala Leu Asp Ala Val Glu Thr Gln Lys Asp Leu Leu
    1430            1435                1440

Gly Thr Ser Gly Leu Met Leu Leu Leu Pro Pro Lys Val Lys Ser
    1445            1450                1455

Glu Glu Val Ala Glu Glu Glu Leu Ser Trp Leu Ser Ala Leu Leu
    1460            1465                1470

Gln Leu Lys Gln Leu Leu Gln Ala Lys Pro Phe Gln Pro Ala Leu
    1475            1480                1485

Pro Leu Val Val Leu Val Pro Ser Ser Arg Gly Asp Ser Ala Gly
    1490            1495                1500

Arg Ala Val Glu Asp Gly Leu Met Leu Gln Asp Leu Val Ser Ala
    1505            1510                1515

Lys Leu Ile Ser Asp Tyr Ile Val Val Glu Ile Pro Asp Ser Val
    1520            1525                1530

Asn Asp Leu Gln Gly Thr Val Lys Val Ser Gly Ala Val Gln Trp
    1535            1540                1545

Leu Ile Ser Gly Cys Pro Gln Ala Leu Asp Leu Cys Cys Gln Thr
    1550            1555                1560

Leu Val Gln Tyr Val Glu Asp Gly Ile Ser Arg Glu Phe Ser Arg
    1565            1570                1575

Arg Phe Phe His Asp Arg Arg Glu Arg Arg Leu Ala Ser Leu Pro
    1580            1585                1590

Ser Gln Glu Pro Ser Thr Ile Ile Glu Leu Phe Asn Ser Val Leu
    1595            1600                1605

Gln Phe Leu Ala Ser Val Val Ser Ser Glu Gln Leu Cys Asp Ile
    1610            1615                1620

Ser Trp Pro Val Met Glu Phe Ala Glu Val Gly Gly Ser Gln Leu
    1625            1630                1635

Leu Pro His Leu His Trp Asn Ser Pro Glu His Leu Ala Trp Leu
    1640            1645                1650

Lys Gln Ala Val Leu Gly Phe Gln Leu Pro Gln Met Asp Leu Pro
    1655            1660                1665

Pro Pro Gly Ala Pro Trp Leu Pro Val Cys Ser Met Val Ile Gln
```

-continued

```
                            1670                1675                1680

Tyr Thr Ser Gln Ile Pro Ser Ser Ser Gln Thr Gln Pro Val Leu
    1685                1690                1695

Gln Ser Gln Ala Glu Asn Leu Leu Cys Arg Thr Tyr Gln Lys Trp
1700                1705                1710

Lys Asn Lys Ser Leu Ser Pro Gly Gln Glu Leu Gly Pro Ser Val
    1715                1720                1725

Ala Glu Ile Pro Trp Asp Ile Ile Thr Leu Cys Ile Asn His
1730                1735                1740

Lys Leu Arg Asp Trp Thr Pro Pro Arg Leu Pro Val Thr Leu Glu
    1745                1750                1755

Ala Leu Ser Glu Asp Gly Gln Ile Cys Val Tyr Phe Phe Lys Asn
1760                1765                1770

Leu Leu Arg Lys Tyr His Val Pro Ser Ser Trp Glu Gln Ala Arg
    1775                1780                1785

Met Gln Thr Gln Arg Glu Leu Gln Leu Ser His Gly Arg Ser Gly
1790                1795                1800

Met Arg Ser Ile His Pro Pro Thr Ser Thr Phe Pro Thr Pro Leu
    1805                1810                1815

Leu His Val His Gln Lys Gly Lys Lys Lys Glu Glu Ser Gly Arg
1820                1825                1830

Glu Gly Ser Leu Ser Thr Glu Asp Leu Leu Arg Gly Ala Ser Ala
    1835                1840                1845

Glu Glu Leu Leu Ala Gln Ser Leu Ser Ser Ser Leu Leu Glu Glu
1850                1855                1860

Lys Glu Glu Asn Lys Arg Phe Glu Asp Gln Leu Gln Gln Trp Leu
    1865                1870                1875

Ser Gln Asp Ser Gln Ala Phe Thr Glu Ser Thr Arg Leu Pro Leu
1880                1885                1890

Tyr Leu Pro Gln Thr Leu Val Ser Phe Pro Asp Ser Ile Lys Thr
    1895                1900                1905

Gln Thr Met Val Lys Thr Ser Thr Ser Pro Gln Asn Ser Gly Thr
1910                1915                1920

Gly Lys Gln Leu Arg Phe Ser Glu Ala Ser Gly Ser Ser Leu Thr
    1925                1930                1935

Glu Lys Leu Lys Leu Leu Glu Arg Leu Ile Gln Ser Ser Arg Ala
1940                1945                1950

Glu Glu Ala Ala Ser Glu Leu His Leu Ser Ala Leu Leu Glu Met
    1955                1960                1965

Val Asp Met
    1970

<210> SEQ ID NO 3
<211> LENGTH: 6114
<212> TYPE: DNA
<213> ORGANISM: Homo sapiens
<220> FEATURE:
<221> NAME/KEY: CDS
<222> LOCATION: (38)..(5977)

<400> SEQUENCE: 3
gtaatactta attaccttct aataattgga gcagaag atg aac cca act aat cct      55
                                        Met Asn Pro Thr Asn Pro
                                          1               5 ttc agt ggg cag cag cct agt gct ttt tcg gcg tct tct agt aat gta    103
Phe Ser Gly Gln Gln Pro Ser Ala Phe Ser Ala Ser Ser Ser Asn Val
         10                  15                  20
```

```
gga aca ctt cca tct aag ccg cca ttt cga ttt ggt caa cct tct ctt      151
Gly Thr Leu Pro Ser Lys Pro Pro Phe Arg Phe Gly Gln Pro Ser Leu
         25                  30                  35 ttt gga caa aac agt acc tta tct ggg aag agc tcg gga ttt tca cag      199
Phe Gly Gln Asn Ser Thr Leu Ser Gly Lys Ser Ser Gly Phe Ser Gln
 40                  45                  50 gta tcc agc ttt cca gcg tct tct gga gta agt cat tcc tct tca gtg      247
Val Ser Ser Phe Pro Ala Ser Ser Gly Val Ser His Ser Ser Ser Val
 55                  60                  65                  70 caa aca tta ggg ttc acc caa acc tca agt gtt gga ccc ttt tct gga      295
Gln Thr Leu Gly Phe Thr Gln Thr Ser Ser Val Gly Pro Phe Ser Gly
                 75                  80                  85 ctt gag cac act tcc acc ttt gtg gct acc tct ggg cct tca agt tca      343
Leu Glu His Thr Ser Thr Phe Val Ala Thr Ser Gly Pro Ser Ser Ser
             90                  95                 100 tct gtg ctg gga aac aca gga ttt agt ttt aaa tca ccc acc agt gtt      391
Ser Val Leu Gly Asn Thr Gly Phe Ser Phe Lys Ser Pro Thr Ser Val
                105                 110                 115 ggg gct ttc cca agc act tct gct ttt gga caa gaa gct gga gaa ata      439
Gly Ala Phe Pro Ser Thr Ser Ala Phe Gly Gln Glu Ala Gly Glu Ile
120                 125                 130 gtg aac tct ggt ttt ggg aaa aca gaa ttc agc ttt aaa cct ctg gaa      487
Val Asn Ser Gly Phe Gly Lys Thr Glu Phe Ser Phe Lys Pro Leu Glu
135                 140                 145                 150 aat gca gtg ttc aaa cca ata ctg ggg gct gaa tct gag cca gag aaa      535
Asn Ala Val Phe Lys Pro Ile Leu Gly Ala Glu Ser Glu Pro Glu Lys
                155                 160                 165 acc cag agc caa att gct tct ggg ttt ttt aca ttt tcc cac cca att      583
Thr Gln Ser Gln Ile Ala Ser Gly Phe Phe Thr Phe Ser His Pro Ile
                170                 175                 180 agt agt gca cct gga ggc ctg gcc cct ttc tct ttt cct caa gta aca      631
Ser Ser Ala Pro Gly Gly Leu Ala Pro Phe Ser Phe Pro Gln Val Thr
            185                 190                 195 agt agt tca gct acc act tca aat ttt acc ttt tca aaa cct gtt agt      679
Ser Ser Ser Ala Thr Thr Ser Asn Phe Thr Phe Ser Lys Pro Val Ser
200                 205                 210 agt aat aat tca tta tct gcc ttt acc cct gct ttg tca aac caa aat      727
Ser Asn Asn Ser Leu Ser Ala Phe Thr Pro Ala Leu Ser Asn Gln Asn
215                 220                 225                 230 gta gag gaa gag aag aga gga cct aag tca ata ttt gga agt tct aat      775
Val Glu Glu Glu Lys Arg Gly Pro Lys Ser Ile Phe Gly Ser Ser Asn
                235                 240                 245 aat agc ttc agt agc ttc cct gta tca tct gcg gtt ttg ggc gaa cct      823
Asn Ser Phe Ser Ser Phe Pro Val Ser Ser Ala Val Leu Gly Glu Pro
                250                 255                 260 ttc cag gct agc aaa gca ggt gtc agg cag ggg tgt gaa gaa gct gtt      871
Phe Gln Ala Ser Lys Ala Gly Val Arg Gln Gly Cys Glu Glu Ala Val
            265                 270                 275 tcc cag gtg gaa cca ctt ccc agc cta atg aaa gga ctg aaa agg aag      919
Ser Gln Val Glu Pro Leu Pro Ser Leu Met Lys Gly Leu Lys Arg Lys
280                 285                 290 gag gac cag gat cgc tcc cca agg aga cat ggc cac gag cca gca gaa      967
Glu Asp Gln Asp Arg Ser Pro Arg Arg His Gly His Glu Pro Ala Glu
295                 300                 305                 310 gat tcg gat cct ctg tcc cgg ggc gat cat cct cca gac aaa cga cct     1015
Asp Ser Asp Pro Leu Ser Arg Gly Asp His Pro Pro Asp Lys Arg Pro
                315                 320                 325 gtc cgc ctg aat cga ccc cgg gga ggt act tta ttt ggt cgg acg ata     1063
Val Arg Leu Asn Arg Pro Arg Gly Gly Thr Leu Phe Gly Arg Thr Ile
                330                 335                 340
```

```
cag gat gtt ttc aaa agc aat aag gaa gta ggt cgt ctg ggc aac aag      1111
Gln Asp Val Phe Lys Ser Asn Lys Glu Val Gly Arg Leu Gly Asn Lys
            345                 350                 355 gag gcc aaa aag gaa act ggc ttt gtt gag tct gca gaa agt gac cac      1159
Glu Ala Lys Lys Glu Thr Gly Phe Val Glu Ser Ala Glu Ser Asp His
    360                 365                 370 atg gct atc cca gga ggg aat cag tct gtc ctg gca cct tcc cgg att      1207
Met Ala Ile Pro Gly Gly Asn Gln Ser Val Leu Ala Pro Ser Arg Ile
375                 380                 385                 390 cca ggt gtg aat aaa gag gaa gaa act gaa agt aga gag aag aaa gaa      1255
Pro Gly Val Asn Lys Glu Glu Glu Thr Glu Ser Arg Glu Lys Lys Glu
                395                 400                 405 gat tct cta aga gga act ccg gcg cgt cag agt aac aga agc gag agc      1303
Asp Ser Leu Arg Gly Thr Pro Ala Arg Gln Ser Asn Arg Ser Glu Ser
            410                 415                 420 aca gac agt ctt ggg ggc ttg tct ccc tct gaa gtc aca gcc atc cag      1351
Thr Asp Ser Leu Gly Gly Leu Ser Pro Ser Glu Val Thr Ala Ile Gln
        425                 430                 435 tgc aag aac atc cct gac tac ctc aac gac agg acc att ctg gag aac      1399
Cys Lys Asn Ile Pro Asp Tyr Leu Asn Asp Arg Thr Ile Leu Glu Asn
440                 445                 450 cat ttt ggc aaa att gct aaa gtg cag cgc atc ttt acc agg cgc agc      1447
His Phe Gly Lys Ile Ala Lys Val Gln Arg Ile Phe Thr Arg Arg Ser
455                 460                 465                 470 aaa aag ctt gca gtg gta cat ttc ttt gat cat gca tct gca gcc ctg      1495
Lys Lys Leu Ala Val Val His Phe Phe Asp His Ala Ser Ala Ala Leu
                475                 480                 485 gct aga aag aag ggg aaa agt ttg cat aaa gac atg gct atc ttt tgg      1543
Ala Arg Lys Lys Gly Lys Ser Leu His Lys Asp Met Ala Ile Phe Trp
            490                 495                 500 cac agg aag aaa ata agc ccc aat aag aaa ccc ttt tcc ctg aag gag      1591
His Arg Lys Lys Ile Ser Pro Asn Lys Lys Pro Phe Ser Leu Lys Glu
        505                 510                 515 aag aaa cca ggt gac ggt gaa gtc agc ccg agc aca gag gat gca ccc      1639
Lys Lys Pro Gly Asp Gly Glu Val Ser Pro Ser Thr Glu Asp Ala Pro
    520                 525                 530 ttt cag cac tct cct ctt ggc aag gcc gca ggg agg act ggt gct agc      1687
Phe Gln His Ser Pro Leu Gly Lys Ala Ala Gly Arg Thr Gly Ala Ser
535                 540                 545                 550 agc ctc ctg aat aaa agc tct cca gtg aag aag cca agt ctt cta aag      1735
Ser Leu Leu Asn Lys Ser Ser Pro Val Lys Lys Pro Ser Leu Leu Lys
                555                 560                 565 gcc cac caa ttc gag gga gac tct ttt gac tca gcc tcc gag ggc tcc      1783
Ala His Gln Phe Glu Gly Asp Ser Phe Asp Ser Ala Ser Glu Gly Ser
            570                 575                 580 gag ggc ctc ggg cca tgt gtg ctc tcc ctc agt acc ctg ata ggc act      1831
Glu Gly Leu Gly Pro Cys Val Leu Ser Leu Ser Thr Leu Ile Gly Thr
        585                 590                 595 gtg gct gag aca tcc aag gag aag tac cgc ctg ctt gac cag aga gac      1879
Val Ala Glu Thr Ser Lys Glu Lys Tyr Arg Leu Leu Asp Gln Arg Asp
    600                 605                 610 agg atc atg cgg caa gct cgg gtg aag aga acc gat ctg gac aaa gcg      1927
Arg Ile Met Arg Gln Ala Arg Val Lys Arg Thr Asp Leu Asp Lys Ala
615                 620                 625                 630 agg act ttt gtt ggc acc tgc ctg gat atg tgt cct gag aag gag agg      1975
Arg Thr Phe Val Gly Thr Cys Leu Asp Met Cys Pro Glu Lys Glu Arg
                635                 640                 645 tac atg cgg gag acc cgt agc cag ctg agc gtg ttc gaa gtg gtc cca      2023
Tyr Met Arg Glu Thr Arg Ser Gln Leu Ser Val Phe Glu Val Val Pro
            650                 655                 660
```

```
ggg act gac cag gtg gac cac gca gca gct gtg aaa gag tac agt cgg    2071
Gly Thr Asp Gln Val Asp His Ala Ala Ala Val Lys Glu Tyr Ser Arg
        665                 670                 675 tcc tcg gcg gat cag gag gag ccc ctg ccc cac gag ctg cgg ccc ttg    2119
Ser Ser Ala Asp Gln Glu Glu Pro Leu Pro His Glu Leu Arg Pro Leu
    680                 685                 690 cca gtg ctc agc agg acc atg gac tac ctg gtg acc cag atc atg gac    2167
Pro Val Leu Ser Arg Thr Met Asp Tyr Leu Val Thr Gln Ile Met Asp
695                 700                 705                 710 cag aag gag ggc agc ctg cgg gat tgg tat gac ttc gtg tgg aac cgc    2215
Gln Lys Glu Gly Ser Leu Arg Asp Trp Tyr Asp Phe Val Trp Asn Arg
                715                 720                 725 acg cgt ggc ata cgg aag gat atc acg cag cag cac ctc tgt gac ccc    2263
Thr Arg Gly Ile Arg Lys Asp Ile Thr Gln Gln His Leu Cys Asp Pro
            730                 735                 740 ctg acg gtg tcc ctg att gag aag tgc acc cgg ttt cac atc cac tgt    2311
Leu Thr Val Ser Leu Ile Glu Lys Cys Thr Arg Phe His Ile His Cys
        745                 750                 755 gcc cac ttc atg tgt gag gag ccc atg tcc tcc ttt gat gcc aag atc    2359
Ala His Phe Met Cys Glu Glu Pro Met Ser Ser Phe Asp Ala Lys Ile
    760                 765                 770 aat aat gag aac atg acc aag tgc ctg cag agc ctg aag gag atg tac    2407
Asn Asn Glu Asn Met Thr Lys Cys Leu Gln Ser Leu Lys Glu Met Tyr
775                 780                 785                 790 cag gac ctg aga aac aag ggt gtc ttc tgt gcc agc gaa gcg gag ttc    2455
Gln Asp Leu Arg Asn Lys Gly Val Phe Cys Ala Ser Glu Ala Glu Phe
                795                 800                 805 cag ggc tac aat gtt ctg ctc agt ctc aac aag gga gac atc cta aga    2503
Gln Gly Tyr Asn Val Leu Leu Ser Leu Asn Lys Gly Asp Ile Leu Arg
            810                 815                 820 gaa gta caa cag ttc cat cct gct gtt aga aac tca tct gag gtg aaa    2551
Glu Val Gln Gln Phe His Pro Ala Val Arg Asn Ser Ser Glu Val Lys
        825                 830                 835 ttt gct gtt cag gct ttt gct gca ttg aac agt aat aat ttt gtg aga    2599
Phe Ala Val Gln Ala Phe Ala Ala Leu Asn Ser Asn Asn Phe Val Arg
    840                 845                 850 ttt ttc aaa ctg gtc cag tca gct tct tac ctg aac gct tgt ctt tta    2647
Phe Phe Lys Leu Val Gln Ser Ala Ser Tyr Leu Asn Ala Cys Leu Leu
855                 860                 865                 870 cac tgt tac ttc agt cag atc cgc aag gat gct ctc cgg gcg ctc aac    2695
His Cys Tyr Phe Ser Gln Ile Arg Lys Asp Ala Leu Arg Ala Leu Asn
                875                 880                 885 ttt gcg tac acg gtg agc aca cag cga tct acc atc ttt ccc ctg gat    2743
Phe Ala Tyr Thr Val Ser Thr Gln Arg Ser Thr Ile Phe Pro Leu Asp
            890                 895                 900 ggt gtg gtg cgc atg ctg ctg ttc aga gac tgt gaa gag gcc acc gac    2791
Gly Val Val Arg Met Leu Leu Phe Arg Asp Cys Glu Glu Ala Thr Asp
        905                 910                 915 ttc ctc acc tgc cac ggc ctc acc gtt tcc gac ggc tgt gtg gag ctg    2839
Phe Leu Thr Cys His Gly Leu Thr Val Ser Asp Gly Cys Val Glu Leu
    920                 925                 930 aac cgg tct gca ttc ctg gaa cca gag gga tta tcc aag acc agg aag    2887
Asn Arg Ser Ala Phe Leu Glu Pro Glu Gly Leu Ser Lys Thr Arg Lys
935                 940                 945                 950 tcg gtg ttt att act agg aag ctg acg gtg tca gtc ggg gaa att gtg    2935
Ser Val Phe Ile Thr Arg Lys Leu Thr Val Ser Val Gly Glu Ile Val
                955                 960                 965 aac gga ggg cca ttg ccc ccc gtc cct cgt cac acc cct gtg tgc agc    2983
Asn Gly Gly Pro Leu Pro Pro Val Pro Arg His Thr Pro Val Cys Ser
            970                 975                 980
```

```
ttc aac tcc cag aac aag tac atc ggg gag agc ctg gcc gcg gag ctg      3031
Phe Asn Ser Gln Asn Lys Tyr Ile Gly Glu Ser Leu Ala Ala Glu Leu
        985                 990                 995 ccc gtc agc acc cag aga ccc ggc tcc gac aca gtg ggc gga ggg          3076
Pro Val Ser Thr Gln Arg Pro Gly Ser Asp Thr Val Gly Gly Gly
    1000                1005                1010 aga gga gag gag tgt ggt gta gag ccg gat gca ccc ctg tcc agt          3121
Arg Gly Glu Glu Cys Gly Val Glu Pro Asp Ala Pro Leu Ser Ser
    1015                1020                1025 ctc cca cag tct cta cca gcc cct gcg ccc tca cca gtg cct ctg          3166
Leu Pro Gln Ser Leu Pro Ala Pro Ala Pro Ser Pro Val Pro Leu
    1030                1035                1040 cct cct gtc ctg gca ctg acc ccg tct gtg gcg ccc agc ctc ttc          3211
Pro Pro Val Leu Ala Leu Thr Pro Ser Val Ala Pro Ser Leu Phe
    1045                1050                1055 cag ctg tct gtg cag cct gaa cca ccg cct cca gag ccc gtg ccc          3256
Gln Leu Ser Val Gln Pro Glu Pro Pro Pro Glu Pro Val Pro
    1060                1065                1070 atg tac tct gac gag gac ctg gcg cag gtg gtg gac gag ctc atc          3301
Met Tyr Ser Asp Glu Asp Leu Ala Gln Val Val Asp Glu Leu Ile
    1075                1080                1085 cag gag gcc ctg cag agg gac tgt gag gaa gtt ggc tct gcg ggt          3346
Gln Glu Ala Leu Gln Arg Asp Cys Glu Glu Val Gly Ser Ala Gly
    1090                1095                1100 gct gcc tac gca gct gcc gcc ctg ggt gtt tct aat gct gct atg          3391
Ala Ala Tyr Ala Ala Ala Ala Leu Gly Val Ser Asn Ala Ala Met
    1105                1110                1115 gag gat ttg tta aca gct gca acc acg ggc att ttg agg cac att          3436
Glu Asp Leu Leu Thr Ala Ala Thr Thr Gly Ile Leu Arg His Ile
    1120                1125                1130 gca gct gaa gaa gtg tct aag gaa aga gag cga agg gag cag gag          3481
Ala Ala Glu Glu Val Ser Lys Glu Arg Glu Arg Arg Glu Gln Glu
    1135                1140                1145 agg cag cgg gct gaa gag gaa agg ttg aaa caa gag aga gag ctg          3526
Arg Gln Arg Ala Glu Glu Glu Arg Leu Lys Gln Glu Arg Glu Leu
    1150                1155                1160 gtg tta agt gag ctg agc cag ggc ctg gcc gtg gag ctg atg gaa          3571
Val Leu Ser Glu Leu Ser Gln Gly Leu Ala Val Glu Leu Met Glu
    1165                1170                1175 cgc gtg atg atg gag ttt gtg agg gaa acc tgc tcc cag gag ttg          3616
Arg Val Met Met Glu Phe Val Arg Glu Thr Cys Ser Gln Glu Leu
    1180                1185                1190 aag aat gca gta gag aca gac cag agg gtc cgt gtg gcc cgt tgc          3661
Lys Asn Ala Val Glu Thr Asp Gln Arg Val Arg Val Ala Arg Cys
    1195                1200                1205 tgt gag gat gtc tgt gcc cac tta gtg gac ttg ttt ctc gtg gag          3706
Cys Glu Asp Val Cys Ala His Leu Val Asp Leu Phe Leu Val Glu
    1210                1215                1220 gaa atc ttc cag act gca aag gag acc ctc cag gag ctt cag tgc          3751
Glu Ile Phe Gln Thr Ala Lys Glu Thr Leu Gln Glu Leu Gln Cys
    1225                1230                1235 ttc tgc aag tat cta cag cgg tgg agg gaa gct gtc aca gcc cgc          3796
Phe Cys Lys Tyr Leu Gln Arg Trp Arg Glu Ala Val Thr Ala Arg
    1240                1245                1250 aag aaa ctg agg cgc caa atg cgg gct ttc cct gct gcg ccc tgc          3841
Lys Lys Leu Arg Arg Gln Met Arg Ala Phe Pro Ala Ala Pro Cys
    1255                1260                1265 tgc gtg gac gtg agc gac cgg ctg agg gcg ctg gcg ccc agc gca          3886
Cys Val Asp Val Ser Asp Arg Leu Arg Ala Leu Ala Pro Ser Ala
    1270                1275                1280
```

| | | | | | | | | | | | |
|---|---|---|---|---|---|---|---|---|---|---|---|
| gag | tgc | ccc | att | gct | gaa | gag | aac | ctg | gcc | agg | ggc | ctc | ctg | gac | 3931 |
| Glu | Cys | Pro | Ile | Ala | Glu | Glu | Asn | Leu | Ala | Arg | Gly | Leu | Leu | Asp | |
| 1285 | | | | 1290 | | | | | 1295 | | | | | | |

| ctg | ggc | cat | gca | ggg | aga | ttg | ggc | atc | tct | tgc | acc | agg | tta | agg | 3976 |
| Leu | Gly | His | Ala | Gly | Arg | Leu | Gly | Ile | Ser | Cys | Thr | Arg | Leu | Arg | |
| 1300 | | | | | 1305 | | | | | 1310 | | | | | |

| cgg | ctc | aga | aac | aag | aca | gct | cac | cag | atg | aag | gtt | cag | cac | ttc | 4021 |
| Arg | Leu | Arg | Asn | Lys | Thr | Ala | His | Gln | Met | Lys | Val | Gln | His | Phe | |
| 1315 | | | | 1320 | | | | | 1325 | | | | | | |

| tac | cag | cag | ctg | ctg | agt | gat | gtg | gca | tgg | gcg | tct | ctg | gac | ctg | 4066 |
| Tyr | Gln | Gln | Leu | Leu | Ser | Asp | Val | Ala | Trp | Ala | Ser | Leu | Asp | Leu | |
| 1330 | | | | 1335 | | | | | 1340 | | | | | | |

| cca | tcc | ctc | gtg | gct | gag | cac | ctc | cct | ggg | agg | cag | gag | cat | gtg | 4111 |
| Pro | Ser | Leu | Val | Ala | Glu | His | Leu | Pro | Gly | Arg | Gln | Glu | His | Val | |
| 1345 | | | | 1350 | | | | | 1355 | | | | | | |

| ttt | tgg | aag | ctg | gtg | ctg | gtg | ttg | ccg | gat | gta | gag | gag | cag | tcc | 4156 |
| Phe | Trp | Lys | Leu | Val | Leu | Val | Leu | Pro | Asp | Val | Glu | Glu | Gln | Ser | |
| 1360 | | | | 1365 | | | | | 1370 | | | | | | |

| cca | gag | agt | tgt | ggc | aga | att | cta | gca | aat | tgg | tta | aaa | gtc | aag | 4201 |
| Pro | Glu | Ser | Cys | Gly | Arg | Ile | Leu | Ala | Asn | Trp | Leu | Lys | Val | Lys | |
| 1375 | | | | 1380 | | | | | 1385 | | | | | | |

| ttc | atg | gga | gat | gaa | ggc | tca | gtg | gat | gac | aca | tcc | agc | gat | gct | 4246 |
| Phe | Met | Gly | Asp | Glu | Gly | Ser | Val | Asp | Asp | Thr | Ser | Ser | Asp | Ala | |
| 1390 | | | | 1395 | | | | | 1400 | | | | | | |

| ggt | ggg | att | cag | acg | ctt | tcg | ctt | ttc | aac | tca | ctt | agc | agc | aaa | 4291 |
| Gly | Gly | Ile | Gln | Thr | Leu | Ser | Leu | Phe | Asn | Ser | Leu | Ser | Ser | Lys | |
| 1405 | | | | 1410 | | | | | 1415 | | | | | | |

| ggg | gat | cag | atg | att | tct | gtt | aac | gtg | tgt | ata | aag | gtg | gcc | cat | 4336 |
| Gly | Asp | Gln | Met | Ile | Ser | Val | Asn | Val | Cys | Ile | Lys | Val | Ala | His | |
| 1420 | | | | 1425 | | | | | 1430 | | | | | | |

| ggc | gcc | ctc | agt | gat | ggt | gcc | att | gat | gct | gtg | gag | aca | cag | aag | 4381 |
| Gly | Ala | Leu | Ser | Asp | Gly | Ala | Ile | Asp | Ala | Val | Glu | Thr | Gln | Lys | |
| 1435 | | | | 1440 | | | | | 1445 | | | | | | |

| gac | ctc | ctg | gga | gcc | agt | ggg | ctc | atg | ctg | ctg | ctt | ccc | ccc | aaa | 4426 |
| Asp | Leu | Leu | Gly | Ala | Ser | Gly | Leu | Met | Leu | Leu | Leu | Pro | Pro | Lys | |
| 1450 | | | | 1455 | | | | | 1460 | | | | | | |

| atg | aag | agt | gag | gac | atg | gca | gag | gag | gac | gtg | tac | tgg | ctg | tcg | 4471 |
| Met | Lys | Ser | Glu | Asp | Met | Ala | Glu | Glu | Asp | Val | Tyr | Trp | Leu | Ser | |
| 1465 | | | | 1470 | | | | | 1475 | | | | | | |

| gcc | ttg | ctg | cag | ctc | aag | cag | ctc | ctg | cag | gct | aag | ccc | ttc | cag | 4516 |
| Ala | Leu | Leu | Gln | Leu | Lys | Gln | Leu | Leu | Gln | Ala | Lys | Pro | Phe | Gln | |
| 1480 | | | | 1485 | | | | | 1490 | | | | | | |

| cct | gcg | ctt | cct | ctg | gtg | gtt | ctt | gtg | cct | agc | cca | gga | ggg | gac | 4561 |
| Pro | Ala | Leu | Pro | Leu | Val | Val | Leu | Val | Pro | Ser | Pro | Gly | Gly | Asp | |
| 1495 | | | | 1500 | | | | | 1505 | | | | | | |

| gcc | gtt | gag | aag | gaa | gta | gaa | gat | ggt | ctg | atg | cta | cag | gac | ttg | 4606 |
| Ala | Val | Glu | Lys | Glu | Val | Glu | Asp | Gly | Leu | Met | Leu | Gln | Asp | Leu | |
| 1510 | | | | 1515 | | | | | 1520 | | | | | | |

| gtt | tca | gct | aag | ctg | att | tca | gat | tac | act | gtt | acc | gag | atc | cct | 4651 |
| Val | Ser | Ala | Lys | Leu | Ile | Ser | Asp | Tyr | Thr | Val | Thr | Glu | Ile | Pro | |
| 1525 | | | | 1530 | | | | | 1535 | | | | | | |

| gat | acc | att | aat | gat | cta | caa | ggt | tca | act | aag | gtt | ttg | caa | gca | 4696 |
| Asp | Thr | Ile | Asn | Asp | Leu | Gln | Gly | Ser | Thr | Lys | Val | Leu | Gln | Ala | |
| 1540 | | | | 1545 | | | | | 1550 | | | | | | |

| gtg | cag | tgg | ctg | gtt | tcc | cac | tgc | ccc | cat | tcc | ctt | gac | ctc | tgc | 4741 |
| Val | Gln | Trp | Leu | Val | Ser | His | Cys | Pro | His | Ser | Leu | Asp | Leu | Cys | |
| 1555 | | | | 1560 | | | | | 1565 | | | | | | |

| tgc | cag | act | ctc | att | cag | tac | gtc | gaa | gac | ggg | att | ggc | cat | gag | 4786 |
| Cys | Gln | Thr | Leu | Ile | Gln | Tyr | Val | Glu | Asp | Gly | Ile | Gly | His | Glu | |
| 1570 | | | | 1575 | | | | | 1580 | | | | | | |

```
ttt agt ggc cgc ttt ttc cat gac aga aga gag agg cgt ctg ggc      4831
Phe Ser Gly Arg Phe Phe His Asp Arg Arg Glu Arg Arg Leu Gly
1585                1590                1595 ggt ctt gct tct cag gag cct ggc gcc atc att gag ctg ttt aac      4876
Gly Leu Ala Ser Gln Glu Pro Gly Ala Ile Ile Glu Leu Phe Asn
    1600                1605                1610 agt gtg ctg cag ttc ctg gct tct gtg gtg tcc tct gaa cag ctg      4921
Ser Val Leu Gln Phe Leu Ala Ser Val Val Ser Ser Glu Gln Leu
1615                1620                1625 tgt gac ctg tcc tgg cct gtc act gag ttt gct gag gca ggg ggc      4966
Cys Asp Leu Ser Trp Pro Val Thr Glu Phe Ala Glu Ala Gly Gly
1630                1635                1640 agc cgg ctg ctt cct cac ctg cac tgg aat gcc cca gag cac ctg      5011
Ser Arg Leu Leu Pro His Leu His Trp Asn Ala Pro Glu His Leu
1645                1650                1655 gcc tgg ctg aag cag gct gtg ctc ggg ttc cag ctt ccg cag atg      5056
Ala Trp Leu Lys Gln Ala Val Leu Gly Phe Gln Leu Pro Gln Met
    1660                1665                1670 gac ctt cca ccc ctg ggg gcc ccc tgg ctc ccc gtg tgc tcc atg      5101
Asp Leu Pro Pro Leu Gly Ala Pro Trp Leu Pro Val Cys Ser Met
1675                1680                1685 gtt gtc cag tac gcc tcc cag atc ccc agc tca cgc cag aca cag      5146
Val Val Gln Tyr Ala Ser Gln Ile Pro Ser Ser Arg Gln Thr Gln
1690                1695                1700 cct gtc ctc cag tcc cag gtg gag aac ctg ctc cac aga acc tac      5191
Pro Val Leu Gln Ser Gln Val Glu Asn Leu Leu His Arg Thr Tyr
1705                1710                1715 tgt agg tgg aag agc aag agt ccc tcc cca gtc cat ggg gca ggc      5236
Cys Arg Trp Lys Ser Lys Ser Pro Ser Pro Val His Gly Ala Gly
1720                1725                1730 ccc tcg gtc atg gag atc cca tgg gat gat ctt atc gcc ttg tgt      5281
Pro Ser Val Met Glu Ile Pro Trp Asp Asp Leu Ile Ala Leu Cys
    1735                1740                1745 atc aac cac aag ctg aga gac tgg acg ccc ccc cgg ctt cct gtt      5326
Ile Asn His Lys Leu Arg Asp Trp Thr Pro Pro Arg Leu Pro Val
1750                1755                1760 aca tca gag gcg ctg agt gaa gat ggt cag ata tgt gtg tat ttt      5371
Thr Ser Glu Ala Leu Ser Glu Asp Gly Gln Ile Cys Val Tyr Phe
1765                1770                1775 ttt aaa aac gat ttg aaa aaa tat gat gtt cct ttg tcg tgg gaa      5416
Phe Lys Asn Asp Leu Lys Lys Tyr Asp Val Pro Leu Ser Trp Glu
    1780                1785                1790 caa gcc agg ttg cag acg cag aag gag cta cag ctg aga gag gga      5461
Gln Ala Arg Leu Gln Thr Gln Lys Glu Leu Gln Leu Arg Glu Gly
1795                1800                1805 cgt ttg gca ata aag cct ttt cat cct tct gca aac aat ttt ccc      5506
Arg Leu Ala Ile Lys Pro Phe His Pro Ser Ala Asn Asn Phe Pro
1810                1815                1820 ata cca ttg ctt cac atg cac cgt aac tgg aag agg agc aca gag      5551
Ile Pro Leu Leu His Met His Arg Asn Trp Lys Arg Ser Thr Glu
    1825                1830                1835 tgt gct caa gag ggg agg att ccc agc aca gag gat ctg atg cga      5596
Cys Ala Gln Glu Gly Arg Ile Pro Ser Thr Glu Asp Leu Met Arg
1840                1845                1850 gga gct tct gct gag gag ctc ttg gcg cag tgt ttg tcg agc agt      5641
Gly Ala Ser Ala Glu Glu Leu Leu Ala Gln Cys Leu Ser Ser Ser
1855                1860                1865 ctg ctg ctg gag aaa gaa gag aac aag agg ttt gaa gat cag ctt      5686
Leu Leu Leu Glu Lys Glu Glu Asn Lys Arg Phe Glu Asp Gln Leu
    1870                1875                1880
```

```
cag caa tgg ttg tct gaa gac tca gga gca ttt acg gat tta act       5731
Gln Gln Trp Leu Ser Glu Asp Ser Gly Ala Phe Thr Asp Leu Thr
    1885                1890                1895 tcc ctt ccc ctc tat ctt cct cag act cta gtg tct ctt tct cac       5776
Ser Leu Pro Leu Tyr Leu Pro Gln Thr Leu Val Ser Leu Ser His
1900                1905                1910 act att gaa cct gtg atg aaa aca tct gta act act agc cca cag       5821
Thr Ile Glu Pro Val Met Lys Thr Ser Val Thr Thr Ser Pro Gln
    1915                1920                1925 agt gac atg atg agg gag caa ctg cag ctg tca gag gcg aca gga       5866
Ser Asp Met Met Arg Glu Gln Leu Gln Leu Ser Glu Ala Thr Gly
1930                1935                1940 acg tgt cta ggc gaa cga cta aag cac ctg gaa agg ctg atc cgg       5911
Thr Cys Leu Gly Glu Arg Leu Lys His Leu Glu Arg Leu Ile Arg
    1945                1950                1955 agt tca agg gaa gag gaa gtt gcc tct gag ctc cat ctc tct gcg       5956
Ser Ser Arg Glu Glu Glu Val Ala Ser Glu Leu His Leu Ser Ala
1960                1965                1970 ctg cta gac atg gtg gac att tgagcagcct gacctgtggg gaggggtct       6007
Leu Leu Asp Met Val Asp Ile
    1975                1980 ctccccgaaga gtttctgttt ttactcaaaa taatgttatt ctcagatgct tgatgcactg   6067
ttggaaatgt gattaattta atcatgcaga taaaccattt aaatgtc                  6114

<210> SEQ ID NO 4
<211> LENGTH: 1980
<212> TYPE: PRT
<213> ORGANISM: Homo sapiens

<400> SEQUENCE: 4

Met Asn Pro Thr Asn Pro Phe Ser Gly Gln Gln Pro Ser Ala Phe Ser
1               5                   10                  15

Ala Ser Ser Ser Asn Val Gly Thr Leu Pro Ser Lys Pro Pro Phe Arg
            20                  25                  30

Phe Gly Gln Pro Ser Leu Phe Gly Gln Asn Ser Thr Leu Ser Gly Lys
        35                  40                  45

Ser Ser Gly Phe Ser Gln Val Ser Ser Phe Pro Ala Ser Ser Gly Val
    50                  55                  60

Ser His Ser Ser Ser Val Gln Thr Leu Gly Phe Thr Gln Thr Ser Ser
65                  70                  75                  80

Val Gly Pro Phe Ser Gly Leu Glu His Thr Ser Thr Phe Val Ala Thr
                85                  90                  95

Ser Gly Pro Ser Ser Ser Ser Val Leu Gly Asn Thr Gly Phe Ser Phe
            100                 105                 110

Lys Ser Pro Thr Ser Val Gly Ala Phe Pro Ser Thr Ser Ala Phe Gly
        115                 120                 125

Gln Glu Ala Gly Glu Ile Val Asn Ser Gly Phe Gly Lys Thr Glu Phe
    130                 135                 140

Ser Phe Lys Pro Leu Glu Asn Ala Val Phe Lys Pro Ile Leu Gly Ala
145                 150                 155                 160

Glu Ser Glu Pro Glu Lys Thr Gln Ser Gln Ile Ala Ser Gly Phe Phe
                165                 170                 175

Thr Phe Ser His Pro Ile Ser Ser Ala Pro Gly Gly Leu Ala Pro Phe
            180                 185                 190

Ser Phe Pro Gln Val Thr Ser Ser Ala Thr Thr Ser Asn Phe Thr
        195                 200                 205
```

```
Phe Ser Lys Pro Val Ser Ser Asn Asn Ser Leu Ser Ala Phe Thr Pro
    210                 215                 220
Ala Leu Ser Asn Gln Asn Val Glu Glu Glu Lys Arg Gly Pro Lys Ser
225                 230                 235                 240
Ile Phe Gly Ser Ser Asn Asn Ser Phe Ser Ser Phe Pro Val Ser Ser
                245                 250                 255
Ala Val Leu Gly Glu Pro Phe Gln Ala Ser Lys Ala Gly Val Arg Gln
                260                 265                 270
Gly Cys Glu Glu Ala Val Ser Gln Val Glu Pro Leu Pro Ser Leu Met
            275                 280                 285
Lys Gly Leu Lys Arg Lys Glu Asp Gln Asp Arg Ser Pro Arg Arg His
290                 295                 300
Gly His Glu Pro Ala Glu Asp Ser Asp Pro Leu Ser Arg Gly Asp His
305                 310                 315                 320
Pro Pro Asp Lys Arg Pro Val Arg Leu Asn Arg Pro Arg Gly Gly Thr
                325                 330                 335
Leu Phe Gly Arg Thr Ile Gln Asp Val Phe Lys Ser Asn Lys Glu Val
                340                 345                 350
Gly Arg Leu Gly Asn Lys Glu Ala Lys Lys Glu Thr Gly Phe Val Glu
            355                 360                 365
Ser Ala Glu Ser Asp His Met Ala Ile Pro Gly Gly Asn Gln Ser Val
        370                 375                 380
Leu Ala Pro Ser Arg Ile Pro Gly Val Asn Lys Glu Glu Thr Glu
385                 390                 395                 400
Ser Arg Glu Lys Lys Glu Asp Ser Leu Arg Gly Thr Pro Ala Arg Gln
                405                 410                 415
Ser Asn Arg Ser Glu Ser Thr Asp Ser Leu Gly Gly Leu Ser Pro Ser
                420                 425                 430
Glu Val Thr Ala Ile Gln Cys Lys Asn Ile Pro Asp Tyr Leu Asn Asp
            435                 440                 445
Arg Thr Ile Leu Glu Asn His Phe Gly Lys Ile Ala Lys Val Gln Arg
    450                 455                 460
Ile Phe Thr Arg Arg Ser Lys Lys Leu Ala Val Val His Phe Asp
465                 470                 475                 480
His Ala Ser Ala Ala Leu Ala Arg Lys Lys Gly Lys Ser Leu His Lys
                485                 490                 495
Asp Met Ala Ile Phe Trp His Arg Lys Lys Ile Ser Pro Asn Lys Lys
                500                 505                 510
Pro Phe Ser Leu Lys Glu Lys Lys Pro Gly Asp Gly Val Ser Pro
            515                 520                 525
Ser Thr Glu Asp Ala Pro Phe Gln His Ser Pro Leu Gly Lys Ala Ala
530                 535                 540
Gly Arg Thr Gly Ala Ser Ser Leu Leu Asn Lys Ser Ser Pro Val Lys
545                 550                 555                 560
Lys Pro Ser Leu Leu Lys Ala His Gln Phe Glu Gly Asp Ser Phe Asp
                565                 570                 575
Ser Ala Ser Glu Gly Ser Glu Gly Leu Gly Pro Cys Val Leu Ser Leu
                580                 585                 590
Ser Thr Leu Ile Gly Thr Val Ala Glu Thr Ser Lys Glu Lys Tyr Arg
                595                 600                 605
Leu Leu Asp Gln Arg Asp Arg Ile Met Arg Gln Ala Arg Val Lys Arg
                610                 615                 620
Thr Asp Leu Asp Lys Ala Arg Thr Phe Val Gly Thr Cys Leu Asp Met
625                 630                 635                 640
```

```
Cys Pro Glu Lys Glu Arg Tyr Met Arg Glu Thr Arg Ser Gln Leu Ser
            645                 650                 655

Val Phe Glu Val Val Pro Gly Thr Asp Gln Val Asp His Ala Ala Ala
            660                 665                 670

Val Lys Glu Tyr Ser Arg Ser Ser Ala Asp Gln Glu Glu Pro Leu Pro
            675                 680                 685

His Glu Leu Arg Pro Leu Pro Val Leu Ser Arg Thr Met Asp Tyr Leu
            690                 695                 700

Val Thr Gln Ile Met Asp Gln Lys Glu Gly Ser Leu Arg Asp Trp Tyr
705                 710                 715                 720

Asp Phe Val Trp Asn Arg Thr Arg Gly Ile Arg Lys Asp Ile Thr Gln
                    725                 730                 735

Gln His Leu Cys Asp Pro Leu Thr Val Ser Leu Ile Glu Lys Cys Thr
                    740                 745                 750

Arg Phe His Ile His Cys Ala His Phe Met Cys Glu Glu Pro Met Ser
                    755                 760                 765

Ser Phe Asp Ala Lys Ile Asn Asn Glu Asn Met Thr Lys Cys Leu Gln
            770                 775                 780

Ser Leu Lys Glu Met Tyr Gln Asp Leu Arg Asn Lys Gly Val Phe Cys
785                 790                 795                 800

Ala Ser Glu Ala Glu Phe Gln Gly Tyr Asn Val Leu Leu Ser Leu Asn
                    805                 810                 815

Lys Gly Asp Ile Leu Arg Glu Val Gln Gln Phe His Pro Ala Val Arg
                    820                 825                 830

Asn Ser Ser Glu Val Lys Phe Ala Val Gln Ala Phe Ala Ala Leu Asn
                    835                 840                 845

Ser Asn Asn Phe Val Arg Phe Phe Lys Leu Val Gln Ser Ala Ser Tyr
            850                 855                 860

Leu Asn Ala Cys Leu Leu His Cys Tyr Phe Ser Gln Ile Arg Lys Asp
865                 870                 875                 880

Ala Leu Arg Ala Leu Asn Phe Ala Tyr Thr Val Ser Thr Gln Arg Ser
                    885                 890                 895

Thr Ile Phe Pro Leu Asp Gly Val Val Arg Met Leu Leu Phe Arg Asp
                    900                 905                 910

Cys Glu Glu Ala Thr Asp Phe Leu Thr Cys His Gly Leu Thr Val Ser
                    915                 920                 925

Asp Gly Cys Val Glu Leu Asn Arg Ser Ala Phe Leu Glu Pro Glu Gly
930                 935                 940

Leu Ser Lys Thr Arg Lys Ser Val Phe Ile Thr Arg Lys Leu Thr Val
945                 950                 955                 960

Ser Val Gly Glu Ile Val Asn Gly Gly Pro Leu Pro Pro Val Pro Arg
                    965                 970                 975

His Thr Pro Val Cys Ser Phe Asn Ser Gln Asn Lys Tyr Ile Gly Glu
                    980                 985                 990

Ser Leu Ala Ala Glu Leu Pro Val Ser Thr Gln Arg Pro Gly Ser Asp
            995                 1000                1005

Thr Val Gly Gly Gly Arg Gly Glu Glu Cys Gly Val Glu Pro Asp
            1010                1015                1020

Ala Pro Leu Ser Ser Leu Pro Gln Ser Leu Pro Ala Pro Ala Pro
            1025                1030                1035

Ser Pro Val Pro Leu Pro Val Leu Ala Leu Thr Pro Ser Val
            1040                1045                1050

Ala Pro Ser Leu Phe Gln Leu Ser Val Gln Pro Glu Pro Pro Pro
```

```
                1055                1060                1065

Pro Glu Pro Val Pro Met Tyr Ser Asp Glu Asp Leu Ala Gln Val
    1070                1075                1080

Val Asp Glu Leu Ile Gln Glu Ala Leu Gln Arg Asp Cys Glu Glu
    1085                1090                1095

Val Gly Ser Ala Gly Ala Ala Tyr Ala Ala Ala Ala Leu Gly Val
    1100                1105                1110

Ser Asn Ala Ala Met Glu Asp Leu Leu Thr Ala Ala Thr Thr Gly
    1115                1120                1125

Ile Leu Arg His Ile Ala Ala Glu Glu Val Ser Lys Glu Arg Glu
    1130                1135                1140

Arg Arg Glu Gln Glu Arg Gln Arg Ala Glu Glu Glu Arg Leu Lys
    1145                1150                1155

Gln Glu Arg Glu Leu Val Leu Ser Glu Leu Ser Gln Gly Leu Ala
    1160                1165                1170

Val Glu Leu Met Glu Arg Val Met Met Glu Phe Val Arg Glu Thr
    1175                1180                1185

Cys Ser Gln Glu Leu Lys Asn Ala Val Glu Thr Asp Gln Arg Val
    1190                1195                1200

Arg Val Ala Arg Cys Cys Glu Asp Val Cys Ala His Leu Val Asp
    1205                1210                1215

Leu Phe Leu Val Glu Glu Ile Phe Gln Thr Ala Lys Glu Thr Leu
    1220                1225                1230

Gln Glu Leu Gln Cys Phe Cys Lys Tyr Leu Gln Arg Trp Arg Glu
    1235                1240                1245

Ala Val Thr Ala Arg Lys Lys Leu Arg Arg Gln Met Arg Ala Phe
    1250                1255                1260

Pro Ala Ala Pro Cys Cys Val Asp Val Ser Asp Arg Leu Arg Ala
    1265                1270                1275

Leu Ala Pro Ser Ala Glu Cys Pro Ile Ala Glu Glu Asn Leu Ala
    1280                1285                1290

Arg Gly Leu Leu Asp Leu Gly His Ala Gly Arg Leu Gly Ile Ser
    1295                1300                1305

Cys Thr Arg Leu Arg Arg Leu Arg Asn Lys Thr Ala His Gln Met
    1310                1315                1320

Lys Val Gln His Phe Tyr Gln Gln Leu Leu Ser Asp Val Ala Trp
    1325                1330                1335

Ala Ser Leu Asp Leu Pro Ser Leu Val Ala Glu His Leu Pro Gly
    1340                1345                1350

Arg Gln Glu His Val Phe Trp Lys Leu Val Leu Leu Pro Asp
    1355                1360                1365

Val Glu Glu Gln Ser Pro Glu Ser Cys Gly Arg Ile Leu Ala Asn
    1370                1375                1380

Trp Leu Lys Val Lys Phe Met Gly Asp Glu Gly Ser Val Asp Asp
    1385                1390                1395

Thr Ser Ser Asp Ala Gly Gly Ile Gln Thr Leu Ser Leu Phe Asn
    1400                1405                1410

Ser Leu Ser Ser Lys Gly Asp Gln Met Ile Ser Val Asn Val Cys
    1415                1420                1425

Ile Lys Val Ala His Gly Ala Leu Ser Asp Gly Ala Ile Asp Ala
    1430                1435                1440

Val Glu Thr Gln Lys Asp Leu Leu Gly Ala Ser Gly Leu Met Leu
    1445                1450                1455
```

```
Leu Leu Pro Pro Lys Met Lys Ser Glu Asp Met Ala Glu Glu Asp
    1460            1465            1470

Val Tyr Trp Leu Ser Ala Leu Leu Gln Leu Lys Gln Leu Leu Gln
    1475            1480            1485

Ala Lys Pro Phe Gln Pro Ala Leu Pro Leu Val Val Leu Val Pro
    1490            1495            1500

Ser Pro Gly Gly Asp Ala Val Glu Lys Glu Val Glu Asp Gly Leu
    1505            1510            1515

Met Leu Gln Asp Leu Val Ser Ala Lys Leu Ile Ser Asp Tyr Thr
    1520            1525            1530

Val Thr Glu Ile Pro Asp Thr Ile Asn Asp Leu Gln Gly Ser Thr
    1535            1540            1545

Lys Val Leu Gln Ala Val Gln Trp Leu Val Ser His Cys Pro His
    1550            1555            1560

Ser Leu Asp Leu Cys Cys Gln Thr Leu Ile Gln Tyr Val Glu Asp
    1565            1570            1575

Gly Ile Gly His Glu Phe Ser Gly Arg Phe Phe His Asp Arg Arg
    1580            1585            1590

Glu Arg Arg Leu Gly Gly Leu Ala Ser Gln Glu Pro Gly Ala Ile
    1595            1600            1605

Ile Glu Leu Phe Asn Ser Val Leu Gln Phe Leu Ala Ser Val Val
    1610            1615            1620

Ser Ser Glu Gln Leu Cys Asp Leu Ser Trp Pro Val Thr Glu Phe
    1625            1630            1635

Ala Glu Ala Gly Gly Ser Arg Leu Leu Pro His Leu His Trp Asn
    1640            1645            1650

Ala Pro Glu His Leu Ala Trp Leu Lys Gln Ala Val Leu Gly Phe
    1655            1660            1665

Gln Leu Pro Gln Met Asp Leu Pro Pro Leu Gly Ala Pro Trp Leu
    1670            1675            1680

Pro Val Cys Ser Met Val Val Gln Tyr Ala Ser Gln Ile Pro Ser
    1685            1690            1695

Ser Arg Gln Thr Gln Pro Val Leu Gln Ser Gln Val Glu Asn Leu
    1700            1705            1710

Leu His Arg Thr Tyr Cys Arg Trp Lys Ser Lys Ser Pro Ser Pro
    1715            1720            1725

Val His Gly Ala Gly Pro Ser Val Met Glu Ile Pro Trp Asp Asp
    1730            1735            1740

Leu Ile Ala Leu Cys Ile Asn His Lys Leu Arg Asp Trp Thr Pro
    1745            1750            1755

Pro Arg Leu Pro Val Thr Ser Glu Ala Leu Ser Glu Asp Gly Gln
    1760            1765            1770

Ile Cys Val Tyr Phe Phe Lys Asn Asp Leu Lys Lys Tyr Asp Val
    1775            1780            1785

Pro Leu Ser Trp Glu Gln Ala Arg Leu Gln Thr Gln Lys Glu Leu
    1790            1795            1800

Gln Leu Arg Glu Gly Arg Leu Ala Ile Lys Pro Phe His Pro Ser
    1805            1810            1815

Ala Asn Asn Phe Pro Ile Pro Leu Leu His Met His Arg Asn Trp
    1820            1825            1830

Lys Arg Ser Thr Glu Cys Ala Gln Glu Gly Arg Ile Pro Ser Thr
    1835            1840            1845

Glu Asp Leu Met Arg Gly Ala Ser Ala Glu Glu Leu Leu Ala Gln
    1850            1855            1860
```

```
Cys Leu Ser Ser Ser Leu Leu Glu Lys Glu Asn Lys Arg
    1865            1870            1875

Phe Glu Asp Gln Leu Gln Gln Trp Leu Ser Glu Ser Gly Ala
1880            1885            1890

Phe Thr Asp Leu Thr Ser Leu Pro Leu Tyr Leu Pro Gln Thr Leu
1895            1900            1905

Val Ser Leu Ser His Thr Ile Glu Pro Val Met Lys Thr Ser Val
    1910            1915            1920

Thr Thr Ser Pro Gln Ser Asp Met Met Arg Glu Gln Leu Gln Leu
    1925            1930            1935

Ser Glu Ala Thr Gly Thr Cys Leu Gly Glu Arg Leu Lys His Leu
    1940            1945            1950

Glu Arg Leu Ile Arg Ser Ser Arg Glu Glu Val Ala Ser Glu
    1955            1960            1965

Leu His Leu Ser Ala Leu Leu Asp Met Val Asp Ile
    1970            1975            1980

<210> SEQ ID NO 5
<211> LENGTH: 33
<212> TYPE: DNA
<213> ORGANISM: Artificial sequence
<220> FEATURE:
<223> OTHER INFORMATION: LVH3 Primer

<400> SEQUENCE: 5
ctataaccat ggaccatgga catactttgt tcc                          33

<210> SEQ ID NO 6
<211> LENGTH: 36
<212> TYPE: DNA
<213> ORGANISM: Artificial sequence
<220> FEATURE:
<223> OTHER INFORMATION: XbaI-CH1-Cu Primer

<400> SEQUENCE: 6
tgcatgcatt ctagagttgc cgttggggtg ctggac                       36

<210> SEQ ID NO 7
<211> LENGTH: 20
<212> TYPE: DNA
<213> ORGANISM: Artificial sequence
<220> FEATURE:
<223> OTHER INFORMATION: Primer used in the preparation of GANP-
      Transgenic (Tg) Mouse

<400> SEQUENCE: 7
tcccgccttc cagctgtgac                                         20

<210> SEQ ID NO 8
<211> LENGTH: 20
<212> TYPE: DNA
<213> ORGANISM: Artificial sequence
<220> FEATURE:
<223> OTHER INFORMATION: Primer used in the preparation of GANP-
      Transgenic (Tg) Mouse

<400> SEQUENCE: 8
gtgctgctgt gttatgtcct                                         20

<210> SEQ ID NO 9
<211> LENGTH: 30
<212> TYPE: DNA
<213> ORGANISM: Artificial sequence
```

<220> FEATURE:
<223> OTHER INFORMATION: neo2 Primer

<400> SEQUENCE: 9
gcctgcttgc cgaatatcat ggtggaaaat                               30

<210> SEQ ID NO 10
<211> LENGTH: 28
<212> TYPE: DNA
<213> ORGANISM: Artificial sequence
<220> FEATURE:
<223> OTHER INFORMATION: CGK3'-2 Primer

<400> SEQUENCE: 10
ggcaccaagc atgcacggag tacacaga                                 28

<210> SEQ ID NO 11
<211> LENGTH: 26
<212> TYPE: DNA
<213> ORGANISM: Artificial sequence
<220> FEATURE:
<223> OTHER INFORMATION: GANP1-5' Primer

<400> SEQUENCE: 11
ggggatccat acccggtgaa cccctt                                   26

<210> SEQ ID NO 12
<211> LENGTH: 28
<212> TYPE: DNA
<213> ORGANISM: Artificial sequence
<220> FEATURE:
<223> OTHER INFORMATION: GANP1-3' Primer

<400> SEQUENCE: 12
gggtcgacgc gcacagactt tcccctga                                 28

<210> SEQ ID NO 13
<211> LENGTH: 28
<212> TYPE: DNA
<213> ORGANISM: Artificial sequence
<220> FEATURE:
<223> OTHER INFORMATION: GANP2-5' Primer

<400> SEQUENCE: 13
gggaattctc ccgccttcca gctgtgac                                 28

<210> SEQ ID NO 14
<211> LENGTH: 28
<212> TYPE: DNA
<213> ORGANISM: Artificial sequence
<220> FEATURE:
<223> OTHER INFORMATION: GANP2-3' Primer

<400> SEQUENCE: 14
gggtcgacgt gctgctgtgt tatgtcct                                 28

<210> SEQ ID NO 15
<211> LENGTH: 28
<212> TYPE: DNA
<213> ORGANISM: Artificial sequence
<220> FEATURE:
<223> OTHER INFORMATION: GANP3-5' Primer

<400> SEQUENCE: 15
gggaattcca tgagctgaga ccctcagc                                 28

```
<210> SEQ ID NO 16
<211> LENGTH: 28
<212> TYPE: DNA
<213> ORGANISM: Artificial sequence
<220> FEATURE:
<223> OTHER INFORMATION: GANP3-3' Primer

<400> SEQUENCE: 16
gggtcgactg aggatgcagg aggcggct                                    28

<210> SEQ ID NO 17
<211> LENGTH: 28
<212> TYPE: DNA
<213> ORGANISM: Artificial sequence
<220> FEATURE:
<223> OTHER INFORMATION: GANP4-5' Primer

<400> SEQUENCE: 17
gggaattcta cgttggagag agcctggc                                    28

<210> SEQ ID NO 18
<211> LENGTH: 28
<212> TYPE: DNA
<213> ORGANISM: Artificial sequence
<220> FEATURE:
<223> OTHER INFORMATION: GANP4-3' Primer

<400> SEQUENCE: 18
gggtcgacca tgctgtcatc tcctgtga                                    28

<210> SEQ ID NO 19
<211> LENGTH: 28
<212> TYPE: DNA
<213> ORGANISM: Artificial sequence
<220> FEATURE:
<223> OTHER INFORMATION: GANP5-5'Primer

<400> SEQUENCE: 19
gggaattcga gaacctggcc aagggtct                                    28

<210> SEQ ID NO 20
<211> LENGTH: 28
<212> TYPE: DNA
<213> ORGANISM: Artificial sequence
<220> FEATURE:
<223> OTHER INFORMATION: GANP5-3'Primer

<400> SEQUENCE: 20
gggtcgacga aaaccgacg gctgaact                                     28

<210> SEQ ID NO 21
<211> LENGTH: 28
<212> TYPE: DNA
<213> ORGANISM: Artificial sequence
<220> FEATURE:
<223> OTHER INFORMATION: GANP6-5' Primer

<400> SEQUENCE: 21
gggaattcaa gcccttccag cctgccct                                    28

<210> SEQ ID NO 22
<211> LENGTH: 28
<212> TYPE: DNA
<213> ORGANISM: Artificial sequence
<220> FEATURE:
<223> OTHER INFORMATION: GANP6-3' Primer

<400> SEQUENCE: 22
```
gggtcgaccg agggaacgtg gtattttc                                    28

<210> SEQ ID NO 23
<211> LENGTH: 28
<212> TYPE: DNA
<213> ORGANISM: Artificial sequence
<220> FEATURE:
<223> OTHER INFORMATION: GANP7-5' Primer

<400> SEQUENCE: 23
ggcccgggcc cgtgggatga catcatca                                    28

<210> SEQ ID NO 24
<211> LENGTH: 28
<212> TYPE: DNA
<213> ORGANISM: Artificial sequence
<220> FEATURE:
<223> OTHER INFORMATION: GANP7-3' Primer

<400> SEQUENCE: 24
ggctcgagca tgtccaccat ctccagca                                    28

<210> SEQ ID NO 25
<211> LENGTH: 41
<212> TYPE: DNA
<213> ORGANISM: Artificial sequence
<220> FEATURE:
<223> OTHER INFORMATION: Gp-gfp-5' Primer

<400> SEQUENCE: 25 gggggatccga attccaccat ggcagtcttc aaaccgatac c                    41

<210> SEQ ID NO 26
<211> LENGTH: 20
<212> TYPE: DNA
<213> ORGANISM: Artificial sequence
<220> FEATURE:
<223> OTHER INFORMATION: Gp-gfp-3' Primer

<400> SEQUENCE: 26 gcagggctc ctcctgatct                                              20

<210> SEQ ID NO 27
<211> LENGTH: 41
<212> TYPE: DNA
<213> ORGANISM: Artificial sequence
<220> FEATURE:
<223> OTHER INFORMATION: Gsac-gfp-5' Primer

<400> SEQUENCE: 27 gggggatccga attccaccat gtccgagggc cttggttctt g                    41

<210> SEQ ID NO 28
<211> LENGTH: 20
<212> TYPE: DNA
<213> ORGANISM: Artificial sequence
<220> FEATURE:
<223> OTHER INFORMATION: Gsac-gfp-3' Primer

<400> SEQUENCE: 28
ctgtcttgtt tctaagccgc                                             20

<210> SEQ ID NO 29
<211> LENGTH: 41
<212> TYPE: DNA
<213> ORGANISM: Artificial sequence

```
<220> FEATURE:
<223> OTHER INFORMATION: Gmap80-gfp-5' Primer

<400> SEQUENCE: 29
ggggatccga attccaccat ggagaacctg gccaagggtc t                41

<210> SEQ ID NO 30
<211> LENGTH: 27
<212> TYPE: DNA
<213> ORGANISM: Artificial sequence
<220> FEATURE:
<223> OTHER INFORMATION: Gmap80-gfp-3' Primer

<400> SEQUENCE: 30
gaggacttgt agatgttttc accatgg                                27

<210> SEQ ID NO 31
<211> LENGTH: 58
<212> TYPE: DNA
<213> ORGANISM: Artificial sequence
<220> FEATURE:
<223> OTHER INFORMATION: FLAG-Gp-5' Primer

<400> SEQUENCE: 31
gggaattcca ccatggatta caaggatgac gacgataagg cagtcttcaa ccgatacc   58

<210> SEQ ID NO 32
<211> LENGTH: 28
<212> TYPE: DNA
<213> ORGANISM: Artificial sequence
<220> FEATURE:
<223> OTHER INFORMATION: FLAG-Gp-3' Primer

<400> SEQUENCE: 32
gggaattcct ccgggtctcc ctcaagta                               28

<210> SEQ ID NO 33
<211> LENGTH: 59
<212> TYPE: DNA
<213> ORGANISM: Artificial sequence
<220> FEATURE:
<223> OTHER INFORMATION: FLAG-Gsac-5' Primer

<400> SEQUENCE: 33
gggaattcca ccatggatta caaggatgac gacgataagt ccgagggcct tggttcttg   59

<210> SEQ ID NO 34
<211> LENGTH: 28
<212> TYPE: DNA
<213> ORGANISM: Artificial sequence
<220> FEATURE:
<223> OTHER INFORMATION: FLAGGsac-3' Primer

<400> SEQUENCE: 34
gggaattcgc tgtcttgttt ctaagccg                               28

<210> SEQ ID NO 35
<211> LENGTH: 59
<212> TYPE: DNA
<213> ORGANISM: Artificial sequence
<220> FEATURE:
<223> OTHER INFORMATION: FLAG-Gmap-5' Primer

<400> SEQUENCE: 35
gggaattcca ccatggatta caaggatgac gacgataagg agaacctggc caagggtct   59
```

```
<210> SEQ ID NO 36
<211> LENGTH: 28
<212> TYPE: DNA
<213> ORGANISM: Artificial sequence
<220> FEATURE:
<223> OTHER INFORMATION: FLAG-Gmap-3' Primer

<400> SEQUENCE: 36
gggaattctg aggacttgta gatgtttt                                         28

<210> SEQ ID NO 37
<211> LENGTH: 98
<212> TYPE: PRT
<213> ORGANISM: Mus musculus
<220> FEATURE:
<221> NAME/KEY: misc_feature
<222> LOCATION: (1)..(98)
<223> OTHER INFORMATION: Fig. 10 WT

<400> SEQUENCE: 37

Gln Val Gln Leu Gln Gln Pro Gly Ala Glu Leu Val Lys Pro Gly Ala
1               5                   10                  15

Ser Val Lys Leu Ser Cys Lys Ala Ser Gly Tyr Thr Phe Thr Ser Tyr
            20                  25                  30

Trp Met His Trp Val Lys Gln Arg Pro Gly Arg Gly Leu Glu Trp Ile
        35                  40                  45

Gly Arg Ile Asp Pro Asn Ser Gly Gly Thr Lys Tyr Asn Glu Lys Phe
    50                  55                  60

Lys Ser Lys Ala Thr Leu Thr Val Asp Lys Pro Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg

<210> SEQ ID NO 38
<211> LENGTH: 294
<212> TYPE: DNA
<213> ORGANISM: Mus musculus
<220> FEATURE:
<221> NAME/KEY: misc_feature
<222> LOCATION: (1)..(294)
<223> OTHER INFORMATION: Fig. 10 WT

<400> SEQUENCE: 38
caggtccaac tgcagcagcc tggggctgag cttgtgaagc ctggggcttc agtgaagctg      60
tcctgcaagg cttctggcta caccttcacc agctactgga tgcactgggt gaagcagagg     120
cctggacgag gccttgagtg gattggaagg attgatccta atagtggtgg tactaagtac     180
aatgagaagt tcaagagcaa ggccacactg actgtagaca aaccctccag cacagcctac     240
atgcagctca gcagcctgac atctgaggac tctgcggtct attattgtgc aaga           294

<210> SEQ ID NO 39
<211> LENGTH: 294
<212> TYPE: DNA
<213> ORGANISM: Mus musculus
<220> FEATURE:
<221> NAME/KEY: misc_feature
<222> LOCATION: (1)..(39)
<223> OTHER INFORMATION: Fig. 10: WT-4

<400> SEQUENCE: 39
caggtccaac tgcagcagcc tggggctgag cttgtgaagc ctggggcttc agtgaagctg      60
tcctgcaagg cttctggcta caccttcacc agctactgga tgcactgggt gaagcagagg     120
```

```
cctggacgag gccttgagtg gattggaagg attgatccta atagtggtgg tactaagtac    180
aatgagaagt tcaagagcaa ggccacactg actgtagaca aaccctccag cacagcctac    240
atgcagctca gcagcctgac atctgaggac tctgcggtct attattgtgc gagt          294
```

<210> SEQ ID NO 40
<211> LENGTH: 294
<212> TYPE: DNA
<213> ORGANISM: Mus musculus
<220> FEATURE:
<221> NAME/KEY: misc_feature
<222> LOCATION: (1)..(294)
<223> OTHER INFORMATION: Fig. 10: WT-5

<400> SEQUENCE: 40

```
caggtccaac tgcagcagcc tggggctgag cttgtgaagc ctggggcttc agtgaagctg    60
tcctgcaagg cttctggcta caccttcacc atctacttaa tgcactgggt gaagcagagg    120
cctggacgag gccttgagtg gattggaagg attgatccta atagtggtgg tactaagtac    180
aatgagaact tcaagagcaa ggccacactg actgtagaca aaccctccag cacagcctac    240
atgcagctca gcagcctgac atctgaggac tctgcggtct attattgtgc aaga          294
```

<210> SEQ ID NO 41
<211> LENGTH: 294
<212> TYPE: DNA
<213> ORGANISM: Mus musculus
<220> FEATURE:
<221> NAME/KEY: misc_feature
<222> LOCATION: (1)..(294)
<223> OTHER INFORMATION: Fig. 10: WT-6

<400> SEQUENCE: 41

```
caggtccaac tgcagcagcc tggggctgag cttgtgaagc ctggggcttc agtgaagctg    60
tcctgcaagg cttctggcta caccttcacc agttacttga tgcactgggt gaagcagggg    120
cctggacgag gccttgagtg gattggaagg attgatccta atagtggtgg tactaagtac    180
aatgagaagt tcaagagcaa ggccacactg actgtagaca aaccctccag cacagcctac    240
atgcagctca gcagcctgac atctgaggac tctgcggtct attattgtgc gagt          294
```

<210> SEQ ID NO 42
<211> LENGTH: 294
<212> TYPE: DNA
<213> ORGANISM: Mus musculus
<220> FEATURE:
<221> NAME/KEY: misc_feature
<222> LOCATION: (1)..(294)
<223> OTHER INFORMATION: Fig. 10: WT-9

<400> SEQUENCE: 42

```
caggtccaac tgcagcagcc tggggctgag cttgtgaagc ctggggcttc agtgaagctg    60
tcctgcaaga cttctggcta ctccttcacc agctacttta tacactgggt gaagcagagg    120
cctggacgag gccttgagtg gattggaagg attgatccta atagtggtgg tactaagtac    180
aatgagaaat tcaagagcag ggccacactg actgtagaca aaccctccag cacagcctac    240
atgcagctca gcagcctgac atctgaggac tctgcggtct attattgtgc aaga          294
```

<210> SEQ ID NO 43
<211> LENGTH: 294
<212> TYPE: DNA
<213> ORGANISM: Mus musculus
<220> FEATURE:
<221> NAME/KEY: misc_feature
<222> LOCATION: (1)..(294)
<223> OTHER INFORMATION: Fig. 10: WT-10

<400> SEQUENCE: 43

```
caggtccaac tgcagcagcc tggggctgag cttgtgaagc ctggggcttc agtgaagctg      60
tcctgcaagg cttctggcta caccttcacc agctactgga tgcactggat gaagcagagg     120
cctggacgag gccttgagtg gattggaagg attgatccta atagtggtgg tactaggtac     180
aatgagaagt tcaagagcaa ggccacactg actgtagaca aaccctccag cacagcctac     240
atgcagctca gcagcctgac atctgaggac tctgcggtct attattgtgc aaga           294
```

<210> SEQ ID NO 44
<211> LENGTH: 294
<212> TYPE: DNA
<213> ORGANISM: Mus musculus
<220> FEATURE:
<221> NAME/KEY: misc_feature
<222> LOCATION: (1)..(294)
<223> OTHER INFORMATION: Fig. 10: WT-11

<400> SEQUENCE: 44

```
caggtccaac tgcagcagcc tggggctgag cttgtgaagc ctggggcttc agtgaagctg      60
tcctgcaagg cttctggcta caccttcacc agctactgga tgcactgggt gaagcagagg     120
cctggacgag gccttgagtg gattggaagg attgatccta atagtggtgg tactaagtac     180
aatgagaagt tcaagagcaa ggccacactg actgtaggca aaccctccag cacagcctac     240
atgcggctca gcagcctgac atctgaggac tctgcggtct attattgtgc acgt           294
```

<210> SEQ ID NO 45
<211> LENGTH: 294
<212> TYPE: DNA
<213> ORGANISM: Mus musculus
<220> FEATURE:
<221> NAME/KEY: misc_feature
<222> LOCATION: (1)..(294)
<223> OTHER INFORMATION: Fig. 10: WT-14

<400> SEQUENCE: 45

```
caggtccaac tgcagcagcc tggggctgag cttgtgaagc ctggggcttc agtgaagctg      60
tcctgcaagg cttctggcta caccttcacc agctactgga tgcactgggt gaagcagagg     120
cctggacgag gccttgagtg gattggaagg attgatccta atagtggtgg tactaagtac     180
aatgagaagt tcaagagcaa ggccacactg actgttgaca aaccctccag cacagcctac     240
atgcagctca gcagcctgac atctgaggac tctgcggtct attattgtgc aaga           294
```

<210> SEQ ID NO 46
<211> LENGTH: 294
<212> TYPE: DNA
<213> ORGANISM: Mus musculus
<220> FEATURE:
<221> NAME/KEY: misc_feature
<222> LOCATION: (1)..(294)
<223> OTHER INFORMATION: Fig. 10: WT-16

<400> SEQUENCE: 46

```
caggtccaac tgcagcagcc tggggctgag cttgtgaagc ctggggcttc agtgaagctg      60
tcctgcaagg cttctggcta caccttcacc aactacttga tgcactgggt gaagcagagg     120
cctggacgag gccttgggtg gattggaagg attgatccta atagtggtgg tactaagtac     180
aatgagaagt tcaagagcaa ggccacactg actgtagaca aaccctccag cacagcctac     240
atgcagctca gcagcctgac atctgaggac tctgcggtct attattgtgc gagt           294
```

-continued

<210> SEQ ID NO 47
<211> LENGTH: 294
<212> TYPE: DNA
<213> ORGANISM: Mus musculus
<220> FEATURE:
<221> NAME/KEY: misc_feature
<222> LOCATION: (1)..(294)
<223> OTHER INFORMATION: Fig. 10: WT-17

<400> SEQUENCE: 47
caggtccaac tgcagcagcc tggggctgag cttgtgaagc ctggggcttc agtgaagctg     60
tcctgcaagg cttctggcta caccttcacc agctactgga tgcactgggt gaagcagagg    120
cctggacgag gccttgagtg gattggaagg attgatccta atagtggtgg ttctaagtac    180
aatgagaagt tcaagagcaa ggccacactg actgtagaca aaccctccag cacagcctac    240
atgcacctca gcagcctgac atctgaggac tctgcggtct attattgtgc aaga          294

<210> SEQ ID NO 48
<211> LENGTH: 294
<212> TYPE: DNA
<213> ORGANISM: Mus musculus
<220> FEATURE:
<221> NAME/KEY: misc_feature
<222> LOCATION: (1)..(294)
<223> OTHER INFORMATION: Fig. 10: WT-18

<400> SEQUENCE: 48
caggtccaac tgcagcagcc tggggctgag cttgtgaagc ctggggcttc agtgaagctg     60
tcctgcaagg cttctggcta caccttcacc agctactgga tgcactgggt gaagcagagg    120
cctggacgag gccttgagtg gattggaagg attgatccta atagtggtgg tactaagtac    180
aatgagaagt tcaagagcaa ggccacactg actgtagaca aaccctccag cacagcctac    240
atgcagctca gcagcctgac atctgaggac tctgcgatct attattgtgc aaga          294

<210> SEQ ID NO 49
<211> LENGTH: 294
<212> TYPE: DNA
<213> ORGANISM: Mus musculus
<220> FEATURE:
<221> NAME/KEY: misc_feature
<222> LOCATION: (1)..(294)
<223> OTHER INFORMATION: Fig. 10: WT-19

<400> SEQUENCE: 49
caggtccaac tgcagcagcc tggggctgag cttgtgaagc ctggggcttc agtgaagctg     60
tcctgcaagg cttctggcta caccttcacc agctactgga tgcactgggt gaagcagagg    120
cctggacgag gccttgagtg gattggaagg attgttccta atagtggtga tactaagtac    180
aatgagaagt tcaagaacaa ggccacactg actgtagaca aaccctccag cacagcctac    240
atgcagctca gcagcctgac atctgaggac tctgcggtct attattgtgc aaga          294

<210> SEQ ID NO 50
<211> LENGTH: 294
<212> TYPE: DNA
<213> ORGANISM: Mus musculus
<220> FEATURE:
<221> NAME/KEY: misc_feature
<222> LOCATION: (1)..(294)
<223> OTHER INFORMATION: Fig. 10: WT-20

<400> SEQUENCE: 50
caggtccaac tgcagcagcc tggggctgag cttgtgaagc ctggggcttc agtgaagctg     60

```
tcctgcaagg cttctggcta ccccttcacc agctactgga tgcactgggt gaagcagagg      120
cctggacgag gccttgagtg gattggaagg attgatccta atagtggtta tactaggtac      180
aatgagaagt tcaagagcaa ggccacactg actgtagaca aaccctccag cacagcctcc      240
atgcagctca gcagcctgac atctgaggac tctgcggtct attactgtgc aaga            294
```

<210> SEQ ID NO 51
<211> LENGTH: 294
<212> TYPE: DNA
<213> ORGANISM: Mus musculus
<220> FEATURE:
<221> NAME/KEY: misc_feature
<222> LOCATION: (1)..(294)
<223> OTHER INFORMATION: Fig. 10: WT-21

<400> SEQUENCE: 51

```
caggtccaac tgcagcagcc tggggctgag cttgtgaagc ctggggcttc agtgaagctg      60
tcctgcaagg cttctggcta ccccttcacc agctactgga tgcactgggt gaagcagagg      120
cctggacgag gccttgagtg gattggaagg attgatccta atagtggtgg tactaagtac      180
aatgagaagt tcaagagcaa ggccacactg actgtagaca aaccctccag cacagcctac      240
atgcagctca gcagcctgac atctgaggac tctgcggtct attattgtgc aagg            294
```

<210> SEQ ID NO 52
<211> LENGTH: 294
<212> TYPE: DNA
<213> ORGANISM: Mus musculus
<220> FEATURE:
<221> NAME/KEY: misc_feature
<222> LOCATION: (1)..(294)
<223> OTHER INFORMATION: Fig. 10: WT-22

<400> SEQUENCE: 52

```
caggtccaac tgcagcagcc tggggctgag cttgtgaagc ctggggcttc agtgaagctg      60
tcctgcaagg cttctggcta ccccttcacc agctactgga tgcactgggt gaagcagagg      120
cctggacgag gccttgagtg gattggaggg attgatccta atagtggtta tactaggtac      180
aatgagaagt tcaagagcaa ggccacactg actgtagaca aaccctccag cacagcctcc      240
atgcagctca gcagcctgac atctgaggac tctgcggtct attattgtgc aaga            294
```

<210> SEQ ID NO 53
<211> LENGTH: 98
<212> TYPE: PRT
<213> ORGANISM: Mus musculus
<220> FEATURE:
<221> NAME/KEY: misc_feature
<222> LOCATION: (1)..(98)
<223> OTHER INFORMATION: Fig. 10 TG

<400> SEQUENCE: 53

```
Gln Val Gln Leu Gln Gln Pro Gly Ala Glu Leu Val Lys Pro Gly Ala
1               5                   10                  15

Ser Val Lys Leu Ser Cys Lys Ala Ser Gly Tyr Thr Phe Thr Ser Tyr
            20                  25                  30

Trp Met His Trp Val Lys Gln Arg Pro Gly Arg Gly Leu Glu Trp Ile
        35                  40                  45

Gly Arg Ile Asp Pro Asn Ser Gly Gly Thr Lys Tyr Asn Glu Lys Phe
    50                  55                  60

Lys Ser Lys Ala Thr Leu Thr Val Asp Lys Pro Ser Ser Thr Ala Tyr
65                  70                  75                  80
```

Met Gln Leu Ser Ser Leu Thr Ser Glu Asp Ser Ala Val Tyr Tyr Cys
            85                  90                  95

Ala Arg

<210> SEQ ID NO 54
<211> LENGTH: 294
<212> TYPE: DNA
<213> ORGANISM: Mus musculus
<220> FEATURE:
<221> NAME/KEY: misc_feature
<222> LOCATION: (1)..(294)
<223> OTHER INFORMATION: Fig. 10 TG

<400> SEQUENCE: 54
caggtccaac tgcagcagcc tggggctgag cttgtgaagc ctggggcttc agtgaagctg      60
tcctgcaagg cttctggcta caccttcacc agctactgga tgcactgggt gaagcagagg     120
cctggacgag gccttgagtg gattggaagg attgatccta atagtggtgg tactaagtac     180
aatgagaagt tcaagagcaa ggccacactg actgtagaca aaccctccag cacagcctac     240
atgcagctca gcagcctgac atctgaggac tctgcggtct attattgtgc aaga           294

<210> SEQ ID NO 55
<211> LENGTH: 294
<212> TYPE: DNA
<213> ORGANISM: Mus musculus
<220> FEATURE:
<221> NAME/KEY: misc_feature
<222> LOCATION: (1)..(294)
<223> OTHER INFORMATION: Fig. 10: Tg-3

<400> SEQUENCE: 55
caggtccaac tgcagcagcc tggggctgag cttgtgaagc ctggggcttc agtgaagctg      60
tcctgcaagg cttctggcta caccttcacc agctacctga tgcactgggt gaagcagagg     120
cctggacgag gccttgagtg gattggaagg attgatccta atcgtggtgg tactaagtac     180
aatgagaagt tcattaacaa ggccacactg actgtagaca aaccctccag cacagcctac     240
atgcagctca gcagcctgac atctgaggac tctgcggtct attattgtgc aaga           294

<210> SEQ ID NO 56
<211> LENGTH: 294
<212> TYPE: DNA
<213> ORGANISM: Mus musculus
<220> FEATURE:
<221> NAME/KEY: misc_feature
<222> LOCATION: (1)..(294)
<223> OTHER INFORMATION: Fig. 10: Tg-4

<400> SEQUENCE: 56
caggtccaac tgcagcagcc tggggctgaa cttgtgaagc ctggggcttc agtgaagctg      60
tcctgcaagg cttctggcta caccttcacc aactacttga tgcactgggt gaagcagagg     120
cctggacgag gccttgagtg gattggaagg attgatccta atagtggtgg tactaagtac     180
aatgagaagt tcaagagcaa ggccacactg actgtagaca aaccctccag cacagcctac     240
atgcagctca gcagcctgac atctgaggac tctgcggtct attattgtgc aaga           294

<210> SEQ ID NO 57
<211> LENGTH: 294
<212> TYPE: DNA
<213> ORGANISM: Mus musculus
<220> FEATURE:
<221> NAME/KEY: misc_feature
<222> LOCATION: (1)..(294)
<223> OTHER INFORMATION: Fig. 10: Tg-5

<400> SEQUENCE: 57
caggtccaac tgcagcagcc tggggctgag cttgtgaagc ctggggcttc agtgaagctg      60
tcctgcaagg cttctggcta caccttcacc agctactgga tgcactgggt gaagcagagg     120
cctggacgag gccttgagtg gattggaagg attgatccta atagtggtgg tactaagtac     180
aatgagaagt tcaagagcaa ggccacactg actgtagaca aaccctccag cacagcctac     240
atgcagctca gcagcctgac acctgaggac tctgcggtct attattgtgc aaga           294

<210> SEQ ID NO 58
<211> LENGTH: 294
<212> TYPE: DNA
<213> ORGANISM: Mus musculus
<220> FEATURE:
<221> NAME/KEY: misc_feature
<222> LOCATION: (1)..(294)
<223> OTHER INFORMATION: Fig. 10: Tg-7

<400> SEQUENCE: 58
caggtccaac tgcagcagcc tggggctgag cttgtgaagc ctggggcttc agtgaagctg      60
tcctgcaagg cttctggcta caccttcacc agctactgga tgcaccgggt gaagcagagg     120
cctggacgag gccttgagtg gattggaagg attgatccta atagtggtgg tactaagtac     180
aatgagaagt tcaagagcaa ggccacactg actgtagaca gaccctccag cacagcctac     240
atgcagctca gcagcctgac atctgaggac tctgcggtct attattgtgc aaga           294

<210> SEQ ID NO 59
<211> LENGTH: 294
<212> TYPE: DNA
<213> ORGANISM: Mus musculus
<220> FEATURE:
<221> NAME/KEY: misc_feature
<222> LOCATION: (1)..(294)
<223> OTHER INFORMATION: Fig. 10: Tg-8

<400> SEQUENCE: 59
caggtccaac tgcagcagcc tggggctgag cttgtgaagc ctgggtcttc agtgaagctg      60
tcctgcaagc cttctggcta caccttcacc acctactgga tacactgggt gaggcagagg     120
cctggacgag gccttgagtg gattggaagg attgatccta atagtggtgg tactaagtac     180
aatgagaagt tcaagagcaa ggccacactg actgtagaca aaccctccag cacagcctac     240
atgcagctca gcagcctgac atctgaggac tctgcggtct attattgtgc aaga           294

<210> SEQ ID NO 60
<211> LENGTH: 294
<212> TYPE: DNA
<213> ORGANISM: Mus musculus
<220> FEATURE:
<221> NAME/KEY: misc_feature
<222> LOCATION: (1)..(294)
<223> OTHER INFORMATION: Fig. 10: Tg-9

<400> SEQUENCE: 60
caggtccaac tgcagcagcc tggggctgag cttgtgaagc ctggggcttc agtgaagctg      60
tcctgcaagg cttctggcta caccttcacc agctacttga tgcactgggt gaagcagagg     120
cctggacgag gccttgagtg gattggaagg attgatccta atagtggtgg tactaagtac     180
aatgagaagt tcaagagcaa ggccacactg actgtagaca aaccctccag cacagcctac     240
atgcagctca gcagcctgac atctgaggac tctgcggtct attattgtgc aaga           294

```
<210> SEQ ID NO 61
<211> LENGTH: 294
<212> TYPE: DNA
<213> ORGANISM: Mus musculus
<220> FEATURE:
<221> NAME/KEY: misc_feature
<222> LOCATION: (1)..(294)
<223> OTHER INFORMATION: Fig. 10: Tg-10

<400> SEQUENCE: 61
caggtccaac tgcagcagcc tggggctgag cttgtgaagc ctggggcttc agtgaagctg      60
tcctgcaagg cttctggcta caccttcaac agttactgga tgcactgggt gaagcagagg     120
cctggacgag gccttgagtg gattggaagg attgatccta atagtggtgg tactaagtac     180
aatgagaagt tcaagagcaa ggccacactg actgtagaca atcctccag cacagcctac      240 atgcagctca gcagcctgac atctgaggac tctgcggtct attattgtgc aaga           294

<210> SEQ ID NO 62
<211> LENGTH: 294
<212> TYPE: DNA
<213> ORGANISM: Mus musculus
<220> FEATURE:
<221> NAME/KEY: misc_feature
<222> LOCATION: (1)..(294)
<223> OTHER INFORMATION: Fig. 10: Tg-11

<400> SEQUENCE: 62
caggtccaac tgcagcagcc tggggctgag cttgtgaagc ctggggcttc agtgaagctg      60
tcctgcaagg cttctggcta caccttcacc agctacttga tgcactgggt gaagcagagg     120
cctggacgag gccttgagtg gattggaagg attgatccta atagtggtgg tactaagtac     180
aatgagaagt tcaagagcaa ggccacactg actgtagaca aaccttccag cacagcctac     240
atgcagctca gcagcctgac atctgaggac tctgcggtct attattgtgc aaga           294

<210> SEQ ID NO 63
<211> LENGTH: 294
<212> TYPE: DNA
<213> ORGANISM: Mus musculus
<220> FEATURE:
<221> NAME/KEY: misc_feature
<222> LOCATION: (1)..(294)
<223> OTHER INFORMATION: Fig. 10: Tg-12

<400> SEQUENCE: 63
caggtccaac tgcagcagcc tggggctgag cttgtgaagc ctggggcttc agtgaagctg      60
tcctgcaagg cttctggcta caccttcacc agctacttga tgcactgggt gaagcagagg     120
cctggacgag gccttgagtg gattggaagg attgatccta atagtggtgg tactaagtac     180
aatgagaagt tcaagagcaa ggccacactg actgtagaca aaccctccag cacagcctac     240
atgcagctca gcagcctgac atctgaggac tctgcggtct attattgtgc aaga           294

<210> SEQ ID NO 64
<211> LENGTH: 294
<212> TYPE: DNA
<213> ORGANISM: Mus musculus
<220> FEATURE:
<221> NAME/KEY: misc_feature
<222> LOCATION: (1)..(294)
<223> OTHER INFORMATION: Fig. 10: Tg-13

<400> SEQUENCE: 64
caggtccaac tgcagcagcc tggggctgag cttgtgaagt ctggggcttc agtgaagctg      60
tcctgcaagg cttctggcta caccttcacc agctacttga tgcactggt gaagcagtgg      120
```
cctggacgag gccttgagtg gattggaagg attgatccta atagtggtgg tactaagtac    180
aatgagaagt tcaagaacaa ggccacactg actgtagaca aaccctccag cacagcctac    240
atgcagctca gcagcctgtc atctgaggac tctgcggtct attattgtgc aaga          294

<210> SEQ ID NO 65
<211> LENGTH: 294
<212> TYPE: DNA
<213> ORGANISM: Mus musculus
<220> FEATURE:
<221> NAME/KEY: misc_feature
<222> LOCATION: (1)..(294)
<223> OTHER INFORMATION: Fig. 10: Tg-14

<400> SEQUENCE: 65
caggtccaac tgcagcagcc tggggctgag cttgtgaagc ctggggcttc agtgaagctg     60
tcctgcaaag cttctggcta caccttcacc agctacttga tgcactgggt gaagcagagg    120
cctggacgag gccttgagtg gattggaagg attgatccca atagtggtgg tactaagtac    180
aatgagaagt tcaggagcag ggccacactg actgtagaca aaccctccag cacagcctac    240
atgcagctca gcagcctgac atctgaggac tctgcggtct attattgtgc aaga          294

<210> SEQ ID NO 66
<211> LENGTH: 294
<212> TYPE: DNA
<213> ORGANISM: Mus musculus
<220> FEATURE:
<221> NAME/KEY: misc_feature
<222> LOCATION: (1)..(294)
<223> OTHER INFORMATION: Fig. 10: Tg-15

<400> SEQUENCE: 66
caggtccgac tgcagcagcc tggggctgag cttgtgaagc ctggggcttc agtgaagctg     60
tcctgcaagg cttctggcta caccttcacc ggctactgga tggactgggt gaagcagagg    120
cctggacgag gccttgagtg gattggaagg atcgatccta atagtggtgg cactaagtac    180
aaagagaagt tcaagagcaa ggccacactg actgtagaca aaccctccag cacagcctac    240
atgcagctca gcagcctgac atctgaggac tctgcggtct attattgtgc aaga          294

<210> SEQ ID NO 67
<211> LENGTH: 294
<212> TYPE: DNA
<213> ORGANISM: Mus musculus
<220> FEATURE:
<221> NAME/KEY: misc_feature
<222> LOCATION: (1)..(294)
<223> OTHER INFORMATION: Fig. 10: Tg-16

<400> SEQUENCE: 67
caggtccaac tgcagcagcc tggggctgag cttgtgaagc ctggggcttc agtgaagctg     60
tcctgcaagg cttctggcta caccttcaat agctacttga tgcactgggt gaagcagagg    120
cctggacgag gccttgagtg gattggaagg attgatccta atagtggtgg tactaagtac    180
aatgagaagt tcaagaacaa ggccacactg actgtagaca aaccctccag cacagcctac    240
atgcacctca gcagcctgac atctgaggac tctgcggtct attattgtgc aaga          294

<210> SEQ ID NO 68
<211> LENGTH: 294
<212> TYPE: DNA
<213> ORGANISM: Mus musculus
<220> FEATURE:
<221> NAME/KEY: misc_feature
<222> LOCATION: (1)..(294)
<223> OTHER INFORMATION: Fig. 10: Tg-17

<400> SEQUENCE: 68

| | | |
|---|---|---|
| caggtccaac tgcagcagcc tggggctgag cttgtgaagc ctggggcttc agtgaagctg | 60 |
| tcctgcaagg cttctggcta caccttcacc agctacttga tgcactgggt gaagcagagg | 120 |
| cctggacgag gccttgagtg gattggaagg attgatccta attctggtgg tactaagtac | 180 |
| aatgagaagt tcaagaccaa ggccacactg actgtagaca aaccctccag cacagcctac | 240 |
| atgcagctca gcagcctgac atctgaggac tctgcggtct attattgtgc aaga | 294 |

<210> SEQ ID NO 69
<211> LENGTH: 294
<212> TYPE: DNA
<213> ORGANISM: Mus musculus
<220> FEATURE:
<221> NAME/KEY: misc_feature
<222> LOCATION: (1)..(294)
<223> OTHER INFORMATION: Fig. 10: Tg-18

<400> SEQUENCE: 69

| | | |
|---|---|---|
| caggtccaac tgcagcagcc tggggctgag cttgtgaagc ctggggcttc agtgaagctg | 60 |
| tcctgcaagg cttctggcta cattttcacc agctacctga tgcactgggt gaagcagagg | 120 |
| cctggacgag gccttgagtg gattggaagg attgatccta atcgtggtgg tactaagtac | 180 |
| aatgagaagt tcattaacaa ggccacactg actgtagaca aaccctccac cacagcctac | 240 |
| atgcagctca gcagcctgac atctgaggac tctgcggtct attattgtgc aaga | 294 |

<210> SEQ ID NO 70
<211> LENGTH: 294
<212> TYPE: DNA
<213> ORGANISM: Mus musculus
<220> FEATURE:
<221> NAME/KEY: misc_feature
<222> LOCATION: (1)..(294)
<223> OTHER INFORMATION: Fig. 10: Tg-20

<400> SEQUENCE: 70

| | | |
|---|---|---|
| caggtccaac tgcagcagcc tggggctgag cttgtgaagc ctggggcttc agtgaagctg | 60 |
| tcctgcaagg cttctggcta caccttcacc agctactgga tgcactgggt gaagcagagg | 120 |
| cctggacgag gccttgagtg gattggaagg attgatccta atagtggtgg tactaggtac | 180 |
| aatgagaggt tcaagagcaa ggccacactg tctgtagaca aaccctccag cacagcctac | 240 |
| atgcagctca gcagcctgac atctgaggac tctgcggtct attattgtgc aaga | 294 |

<210> SEQ ID NO 71
<211> LENGTH: 294
<212> TYPE: DNA
<213> ORGANISM: Mus musculus
<220> FEATURE:
<221> NAME/KEY: misc_feature
<222> LOCATION: (1)..(294)
<223> OTHER INFORMATION: Fig. 10: Tg-21

<400> SEQUENCE: 71

| | | |
|---|---|---|
| caggtccaac tgcagcagcc tggggctgag cttgtgaagc ctggggcttc agtgaagctg | 60 |
| tcctgcaagg cttctggcta caccttcacc agctacttga tgcactgggt gaagcagagg | 120 |
| cctggacgag gccttgagtg gattggaagg attgatccta atagtggtgg tactaagtac | 180 |
| aatgagaagt tcaagagcaa ggccacactg actgtagaca aaccctccag cacagcctac | 240 |
| atgcagctca gcagcctgac atctgaggac tctgcggtct attattgtgc aaga | 294 |

<210> SEQ ID NO 72
<211> LENGTH: 294
<212> TYPE: DNA
<213> ORGANISM: Mus musculus
<220> FEATURE:
<221> NAME/KEY: misc_feature
<222> LOCATION: (1)..(294)
<223> OTHER INFORMATION: Fig. 10: Tg-23

<400> SEQUENCE: 72
caggtccaac tgcagcagcc tggggctgag cttgtgaagc ctggggcttc agtgaagctg    60
tcctgcaagg cttctggcta caccttcacc agctacttga tgcactgggt gaagcagagg   120
cctggacgag gccttgagtg gattggaagg attgatccta atactggtgg tactaagtac   180
gatgagaagt tcaagaccaa ggccacactg actgtagaca aaccctccag cacagcctac   240
atgcagctca gcagtctgac atctgaggac tctgcggtct attattgtgc aaga         294

<210> SEQ ID NO 73
<211> LENGTH: 98
<212> TYPE: PRT
<213> ORGANISM: Mus musculus
<220> FEATURE:
<221> NAME/KEY: misc_feature
<222> LOCATION: (1)..(98)
<223> OTHER INFORMATION: Fig. 20A-20F Cre-flox/+

<400> SEQUENCE: 73

Gln Val Gln Leu Gln Gln Pro Gly Ala Glu Leu Val Lys Pro Gly Ala
1               5                   10                  15

Ser Val Lys Leu Ser Cys Lys Ala Ser Gly Tyr Thr Phe Thr Ser Tyr
            20                  25                  30

Trp Met His Trp Val Lys Gln Arg Pro Gly Arg Gly Leu Glu Trp Ile
        35                  40                  45

Gly Arg Ile Asp Pro Asn Ser Gly Gly Thr Lys Tyr Asn Glu Lys Phe
    50                  55                  60

Lys Ser Lys Ala Thr Leu Thr Val Asp Lys Pro Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg

<210> SEQ ID NO 74
<211> LENGTH: 294
<212> TYPE: DNA
<213> ORGANISM: Mus musculus
<220> FEATURE:
<221> NAME/KEY: misc_feature
<222> LOCATION: (1)..(294)
<223> OTHER INFORMATION: Fig. 20A-20F Cre-flox/+

<400> SEQUENCE: 74
caggtccaac tgcagcagcc tggggctgag cttgtgaagc ctggggcttc agtgaagctg    60
tcctgcaagg cttctggcta caccttcacc agctactgga tgcactgggt gaagcagagg   120
cctggacgag gccttgagtg gattggaagg attgatccta atagtggtgg tactaagtac   180
aatgagaagt tcaagagcaa ggccacactg actgtagaca aaccctccag cacagcctac   240
atgcagctca gcagcctgac atctgaggac tctgcggtct attattgtgc aaga         294

<210> SEQ ID NO 75
<211> LENGTH: 294

```
<212> TYPE: DNA
<213> ORGANISM: Mus musculus
<220> FEATURE:
<221> NAME/KEY: misc_feature
<222> LOCATION: (1)..(294)
<223> OTHER INFORMATION: Fig. 20: 1-5

<400> SEQUENCE: 75
caggtccaac tgcagcagcc tggggctgag cttgtgaagc ctggggcttc agtgattctg    60
tcctgcaagg cttctgccta caccttcacc agttactgga tgcactgggt gaagcagagg   120
cctggacgag gccttgagtg gattggaagg attgatccta atagtggtgg tactaagtac   180
aatgagaagt tcaagagcaa ggccacactg actgtagaca aaccctccag cacagcctac   240
atgcagctca gcagcctgac atctgaggac tctgcggtct attattgtgc aaga         294

<210> SEQ ID NO 76
<211> LENGTH: 294
<212> TYPE: DNA
<213> ORGANISM: Mus musculus
<220> FEATURE:
<221> NAME/KEY: misc_feature
<222> LOCATION: (1)..(294)
<223> OTHER INFORMATION: Fig. 20: 1-6

<400> SEQUENCE: 76
caggtccaac tgcagcagcc tggggctgaa cttgtgaagc ctggggcttc agtgaagctg    60
tcctgcaagg cttctggcta caccttcacc agctactgga tgcactgggt gaagcagagg   120
cctggacgag gccttgagtg gattggaagg attgatccta atagtggtgg tactaagtac   180
aatgagaagt tcaagagcaa ggccacactg actgtagaca aaccctccag cacagcctac   240
atgcagctca gcagcctgac atctgaggac tctgcggtct attattgtgc aaga         294

<210> SEQ ID NO 77
<211> LENGTH: 294
<212> TYPE: DNA
<213> ORGANISM: Mus musculus
<220> FEATURE:
<221> NAME/KEY: misc_feature
<222> LOCATION: (1)..(294)
<223> OTHER INFORMATION: Fig. 20: 3-1

<400> SEQUENCE: 77
caggtccaac tgcagcagcc tggggctgag cttgtgaagc ctggggcttc agtgaagctg    60
tcctgcaagg cttctggcta caccttcacc agctatagga tgcactgggt gaagcagagg   120
cctggacgag gccttgagtg gattggaagg attgatccta atagtggtga tacaaagtac   180
aatgagaagt tcaagagcaa ggccacactg actgtagaca aaccctccag cacagcctac   240
atgcagctca gcagcctgac atctgaggac tctgcggtct attattgtgc aaga         294

<210> SEQ ID NO 78
<211> LENGTH: 294
<212> TYPE: DNA
<213> ORGANISM: Mus musculus
<220> FEATURE:
<221> NAME/KEY: misc_feature
<222> LOCATION: (1)..(294)
<223> OTHER INFORMATION: Fig. 20: 3-2

<400> SEQUENCE: 78
caggtccaac tgcagcagcc tggggctgag cttgtgaggc ctggggcttc agtgaagctg    60
tcctgcaagg cttctggcta caccttcacc acctacttga ttcactgggt gaagcagagg   120
cctggacgag gccttgagtg gattggaagg attgatccta tgagtggtgg cagtaggtac   180
```

```
aatgagtact tcaagagcaa ggccacactg actgtagaca aaccctccag cacagcctac    240
atgcagctca gcagcctgac atctgaggac actgcggtcg attattgtgc aaga          294
```

<210> SEQ ID NO 79
<211> LENGTH: 294
<212> TYPE: DNA
<213> ORGANISM: Mus musculus
<220> FEATURE:
<221> NAME/KEY: misc_feature
<222> LOCATION: (1)..(294)
<223> OTHER INFORMATION: Fig. 20: 3-3

<400> SEQUENCE: 79

```
caggtccaac tgcagcagcc tggggctgag cttgtgaagc ctggggcttc agtgaacctg    60
tcctgcaagg cttctggcta aatttttcacc agctagtgga tgcactgggt gaagcagagg   120
cctggacgag gccttgagtg gattggaagg attgatccta atagtggtgg tactaagtac    180
aatgagaagt tcaagagcaa ggccacattg actgtagaca aaccctccag cacagcctac    240
atgcagctca gcagcctgac atctgaggac tctgcggtct attattgtgc aaga          294
```

<210> SEQ ID NO 80
<211> LENGTH: 294
<212> TYPE: DNA
<213> ORGANISM: Mus musculus
<220> FEATURE:
<221> NAME/KEY: misc_feature
<222> LOCATION: (1)..(294)
<223> OTHER INFORMATION: Fig. 20: 4-2

<400> SEQUENCE: 80

```
caggtccaac tgcagcagcc tggggctgag cttgtgaagc ctgggggttc agtgaagctg    60
tcctgcaagg cttctggtta caccctcacc acctacttaa tgcactgggt gaagcagagg   120
cctggacgag gccttgagtg gattggaagg attgatccta atagtggtgg tactaagtac    180
aatgagaagt tcaagagcaa ggccacactg actatagaca aaccctccag cacagcctac    240
atgcagctca gcagcctgac atctgaggac tctgcggtct attattgtgc aagg          294
```

<210> SEQ ID NO 81
<211> LENGTH: 294
<212> TYPE: DNA
<213> ORGANISM: Mus musculus
<220> FEATURE:
<221> NAME/KEY: misc_feature
<222> LOCATION: (1)..(294)
<223> OTHER INFORMATION: Fig. 20: 4-4

<400> SEQUENCE: 81

```
caggtccaac tgcagcagcc tggggctgag cttgtgaagc ctgggggttc agtgaagctg    60
tcctgcaagg cttctggcta caccctcacc acctacttaa tgcactgggt gaagcagagg   120
cctggacgag gccttgagtg gattggaagg attgatccta atagtggtgg tactaagtac    180
aatgagaagt tcaagagcaa ggccacactg actatagaca aaccctccag cacagcctac    240
atgcagctca gcagcctgac atctgaggac tctgcggtct attattgtgc aagg          294
```

<210> SEQ ID NO 82
<211> LENGTH: 294
<212> TYPE: DNA
<213> ORGANISM: Mus musculus
<220> FEATURE:
<221> NAME/KEY: misc_feature
<222> LOCATION: (1)..(294)
<223> OTHER INFORMATION: Fig. 20: 4-6

<400> SEQUENCE: 82
caggtccaac tgcagcagcc tggggctgag cttgtgaagc ctggggcttc agtgaagctg    60
tcctgcaagg cttctggcta caccctcacc acctacttaa tgcactgggt gaagcagagg   120
cctggacgag gccttgagtg gattggaagg attgatccta atagtggtgg tactaagtac   180
aatgagaagt tcaagagcaa ggccacactg actatagaca aaccctccag cacagcctac   240
atgcagctca gcagcctgac atctgaggac tctgcggtct attattgtgc aagg         294

<210> SEQ ID NO 83
<211> LENGTH: 294
<212> TYPE: DNA
<213> ORGANISM: Mus musculus
<220> FEATURE:
<221> NAME/KEY: misc_feature
<222> LOCATION: (1)..(294)
<223> OTHER INFORMATION: Fig. 20: 1-8

<400> SEQUENCE: 83
caggtccaac tgcagcagcc tggggctgag cttgtgaagc ctggggcttc agtgaagctg    60
tcctgcaagg cttctggcta caccttcacc acctacttga tacactgggt gaagcagagg   120
cctggacgag gccttgagtg gattggaagg attgatccta aaagtggtgg tactaagtac   180
agtgagaagt tcaagagcaa ggccacactg actgtagacc aaccctccag cacagcctac   240
atgcagttca gcagcctgac atctgaggac tctgcggtct attattgtgc aaga         294

<210> SEQ ID NO 84
<211> LENGTH: 294
<212> TYPE: DNA
<213> ORGANISM: Mus musculus
<220> FEATURE:
<221> NAME/KEY: misc_feature
<222> LOCATION: (1)..(294)
<223> OTHER INFORMATION: Fig. 20: 1-10

<400> SEQUENCE: 84
caggtccaac tgcagcagcc tggggctgag cttgtgaagc ctggggcttc agtgaagctg    60
tcctgcaagg cttctggcta caccttcacc acctacttga ttcactgggt gaagcagagg   120
cctggacgag gccttgagtg gattggaagg gttgatccta atactggtgg tactaagtac   180
aatgagaagt tcaagagcaa ggccacactg actgtagaca aaccctccag cacagcctac   240
atgcagctca gcagcctgac atctgaggac tctgcggtct attattgtgc aaga         294

<210> SEQ ID NO 85
<211> LENGTH: 294
<212> TYPE: DNA
<213> ORGANISM: Mus musculus
<220> FEATURE:
<221> NAME/KEY: misc_feature
<222> LOCATION: (1)..(294)
<223> OTHER INFORMATION: Fig. 20: 4-7

<400> SEQUENCE: 85
caggtccaac tgcagcagcc tggggctgag cttgtgaagc ctgggggttc agtgaagctg    60
tcctgcaagg cttctggcta caccctcacc acctacttaa tgcactgggt gaagcagagg   120
cctggacgag gccttgagtg gattggaagg attgatccta atagtggtga tactaagtac   180
aatgagaagt tcaagagcaa ggccacactg actgtagaca aaccctccag cacagcctac   240
atgcagctca acagcctgac atctgaggac tctgcggtct attattgtgc aaga         294

```
<210> SEQ ID NO 86
<211> LENGTH: 294
<212> TYPE: DNA
<213> ORGANISM: Mus musculus
<220> FEATURE:
<221> NAME/KEY: misc_feature
<222> LOCATION: (1)..(294)
<223> OTHER INFORMATION: Fig. 20: 6-1

<400> SEQUENCE: 86
caggtccaac tgcagcagcc tgggactgag cttgtgaagc ctggggcttc agtgaagctg      60
tcctgcaagg cttctggctt caccttcacc agctacttga tgcactgggt gaaacagagg     120
cctggacgag gccttgagtg gattggaagg attgatccta atagtggtgg tactaagtac     180
aatgagacgt tcaagaacaa ggccacactg actgtagaca aaccctccag cacagcctac     240
atgcagctca gcagcctgac atctgaggac tctgcggtct attattgtgc aaga           294

<210> SEQ ID NO 87
<211> LENGTH: 294
<212> TYPE: DNA
<213> ORGANISM: Mus musculus
<220> FEATURE:
<221> NAME/KEY: misc_feature
<222> LOCATION: (1)..(294)
<223> OTHER INFORMATION: Fig. 20: 6-2

<400> SEQUENCE: 87
caggtccaac tgcagcagcc tggggctgag ctagtgaagc ctggggcttc agtgaaggtg      60
tcctgcaagg cttctggcta caccttcacc agctacttga tgcactgggt gaagcagagg     120
cctggacgag gccttgagtg gattggaagg attgatccta atagtggtag tactaagtac     180
aatgagaagt tcaagaccaa ggccacactg actgtagaca aaccctccag tacagcctac     240
atgcagctca gcagcctgac atctgaggac tctgcggtct attattgtgc aaga           294

<210> SEQ ID NO 88
<211> LENGTH: 294
<212> TYPE: DNA
<213> ORGANISM: Mus musculus
<220> FEATURE:
<221> NAME/KEY: misc_feature
<222> LOCATION: (1)..(294)
<223> OTHER INFORMATION: Fig. 20: 7-1

<400> SEQUENCE: 88
caggtccaac tgcagcagcc tggggctgag cttgtgaagc ctggggcttc agtgaagctg      60
tcctgcaagg cttctggcta caccttcacc aactacttga tgcactgggt gaagcagagg     120
cctggacgag gccttgagtg gattggaagg attgatccta atagtggtgg tactaagtac     180
aatgagacgt tcaagaacaa ggccacactg actgtagaca aaccctccag cacagcctac     240
atgcagctca gcagcctgac atctgaggac tctgcggtct attattgtgc aaga           294

<210> SEQ ID NO 89
<211> LENGTH: 98
<212> TYPE: PRT
<213> ORGANISM: Mus musculus
<220> FEATURE:
<221> NAME/KEY: misc_feature
<222> LOCATION: (1)..(98)
<223> OTHER INFORMATION: Fig.20G-20L B-Ganp-/-

<400> SEQUENCE: 89

Gln Val Gln Leu Gln Gln Pro Gly Ala Glu Leu Val Lys Pro Gly Ala
1               5                   10                  15
```

```
Ser Val Lys Leu Ser Cys Lys Ala Ser Gly Tyr Thr Phe Thr Ser Tyr
            20                  25                  30

Trp Met His Trp Val Lys Gln Arg Pro Gly Arg Gly Leu Glu Trp Ile
        35                  40                  45

Gly Arg Ile Asp Pro Asn Ser Gly Gly Thr Lys Tyr Asn Glu Lys Phe
    50                  55                  60

Lys Ser Lys Ala Thr Leu Thr Val Asp Lys Pro Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg

<210> SEQ ID NO 90
<211> LENGTH: 294
<212> TYPE: DNA
<213> ORGANISM: Mus musculus
<220> FEATURE:
<221> NAME/KEY: misc_feature
<222> LOCATION: (1)..(98)
<223> OTHER INFORMATION: Fig.20G-20L B-Ganp-/-

<400> SEQUENCE: 90
caggtccaac tgcagcagcc tggggctgag cttgtgaagc ctggggcttc agtgaagctg     60
tcctgcaagg cttctggcta ccttcacc agctactgga tgcactgggt gaagcagagg     120
cctggacgag gccttgagtg gattggaagg attgatccta atagtggtgg tactaagtac    180
aatgagaagt tcaagagcaa ggccacactg actgtagaca aaccctccag cacagcctac    240
atgcagctca gcagcctgac atctgaggac tctgcggtct attattgtgc aaga          294

<210> SEQ ID NO 91
<211> LENGTH: 294
<212> TYPE: DNA
<213> ORGANISM: Mus musculus
<220> FEATURE:
<221> NAME/KEY: misc_feature
<222> LOCATION: (1)..(294)
<223> OTHER INFORMATION: Fig. 20: 1-1

<400> SEQUENCE: 91
caggtccaac tgcagcagcc tggggctgag cttgtgaagc ctggggcttc agtgaagctg     60
tcctgcaagg cttctggcta ccttcacc agctactgga tgcactgggt gaagcagagg     120
cctggacgag gccttgagtg gattggaagg attgatccta atagtggtgg tactaagtac    180
aatgagaagt tcaagagtaa ggccacactg actgtagaca aaccctccag cacagcctac    240
atgcagctca gcagcctgac atctgaggac tctgcggtct attattgtgc acga          294

<210> SEQ ID NO 92
<211> LENGTH: 294
<212> TYPE: DNA
<213> ORGANISM: Mus musculus
<220> FEATURE:
<221> NAME/KEY: misc_feature
<222> LOCATION: (1)..(294)
<223> OTHER INFORMATION: Fig. 20: 1-5

<400> SEQUENCE: 92
caggtccaac tgcagcagcc tggggctgag cttgtgaagc ctggggcttc agtgattctg     60
tcctgcaagg cttctgccta ccttcacc agttactgga tgcactgggt gaagcagagg     120
cctggacgag gccttgagtg gattggaagg attgatccta atagtggtgg tactaagtac    180
aatgagaagt tcaagagcaa ggccacactg actgtagaca aaccctccag cacagcctac    240
```

```
atgcagctca gcagcctgac atctgaggac tctgcggtct attattgtgc aaga         294

<210> SEQ ID NO 93
<211> LENGTH: 294
<212> TYPE: DNA
<213> ORGANISM: Mus musculus
<220> FEATURE:
<221> NAME/KEY: misc_feature
<222> LOCATION: (1)..(294)
<223> OTHER INFORMATION: Fig. 20: 1-6

<400> SEQUENCE: 93
caggtccaac tgcagcagcc tggggctgag cttgtgaagc ctggggcttc agtgaagctg    60
tcctgcaagg cttctggcta caccttcacc agctactgga tgcactgggt gaagcagagg   120
cctggacgag gccttgagtg gattggaagg attgatccta atagtggtgg tactaagtac   180
aatgagaagt tcaagagcaa ggccacactg actgtagaca aaccctccag cacagcctac   240
atgcaactca gcagcctgac atctgaggac tctgcggtct attattgtgc aaga         294

<210> SEQ ID NO 94
<211> LENGTH: 294
<212> TYPE: DNA
<213> ORGANISM: Mus musculus
<220> FEATURE:
<221> NAME/KEY: misc_feature
<222> LOCATION: (1)..(294)
<223> OTHER INFORMATION: Fig. 20: 2-2

<400> SEQUENCE: 94
caggtccaac tgcagcagcc tggggctgag cttgtgaagc ctggggcttc agtgaagctg    60
tcctgcaagg cttcgggcta caccttcacc aactattgga tgcactgggt gaagcagagg   120
cctggacgag gccttgagtg gattggaagg attgatccta atagtggtgg ttctaagtac   180
aatgagaagt tcaagagcaa ggccacactg actgcagaca aaccctccag cacagcctac   240
atgcagctca gcagcctgac atctgaggac tctgcggtct attactgtgc aaga         294

<210> SEQ ID NO 95
<211> LENGTH: 294
<212> TYPE: DNA
<213> ORGANISM: Mus musculus
<220> FEATURE:
<221> NAME/KEY: misc_feature
<222> LOCATION: (1)..(294)
<223> OTHER INFORMATION: Fig. 20: 2-3

<400> SEQUENCE: 95
caggtccaac tgcagcagcc tggggctgag cttgtgaagc ctggggcttc agtgaagctg    60
tcctgcaagg cttctggcta caccttcacc aactactgga tgcactgggt gaagcagagg   120
cctggacgag gccttgagtg gattggaagt attgatccta atagtggtgg tactaagtac   180
aatgagaagt tcaagaacaa ggccacacta actgtgacac aaccctccag cacagcctac   240
atgcagctca gcagcctgac atctgaggac tctgcggtct attattgtgc aaga         294

<210> SEQ ID NO 96
<211> LENGTH: 294
<212> TYPE: DNA
<213> ORGANISM: Mus musculus
<220> FEATURE:
<221> NAME/KEY: misc_feature
<222> LOCATION: (1)..(294)
<223> OTHER INFORMATION: Fig. 20: 4-3

<400> SEQUENCE: 96
```

```
caggtccaac tgcagcagcc tgggactgaa ctggtgaagc ctggggcttc agtgaagctg      60
tcctgcaagg cttctggcta caccttcacc agctacttga tgcactgggt gaagcagagg     120
cctggacgag gccttgagtg gattggaaat attaatccta atagtggtgg tactaactac     180
aatgagaagt tcaagagcaa ggccacactg actgtagaca aatcctccag cacagcctac     240
atgcagctca gcagcctgac atctgaggac tctgcggtct attactgtgc aaga           294

<210> SEQ ID NO 97
<211> LENGTH: 294
<212> TYPE: DNA
<213> ORGANISM: Mus musculus
<220> FEATURE:
<221> NAME/KEY: misc_feature
<222> LOCATION: (1)..(294)
<223> OTHER INFORMATION: Fig. 20: 4-4

<400> SEQUENCE: 97
caggtccaac tgcagcagcc tggggctgag cttgtgaagc ctggggcttc agtgaagctg      60
tcctgcaagg cttctggcta caccttcacc aactactgga tgcactgggt gaagcagagg     120
cctggacgag gccttgagtg gattggaagg attgatccta atggtggtgg tactaagtac     180
aatgagaagt tcaagaccaa ggccacactg actgtagaca aaccctccag cacagcctac     240
atgcagctca gcagcctgac atctgaggac tctgcggtct attattgtgc aaga           294

<210> SEQ ID NO 98
<211> LENGTH: 294
<212> TYPE: DNA
<213> ORGANISM: Mus musculus
<220> FEATURE:
<221> NAME/KEY: misc_feature
<222> LOCATION: (1)..(294)
<223> OTHER INFORMATION: Fig. 20: 6-1

<400> SEQUENCE: 98
caggtccaac tgcagcagcc tggggctgag cttgtgaagc ctggggcttc agtgaagctg      60
tcctgcaagg cttctggcta cactttaacc agctactgga tgcactgggt gaagcagagg     120
cctggacgag gccttgagtg gattggaagg attgatccta atagtggtgg tactaagtat     180
aatgaggagt tcaagagcaa ggccacactg actgtagaca aaccctccag cacagcctac     240
atgcagctca gcagcctgac atctgaggac tctgcggtct actattgtgc aaga           294

<210> SEQ ID NO 99
<211> LENGTH: 294
<212> TYPE: DNA
<213> ORGANISM: Mus musculus
<220> FEATURE:
<221> NAME/KEY: misc_feature
<222> LOCATION: (1)..(294)
<223> OTHER INFORMATION: Fig. 20: 6-2

<400> SEQUENCE: 99
caggtccaac tgcagcagcc tggggctgag cttgtgaagc ctggggcttc agtgaagctg      60
tcctgcaagg cttctggcta cactttaacc agctactgga tgcactgggt gaagcagagg     120
cctggacgag gccttgagtg gattggaagg attgatccta atagtggtgg tactaagtat     180
aatgagaagt tcaagagcaa ggccacactg actgtagaca aaccctccag cacagcctac     240
atgcagctca gcagcctgac atctgaggac tctgcggtct actattgtgc aaga           294

<210> SEQ ID NO 100
<211> LENGTH: 294
```

```
<212> TYPE: DNA
<213> ORGANISM: Mus musculus
<220> FEATURE:
<221> NAME/KEY: misc_feature
<222> LOCATION: (1)..(294)
<223> OTHER INFORMATION: Fig. 20: 7-1

<400> SEQUENCE: 100
caggtccaac tgcagcagcc tggggctgag cttgtgaagc ctggggcttc agtgaagctg      60
tcctgcaagg cttctggcta caccttcacc agctgctgga tgcactgggt gaagcagagg     120
cctggacgag gccttgagtg gattggaagg attgatccta atggtggtgg tactaagttc     180
gatgagaagt tcaagagcaa ggccacactg actgtagaca aaccctccag cacagcctat     240
atgcaactca gcagcctgac atctgaggac tctgcggtct attattgtgc aaga           294

<210> SEQ ID NO 101
<211> LENGTH: 294
<212> TYPE: DNA
<213> ORGANISM: Mus musculus
<220> FEATURE:
<221> NAME/KEY: misc_feature
<222> LOCATION: (1)..(294)
<223> OTHER INFORMATION: Fig. 20: 8-1

<400> SEQUENCE: 101
caggtccaac tgcagcagcc tggggctgag cttgtgaagc ctggggcttc agtgaagctg      60
tcctgcaagg cttctggcta caccttcacc aactacttga tgcactgggt gaagcagagg     120
cctggacgag gccttgagtg gattggaagg attgatccta atagtggtgg tactaagtac     180
aatgagaagt tcaagagcaa ggccacactg actgtagaca aaccctccag cacagcctac     240
atgcagctca gcagcctgac atctgaggac tctgcggtct attattgtgc aaga           294

<210> SEQ ID NO 102
<211> LENGTH: 294
<212> TYPE: DNA
<213> ORGANISM: Mus musculus
<220> FEATURE:
<221> NAME/KEY: misc_feature
<222> LOCATION: (1)..(294)
<223> OTHER INFORMATION: Fig. 20: 8-2

<400> SEQUENCE: 102
caggtccaac tgcagcagcc tggggctgag cttgtgaagc ctggggcttc agtgaagctg      60
tcctgcaagg cttctggcta caccttcacc agctactgga tgcactgggt gaagcagagg     120
cctggacgag gccttgagtg gattggaagg attgatccta atggtggtgg tactaaatac     180
aatgagaggt tcaagagcaa ggccacactg actgtagaca aaccctccag cacagcctac     240
atgcagttca gcagcctgac atctgaggac tctgcggtct attattgtgc aaga           294

<210> SEQ ID NO 103
<211> LENGTH: 294
<212> TYPE: DNA
<213> ORGANISM: Mus musculus
<220> FEATURE:
<221> NAME/KEY: misc_feature
<222> LOCATION: (1)..(294)
<223> OTHER INFORMATION: Fig. 20: 9-1

<400> SEQUENCE: 103
caggtccaac tgcagcagcc tggggctgag cttgtgaagc ctggggcttc agtgaagctg      60
tcctgcaagg cttctggcta caccttcacc aactactgga tgcactgggt gaagcagagg     120
cctggacgag gccttgagtg gattggaagg attgatccta atagtggtgg tgccaagtac     180
```

```
aatgagaagt tcaagagcaa ggccacactg actgtagaca aaccttccag cacagcctac      240
atgcagctca gcagcctgac atctgaggac tctgcggtct attattgtgc aaga            294

<210> SEQ ID NO 104
<211> LENGTH: 294
<212> TYPE: DNA
<213> ORGANISM: Mus musculus
<220> FEATURE:
<221> NAME/KEY: misc_feature
<222> LOCATION: (1)..(294)
<223> OTHER INFORMATION: Fig. 20: 9-3

<400> SEQUENCE: 104
caggtccaac tgcagcagcc tggggctgag cttgtgaagc ctggggcttc agtgaagctg       60
tcctgcaaga cttctggcta caccttcacc acctactggc tgcactgggt gaagcagagg      120
cctggacgag gccttgagtg gattgggagg attgatccta atagtggcgg tactaagtac      180
aatgagaagt tcaagagcaa ggccacactg actgtagaca aaccctccag cacagcctac      240
atgcagctca gcagcctgac atctgaggac tctgcggtct attattgtgc aaga            294

<210> SEQ ID NO 105
<211> LENGTH: 294
<212> TYPE: DNA
<213> ORGANISM: Mus musculus
<220> FEATURE:
<221> NAME/KEY: misc_feature
<222> LOCATION: (1)..(294)
<223> OTHER INFORMATION: Fig. 20: 9-4

<400> SEQUENCE: 105
caggtccaac tgcagcagcc tggggctgag cttgtgaagc ctggggcttc agtgaagctg       60
tcctgcaagg cttctggcta caccttcacc agctattgga tgcactgggt gaagcagagg      120
cctggacgag gccttgagtg gattggaagg attgatccta atagtggtgg tactaagtac      180
aatgagaagt tcaagagcaa ggccacactg actgtagaca aatcctccag cacagcctac      240
atgcagctca gcagcctgac atctgaggac tctgcggtct attattgtgc aaga            294
```